(12) United States Patent  
Walker et al.

(10) Patent No.: US 6,911,543 B2  
(45) Date of Patent: Jun. 28, 2005

(54) AZABICYCLIC-SUBSTITUTED FUSED-HETEROARYL COMPOUNDS FOR THE TREATMENT OF DISEASE

(75) Inventors: Daniel Patrick Walker, Mystic, CT (US); David W. Piotrowski, Waterford, CT (US); Eric Jon Jacobsen, Chesterfield, MO (US); Brad A. Acker, Saint Charles, MO (US); Donn G. Wishka, Mystic, CT (US); Steven Charles Reitz, Holland, OH (US)

(73) Assignee: Pfizer Inc., New York, NY (US)

( * ) Notice: Subject to any disclaimer, the term of this patent is extended or adjusted under 35 U.S.C. 154(b) by 3 days.

(21) Appl. No.: 10/262,257

(22) Filed: Oct. 1, 2002

(65) Prior Publication Data

US 2003/0153595 A1 Aug. 14, 2003

Related U.S. Application Data

(60) Provisional application No. 60/334,886, filed on Nov. 15, 2001, and provisional application No. 60/326,565, filed on Oct. 2, 2001.

(51) Int. Cl.[7] .................. C07D 491/048; C07D 495/04
(52) U.S. Cl. .............. 546/80; 546/86; 546/87; 546/89; 546/113; 546/114; 546/115; 546/116; 540/582
(58) Field of Search .................. 546/80, 86, 87, 546/89, 113, 114, 115, 116; 540/582; 514/291, 292, 300, 301, 302

(56) References Cited

U.S. PATENT DOCUMENTS

| | | | |
|---|---|---|---|
| 4,605,652 A | 8/1986 | Welstead, Jr. | 514/214 |
| 4,612,319 A | 9/1986 | King | 514/305 |

(Continued)

FOREIGN PATENT DOCUMENTS

| | | | |
|---|---|---|---|
| DE | 3810552 | 3/1998 | C07D/451/12 |
| EP | 0030254 B1 | 8/1980 | C07D/471/04 |

(Continued)

OTHER PUBLICATIONS

Cooper and Millar, *J. Neurochem*, 1997, 68(5), pp. 2140–2151.

(Continued)

*Primary Examiner*—Bernard Dentz  
(74) *Attorney, Agent, or Firm*—Eileen M. Ebel; Peter C. Richardson; Lorraine B. Ling

(57) ABSTRACT

The invention provides compounds of Formula I:

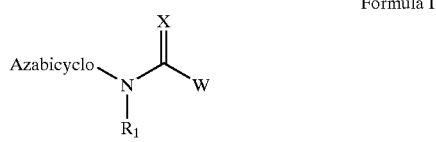

Formula I wherein Azabicyclo is

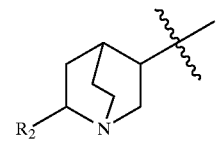

I

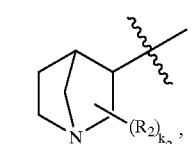

II

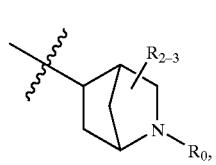

III

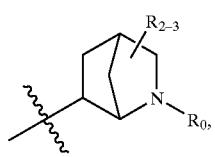

IV

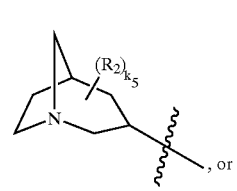

V

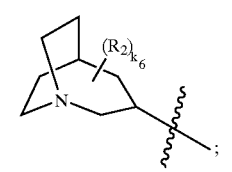

, or

VI

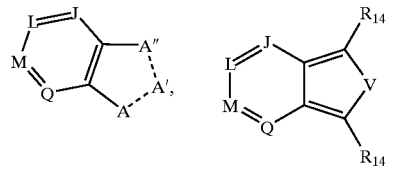

;

W is

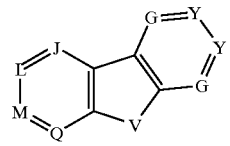

or

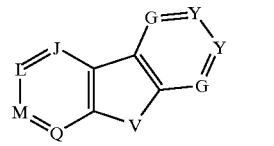

These compounds may be in the form of pharmaceutical salts or compositions, racemic mixtures, or pure enantiomers thereof. The compounds of Formula I are useful in pharmaceuticals in which α7 is known to be involved.

15 Claims, No Drawings

U.S. PATENT DOCUMENTS

| | | | |
|---|---|---|---|
| 4,721,720 A | 1/1988 | Wootton et al. .............. | 514/304 |
| 4,797,406 A | 1/1989 | Richardson et al. ......... | 514/299 |
| 4,798,829 A | 1/1989 | King et al. .................. | 514/214 |
| 4,803,199 A | 2/1989 | Donatsch et al. ........... | 514/214 |
| 4,822,795 A | 4/1989 | King ........................... | 514/214 |
| 4,835,162 A | 5/1989 | Abood ........................ | 514/305 |
| 4,845,092 A | 7/1989 | Sanger ........................ | 514/216 |
| 4,882,327 A | 11/1989 | King ........................... | 514/214 |
| 4,888,353 A | 12/1989 | Lednicer et al. ............. | 514/422 |
| 4,910,193 A | 3/1990 | Buchheit ..................... | 514/216 |
| 4,920,127 A | 4/1990 | King et al. .................. | 514/278 |
| 4,920,219 A | 4/1990 | Pelletier et al. .............. | 540/523 |
| 4,921,982 A | 5/1990 | Cohen ......................... | 549/462 |
| 4,935,511 A | 6/1990 | Youssefyeh et al. ......... | 540/552 |
| 4,937,247 A | 6/1990 | King ........................... | 514/299 |
| 4,973,594 A | 11/1990 | Tyers .......................... | 514/299 |
| 4,983,600 A | 1/1991 | Ward et al. .................. | 514/214 |
| 4,985,437 A | 1/1991 | Tyers .......................... | 514/304 |
| 5,039,680 A | 8/1991 | Imperato et al. ............. | 514/304 |
| 5,217,975 A | 6/1993 | Wadsworth et al. ......... | 514/299 |
| 5,260,303 A | 11/1993 | Becker et al. ............... | 514/300 |
| 5,322,951 A | 6/1994 | King et al. ................ | 548/312.1 |
| 5,342,845 A | 8/1994 | Chokai et al. ............... | 514/305 |
| 5,352,685 A | 10/1994 | Maruyama et al. .......... | 514/301 |
| 5,362,740 A | 11/1994 | Bedeschi et al. ............ | 514/299 |
| 5,434,161 A | 7/1995 | Becker et al. ............... | 514/300 |
| 5,543,426 A | 8/1996 | Dixon et al. ................. | 514/410 |
| 5,561,149 A | 10/1996 | Azria et al. .................. | 514/397 |
| 5,599,937 A | 2/1997 | Glas et al. ................... | 546/133 |
| 5,750,536 A | 5/1998 | Mantovanini et al. ....... | 514/300 |
| 5,977,144 A | 11/1999 | Meyer et al. ................. | 514/334 |
| 5,998,429 A | 12/1999 | Macor et al. ................ | 514/299 |
| 6,054,464 A | 4/2000 | Macor et al. ................ | 514/299 |
| 6,441,049 B2 | 8/2002 | Reitz et al. .................. | 514/657 |
| 2002/0016334 A1 | 2/2002 | Coe et al. .................... | 514/203 |
| 2003/0045540 A1 | 3/2003 | Wishka et al. | |
| 2003/0130304 A1 * | 7/2003 | Yamazaki ................... | 514/301 |

FOREIGN PATENT DOCUMENTS

| | | | | |
|---|---|---|---|---|
| EP | 0635508 | | 4/1992 | ......... C07D/495/04 |
| EP | 483 836 | A1 | 5/1992 | ......... C07D/519/00 |
| EP | 496 064 | A1 | 7/1992 | ......... C07D/405/12 |
| EP | 512 350 | A2 | 11/1992 | ......... C07D/453/02 |
| JP | WO 90/14347 | A | 11/1990 | ......... C07D/453/02 |
| JP | 2002-30084 | | 1/2002 | |
| WO | WO 91/09593 | | 7/1991 | ......... A61K/31/00 |
| WO | WO 91/17161 | | 11/1991 | ......... C07D/451/14 |
| WO | WO 92/10494 | | 6/1992 | ......... C07D/451/00 |
| WO | WO 93/09116 | | 5/1993 | ......... C07D/453/02 |
| WO | WO 95/04742 | | 2/1995 | ......... C07D/519/00 |
| WO | WO 95/27490 | | 10/1995 | ......... A61K/31/445 |
| WO | WO 96/33186 | | 10/1996 | ......... C07D/307/79 |
| WO | WO 97/35860 | | 10/1997 | ......... C07D/451/14 |
| WO | WO 98/54181 | | 12/1998 | ......... C07D/451/02 |
| WO | WO 99/20633 | | 4/1999 | ......... C07D/519/00 |
| WO | WO 00/42044 | | 7/2000 | ......... C07D/491/22 |
| WO | WO 00/73431 | A2 | 12/2000 | ........... C12N/15/00 |
| WO | WO 01/36417 | A1 | 5/2001 | ......... C07D/451/04 |
| WO | WO 01/60821 | A1 | 8/2001 | ......... C07D/453/02 |
| WO | WO 2001058898 | * | 8/2001 | |
| WO | WO 01/76576 | A2 | 10/2001 | ......... A61K/31/00 |
| WO | WO 02/15662 | A2 | 2/2002 | |
| WO | WO 02/16358 | A2 | 2/2002 | ......... C07D/453/02 |
| WO | WO 03/055878 | A1 | 7/2003 | |
| WO | WO 03/078431 | A1 | 9/2003 | |
| WO | WO 03/087102 | A1 | 10/2003 | |
| WO | WO 03/087103 | A1 | 10/2003 | |
| WO | WO 03/087104 | A1 | 10/2003 | |

OTHER PUBLICATIONS

Eisele et al., *Chimaeric nicotinic–serotonergic receptor combines distinct ligand binding and channel specificities*, Nature, 366(6454), pp. 479–483, 1993.

*Bioorg. & Med. Chem. Lett.* 11 (2001) 319–321.

*Behavioral Brain Res.*, 113 (2000) 169–181.

*Eur. J. Med. Chem.*, 34(1999) 415–422.

*Journal of Pharmacology and Experimental Therapeutics.*, 03(1998) 886–896.

* cited by examiner

AZABICYCLIC-SUBSTITUTED FUSED-HETEROARYL COMPOUNDS FOR THE TREATMENT OF DISEASE

CROSS-REFERENCE TO RELATED APPLICATIONS

This application claims priority from Provisional Applications 60/334,886 filed Nov. 15, 2001 and 60/326,565 filed Oct. 2, 2001.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, not all of the activities are desirable. In fact, one of the least desirable properties of nicotine is its addictive nature and the low ratio between efficacy and safety. The present invention relates to molecules that have a greater effect upon the α7 nAChRs as compared to other closely related members of this large ligand-gated receptor family. Thus, the invention provides compounds that are active drug molecules with fewer side effects.

BACKGROUND OF THE INVENTION

Cell surface receptors are, in general, excellent and validated drug targets. nAChRs comprise a large family of ligand-gated ion channels that control neuronal activity and brain function. These receptors have a pentameric structure. In mammals, this gene family is composed of nine alpha and four beta subunits that co-assemble to form multiple subtypes of receptors that have a distinctive pharmacology. Acetylcholine is the endogenous regulator of all of the subtypes, while nicotine non-selectively activates all nAChRs.

The α7 nAChR is one receptor system that has proved to be a difficult target for testing. Native α7 nAChR is not routinely able to be stably expressed in most mammalian cell lines (Cooper and Millar, *J. Neurochem.*, 1997, 68(5) :2140–51). Another feature that makes functional assays of α7 nAChR challenging is that the receptor is rapidly (100 milliseconds) inactivated. This rapid inactivation greatly limits the functional assays that can be used to measure channel activity.

Recently, Eisele et al. has indicated that a chimeric receptor formed between the N-terminal ligand binding domain of the α7 nAChR (Eisele et al., Nature, 366(6454), p 479–83, 1993), and the pore forming C-terminal domain of the 5-$HT_3$ receptor expressed well in Xenopus oocytes while retaining nicotinic agonist sensitivity. Eisele et al. used the N-terminus of the avian (chick) form of the α7 nAChR receptor and the C-terminus of the mouse form of the 5-$HT_3$ gene. However, under physiological conditions the α7 nAChR is a calcium channel while the 5-$HT_3$R is a sodium and potassium channel. Indeed, Eisele et al. teaches that the chicken α7 nAChR/mouse 5-$HT_3$R behaves quite differently than the native α7 nAChR with the pore element not conducting calcium but actually being blocked by calcium ions. WO 00/73431 A2 reports on assay conditions under which the 5-$HT_3$R can be made to conduct calcium. This assay may be used to screen for agonist activity at this receptor.

U.S. Pat. No. 6,054,464 discloses azabicyclic esters of carbamic acids useful in therapy, especially in the treatment or prophylaxis of psychotic disorders and intellectual impairment disorders, as well as intermediates and use of intermediates in synthesis.

U.S. Pat. No. 5,977,144 discloses compositions for benzylidene- and cinnamylidene-anabaseines and methods for using these compositions for treating conditions associated with defects or malfunctioning of nicotinic subtypes brain receptors. These compositions target the α7 receptor subtype with little or no activation of the α4β2 or other receptor subtypes.

U.S. Pat. No. 5,599,937 discloses heteroaromatic quinuclidines used for treating diseases related to muscarinic receptor function.

U.S. Pat. No. 5,561,149 discloses the use of a mono or bicyclic carbocyclic, or heterocyclic carboxylic acid, ester or amide or an imidazolyl carbazol in the manufacture of a medicament suitable for the treatment of stress-related psychiatric disorders, for increasing vigilance, for the treatment of rhinitis or serotonin-induced disorders and/or coadministration with another active agent to increase the bioavailability thereof, or for nasal administration.

U.S. Pat. No. 5,543,426 discloses the use of certain 3,7-disubstituted indole compounds for treating depression or cognitive disorders.

U.S. Pat. No. 5,434,161 discloses imidazopyridines as serotonergic 5-$HT_3$ antagonists.

U.S. Pat. No. 5,362,740 discloses dihydrobenzofuran carboxamides useful in treating CNS disorders, but motility disorders, and/or emisis and/or pain in mammals, and/or migraine.

U.S. Pat. No. 5,352,685 discloses thieno[3,2-b]pyridine derivatives effective for the prevention and therapeutical treatment of the symptoms caused by gastric hypanakinesis, such as heartburn, abdominal distension feeling, anorexia, unpleasant feeling on upper abdomen, abdominalgia, nausea, vomiting, etc. caused by the underlying diseases such as acute and chronic gastritis, stomach and duodenum ulcer, gastroneurosis, gastroptosis, etc.

U.S. Pat. No. 5,342,845 discloses indole derivatives and drugs. The compound of the invention is disclosed as being effective as a gastrointestinal motor activity regulator, antimigraine, antipsychotic or antianxiety drug and for dementia or orthostatic hypotension.

U.S. Pat. No. 5,322,951 discloses certain 1-(2,3-dihydro-indole)carbonyl intermediates useful for preparing 1-(2,3-dihydro)-1-carboxamide final products that possess 5-HT M-receptor antagonist activity.

U.S. Pat. No. 5,272,154 discloses 3,7 substituted indole and indazole compounds and pharmaceutical compositions containing them and are disclosed as being useful for the treatment of psychiatric disorders.

U.S. Pat. No. 5,217,975 discloses azabicyclic compounds for treating dementia.

U.S. Pat. No. 5,039,680 discloses 5-$HT_3$ antagonists in preventing or reducing dependency on dependency-inducing agents.

U.S. Pat. No. 5,001,133 discloses substituted benzoic acid heterocyclic amides and esters as being serotonin M antagonists.

U.S. Pat. No. 4,985,437 discloses the use of certain compounds which act as antagonists of 5-hydroxytryptamine (5-HT) at 5-$HT_3$ receptors for the treatment of cognitive disorders such as attentional and memory deficits and dementia states.

U.S. Pat. No. 4,983,600 discloses heterocyclic compounds useful as 5-HT$_3$ antagonists.

U.S. Pat. No. 4,973,594 discloses the use of compounds which act as antagonists of 5-hydroxytryptamine (5-HT) at 5-HT$_3$ receptors for the treatment of depression.

U.S. Pat. No. 4,937,247 discloses 1-acyl indazoles that are disclosed as having 5-HT$_3$ antagonist activity.

U.S. Pat. No. 4,935,511 discloses benzoxazine and benzoxazepin carboxamide 5-HT$_3$ antagonists properties including CNS, anti-emetic and gastric prokinetic activity and which are void of any significant D$_2$ receptor binding affinity.

U.S. Pat. No. 4,921,982 discloses 5-halo-2,3-dihydro-2,2-dimethylbenzofuran-7-carboxylic acids which are useful as intermediates for 5-HT$_3$ antagonists.

U.S. Pat. No. 4,920,219 discloses substituted saturated and unsaturated indole quinoline and benzazepine carboxamides and their valuable use as 5-HT$_3$ antagonists havinig CNS and gastric prokinetic activity void of any significant D$_2$ receptor binding properties.

U.S. Pat. No. 4,920,127 discloses substituted indoles and their use as 5-HT$_3$ receptor antagonists.

U.S. Pat. No. 4,910,193 discloses treatment of gastrointestinal disorders.

U.S. Pat. No. 4,888,353 discloses carboxamides useful as antiemetic or antipsychotic agents.

U.S. Pat. No. 4,882,327 discloses certain heterocyclic N-substituted carboxamides having 5-HT$_3$ receptor antagonist activity.

U.S. Pat. No. 4,845,092 discloses a method of treatment of visceral pain in mammals, including humans.

U.S. Pat. No. 4,835,162 discloses agonists and antagonists to nicotine as smoking deterrents.

U.S. Pat. No. 4,822,795 discloses pharmaceutically useful esters and amides.

U.S. Pat. No. 4,803,199 discloses pharmaceutically useful heterocyclic acid esters and amides or alkylene bridged peperidines as serotonin M antagonists.

U.S. Pat. No. 4,798,829 discloses 1-azabicyclo[3.2.2] nonane derivatives having gastric motility enhancing activity and/or anti-emetic activity and/or 5-HT receptor antagonist activity.

U.S. Pat. No. 4,797,406 discloses amides and esters containing bridged piperidines and use as serotonin M antagonists.

U.S. Pat. No. 4,721,720 discloses a method of treating emesis, anxiety and/or irritable bowl syndrome.

U.S. Pat. No. 4,612,319 discloses bridged quinolizinidinylamides, compositions containing them and methods for their use.

U.S. Pat. No. 4,605,652 discloses a method of enhancing memory or correcting memory deficiency with arylamido (and arylthioamido)-azabicycloalkanes, and the pharmaceutically acceptable acid addition salts, hydrates and alcoholates thereof.

WO 01/60821 A1 discloses novel biarylcarboxamides and their use in therapy, especially in the treatement of prophylaxis of psychotic and intellectual impairment conditions.

WO 01/36417 A1 discloses novel N-azabicyclo-amide derivatives and use in therapy, especially in the treatment of prophylaxis of psychotic disorders and intellectual impairment disorders.

WO 00/73431 A2 discloses two binding assays to directly measure the affinity and selectivity of compounds at the α7 nAChR and the 5-HT$_3$R. The combined use of these functional and binding assays may be used to identify compounds that are selective agonists of the α7 nAChR.

WO 99/20633 discloses benzoazine derivatives having an antagonist activity for 5-HT$_3$/5-HT$_4$ receptors.

WO 97/35860 discloses novel benzimidazol derivatives having an affinity for the serotoninergic 5-HT$_3$/5-HT$_4$ receptors.

WO 96/33186 discloses substituted dihydrobenzofuran derivatives as 5-HT$_4$ agonists.

WO 95/27490 discloses serotonin antagonists (5-HT$_3$) for treating fibromyalgia.

WO 95/04742 discloses tropyl 7-azaindol-3-ylcarboxyamides as antitussive agents.

WO 92/10494 discloses novel compounds that are 5-HT$_3$ receptor antagonists.

WO 91/17161 discloses isoquinoline amides and esters as 5-HT$_3$ receptor antagonists.

WO 91/09593 discloses 5-HT$_3$ antagonists for treatment of nausea, bradycardia or hypotension associated myocardial instability.

WO 90/14347 A as abstracted in chemical abstract 1991:143,158 discloses N-quinuclidinyl-indolecarboxamide derivatives as being antiemetics.

EP 512 350 A2 discloses 3-(indolyl-2-carboxamido) quinuclidines useful for treating diseases characterized by an excess or enhanced sensitivity to serotonin, e.g., psychosis, nausea, vomiting, dementia or other cognitive diseases, migraine, diabetes. The compound may be used to control anxiety, aggression, depression, and pain. The compounds are disclosed as serotonin 5-HT$_3$ antagonists.

EP 496 064 A1 discloses a process for the preparation of substituted benzofuran derivatives. The compounds are disclosed as being useful 5-HT$_3$ receptor antagonists.

EP 483 836 A1 discloses pyrazolo[1,5-a]pyridine-3-carboxylic acid derivatives, their preparation process, and serotonin receptor antagonists containing them as active ingredients.

DE 3810552 A1 discloses esters and amides of indolyl-, benzo[b]thiophenyl-, benzo[b]furancarboxylic acids or 4-amino-2 methoxy-benzoic acids with N-heterocyclic or N-heterobicyclic alcohols or amines. The compounds disclosed have activity against pain especially migraine, as an anti-arrhythmic for gastrointestinal disturbances, stomach disturbances, gastritis ulcer, gall bladder, spastic colon, Crohn's disease, ulcerative colitis, carcinoid syndrome, diarrhea of various types. The compounds are also disclosed as speeding stomach emptying, controlling gastro duodenal and gastro esophageal reflux, disturbances of esophageal motility, hiatal hernia, cardiac insufficiency, hypotonic stomach, paralytic ileus, manic depressive psychosis and other psychoses. The compounds are also disclosed as useful for stress related diseases, senility, and enhancement of nasal absorption of other agents, e.g., in the treatment of emesis.

In *Bioorg. & Med. Chem. Lett.* 11 (2001) 319–321, the 5-HT$_3$ antagonist tropisetron (ICS 205-930) is discussed as a potent and selective α7 nicotinic receptor partial agonist.

In *Behavioral Brain Res.*, 113 (2000) 169–181, it is discussed that the brain α7 nicotinic receptor may be an important therapeutic target for the treatment of Alzheimer's disease using DMXBA which is known as GTS-21.

In *Bioorg. & Med. Chem. Lett.* 9 (1999) 1895–1900, it is discussed the discovery of a highly potent, functionally-selective muscarinic M1 agonist.

In *Bioorg. & Med. Chem. Lett.* 4 (1994) 695–698, it is discussed pyrazolo[1,5-a]pyridines and pyrazolo[1,5-b]pyridazines as 5-HT₃ antagonists.

In *Eur. J Med. Chem.*, 34 (1999) 415–422, benzimidazole-2-carboxylic acid amides and esters are discussed as a new structural class of 5-HT₃ ligands.

SUMMARY OF THE INVENTION

The present invention discloses compounds of the Formula I:

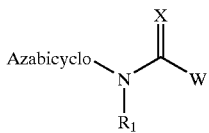

Formula I wherein Azabicyclo is

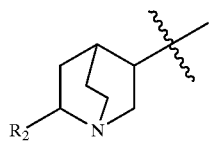  I

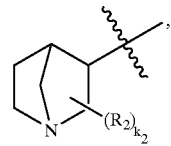  II

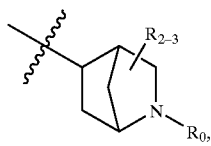  III

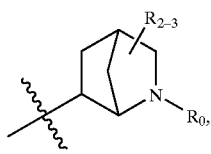  IV

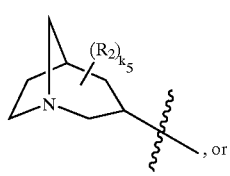  V

, or

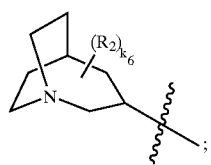  VI

W is

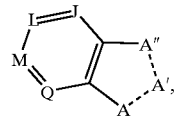  (a)

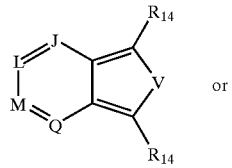  or  (b)

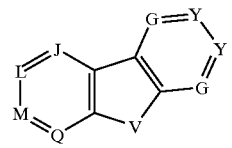  (c)

provided that the bond between the —C(=X)— group and the W group may be attached at any available carbon atom within the W group as provided in $R_3$, $R_6$, and $R_{15}$;

X is O, or S;

$R_0$ is H, lower alkyl, substituted lower alkyl, or halogenated lower alkyl;

Each $R_1$ is H, alkyl, cycloalkyl, halogenated alkyl, substituted phenyl, or substituted naphthyl;

Each $R_2$ is alkyl, halogenated alkyl, substituted alkyl, cycloalkyl, aryl, F, Cl, Br, I, or $R_2$ is absent provided that $k_2$, $k_5$, or $k_6$ is 0;

$R_{2-3}$ is H, alkyl, substituted alkyl, halogenated alkyl, F, Cl, Br, or I;

$k_2$ is 0 or 1;

$k_5$ and $k_6$ are independently 0, 1, or 2;

A - - - A' - - - A'' is $N(R_4)$—$C(R_3)$=$C(R_3)$, N=$C(R_3)$—$C(R_{15})_2$, $C(R_3)$=$C(R_3)$ —$N(R_4)$, $C(R_3)_2$—$N(R_4)$—$C(R_3)_2$, $C(R_{15})_2$—$C(R_3)$=N,$N(R_4)$—$C(R_3)_2$—$C(R_3)_2$, $C(R_3)_2$—$C(R_3)_2$—$N(R_4)$, O—$C(R_3)$=$C(R_3)$, O—$C(R_3)_2$—$C(R_3)_2$, $C(R_3)_2$—O—$C(R_3)_2$, $C(R_3)$=$C(R_3)$—O, $C(R_3)_2$—$C(R_3)_2$—O, S—$C(R_3)$=$C(R_3)$, S—$C(R_3)_2$—$C(R_3)_2$, $C(R_3)_2$—S—$C(R_3)_2$, $C(R_3)$=$C(R_3)$—S, or $C(R_3)_2$—$C(R_3)_2$—S;

Each $R_3$ is independently a bond to the core molecule provided that only one $R_3$ and no $R_6$ or $R_{15}$ is also said bond, H, alkyl, substituted alkyl, halogenated alkyl, alkenyl, substituted alkenyl, halogenated alkenyl, alkynyl, substituted alkynyl, halogenated alkynyl, —CN, —NO₂, F, Br, Cl, I, —$OR_{19}$, —$C(O)N(R_{10})_2$, —$N(R_{10})_2$, —$SR_{19}$, —$S(O)_2R_{19}$, —$C(O)R_{19}$, —$CO_2R_{19}$, aryl, $R_7$, or $R_9$;

J, L, M, and Q are N or $C(R_6)$ provided that only one of J, L, M, or Q, is N and the others are $C(R_6)$, further provided that when the core molecule is attached to the pyridinyl moiety at M, Q is C(H), and further provided that there is only one attachment to the core molecule;

G and Y are $C(R_6)$, provided that when the molecule is attached to the phenyl moiety at Y, G is CH;

$R_4$ is H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, or $R_9$;

Each $R_5$ is independently H, lower alkyl, or lower alkenyl;

Each $R_6$ is independently H, F, Br, I, Cl, —CN, —CF$_3$, —OR$_5$, —SR$_5$, —N(R$_5$)$_2$, or a bond to the core molecule provided that only one $R_6$ and no $R_3$ or $R_{15}$ is said bond;

V is selected from O, S, or N(R$_4$);

$R_7$ is 5-membered heteroaromatic mono-cyclic moieties containing within the ring 1–3 heteroatoms independently selected from the group consisting of =N—, —N(R$_{17}$)—, —O—, and —S—, and having 0–1 substituent selected from $R_{18}$ and further having 0–3 substituents independently selected from F, Cl, Br, or I, or $R_7$ is 9-membered fused-ring moieties having a 6-membered ring fused to a 5-membered ring including the formula

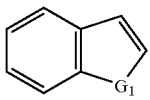

wherein G$_1$ is O, S, or NR$_{17}$,

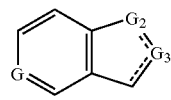

wherein G$_1$ is O, S or NR$_{17}$,
wherein G is C(R$_{16}$) or N, and each G$_2$ and G$_3$ are independently selected from C(R$_{16}$)$_2$, C(R$_{16}$), O, S, N, and N(R$_{18}$), provided that both G$_2$ and G$_3$ are not simultaneously O, simultaneously S, or simultaneously O and S, or

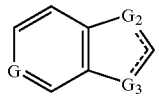

wherein G is C(R$_{16}$) or N, and each G$_2$ and G$_3$ are independently selected from C(R$_{16}$)$_2$, C(R$_{16}$), O, S, N, and N(R$_{17}$), each 9-membered fused-ring moiety having 0–1 substituent selected from $R_{18}$ and further having 0–3 substituent(s) independently selected from F, Cl, Br, or I, wherein the $R_7$ moiety attaches to other substituents as defined in formula I at any position on either ring as valency allows;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R$_7$, R$_9$, phenyl, or substituted phenyl;

$R_9$ is 6-membered heteroaromatic mono-cyclic moieties containing within the ring 1–3 heteroatoms selected from =N— and having 0–1 substituent selected from $R_{18}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{18}$ and 0–3 substituent(s) independently selected from F, Cl, Br, or I, and having a bond directly or indirectly attached to the core molecule where valency allows;

Each $R_{10}$ is independently H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_{11}$ is independently H, alkyl, cycloalkyl, heterocycloalkyl, halogenated alkyl, halogenated cycloalkyl, or halogenated heterocycloalkyl;

$R_{12}$ is —NO$_2$, —CN, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —C(O)NR$_{11}$R$_{11}$, —NR$_{11}$C(O)R$_{11}$, —S(O)$_2$NR$\,$R$_{11}$, or —NR$_{11}$S(O)$_2$R$_{11}$;

$R_{13}$ is —CN, —CF$_3$, —NO$_2$, —OR$_{11}$, —SR$_{11}$, —NR R$_{11}$, —C(O)R$_{11}$, —C(O)NR$_{11}$R$_{11}$, —NR$_{11}$C(O)R$_{11}$, —S(O)$_2$NR$_{11}$R$_{11}$, or —NR$_{11}$S(O)$_2$R$_{11}$;

Each $R_{14}$ is H, alkyl, substituted alkyl, halogenated alkyl, alkenyl, substituted alkenyl, halogenated alkenyl, alkynyl, substituted alkynyl, halogenated alkynyl, F, Br, Cl, I, —CN, —NO$_2$, —OR$_{19}$, —C(O)N(R$_{10}$)$_2$, —N(R$_{10}$)$_2$, —SR$_{19}$, —S(O)$_2$R$_{19}$, —C(O)R$_{19}$, —CO$_2$R$_{19}$, aryl, R$_7$ or R$_9$;

Each $R_{15}$ is independently alkyl, substituted alkyl, halogenated alkyl, alkenyl, substituted alkenyl, halogenated alkenyl, alkynyl, substituted alkynyl, halogenated alkynyl, F, Br, Cl, I, —CN, —NO$_2$, —OR$_{19}$, —C(O)N(R$_{10}$)$_2$, —N(R$_{10}$)$_2$, —SR$_{19}$, —CO$_2$R$_{19}$, aryl, R$_7$, R$_9$, or a bond to the core molecule provided that only one $R_{15}$ and no $R_6$ or $R_3$ is said bond;

Each $R_{16}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, F, Cl, Br, I, —NO$_2$, —CN, —OR$_{11}$, —SR$_{11}$, —NR$_{11}$R$_{11}$, —C(O)R$_{11}$, —C(O)NR$_{11}$ R$_{11}$, —NR$_{11}$C(O)R$_1$, —S(O)$_2$NR$_{11}$R$_{11}$, —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

$R_{17}$ is H, alkyl, halogenated alkyl, substituted alkyl, cycloalkyl, halogenated cycloalkyl, substituted cycloalkyl, phenyl, —SO$_2$R$_8$, or phenyl having 1 substituent selected from $R_{18}$ and further having 0–3 substituents independently selected from F, Cl, Br, or I;

$R_{18}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$, —S(O)$_2$R$_{11}$, —NO$_2$, alkyl substituted with 1–4 substituent(s) independently selected from F, Cl, Br, I, or R$_{13}$, cycloalkyl substituted with 1–4 substituent(s) independently selected from F, Cl, Br, I, or R$_{13}$, or heterocycloalkyl substituted with 1–4 substituent(s) independently selected from F, Cl, Br, I, or R$_{13}$;

$R_{19}$ is H, alkyl, cycloalkyl, substituted alkyl, halogenated alkyl, substituted phenyl, or substituted naphthyl;

or pharmaceutical composition, pharmaceutically acceptable salt, racemic mixture, or pure enantiomer thereof.

The compound of Formula I are used to treat a disease or condition, wherein the diseases, disorders, and/or condition is any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

Embodiments of the invention may include one or more or combination of the following.

The compound of Formula I, wherein X is O.

The compound of Formula I, where X is S.

The compound of Formula I, where Azabicyclo is any one or more of I, II, III, IV, V, or VI.

The compound of Formula I, where W is any one or more of (a), (b), or (c).

The compound of Formula I, where W is any one or more of the following: thieno[2,3-b]pyridin-2-yl, thieno[2,3-b]pyridin-5-yl, thieno[2,3-b]pyridin-6-yl, thieno[3,2-b]pyridin-2-yl, thieno[3,2-b]pyridin-5-yl, thieno[3,2-b]pyridin-6-yl, thieno[2,3-c]pyridin-2-yl, thieno[2,3-c]pyridin-5-yl, thieno[3,2-c]pyridin-2-yl, thieno[3,2-c]pyridin-6-yl, furo[3,2-c]pyridin-2-yl, furo[3,2-c]pyridin-6-yl, furo[2,3-b]pyridin-2-yl, furo[2,3-c]pyridin-2-yl, furo[2,3-c]pyridin-5-yl, 2,3-dihydrofuro[2,3-c]pyridin-5-yl, 1H-pyrrolo[2,3-c]pyridin-5-yl, thieno[3,4-c]pyridin-6-yl, benzothieno[3,2-c]pyridine-3-yl, benzothieno[2,3-c]pyridin-3-yl, benzofuro[3,2-c]pyridin-3-yl, or benzofuro[2,3-c]pyridin-3-yl, any of which is optionally substituted on up to 4 different carbon atoms as valency allows and as allowed by the definition of W with F, Br, Cl, I, —CN, —NO$_2$, —CF$_3$, —OR$_5$, —OR$_{19}$, —SR$_5$, —SR$_{19}$, —N(R$_5$)$_2$, —N(R$_{10}$)$_2$, —C(O)R$_{19}$, —CO$_2$R$_{19}$, —C(O)N(R$_{10}$)$_2$, —S(O)$_2$R$_{19}$, alkyl, substituted alkyl, halogenated alkyl, alkenyl, substituted alkenyl, halogenated alkenyl, alkynyl, substituted alkynyl, halogenated alkynyl, aryl, R$_7$, R$_9$, and further where any of which is optionally substituted on a nitrogen as allowed by the definition of W with alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R$_7$, or R$_{19}$, provided that one carbon is used to bond W to the core molecule. One of ordinary skill in the art will recognize what substitution is allowed by comparing the named moieties with the allowed moieties for W.

The compound of Formula I, where (a), (b), or (c) is optionally substituted as the definition of W allows with up to four substituents being F, Br, Cl, I, —CN, —CF$_3$, —OR$_5$, —SR$_5$, —N(R$_5$)$_2$, —C(O)R$_5$, —CO$_2$R$_5$, —C(O)N(R$_{10}$)$_2$, —S(O)$_2$R$_5$, lower alkyl, lower substituted alkyl, or lower alkynyl, where R$_{10}$ is H, lower halogenated alkyl, or lower alkyl optionally substituted with —CN, —CF$_3$, —NO$_2$, —OR$_{11}$, —SR$_{11}$, —NR$_{11}$R$_{11}$, —C(O)R$_{11}$, —C(O)NR$_{11}$R$_{11}$, —NR$_{11}$C(O)R$_{11}$, —S(O)$_2$NR$_{11}$R$_{11}$, or —NR$_{11}$S(O)$_2$R$_{11}$, where R$_{11}$ is H, lower alkyl, lower halogenated alkyl, lower substituted alkyl. One of ordinary skill in the art will recognize that where —OR$_{19}$, —SR$_{19}$, —C(O)R$_{19}$, or —CO$_2$R$_{19}$ is an allowed substituent, —OR$_5$, —SR$_5$, —C(O)R$_5$, or —CO$_2$R$_5$ is also allowed due to the groups within R$_5$ being a subgroup of what is in R$_{19}$. Furthermore, one of ordinary skill in the art can identify which substituents are allowed on carbon or nitrogen as allowed by the definition of W.

Lower alkynyl is straight- and branched-chained moieties having from 2–4 carbon atoms and having at least one carbon-carbon triple bond.

Another group of compounds of Formula I include compounds where R$_1$ is H, alkyl, or cycloalkyl.

Another group of compounds of Formula I include compounds where Azabicyclo is II, V, or VI and where each k$_2$, k$_5$, and k$_6$ is independently 0 or 1. Another group of compounds of Formula I include compounds where R$_2$ is alkyl, halogenated alkyl, substituted alkyl, or is absent provided that k$_2$, k$_5$, or k$_6$ is 0. Another group of compounds of Formula I include compounds where R$_1$ is H or lower alkyl, and wherein R$_2$ is lower alkyl or is absent provided that k$_2$, k$_5$, or k$_6$ is 0.

Another group of compounds of Formula I include compounds where Azabicyclo is I and where R$_2$ is alkyl, halogenated alkyl, or substituted alkyl, or where Azabicyclo is III or IV and where R$_{2-3}$ is H, alkyl, or substituted alkyl.

The compound of Formula I, where the compound is any one or more or combination of the following as the free base, or pharmaceutally acceptable salt thereof as a pure enantiomer or racemic mixture thereof:

Exo-4(S)-N-(1-azabicyclo[2.2.1]hept-3-yl)furo[2,3-c]pyridine-5-carboxamide;

Exo-4(R)-N-(1-azabicyclo[2.2.1]hept-3-yl)furo[2,3-c]pyridine-5-carboxamide;

Exo-N-(1-azabicyclo[2.2.1]hept-3-yl)furo[2,3-c]pyridine-5-carboxamide;

(+)-N-[endo-1-azabicyclo[2.2.1]hept-3-yl]furo[2,3-c]pyridine-5-carboxamide;

(−)-N-[endo-1-azabicyclo[2.2.1]hept-3-yl]furo[2,3-c]pyridine-5-carboxamide;

N-(1-(6-methyl)-azabicyclo[2.2.1]hept-3-yl)furo[2,3-c]pyridine-5-carboxamide;

N-((3R,5R)-1-azabicyclo[3.2.1]oct-3-yl)furo[2,3-c]pyridine-5-carboxamide;

N-(1-azabicyclo[3.2.2]non-3-yl)furo[2,3-c]pyridine-5-carboxamide;

N-[(exo)-azabicyclo[2.2.1]hept-3-yl]furo[3,2-c]pyridine-6-carboxamide;

N-(1-(6-methyl)-azabicyclo[2.2.1]hept-3-yl)furo[3,2-c]pyridine-6-carboxamide;

N-((3R,5R)-1-azabicyclo[3.2.1]oct-3-yl)furo[3,2-c]pyridine-6-carboxamide;

N-(1-azabicyclo[3.2.2]non-3-yl)furo[3,2-c]pyridine-6-carboxamide;

N-(1-azabicyclo[2.2.1]-hept-3-yl)-2,3-dihydrofuro[2,3-c]pyridine-5-carboxamide;

N-(1-(6-methyl)-azabicyclo[2.2.1]hept-3-yl)-2,3-dihydrofuro[2,3-c]pyridine-5-carboxamide;

N-((3R,5R)-1-azabicyclo[3.2.1]oct-3-yl)-2,3-dihydrofuro[2,3-c]pyridine-5-carboxamide;
N-(1-azabicyclo[3.2.2]non-3-yl)-2,3-dihydrofuro[2,3-c]pyridine-5-carboxamide;
N-(1-azabicyclo[2.2.1]hept-3-yl)-7-chlorofuro[2,3-c]pyridine-5-carboxamide;
N-(1-(6-methyl)-azabicyclo[2.2.1]hept-3-yl)-7-chlorofuro[2,3-c]pyridine-5-carboxamide;
N-((3R,5R)-1-azabicyclo[3.2.1]oct-3-yl)-7-chlorofuro[2,3-c]pyridine-5-carboxamide;
N-(1-azabicyclo[2.2.1]hept-3-yl)-3,3-dimethyl-2,3-dihydrofuro[2,3-c]pyridine-5-carboxamide;
N-(1-(6-methyl)-azabicyclo[2.2.1]hept-3-yl)-3,3-dimethyl-2,3-dihydrofuro[2,3-c]pyridine-5-carboxamide;
N-((3R,5R)-1-azabicyclo[3.2.1]oct-3-yl)-3,3-dimethyl-2,3-dihydrofuro[2,3-c]pyridine-5-carboximide;
N-(1-azabicyclo[2.2.1]hept-3-yl)-2-methylfuro[2,3-c]pyridine-5-carboxamide;
N-(1-(6-methyl)-azabicyclo[2.2.1]hept-3-yl)-2-methylfuro[2,3-c]pyridine-5-carboxamide;
N-((3R,5R)-1-azabicyclo[3.2.1]oct-3-yl)-2-methylfuro[2,3-c]pyridine-5-carboxamide;
Exo-4(S)-N-(1-azabicyclo[2.2.1]hept-3-yl)-3-methylfuro[2,3-c]pyridine-5-carboxamide;
N-(1-(6-methyl)-azabicyclo[2.2.1]hept-3-yl)-3-methylfuro[2,3-c]pyridine-5-carboxamide;
(exo)-N-[1-Azabicyclo[3.2.1]oct-3-yl]-3-methylfuro[2,3-c]pyridine-5-carboxamide;
(3R,5R)-N-[1-azabicyclo[3.2.1]oct-3-yl]-3-methylfuro[2,3-c]pyridine-5-carboximide
Exo-4(S)-N-(1-azabicyclo[2.2.1]hept-3-yl)-3-ethylfuro[2,3-c]pyridine-5-carboxamide;
N-(1-(6-methyl)-azabicyclo[2.2.1]hept-3-yl)-3-ethylfuro[2,3-c]pyridine-5-carboxamide;
N-((3R,5R)-1-azabicyclo[3.2.1]oct-3-yl)-3-ethylfuro[2,3-c]pyridine-5-carboxamide;
N-(1-azabicyclo[2.2.1]hept-3-yl)-furo[2,3-b]pyridine-2-carboxamide;
N-(1-(6-methyl)-azabicyclo[2.2.1]hept-3-yl)-furo[2,3-b]pyridine-2-carboxamide;
N-((3R,5R)-1-azabicyclo[3.2.1]oct-3-yl)-furo[2,3-b]pyridine-2-carboxamide;
N-(1-azabicyclo[3.2.2]non-3-yl)-furo[2,3-b]pyridine-2-carboxamide;
Exo-4(S)-N-(1-azabicyclo[2.2.1]hept-3-yl)-3-isopropylfuro[2,3-c]pyridine-5-carboxamide;
N-(1-(6-methyl)-azabicyclo[2.2.1]hept-3-yl)-3-isopropylfuro[2,3-c]pyridine-5-carboxamide;
N-((3R,5R)-1-azabicyclo[3.2.1]oct-3-yl)-3-isopropylfuro[2,3-c]pyridine-5-carboxamide;
N-(1-azabicyclo[2.2.1]hept-3-yl)-7-(methylsulfanyl)furo[2,3-c]pyridine-5-carboxamide;
N-(1-(6-methyl)-azabicyclo[2.2.1]hept-3-yl)-7-(methylsulfanyl)furo[2,3-c]pyridine-5-carboxamide;
N-((3R,5R)-1-azabicyclo[3.2.1]oct-3-yl)-7-(methylsulfanyl)furo[2,3-c]pyridine-5-carboxamide;
N-(1-azabicyclo[2.2.1]hept-3-yl)-thieno[2,3-b]pyridine-2-carboxamide;
N-(1-(6-methyl)-azabicyclo[2.2.1]hept-3-yl)-thieno[2,3-b]pyridine-2-carboxamide;
N-((3R,5R)-1-azabicyclo[3.2.1]oct-3-yl)-thieno[2,3-b]pyridine-2-carboxamide;
N-(1-azabicyclo[3.2.2]non-3-yl)-thieno[2,3-b]pyridine-2-carboxamide;
N-(1-azabicyclo[2.2.1]hept-3-yl)-thieno[2,3-b]pyridine-5-carboxamide;
N-(1-(6-methyl)-azabicyclo[2.2.1]hept-3-yl)-thieno[2,3-b]pyridine-5-carboxamide;
N-((3R,5R)-1-azabicyclo[3.2.1]oct-3-yl)thieno[2,3-b]pyridine-5-carboxamide;
N-(1-azabicyclo[3.2.2]non-3-yl)-thieno[2,3-b]pyridine-5-carboxamide;
N-(1-azabicyclo[2.2.1]hept-3-yl)-thieno[2,3-b]pyridine-6-carboxamide;
N-(1-(6-methyl)-azabicyclo[2.2.1]hept-3-yl)-thieno[2,3-b]pyridine-6-carboxamide,
N-((3R,5R)-1-azabicyclo[3.2.1]oct-3-yl)-thieno[2,3-b]pyridine-6-carboxamide;
N-(1-azabicyclo[3.2.2]non-3-yl)-thieno[2,3-b]pyridine-6-carboxamide;
N-(1-azabicyclo[2.2.1]hept-3-yl)-thieno[2,3-c]pyridine-2-carboxamide;
N-(1-(6-methyl)-azabicyclo[2.2.1]hept-3-yl)-thieno[2,3-c]pyridine-2-carboxamide;
N-((3R,5R)-1-azabicyclo[3.2.1]oct-3-yl)-thieno[2,3-c]pyridine-2-carboxamide;
N-(1-azabicyclo[3.2.2]non-3-yl)-thieno[2,3-c]pyridine-2-carboxamide;
N-(1-azabicyclo[2.2.1]hept-3-yl)-thieno[3,2-b]pyridine-2-carboxamide;
N-(1-(6-methyl)-azabicyclo[2.2.1]hept-3-yl)-thieno[3,2-b]pyridine-2-carboxamide;
N-((3R,5R)-1-azabicyclo[3.2.1]oct-3-yl)-thieno[3,2-b]pyridine-2-carboxamide;
N-(1-azabicyclo[3.2.2]non-3-yl)-thieno[3,2-b]pyridine-2-carboxamide;
N-(1-azabicyclo[2.2.1]hept-3-yl)-thieno[3,2-b]pyridine-5-carboxamide;
N-(1-(6-methyl)-azabicyclo[2.2.1]hept-3-yl)-thieno[3,2-b]pyridine-5-carboxamide;
N-((3R,5R)-1-azabicyclo[3.2.1]oct-3-yl)-thieno[3,2-b]pyridine-5-carboxamide;
N-(1-azabicyclo[3.2.2]non-3-yl)-thieno[3,2-b]pyridine-5-carboxamide;
N-(1-azabicyclo[2.2.1]hept-3-yl)-thieno[3,2-b]pyridine-6-carboxamide;
N-(1-(6-methyl)-azabicyclo[2.2.1]hept-3-yl)-thieno[3,2-b]pyridine-6-carboxamide;
N-((3R,5R)-1-azabicyclo[3.2.1]oct-3-yl)-thieno[3,2-b]pyridine-6-carboxamide;
N-(1-azabicyclo[3.2.2]non-3-yl)-thieno[3,2-b]pyridine-6-carboxamide;
N-(1-azabicyclo[2.2.1]hept-3-yl)-thieno[3,2-c]pyridine-2-carboxamide;
N-(1-(6-methyl)-azabicyclo[2.2.1]hept-3-yl)-thieno[3,2-c]pyridine-2-carboxamide;
N-(2-azabicyclo[2.2.1]hept-6-yl)-thieno[3,2-c]pyridine-2-carboxamide;
N-(2-azabicyclo[2.2.1]hept-6-yl)-thieno[3,2-c]pyridine-2-carboxamide;
Exo-4(S)-N-(1-azabicyclo[2.2.1]hept-3-yl)-thieno[2,3-c]pyridine-5-carboxamide;
N-(1-(6-methyl)-azabicyclo[2.2.1]hept-3-yl)-thieno[2,3-c]pyridine-5-carboxamide;
N-((3R,5R)-1-azabicyclo[3.2.1]oct-3-yl)-thieno[2,3-c]pyridine-5-carboxamide;
N-(1-azabicyclo[3.2.2]non-3-yl)-thieno[2,3-c]pyridine-5-carboxamide;
Exo-4(S)-N-(1-azabicyclo[2.2.1]hept-3-yl)-thieno[3,2-c]pyridine-6-carboxamide;
N-(1-(6-methyl)-azabicyclo[2.2.1]hept-3-yl)-thieno[3,2-c]pyridine-6-carboxamide;
N-((3R,5R)-1-azabicyclo[3.2.1]oct-3-yl)-thieno[3,2-c]pyridine-6-carboxamide;
N-(1-azabicyclo[3.2.2]non-3-yl)-thieno[3,2-c]pyridine-6-carboxamide;

N-(1-azabicyclo[2.2.1]hept-3-yl)-1H-pyrrolo[2,3-c]pyridine-5-carboxamide;
N-(1-(6-methyl)-azabicyclo[2.2.1]hept-3-yl)-1H-pyrrolo[2,3-c]pyridine-5-carboxamide;
N-((3R,5R)-1-azabicyclo[3.2.1]oct-3-yl)-1H-pyrrolo[2,3-c]pyridine-5-carboxamide;
N-(1-azabicyclo[3.2.2]non-3-yl)-1H-pyrrolo[2,3-c]pyridine-5-carboxamide;
N-(1-azabicyclo[2.2.1]hept-3-yl)-1-methyl-1H-pyrrolo[2,3-c]pyridine-5-carboxamide;
N-(1-(6-methyl)-azabicyclo[2.2.1]hept-3-yl)-1-methyl-1H-pyrrolo[2,3-c]pyridine-5-carboxamide;
N-((3R,5R)-1-azabicyclo[3.2.1]oct-3-yl)-1-methyl-1H-pyrrolo[2,3-c]pyridine-5-carboxamide;
N-(exo-(4S)-1-azabicyclo[2.2.1]hept-3-yl)-3-bromofuro[2,3-c]pyridine-5-carboxamide;
N-(1-(6-methyl)-azabicyclo[2.2.1]hept-3-yl)-3-bromofuro[2,3-c]pyridine-5-carboxamide;
N-((3R,5R)-1-azabicyclo[3.2.1]oct-3-yl)-3-bromofuro[2,3-c]pyridine-5-carboxamide;
N-[exo-(4S)-1-azabicyclo[2.2.1]hept-3-yl]-3-chlorofuro[2,3-c]pyridine-5-carboxamide;
N-(1-(6-methyl)-azabicyclo[2.2.1]hept-3-yl)-3-chlorofuro[2,3-c]pyridine-5-carboxamide; or
N-((3R,5R)-1-azabicyclo[3.2.1]oct-3-yl)-3-chlorofuro[2,3-c]pyridine-5-carboxamide.

For all compounds identified, the naming of a specific enantiomer does not limit the scope of the invention, but is for exemplification. The naming of a specific enantiomer includes racemic mixtures of that compound. For example, naming exo-4(S)-N-(1-azabicyclo[2.2.1]hept-3-yl)furo[2,3-c]pyridine-5-carboxamide includes within the scope of the present invention exo-(rac)-N-(1-azabicyclo[2.2.1]hept-3-yl)furo[2,3-c]pyridine-5-carboxamide. When a pure enantiomer is discussed, the compound is a racemic mixture or the pure enantiomer pure thereof. When Azabicyclo is II, pure enantiomers include exo-4(S)1-azabicyclo[2.2.1]hept-3-yl. When Azabicyclo is V, pure enantiomers include exo-3(R),5(R)1-azabicyclo[3.2.1]oct-3-yl.

The compound of Formula I, where the compound is any one or more or combination of the following as the free base, or pharmaceutally acceptable salt thereof as a pure enantiomer or racemic mixture thereof:

N-[exo-4(S)-1-azabicyclo[2.2.1]hept-3-yl]-2-vinylfuro[3,2-c]pyridine-6-carboxamide;
N-[exo-4(S)-1-azabicyclo[2.2.1]hept-3-yl]-2-ethynylfuro[3,2-c]pyridine-6-carboxamide;
N-[exo-4(S)-1-azabicyclo[2.2.1]hept-3-yl]-2-prop-1-ynylfuro[3,2-c]pyridine-6-carboxamide;
N-[exo-4(S)-1-azabicyclo[2.2.1]hept-3-yl]-2-(3-hydroxyprop-1-ynyl)furo[3,2-c]pyridine-6-carboxamide;
methyl 3-(6-{[exo-4(S)-1-azabicyclo[2.2.1]hept-3-ylamino]carbonyl}furo[3,2-c]pyridin-2-yl)prop-2-ynoate;
2-(3-amino-3-oxoprop-1-ynyl)-N-[exo-4(S)-1-azabicyclo[2.2.1]hept-3-yl]furo[3,2-c]pyridine-6-carboxamide;
N-[exo-4(S)-1-azabicyclo[2.2.1]hept-3-yl]-2-cyanofuro[3,2-c]pyridine-6-carboxamide;
N-[exo-4(S)-1-azabicyclo[2.2.1]hept-3-yl]-2-chlorofuro[3,2-c]pyridine-6-carboxamide;
N-[exo-4(S)-1-azabicyclo[2.2.1]hept-3-yl]-2-fluorofuro[3,2-c]pyridine-6-carboxamide;
N-[exo-4(S)-1-azabicyclo[2.2.1]hept-3-yl]-2-iodofuro[3,2-c]pyridine-6-carboxamide;
N-[exo-4(S)-1-azabicyclo[2.2.1]hept-3-yl]-2-trifluoromethylfuro[3,2-c]pyridine-6-carboxamide;
N-[exo-4(S)-1-azabicyclo[2.2.1]hept-3-yl]-2-(methylthio)furo[3,2-c]pyridine-6-carboxamide;
N-[exo-4(S)-1-azabicyclo[2.2.1]hept-3-yl]-2-(methylamino)furo[3,2-c]pyridine-6-carboxamide;
N-[exo-4(S)-1-azabicyclo[2.2.1]hept-3-yl]-2-(formylamino)furo[3,2-c]pyridine-6-carboxamide;
N-[exo-4(S)-1-azabicyclo[2.2.1]hept-3-yl]-2-[formyl(methyl)amino]furo[3,2-c]pyridine-6-carboxamide;
N-[exo-4(S)-1-azabicyclo[2.2.1]hept-3-yl]-2-[(trifluoroacetyl)amino]furo[3,2-c]pyridine-6-carboxamide;
N-6-[exo-4(S)-1-azabicyclo[2.2.1]hept-3-yl]furo[3,2-c]pyridine-2,6-dicarboxamide;
N-[exo-4(S)-1-azabicyclo[2.2.1]hept-3-yl]-2-formylfuro[3,2-c]pyridine-6-carboxamide;
N-[exo-4(S)-1-azabicyclo[2.2.1]hept-3-yl]-2-(trifluoroacetyl)furo[3,2-c]pyridine-6-carboxamide;
N-[exo-4(S)-1-azabicyclo[2.2.1]hept-3-yl]-2-(methylsulfonyl)furo[3,2-c]pyridine-6-carboxamide;
methyl 6-{[exo-4(S)-1-azabicyclo[2.2.1]hept-3-ylamino]carbonyl}furo[3,2-c]pyridine-2-carboxylate;
N-[exo-4(S)-1-azabicyclo[2.2.1]hept-3-yl]-2-vinylthieno[3,2-c]pyridine-6-carboxamide;
N-[exo-4(S)-1-azabicyclo[2.2.1]hept-3-yl]-2-ethynylthieno[3,2-c]pyridine-6-carboxamide;
N-[exo-4(S)-1-azabicyclo[2.2.1]hept-3-yl]-2-prop-1-ynylthieno[3,2-c]pyridine-6-carboxamide;
N-[exo-4(S)-1-azabicyclo[2.2.1]hept-3-yl]-2-(3-hydroxyprop-1-ynyl)thieno[3,2-c]pyridine-6-carboxamide;
methyl 3-(6-{[exo-4(S)-1-azabicyclo[2.2.1]hept-3-ylamino]carbonyl}thieno[3,2-c]pyridin-2-yl)prop-2-ynoate;
2-(3-amino-3-oxoprop-1-ynyl)-N-[exo-4(S)-1-azabicyclo[2.2.1]hept-3-yl]thieno[3,2-c]pyridine-6-carboxamide;
N-[exo-4(S)-1-azabicyclo[2.2.1]hept-3-yl]-2-cyanothieno[3,2-c]pyridine-6-carboxamide;
N-[exo-4(S)-1-azabicyclo[2.2.1]hept-3-yl]-2-chlorothieno[3,2-c]pyridine-6-carboxamide;
N-[exo-4(S)-1-azabicyclo[2.2.1]hept-3-yl]-2-fluorothieno[3,2-c]pyridine-6-carboxamide;
N-[exo-4(S)-1-azabicyclo[2.2.1]hept-3-yl]-2-iodothieno[3,2-c]pyridine-6-carboxamide;
N-[exo-4(S)-1-azabicyclo[2.2.1]hept-3-yl]-2-trifluoromethylthieno[3,2-c]pyridine-6-carboxamide;
N-[exo-4(S)-1-azabicyclo[2.2.1]hept-3-yl]-2-(methylthio)thieno[3,2-c]pyridine-6-carboxamide;
N-[exo-4(S)-1-azabicyclo[2.2.1]hept-3-yl]-2-(methylamino)thieno[3,2-c]pyridine-6-carboxamide;
N-[exo-4(S)-1-azabicyclo[2.2.1]hept-3-yl]-2-(formylamino)thieno[3,2-c]pyridine-6-carboxamide;
N-[exo-4(S)-1-azabicyclo[2.2.1]hept-3-yl]-2-[formyl(methyl)amino]thieno[3,2-c]pyridine-6-carboxamide;
N-[exo-4(S)-1-azabicyclo[2.2.1]hept-3-yl]-2-[(trifluoroacetyl)amino]thieno[3,2-c]pyridine-6-carboxamide;
N-[exo-4(S)-1-azabicyclo[2.2.1]hept-3-yl]-2-(cyclopropylamino)thieno[3,2-c]pyridine-6-carboxamide;
N-[exo-4(S)-1-azabicyclo[2.2.1]hept-3-yl]-2-[dimethylamino]thieno[3,2-c]pyridine-6-carboxamide;
N-6-[exo-4(S)-1-azabicyclo[2.2.1]hept-3-yl]thieno[3,2-c]pyridine-2,6-dicarboxamide;
N-[exo-4(S)-1-azabicyclo[2.2.1]hept-3-yl]-2-formylthieno[3,2-c]pyridine-6-carboxamide;
2-acetyl-N-[exo-4(S)-1-azabicyclo[2.2.1]hept-3-yl]thieno[3,2-c]pyridine-6-carboxamide;
N-[exo-4(S)-1-azabicyclo[2.2.1]hept-3-yl]-2-(trifluoroacetyl)thieno[3,2-c]pyridine-6-carboxamide;
N-[exo-4(S)-1-azabicyclo[2.2.1]hept-3-yl]-2-(methylsulfonyl)thieno[3,2-c]pyridine-6-carboxamide;

methyl 6-{[exo-4(S)-1-azabicyclo[2.2.1]hept-3-ylamino]carbonyl}thieno[3,2-c]pyridine-2-carboxylate N-[exo-4(S)-1-azabicyclo[2.2.1]hept-3-yl]-3-vinylfuro[2,3-c]pyridine-5-carboxamide;

N-[exo-4(S)-1-azabicyclo[2.2.1]hept-3-yl]-3-ethynylfuro[2,3-c]pyridine-5-carboxamide;

N-[exo-4(S)-1-azabicyclo[2.2.1]hept-3-yl]-3-prop-1-ynylfuro[2,3-c]pyridine-5-carboxamide;

N-[exo-4(S)-1-azabicyclo[2.2.1]hept-3-yl]-3-(3-hydroxyprop-1-ynyl)furo[2,3-c]pyridine-5-carboxamide;

methyl 3-(5-{[exo-4(S)-1-azabicyclo[2.2.1]hept-3-ylamino]carbonyl}furo[2,3-c]pyridin-3-yl)prop-2-ynoate;

3-(3-amino-3-oxoprop-1-ynyl)-N-[exo-4(S)-1-azabicyclo[2.2.1]hept-3-yl]furo[2,3-c]pyridine-5-carboxamide;

N-[exo-4(S)-1-azabicyclo[2.2.1]hept-3-yl]-3-cyanofuro[2,3-c]pyridine-5-carboxamide;

N-[exo-4(S)-1-azabicyclo[2.2.1]hept-3-yl]-3-fluorofuro[2,3-c]pyridine-5-carboxamide;

N-[exo-4(S)-1-azabicyclo[2.2.1]hept-3-yl]-3-iodofuro[2,3-c]pyridine-5-carboxamide;

N-[exo-4(S)-1-azabicyclo[2.2.1]hept-3-yl]-3-trifluoromethylfuro[2,3-c]pyridine-5-carboxamide;

N-[exo-4(S)-1-azabicyclo[2.2.1]hept-3-yl]-3-(methylthio)furo[2,3-c]pyridine-5-carboxamide;

N-[exo-4(S)-1-azabicyclo[2.2.1]hept-3-yl]-3-(methylamino)furo[2,3-c]pyridine-5-carboxamide;

N-[exo-4(S)-1-azabicyclo[2.2.1]hept-3-yl]-3-(formylamino)furo[2,3-c]pyridine-5-carboxamide;

N-[exo-4(S)-1-azabicyclo[2.2.1]hept-3-yl]-3-[formyl(methyl)amino]furo[2,3-c]pyridine-5-carboxamide;

N-[exo-4(S)-1-azabicyclo[2.2.1]hept-3-yl]-3-[(trifluoroacetyl)amino]furo[2,3-c]pyridine-5-carboxamide;

N-[exo-4(S)-1-azabicyclo[2.2.1]hept-3-yl]-3-(cyclopropylamino)furo[2,3-c]pyridine-5-carboxamide;

N-[exo-4(S)-1-azabicyclo[2.2.1]hept-3-yl]-3-[dimethylamino]furo[2,3-c]pyridine-5-carboxamide;

N-5-[exo-4(S)-1-azabicyclo[2.2.1]hept-3-yl]furo[2,3-c]pyridine-3,5-dicarboxamide;

N-[exo-4(S)-1-azabicyclo[2.2.1]hept-3-yl]-3-formylfuro[2,3-c]pyridine-5-carboxamide;

N-[exo-4(S)-1-azabicyclo[2.2.1]hept-3-yl]-3-(trifluoroacetyl)furo[2,3-c]pyridine-5-carboxamide;

N-[exo-4(S)-1-azabicyclo[2.2.1]hept-3-yl]-3-(methylsulfonyl)furo[2,3-c]pyridine-5-carboxamide;

methyl 5-{[exo-4(S)-1-azabicyclo[2.2.1]hept-3-ylamino]carbonyl}furo[2,3-c]pyridine-3-carboxylate;

N-[exo-4(S)-1-azabicyclo[2.2.1]hept-3-yl]-3-vinylthieno[2,3-c]pyridine-5-carboxamide;

N-[exo-4(S)-1-azabicyclo[2.2.1]hept-3-yl]-3-ethynylthieno[2,3-c]pyridine-5-carboxamide;

N-[exo-4(S)-1-azabicyclo[2.2.1]hept-3-yl]-3-prop-1-ynylthieno[2,3-c]pyridine-5-carboxamide;

N-[exo-4(S)-1-azabicyclo[2.2.1]hept-3-yl]-3-(3-hydroxyprop-1-ynyl)thieno[2,3-c]pyridine-5-carboxamide;

methyl 3-(5-{[exo-4(S)-1-azabicyclo[2.2.1]hept-3-ylamino]carbonyl}thieno[2,3-c]pyridin-3-yl)prop-2-ynoate;

3-(3-amino-3-oxoprop-1-ynyl)-N-[exo-4(S)-1-azabicyclo[2.2.1]hept-3-yl]thieno[2,3-c]pyridine-5-carboxamide;

N-[exo-4(S)-1-azabicyclo[2.2.1]hept-3-yl]-3-cyanothieno[2,3-c]pyridine-5-carboxamide;

N-[exo-4(S)-1-azabicyclo[2.2.1]hept-3-yl]-3-chlorothieno[2,3-c]pyridine-5-carboxamide;

N-[exo-4(S)-1-azabicyclo[2.2.1]hept-3-yl]-3-fluorothieno[2,3-c]pyridine-5-carboxamide;

N-[exo-4(S)-1-azabicyclo[2.2.1]hept-3-yl]-3-iodothieno[2,3-c]pyridine-5-carboxamide;

N-[exo-4(S)-1-azabicyclo[2.2.1]hept-3-yl]-3-trifluoromethylthieno[2,3-c]pyridine-5-carboxamide;

N-[exo-4(S)-1-azabicyclo[2.2.1]hept-3-yl]-3-(methylthio)thieno[2,3-c]pyridine-5-carboxamide;

N-[exo-4(S)-1-azabicyclo[2.2.1]hept-3-yl]-3-(methylamino)thieno[2,3-c]pyridine-5-carboxamide;

N-[exo-4(S)-1-azabicyclo[2.2.1]hept-3-yl]-3-(formylamino)thieno[2,3-c]pyridine-5-carboxamide;

N-[exo-4(S)-1-azabicyclo[2.2.1]hept-3-yl]-3-[formyl(methyl)amino]thieno[2,3-c]pyridine-5-carboxamide;

N-[exo-4(S)-1-azabicyclo[2.2.1]hept-3-yl]-3-[(trifluoroacetyl)amino]thieno[2,3-c]pyridine-5-carboxamide;

N-[exo-4(S)-1-azabicyclo[2.2.1]hept-3-yl]-3-(cyclopropylamino)thieno[2,3-c]pyridine-5-carboxamide;

N-[exo-4(S)-1-azabicyclo[2.2.1]hept-3-yl]-3-[dimethylamino]thieno[2,3-c]pyridine-5-carboxamide;

N-5-[exo-4(S)-1-azabicyclo[2.2.1]hept-3-yl]thieno[2,3-c]pyridine-3,5-dicarboxamide;

N-[exo-4(S)-1-azabicyclo[2.2.1]hept-3-yl]-3-formylthieno[2,3-c]pyridine-5-carboxamide;

N-[exo-4(S)-1-azabicyclo[2.2.1]hept-3-yl]-3-(trifluoroacetyl)thieno[2,3-c]pyridine-5-carboxamide;

N-[exo-4(S)-1-azabicyclo[2.2.1]hept-3-yl]-3-(methylsulfonyl)thieno[2,3-c]pyridine-5-carboxamide;

methyl 5-{[exo-4(S)-1-azabicyclo[2.2.1]hept-3-ylamino]carbonyl}thieno[2,3-c]pyridine-3-carboxylate;

N-[exo-4(S)-1-azabicyclo[2.2.1]hept-3-yl]-3-(phenylethynyl)furo[2,3-c]pyridine-5-carboxamide;

N-[exo-4(S)-1-azabicyclo[2.2.1]hept-3-yl]-3-(3,3,3-trifluoroprop-1-ynyl)furo[2,3-c]pyridine-5-carboxamide;

N-[exo-4(S)-1-azabicyclo[2.2.1]hept-3-yl]-3-(3,3-difluoroprop-1-ynyl)furo[2,3-c]pyridine-5-carboxamide;

N-[exo-4(S)-1-azabicyclo[2.2.1]hept-3-yl]-3-(phenylethynyl)thieno[2,3-c]pyridine-5-carboxamide;

N-[exo-4(S)-1-azabicyclo[2.2.1]hept-3-yl]-3-(3,3,3-trifluoroprop-1-ynyl)thieno[2,3-c]pyridine-5-carboxamide;

N-[exo-4(S)-1-azabicyclo[2.2.1]hept-3-yl]-3-(3,3-difluoroprop-1-ynyl)thieno[2,3-c]pyridine-5-carboxamide;

N-[exo-4(S)-1-azabicyclo[2.2.1]hept-3-yl]-2-(phenylethynyl)thieno[3,2-c]pyridine-5-carboxamide;

N-[exo-4(S)-1-azabicyclo[2.2.1]hept-3-yl]-2-(3,3,3-trifluoroprop-1-ynyl)thieno[3,2-c]pyridine-5-carboxamide;

N-[exo-4(S)-1-azabicyclo[2.2.1]hept-3-yl]-2-(3,3-difluoroprop-1-ynyl)thieno[3,2-c]pyridine-5-carboxamide;

N-((3R,5R)-1-azabicyclo[3.2.1]oct-3-yl)-2-methyl-furo[3,2-c]pyridine-6-carboxamide;

N-((3R,5R)-1-azabicyclo[3.2.1]oct-3-yl)-3-methyl-furo[3,2-c]pyridine-6-carboxamide;

N-((3R,5R)-1-azabicyclo[3.2.1]oct-3-yl)-2-ethyl-furo[3,2-c]pyridine-6-carboxamide;

N-((3R,5R)-1-azabicyclo[3.2.1]oct-3-yl)-3-ethyl-furo[3,2-c]pyridine-6-carboxamide;

N-((3R,5R)-1-azabicyclo[3.2.1]oct-3-yl)-4-methyl-furo[3,2-c]pyridine-6-carboxamide;

N-((3R,5R)-1-azabicyclo[3.2.1]oct-3-yl)-4-methylthio-furo[3,2-c]pyridine-6-carboxamide;

N-((3R,5R)-1-azabicyclo[3.2.1]oct-3-yl)-4-methoxy-furo[3,2-c]pyridine-6-carboxamide;

N-((3R,5R)-1-azabicyclo[3.2.1]oct-3-yl)-4-chloro-furo[3,2-c]pyridine-6-carboxamide;

N-((3R,5R)-1-azabicyclo[3.2.1]oct-3-yl)-2-vinylfuro[3,2-c]pyridine-6-carboxamide;

N-((3R,5R)-1-azabicyclo[3.2.1]oct-3-yl)-2-ethynylfuro[3,2-c]pyridine-6-carboxamide;
N-((3R,5R)-1-azabicyclo[3.2.1]oct-3-yl)-2-prop-1-ynylfuro[3,2-c]pyridine-6-carboxamide;
N-((3R,5R)-1-azabicyclo[3.2.1]oct-3-yl)-2-cyanofuro[3,2-c]pyridine-6-carboxamide;
N-((3R,5R)-1-azabicyclo[3.2.1]oct-3-yl)-3-ethynylfuro[3,2-c]pyridine-6-carboxamide;
N-((3R,5R)-1-azabicyclo[3.2.1]oct-3-yl)-3-prop-1-ynylfuro[3,2-c]pyridine-6-carboxamide;
N-((3R,5R)-1-azabicyclo[3.2.1]oct-3-yl)-3-cyanofuro[3,2-c]pyridine-6-carboxamide;
N-((3R,5R)-1-azabicyclo[3.2.1]oct-3-yl)-2-fluorofuro[3,2-c]pyridine-6-carboxamide;
N-((3R,5R)-1-azabicyclo[3.2.1]oct-3-yl)-2-chlorofuro[3,2-c]pyridine-6-carboxamide;
N-((3R,5R)-1-azabicyclo[3.2.1]oct-3-yl)-2-bromofuro[3,2-c]pyridine-6-carboxamide;
N-((3R,5R)-1-azabicyclo[3.2.1]oct-3-yl)-2-iodofuro[3,2-c]pyridine-6-carboxamide;
N-((3R,5R)-1-azabicyclo[3.2.1]oct-3-yl)-2-trifluoromethylfuro[3,2-c]pyridine-6-carboxamide;
N-((3R,5R)-1-azabicyclo[3.2.1]oct-3-yl)-3-trifluoromethylfuro[3,2-c]pyridine-6-carboxamide;
N-((3R,5R)-1-azabicyclo[3.2.1]oct-3-yl)-2-mercaptofuro[3,2-c]pyridine-6-carboxamide;
N-((3R,5R)-1-azabicyclo[3.2.1]oct-3-yl)-2-(methylthio)furo[3,2-c]pyridine-6-carboxamide;
N-((3R,5R)-1-azabicyclo[3.2.1]oct-3-yl)-2-(methylamino)furo[3,2-c]pyridine-6-carboxamide;
N-((3R,5R)-1-azabicyclo[3.2.1]oct-3-yl)-2-(formylamino)furo[3,2-c]pyridine-6-carboxamide;
2-(acetylamino)-N-((3R,5R)-1-azabicyclo[3.2.1]oct-3-yl)furo[3,2-c]pyridine-6-carboxamide;
2-(acetyl(methyl)amino)-N-((3R,5R)-1-azabicyclo[3.2.1]oct-3-yl)furo[3,2-c]pyridine-6-carboxamide;
N-((3R,5R)-1-azabicyclo[3.2.1]oct-3-yl)-2-[(trifluoroacetyl)amino]furo[3,2-c]pyridine-6-carboxamide;
N-((3R,5R)-1-azabicyclo[3.2.1]oct-3-yl)-2-(benzoylamino)furo[3,2-c]pyridine-6-carboxamide;
N-((3R,5R)-1-azabicyclo[3.2.1]oct-3-yl)-2-(diethylamino)furo[3,2-c]pyridine-6-carboxamide;
N-((3R,5R)-1-azabicyclo[3.2.1]oct-3-yl)-2-(diisopropylamino)furo[3,2-c]pyridine-6-carboxamide;
N-((3R,5R)-1-azabicyclo[3.2.1]oct-3-yl)-2-(pyrrolidin-1-yl)furo[3,2-c]pyridine-6-carboxamide;
N-((3R,5R)-1-azabicyclo[3.2.1]oct-3-yl)-2-(piperidin-1-yl)furo[3,2-c]pyridine-6-carboxamide;
N-((3R,5R)-1-azabicyclo[3.2.1]oct-3-yl)-2-(morpholin-4-yl)furo[3,2-c]pyridine-6-carboxamide;
N-((3R,5R)-1-azabicyclo[3.2.1]oct-3-yl)-2-(thiomorpholin-4yl)furo[3,2-c]pyridine-6-carboximide;
N-((3R,5R)-1-azabicyclo[3.2.1]oct-3-yl)-2-(piperazin-1-yl)furo[3,2-c]pyridine-6-carboxamide;
N-((3R,5R)-1-azabicyclo[3.2.1]oct-3-yl)-2-(4-methylpiperazin-1-yl)furo[3,2-c]pyridine-6-carboxamide;
N-((3R,5R)-1-azabicyclo[3.2.1]oct-3-yl)-2-(cyclopropylamino)furo[3,2-c]pyridine-6-carboxamide;
N-((3R,5R)-1-azabicyclo[3.2.1]oct-3-yl)-2-[dimethylamino]furo[3,2-c]pyridine-6-carboxamide;
N-((3R,5R)-1-azabicyclo[3.2.1]oct-3-yl)-2-(pyrrolidin-1-ylcarbonyl)furo[3,2-c]pyridine-6-carboxamide;
N-((3R,5R)-1-azabicyclo[3.2.1]oct-3-yl)-2-(piperidin-1-ylcarbonyl)furo[3,2-c]pyridine-6-carboxamide;
N-((3R,5R)-1-azabicyclo[3.2.1]oct-3-yl)-2-(piperazin-1-ylcarbonyl)furo[3,2-c]pyridine-6-carboxamide;
N-((3R,5R)-1-azabicyclo[3.2.1]oct-3-yl)-2-[(4-methylpiperazin-1-yl)carbonyl]furo[3,2-c]pyridine-6-carboxamide;
N-((3R,5R)-1-azabicyclo[3.2.1]oct-3-yl)-2-(morpholin-4-ylcarbonyl)furo[3,2-c]pyridine-6-carboxamide;
N-((3R,5R)-1-azabicyclo[3.2.1]oct-3-yl)-2-(thiomorpholin-4-ylcarbonyl)furo[3,2-c]pyridine-6-carboxamide;
N-((3R,5R)-1-azabicyclo[3.2.1]oct-3-yl)-2-(aziridin-1-ylcarbonyl)furo[3,2-c]pyridine-6-carboxamide;
N-((3R,5R)-1-azabicyclo[3.2.1]oct-3-yl)-2-(azetidin-1-ylcarbonyl)furo[3,2-c]pyridine-6-carboxamide;
N-((3R,5R)-1-azabicyclo[3.2.1]oct-3-yl)-2-formylfuro[3,2-c]pyridine-6-carboxamide;
2-acetyl-N-((3R,5R)-1-azabicyclo[3.2.1]oct-3-yl)furo[3,2-c]pyridine-6-carboxamide;
N-((3R,5R)-1-azabicyclo[3.2.1]oct-3-yl)-2-(trifluoroacetyl)furo[3,2-c]pyridine-6-carboxamide;
N-((3R,5R)-1-azabicyclo[3.2.1]oct-3-yl)-2-[(phenyl)sulfonyl]furo[3,2-c]pyridine-6-carboxamide;
N-((3R,5R)-1-azabicyclo[3.2.1]oct-3-yl)-2-(methylsulfonyl)furo[3,2-c]pyridine-6-carboxamide;
N-((3R,5R)-1-azabicyclo[3.2.1]oct-3-yl)-4-methyl-thieno[3,2-c]pyridine-6-carboxamide;
N-((3R,5R)-1-azabicyclo[3.2.1]oct-3-yl)-4-methylthio-thieno[3,2-c]pyridine-6-carboxamide;
N-((3R,5R)-1-azabicyclo[3.2.1]oct-3-yl)-4-methoxy-thieno[3,2-c]pyridine-6-carboxamide;
N-((3R,5R)-1-azabicyclo[3.2.1]oct-3-yl)-4-chloro-thieno[3,2-c]pyridine-6-carboxamide;
N-((3R,5R)-1-azabicyclo[3.2.1]oct-3-yl)-2-vinylthieno[3,2-c]pyridine-6-carboxamide;
N-((3R,5R)-1-azabicyclo[3.2.1]oct-3-yl)-2-ethynylthieno[3,2-c]pyridine-6-carboxamide;
N-((3R,5R)-1-azabicyclo[3.2.1]oct-3-yl)-2-prop-1-ynylthieno[3,2-c]pyridine-6-carboxamide;
N-((3R,5R)-1-azabicyclo[3.2.1]oct-3-yl)-2-cyanothieno[3,2-c]pyridine-6-carboxamide;
N-((3R,5R)-1-azabicyclo[3.2.1]oct-3-yl)-2-fluorothieno[3,2-c]pyridine-6-carboxamide;
N-((3R,5R)-1-azabicyclo[3.2.1]oct-3-yl)-2-chlorothieno[3,2-c]pyridine-6-carboxamide;
N-((3R,5R)-1-azabicyclo[3.2.1]oct-3-yl)-2-bromothieno[3,2-c]pyridine-6-carboxamide;
N-((3R,5R)-1-azabicyclo[3.2.1]oct-3-yl)-2-iodothieno[3,2-c]pyridine-6-carboxamide;
N-((3R,5R)-1-azabicyclo[3.2.1]oct-3-yl)-2-trifluoromethylthieno[3,2-c]pyridine-6-carboxamide;
N-((3R,5R)-1-azabicyclo[3.2.1]oct-3-yl)-2-mercaptothieno[3,2-c]pyridine-6-carboxamide;
N-((3R,5R)-1-azabicyclo[3.2.1]oct-3-yl)-2-(methylthio)thieno[3,2-c]pyridine-6-carboxamide;
N-((3R,5R)-1-azabicyclo[3.2.1]oct-3-yl)-2-(methylamino)thieno[3,2-c]pyridine-6-carboxamide;
N-((3R,5R)-1-azabicyclo[3.2.1]oct-3-yl)-2-(formylamino)thieno[3,2-c]pyridine-6-carboxamide;
2-(acetylamino)-N-((3R,5R)-1-azabicyclo[3.2.1]oct-3-yl)thieno[3,2-c]pyridine-6-carboxamide;
2-(acetyl(methyl)amino)-N-((3R,5R)-1-azabicyclo[3.2.1]oct-3-yl)thieno[3,2-c]pyridine-6-carboxamide;
N-((3R,5R)-1-azabicyclo[3.2.1]oct-3-yl)-2-[(trifluoroacetyl)amino]thieno[3,2-c]pyridine-6-carboxamide;
N-((3R,5R)-1-azabicyclo[3.2.1]oct-3-yl)-2-(benzoylamino)thieno[3,2-c]pyridine-6-carboxamide;
N-((3R,5R)-1-azabicyclo[3.2.1]oct-3-yl)-2-(diethylamino)thieno[3,2-c]pyridine-6-carboxamide;
N-((3R,5R)-1-azabicyclo[3.2.1]oct-3-yl)-2-(diisopropylamino)thieno[3,2-c]pyridine-6-carboxamide;

N-((3R,5R)-1-azabicyclo[3.2.1]oct-3-yl)-2-(pyrrolidin-1-yl)thieno[3,2-c]pyridine-6-carboximide;
N-((3R,5R)-1-azabicyclo[3.2.1]oct-3-yl)-2-(piperidin-1-yl)thieno[3,2-c]pyridine-6-carboxamide;
N-((3R,5R)-1-azabicyclo[3.2.1]oct-3-yl)-2-(morpholin-4-yl)thieno[3,2-c]pyridine-6-carboxamide;
N-((3R,5R)-1-azabicyclo[3.2.1]oct-3-yl)-2-(thiomorpholin-4yl)thieno[3,2-c]pyridine -6-carboxamide;
N-((3R,5R)-1-azabicyclo[3.2.1]oct-3-yl)-2-(piperazin-1-yl)thieno[3,2-c]pyridine-6-carboxamide;
N-((3R,5R)-1-azabicyclo[3.2.1]oct-3-yl)-2-(4-methylpiperazin-1-yl)thieno[3,2-c]pyridine-6-carboxamide;
N-((3R,5R)-1-azabicyclo[3.2.1]oct-3-yl)-2-(cyclopropylamino)thieno[3,2-c]pyridine-6-carboxamide;
N-((3R,5R)-1-azabicyclo[3.2.1]oct-3-yl)-2-[dimethylamino]thieno[3,2-c]pyridine-6-carboxamide;
N-((3R,5R)-1-azabicyclo[3.2.1]oct-3-yl)-2-(pyrrolidin-1-ylcarbonyl)thieno[3,2-c]pyridine-6-carboxamide;
N-((3R,5R)-1-azabicyclo[3.2.1]oct-3-yl)-2-(piperidin-1-ylcarbonyl)thieno[3,2-c]pyridine-6-carboxamide;
N-((3R,5R)-1-azabicyclo[3.2.1]oct-3-yl)-2-(piperazin-1-ylcarbonyl)thieno[3,2-c]pyridine-6-carboxamide;
N-((3R,5R)-1-azabicyclo[3.2.1]oct-3-yl)-2-[(4-methylpiperazin-1-yl)carbonyl]thieno[3,2-c]pyridine-6-carboxamide;
N-((3R,5R)-1-azabicyclo[3.2.1]oct-3-yl)-2-(morpholin-4-ylcarbonyl)thieno[3,2-c]pyridine-6-carboxamide;
N-((3R,5R)-1-azabicyclo[3.2.1]oct-3-yl)-2-(thiomorpholin-4-ylcarbonyl)thieno[3,2-c]pyridine-6-carboxamide;
N-((3R,5R)-1-azabicyclo[3.2.1]oct-3-yl)-2-(aziridin-1-ylcarbonyl)thieno[3,2-c]pyridine-6-carboxamide;
N-((3R,5R)-1-azabicyclo[3.2.1]oct-3-yl)-2-(azetidin-1-ylcarbonyl)thieno[3,2-c]pyridine-6-carboxamide;
N-((3R,5R)-1-azabicyclo[3.2.1]oct-3-yl)-2-formylthieno[3,2-c]pyridine-6-carboxamide;
2-acetyl-N-((3R,5R)-1-azabicyclo[3.2.1]oct-3-yl)thieno[3,2-c]pyridine-6-carboxamide;
N-((3R,5R)-1-azabicyclo[3.2.1]oct-3-yl)-2-(trifluoroacetyl)thieno[3,2-c]pyridine-6-carboxamide;
N-((3R,5R)-1-azabicyclo[3.2.1]oct-3-yl)-2-[(phenyl)sulfonyl]thieno[3,2-c]pyridine-6-carboxamide;
N-((3R,5R)-1-azabicyclo[3.2.1]oct-3-yl)-2-(methylsulfonyl)thieno[3,2-c]pyridine-6-carboxamide;
N-((3R,5R)-1-azabicyclo[3.2.1]oct-3-yl)-3-vinylfuro[2,3-c]pyridine-5-carboxamide;
N-((3R,5R)-1-azabicyclo[3.2.1]oct-3-yl)-7-methyl-furo[2,3-c]pyridine-5-carboxamide;
N-((3R,5R)-1-azabicyclo[3.2.1]oct-3-yl)-7-methoxy-furo[2,3-c]pyridine-5-carboxamide;
N-((3R,5R)-1-azabicyclo[3.2.1]oct-3-yl)-3-ethynylfuro[2,3-c]pyridine-5-carboxamide;
N-((3R,5R)-1-azabicyclo[3.2.1]oct-3-yl)-3-prop-1-ynylfuro[2,3-c]pyridine-5-carboxamide;
N-((3R,5R)-1-azabicyclo[3.2.1]oct-3-yl)-3-cyanofuro[2,3-c]pyridine-5-carboxamide;
N-((3R,5R)-1-azabicyclo[3.2.1]oct-3-yl)-3-fluorofuro[2,3-c]pyridine-5-carboxamide;
N-((3R,5R)-1-azabicyclo[3.2.1]oct-3-yl)-3-iodofuro[2,3-c]pyridine-5-carboxamide;
N-((3R,5R)-1-azabicyclo[3.2.1]oct-3-yl)-3-trifluoromethylfuro[2,3-c]pyridine-5-carboxamide;
N-((3R,5R)-1-azabicyclo[3.2.1]oct-3-yl)-3-mercaptofuro[2,3-c]pyridine-5-carboxamide;
N-((3R,5R)-1-azabicyclo[3.2.1.]oct-3-yl)-3-(methylthio)furo[2,3-c]pyridine-5-carboxamide;
N-((3R,5R)-1-azabicyclo[3.2.1]oct-3-yl)-3-(methylamino)furo[2,3-c]pyridine-5-carboxamide;
N-((3R,5R)-1-azabicyclo[3.2.1]oct-3-yl)-3-(formylamino)furo[2,3-c]pyridine-5-carboxamide;
3-(acetylamino)-N-((3R,5R)-1-azabicyclo[3.2.1]oct-3-yl)furo[2,3-c]pyridine-5-carboxamide;
3-(acetyl(methyl)amino)-N-((3R,5R)-1-azabicyclo[3.2.1]oct-3-yl)furo[2,3-c]pyridine-5-carboxamide;
N-((3R,5R)-1-azabicyclo[3.2.1]oct-3-yl)-3-[(trifluoroacetyl)amino]furo[2,3-c]pyridine-5-carboxamide;
N-((3R,5R)-1-azabicyclo[3.2.1]oct-3-yl)-3-(benzoylamino)furo[2,3-c]pyridine-5-carboxamide;
N-((3R,5R)-1-azabicyclo[3.2.1]oct-3-yl)-3-(diethylamino)furo[2,3-c]pyridine-5-carboxamide;
N-((3R,5R)-1-azabicyclo[3.2.1]oct-3-yl)-3-(diisopropylamino)furo[2,3-c]pyridine-5-carboxamide;
N-((3R,5R)-1-azabicyclo[3.2.1]oct-3-yl)-3-(pyrrolidin-1-yl)furo[2,3-c]pyridine -5-carboxamide;
N-((3R,5R)-1-azabicyclo[3.2.1]oct-3-yl)-3-(piperidin-1-yl)furo[2,3-c]pyridine -5-carboxamide;
N-((3R,5R)-1-azabicyclo[3.2.1]oct-3-yl)-3-(morpholin-4-yl)furo[2,3-c]pyridine -5-carboxamide;
N-((3R,5R)-1-azabicyclo[3.2.1]oct-3-yl)-3-(thiomorpholin-4yl)furo[2,3-c]pyridine -5-carboxamide;
N-((3R,5R)-1-azabicyclo[3.2.1]oct-3-yl)-3-(piperazin-1-yl)furo[2,3-c]pyridine-5-carboxamide;
N-((3R,5R)-1-azabicyclo[3.2.1]oct-3-yl)-3-(4-methylpiperazin-1-yl)furo[2,3-c]pyridine-5-carboxamide;
N-((3R,5R)-1-azabicyclo[3.2.1]oct-3-yl)-3-(cyclopropylamino)furo[2,3-c]pyridine-5-carboxamide;
N-((3R,5R)-1-azabicyclo[3.2.1]oct-3-yl)-3-[dimethylamino]furo[2,3-c]pyridine-5-carboxamide;
N-((3R,5R)-1-azabicyclo[3.2.1]oct-3-yl)-3-(pyrrolidin-1-ylcarbonyl)furo[2,3-c]pyridine-5-carboxamide;
N-((3R,5R)-1-azabicyclo[3.2.1]oct-3-yl)-3-(piperidin-1-ylcarbonyl)furo[2,3-c]pyridine-5-carboxamide;
N-((3R,5R)-1-azabicyclo[3.2.1]oct-3-yl)-3-(piperazin-1-ylcarbonyl)furo[2,3-c]pyridine-5-carboxamide;
N-((3R,5R)-1-azabicyclo[3.2.1]oct-3-yl)-3-[(4-methylpiperazin-1-yl)carbonyl]furo[2,3-c]pyridine-5-carboxamide;
N-((3R,5R)-1-azabicyclo[3.2.1]oct-3-yl)-3-(morpholin-4-ylcarbonyl)furo[2,3-c]pyridine-5-carboxamide;
N-((3R,5R)-1-azabicyclo[3.2.1]oct-3-yl)-3-(thiomorpholin-4-ylcarbonyl)furo[2,3-c]pyridine-5-carboxamide;
N-((3R,5R)-1-azabicyclo[3.2.1]oct-3-yl)-3-(aziridin-1-ylcarbonyl)furo[2,3-c]pyridine-5-carboxamide;
N-((3R,5R)-1-azabicyclo[3.2.1]oct-3-yl)-3-(azetidin-1-ylcarbonyl)furo[2,3-c]pyridine-5-carboxamide;
N-((3R,5R)-1-azabicyclo[3.2.1]oct-3-yl)-3-formylfuro[2,3-c]pyridine-5-carboxamide;
3-acetyl-N-((3R,5R)-1-azabicyclo[3.2.1]oct-3-yl)furo[2,3-c]pyridine-5-carboxamide;
N-((3R,5R)-1-azabicyclo[3.2.1]oct-3-yl)-3-(trifluoroacetyl)furo[2,3-c]pyridine-5-carboxamide;
N-((3R,5R)-1-azabicyclo[3.2.1]oct-3-yl)-3-[(phenyl)sulfonyl]furo[2,3-c]pyridine-5-carboxamide;
N-((3R,5R)-1-azabicyclo[3.2.1]oct-3-yl)-3-(methylsulfonyl)furo[2,3-c]pyridine-5-carboxamide;
N-((3R,5R)-1-azabicyclo[3.2.1]oct-3-yl)-2-ethyl-furo[2,3-c]pyridine-5-carboxamide;
N-((3R,5R)-1-azabicyclo[3.2.1]oct-3-yl)-2-ethynylfuro[2,3-c]pyridine-5-carboxamide;
N-((3R,5R)-1-azabicyclo[3.2.1]oct-3-yl)-2-prop-1-ynylfuro[2,3-c]pyridine-5-carboxamide;

N-((3R,5R)-1-azabicyclo[3.2.1]oct-3-yl)-2-cyanofuro[2,3-c]pyridine-5-carboxamide;
N-((3R,5R)-1-azabicyclo[3.2.1]oct-3-yl)-2-fluorofuro[2,3-c]pyridine-5-carboxamide;
N-((3R,5R)-1-azabicyclo[3.2.1]oct-3-yl)-2-chlorofuro[2,3-c]pyridine-5-carboxamide;
N-((3R,5R)-1-azabicyclo[3.2.1]oct-3-yl)-2-bromofuro[2,3-c]pyridine-5-carboxamide;
N-((3R,5R)-1-azabicyclo[3.2.1]oct-3-yl)-2-iodofuro[2,3-c]pyridine-5-carboxamide;
N-((3R,5R)-1-azabicyclo[3.2.1]oct-3-yl)-2-trifluoromethylfuro[2,3-c]pyridine-5-carboxamide;
N-((3R,5R)-1-azabicyclo[3.2.1]oct-3-yl)-2-mercaptofuro[2,3-c]pyridine-5-carboxamide;
N-((3R,5R)-1-azabicyclo[3.2.1]oct-3-yl)-2-(methylthio)furo[2,3-c]pyridine-5-carboxamide;
N-((3R,5R)-1-azabicyclo[3.2.1]oct-3-yl)-2-(methylamino)furo[2,3-c]pyridine-5-carboxamide;
N-((3R,5R)-1-azabicyclo[3.2.1]oct-3-yl)-2-(formylamino)furo[2,3-c]pyridine-5-carboxamide;
2-(acetylamino)-N-((3R,5R)-1-azabicyclo[3.2.1]oct-3-yl)furo[2,3-c]pyridine-5-carboxamide;
2-(acetyl(methyl)amino)-N-((3R,5R)-1-azabicyclo[3.2.1]oct-3-yl)furo[2,3-c]pyridine-5-carboxamide;
N-((3R,5R)-1-azabicyclo[3.2.1]oct-3-yl)-2-[(trifluoroacetyl)amino]furo[2,3-c]pyridine-5-carboxamide;
N-((3R,5R)-1-azabicyclo[3.2.1]oct-3-yl)-2-(benzoylamino)furo[2,3-c]pyridine-5-carboxamide;
N-((3R,5R)-1-azabicyclo[3.2.1]oct-3-yl)-2-(diethylamino)furo[2,3-c]pyridine-5-carboxamide;
N-((3R,5R)-1-azabicyclo[3.2.1]oct-3-yl)-2-(diisopropylamino)furo[2,3-c]pyridine-5-carboxamide;
N-((3R,5R)-1-azabicyclo[3.2.1]oct-3-yl)-2-(pyrrolidin-1-yl)furo[2,3-c]pyridine-5-carboximide;
N-((3R,5R)-1-azabicyclo[3.2.1]oct-3-yl)-2-(piperidin-1-yl)furo[2,3-c]pyridine-5-carboxamide;
N-((3R,5R)-1-azabicyclo[3.2.1]oct-3-yl)-2-(morpholin-4-yl)furo[2,3-c]pyridine-5-carboxamide;
N-((3R,5R)-1-azabicyclo[3.2.1]oct-3-yl)-2-(thiomorpholin-4yl)furo[2,3-c]pyridine-5-carboximide;
N-((3R,5R)-1-azabicyclo[3.2.1]oct-3-yl)-2-(piperazin-1-yl)furo[2,3-c]pyridine-5-carboxamide;
N-((3R,5R)-1-azabicyclo[3.2.1]oct-3-yl)-2-(4-methylpiperazin-1-yl)furo[2,3-c]pyridine-5-carboxamide;
N-((3R,5R)-1-azabicyclo[3.2.1]oct-3-yl)-2-(cyclopropylamino)furo[2,3-c]pyridine-5-carboxamide;
N-((3R,5R)-1-azabicyclo[3.2.1]oct-3-yl)-2-[dimethylamino]furo[2,3-c]pyridine-5-carboxamide;
N-((3R,5R)-1-azabicyclo[3.2.1]oct-3-yl)-2-(pyrrolidin-1-ylcarbonyl)furo[2,3-c]pyridine-5-carboxamide;
N-((3R,5R)-1-azabicyclo[3.2.1]oct-3-yl)-2-(piperidin-1-ylcarbonyl)furo[2,3-c]pyridine-5-carboxamide;
N-((3R,5R)-1-azabicyclo[3.2.1]oct-3-yl)-2-(piperazin-1-ylcarbonyl)furo[2,3-c]pyridine-5-carboxamide;
N-((3R,5R)-1-azabicyclo[3.2.1]oct-3-yl)-2-[(4-methylpiperazin-1-yl)carbonyl]furo[2,3-c]pyridine-5-carboxamide;
N-((3R,5R)-1-azabicyclo[3.2.1]oct-3-yl)-2-(morpholin-4-ylcarbonyl)furo[2,3-c]pyridine-5-carboxamide;
N-((3R,5R)-1-azabicyclo[3.2.1]oct-3-yl)-2-(thiomorpholin-4-ylcarbonyl)furo[2,3-c]pyridine-5-carboxamide;
N-((3R,5R)-1-azabicyclo[3.2.1]oct-3-yl)-2-(aziridin-1-ylcarbonyl)furo[2,3-c]pyridine-5-carboxamide;
N-((3R,5R)-1-azabicyclo[3.2.1]oct-3-yl)-2-(azetidin-1-ylcarbonyl)furo[2,3-c]pyridine-5-carboxamide;
N-((3R,5R)-1-azabicyclo[3.2.1]oct-3-yl)-2-formylfuro[2,3-c]pyridine-5-carboxamide;
2-acetyl-N-((3R,5R)-1-azabicyclo[3.2.1]oct-3-yl)furo[2,3-c]pyridine-5-carboxamide;
N-((3R,5R)-1-azabicyclo[3.2.1]oct-3-yl)-2-(trifluoroacetyl)furo[2,3-c]pyridine-5-carboxamide;
N-((3R,5R)-1-azabicyclo[3.2.1]oct-3-yl)-2-[(phenyl)sulfonyl]furo[2,3-c]pyridine-5-carboxamide;
N-((3R,5R)-1-azabicyclo[3.2.1]oct-3-yl)-2-(methylsulfonyl)furo[2,3-c]pyridine-5-carboxamide;
N-((3R,5R)-1-azabicyclo[3.2.1]oct-3-yl)-7-methyl-thieno[2,3-c]pyridine-5-carboxamide;
N-((3R,5R)-1-azabicyclo[3.2.1]oct-3-yl)-7-methylthio-thieno[2,3-c]pyridine-5-carboxamide;
N-((3R,5R)-1-azabicyclo[3.2.1]oct-3-yl)-7-methoxy-thieno[2,3-c]pyridine-5-carboxamide;
N-((3R,5R)-1-azabicyclo[3.2.1]oct-3-yl)-7-chloro-thieno[2,3-c]pyridine-5-carboxamide;
N-((3R,5R)-1-azabicyclo[3.2.1]oct-3-yl)-3-vinylthieno[2,3-c]pyridine-5-carboxamide;
N-((3R,5R)-1-azabicyclo[3.2.1]oct-3-yl)-3-ethynylthieno[2,3-c]pyridine-5-carboxamide;
N-((3R,5R)-1-azabicyclo[3.2.1]oct-3-yl)-3-prop-1-ynylthieno[2,3-c]pyridine-5-carboxamide;
N-((3R,5R)-1-azabicyclo[3.2.1]oct-3-yl)-3-cyanothieno[2,3-c]pyridine-5-carboxamide;
N-((3R,5R)-1-azabicyclo[3.2.1]oct-3-yl)-3-fluorothieno[2,3-c]pyridine-5-carboxamide;
N-((3R,5R)-1-azabicyclo[3.2.1]oct-3-yl)-3-chlorothieno[2,3-c]pyridine-5-carboxamide;
N-((3R,5R)-1-azabicyclo[3.2.1]oct-3-yl)-3-bromothieno[2,3-c]pyridine-5-carboxamide;
N-((3R,5R)-1-azabicyclo[3.2.1]oct-3-yl)-3-iodothieno[2,3-c]pyridine-5-carboxamide;
N-((3R,5R)-1-azabicyclo[3.2.1]oct-3-yl)-3-trifluoromethylthieno[2,3-c]pyridine-5-carboxamide;
N-((3R,5R)-1-azabicyclo[3.2.1]oct-3-yl)-3-mercaptothieno[2,3-c]pyridine-5-carboxamide;
N-((3R,5R)-1-azabicyclo[3.2.1]oct-3-yl)-3-(methylthio)thieno[2,3-c]pyridine-5-carboxamide;
N-((3R,5R)-1-azabicyclo[3.2.1]oct-3-yl)-3-(methylamino)thieno[2,3-c]pyridine-5-carboxamide;
N-((3R,5R)-1-azabicyclo[3.2.1]oct-3-yl)-3-(formylamino)thieno[2,3-c]pyridine-5-carboxamide;
3-(acetylamino)-N-((3R,5R)-1-azabicyclo[3.2.1]oct-3-yl)thieno[2,3-c]pyridine-5-carboxamide;
3-(acetyl(methyl)amino)-N-((3R,5R)-1-azabicyclo[3.2.1]oct-3-yl)thieno[2,3-c]pyridine-5-carboxamide;
N-((3R,5R)-1-azabicyclo[3.2.1]oct-3-yl)-3-[(trifluoroacetyl)amino]thieno[2,3-c]pyridine-5-carboxamide;
N-((3R,5R)-1-azabicyclo[3.2.1]oct-3-yl)-3-(benzoylamino)thieno[2,3-c]pyridine-5-carboxamide;
N-((3R,5R)-1-azabicyclo[3.2.1]oct-3-yl)-3-(diethylamino)thieno[2,3-c]pyridine-5-carboxamide;
N-((3R,5R)-1-azabicyclo[3.2.1]oct-3-yl)-3-(diisopropylamino)thieno[2,3-c]pyridine-5-carboxamide;
N-((3R,5R)-1-azabicyclo[3.2.1]oct-3-yl)-3-(pyrrolidin-1-yl)thieno[2,3-c]pyridine-5-carboxamide;
N-((3R,5R)-1-azabicyclo[3.2.1]oct-3-yl)-3-(piperidin-1-yl)thieno[2,3-c]pyridine-5-carboxamide;
N-((3R,5R)-1-azabicyclo[3.2.1]oct-3-yl)-3-(morpholin-4-yl)thieno[2,3-c]pyridine-5-carboxamide;
N-((3R,5R)-1-azabicyclo[3.2.1]oct-3-yl)-3-(thiomorpholin-4yl)thieno[2,3-c]pyridine-5-carboxamide;
N-((3R,5R)-1-azabicyclo[3.2.1]oct-3-yl)-3-(piperazin-1-yl)thieno[2,3-c]pyridine-5-carboxamide;

N-((3R,5R)-1-azabicyclo[3.2.1]oct-3-yl)-3-(4-methylpiperazin-1-yl)thieno[2,3-c]pyridine-5-carboxamide;
N-((3R,5R)-1-azabicyclo[3.2.1]oct-3-yl)-3-(cyclopropylamino)thieno[2,3-c]pyridine-5-carboxamide;
N-((3R,5R)-1-azabicyclo[3.2.1]oct-3-yl)-3-[dimethylamino]thieno[2,3-c]pyridine-5-carboxamide;
N-((3R,5R)-1-azabicyclo[3.2.1]oct-3-yl)-3-(pyrrolidin-1-ylcarbonyl)thieno[2,3-c]pyridine-5-carboxamide;
N-((3R,5R)-1-azabicyclo[3.2.1]oct-3-yl)-3-(piperidin-1-ylcarbonyl)thieno[2,3-c]pyridine-5-carboxamide;
N-((3R,5R)-1-azabicyclo[3.2.1]oct-3-yl)-3-(piperazin-1-ylcarbonyl)thieno[2,3-c]pyridine-5-carboxamide;
N-((3R,5R)-1-azabicyclo[3.2.1]oct-3-yl)-3-[(4-methylpiperazin-1-yl)carbonyl]thieno[2,3-c]pyridine-5-carboxamide;
N-((3R,5R)-1-azabicyclo[3.2.1]oct-3-yl)-3-(morpholin-4-ylcarbonyl)thieno[2,3-c]pyridine-5-carboxamide;
N-((3R,5R)-1-azabicyclo[3.2.1]oct-3-yl)-3-(thiomorpholin-4-ylcarbonyl)thieno[2,3-c]pyridine-5-carboxamide;
N-((3R,5R)-1-azabicyclo[3.2.1]oct-3-yl)-3-(aziridin-1-ylcarbonyl)thieno[2,3-c]pyridine-5-carboxamide;
N-((3R,5R)-1-azabicyclo[3.2.1]oct-3-yl)-3-(azetidin-1-ylcarbonyl)thieno[2,3-c]pyridine-5-carboxamide;
N-((3R,5R)-1-azabicyclo[3.2.1]oct-3-yl)-3-formylthieno[2,3-c]pyridine-5-carboxamide;
3-acetyl-N-((3R,5R)-1-azabicyclo[3.2.1]oct-3-yl)thieno[2,3-c]pyridine-5-carboxamide;
N-((3R,5R)-1-azabicyclo[3.2.1]oct-3-yl)-3-(trifluoroacetyl)thieno[2,3-c]pyridine-5-carboxamide;
N-((3R,5R)-1-azabicyclo[3.2.1]oct-3-yl)-3-[(phenyl)sulfonyl]lthieno[2,3-c]pyridine -5-carboxamide; or
N-((3R,5R)-1-azabicyclo[3.2.1]oct-3-yl)-3-(methylsulfonyl)thieno[2,3-c]pyridine-5-carboxamide.

The compound of Formula I, where the compound is any one or more or combination of the following as the free base, or pharmaceutically acceptable salt thereof as a pure enantiomer or racemic mixture thereof:
N-(1-(6-methyl)-azabicyclo[2.2.2]oct-3-yl)furo[2,3-c]pyridine-5-carboxamide;
N-(2-azabicyclo[2.2.1]hept-5-yl)furo[2,3-c]pyridine-5-carboxamide;
N-(2-azabicyclo[2.2.1]hept-6-yl)furo[2,3-c]pyridine-5-carboxamide;
N-(1-(6-methyl)-azabicyclo[2.2.2]oct-3-yl)furo[3,2-c]pyridine-6-carboxamide;
N-(2-azabicyclo[2.2.1]hept-5-yl)furo[3,2-c]pyridine-6-carboxamide;
N-(2-azabicyclo[2.2.1]hept-6-yl)furo[3,2-c]pyridine-6-carboxamide;
N-(1-(6-methyl)-azabicyclo[2.2.2]oct-3-yl)-2,3-dihydrofuro[2,3-c]pyridine-5-carboxamide;
N-(2-azabicyclo[2.2.1]hept-5-yl)-2,3-dihydrofuro[2,3-c]pyridine-5-carboxamide;
N-(2-azabicyclo[2.2.1]hept-6-yl)-2,3-dihydrofuro[2,3-c]pyridine-5-carboxamide;
N-(1-(6-methyl)-azabicyclo[2.2.2]oct-3-yl)-7-chlorofuro[2,3-c]pyridine-5-carboxamide;
N-(2-azabicyclo[2.2.1]hept-5-yl)-7-chlorofuro[2,3-c]pyridine-5-carboxamide;
N-(2-azabicyclo[2.2.1]hept-6-yl)-7-chlorofuro[2,3-c]pyridine-5-carboxamide;
N-(1-(6-methyl)-azabicyclo[2.2.2]oct-3-yl)-3,3-dimethyl-2,3-dihydrofuro[2,3-c]pyridine-5-carboxamide;
N-(2-azabicyclo[2.2.1]hept-5-yl)-3,3-dimethyl-2,3-dihydrofuro[2,3-c]pyridine-5-carboxamide;
N-(2-azabicyclo[2.2.1]hept-6-yl)-3,3-dimethyl-2,3-dihydrofuro[2,3-c]pyridine-5-carboxamide;
N-(-(6-methyl)-azabicyclo[2.2.2]oct-3-yl)-2-methylfuro[2,3-c]pyridine-5-carboxamide;
N-(2-azabicyclo[2.2.1]hept-5-yl)-2-methylfuro[2,3-c]pyridine-5-carboxamide;
N-(2-azabicyclo[2.2.1]hept-6-yl)-2-methylfuro[2,3-c]pyridine-5-carboxamide;
N-(1-(6-methyl)-azabicyclo[2.2.2]oct-3-yl)-3-methylfuro[2,3-c]pyridine-5-carboxamide;
N-(2-azabicyclo[2.2.1]hept-5-yl)-3-methylfuro[2,3-c]pyridine-5-carboxamide;
N-(2-azabicyclo[2.2.1]hept-6-yl)-3-methylfuro[2,3-c]pyridine-5-carboxamide;
N-(1-(6-methyl)-azabicyclo[2.2.2]oct-3-yl)-3-ethylfuro[2,3-c]pyridine-5-carboxamide;
N-(2-azabicyclo[2.2.1]hept-5-yl)-3-ethylfuro[2,3-c]pyridine-5-carboxamide;
N-(2-azabicyclo[2.2.1]hept-6-yl)-3-ethylfuro[2,3-c]pyridine-5-carboxamide;
N-(1-(6-methyl)-azabicyclo[2.2.2]oct-3-yl)-furo[2,3-b]pyridine-2-carboxamide;
N-(2-azabicyclo[2.2.1]hept-5-yl)-furo[2,3-b]pyridine-2-carboxamide;
N-(2-azabicyclo[2.2.1]hept-6-yl)-furo[2,3-b]pyridine-2-carboxamide;
N-(1-(6-methyl)-azabicyclo[2.2.2]oct-3-yl)-3-isopropylfuro[2,3-c]pyridine-5-carboxamide;
N-(2-azabicyclo[2.2.1]hept-5-yl)-3-isopropylfuro[2,3-c]pyridine-5-carboxamide;
N-(2-azabicyclo[2.2.1]hept-6-yl)-3-isopropylfuro[2,3-c]pyridine-5-carboxamide;
N-(1-(6-methyl)-azabicyclo[2.2.2]oct-3-yl)-7-(methylsulfanyl)furo[2,3-c]pyridine-5-carboxamide;
N-(2-azabicyclo[2.2.1]hept-5-yl)-7-(methylsulfanyl)furo[2,3-c]pyridine-5-carboxamide;
N-(2-azabicyclo[2.2.1]hept-6-yl)-7-(methylsulfanyl)furo[2,3-c]pyridine-5-carboxamide;
N-(1-(6-methyl)-azabicyclo[2.2.2]oct-3-yl)-thieno[2,3-b]pyridine-2-carboxamide;
N-(2-azabicyclo[2.2.1]hept-5-yl)-thieno[2,3-b]pyridine-2-carboxamide;
N-(2-azabicyclo[2.2.1]hept-6-yl)-thieno[2,3-b]pyridine-2-carboxamide;
N-(1-(6-methyl)-azabicyclo[2.2.2]oct-3-yl)-thieno[2,3-b]pyridine-5-carboxamide;
N-(2-azabicyclo[2.2.1]bept-5-yl)-thieno[2,3-b]pyridine-5-carboxamide;
N-(2-azabicyclo[2.2.1]hept-6-yl)-thieno[2,3-b]pyridine-5-carboxamide;
N-(1-(6-methyl)-azabicyclo[2.2.2]oct-3-yl)-thieno[2,3-b]pyridine-6-carboxamide;
N-(2-azabicyclo[2.2.1]hept-5-yl)-thieno[2,3-b]pyridine-6-carboxamide;
N-(2-azabicyclo[2.2.1]hept-6-yl)-thieno[2,3-b]pyridine-6-carboxamide;
N-(1-(6-methyl)-azabicyclo[2.2.2]oct-3-yl)-thieno[2,3-c]pyridine-2-carboxamide;
N-(2-azabicyclo[2.2.1]hept-5-yl)-thieno[2,3-c]pyridine-2-carboxamide;
N-(2-azabicyclo[2.2.1]hept-6-yl)-thieno[2,3-c]pyridine-2-carboxamide;
N-(1-(6-methyl)-azabicyclo[2.2.2]oct-3-yl)-thieno[3,2-b]pyridine-2-carboxamide;
N-(2-azabicyclo[2.2.1]hept-5-yl)-thieno[3,2-b]pyridine-2-carboxamide;
N-(2-azabicyclo[2.2.1]hept-6-yl)-thieno[3,2-b]pyridine-2-carboxamide;

N-(1-(6-methyl)-azabicyclo[2.2.2]oct-3-yl)-thieno[3,2-b]
pyridine-5-carboxamide;
N-(2-azabicyclo[2.2.1]hept-5-yl)-thieno[3,2-b]pyridine-5-
carboxamide;
N-(2-azabicyclo[2.2.1]hept-6-yl)-thieno[3,2-b]pyridine-5-
carboxamide;
N-(1-(6-methyl)-azabicyclo[2.2.2]oct-3-yl)-thieno[3,2-b]
pyridine-6-carboxamide;
N-(2-azabicyclo[2.2.1]hept-5-yl)-thieno[3,2-b]pyridine-6-
carboxamide;
N-(2-azabicyclo[2.2.1]hept-6-yl)-thieno[3,2-b]pyridine-6-
carboxamide;
N-(1-(6-methyl)-azabicyclo[2.2.2]oct-3-yl)-thieno[3,2-c]
pyridine-2-carboxamide;
N-(2-azabicyclo[2.2.1]hept-5-yl)-thieno[3,2-c]pyridine-2-
carboxamide;
N-(2-azabicyclo[2.2.1]hept-6-yl)-thieno[3,2-c]pyridine-2-
carboxamide;
N-(1-(6-methyl)-azabicyclo[2.2.2]oct-3-yl)-thieno[2,3-c]
pyridine-5-carboxamide;
N-(2-azabicyclo[2.2.1]hept-5-yl)-thieno[2,3-c]pyridine-5-
carboxamide;
N-(2-azabicyclo[2.2.1]hept-6-yl)-thieno[2,3-c]pyridine-5-
carboxamide;
N-(1-(6-methyl)-azabicyclo[2.2.2]oct-3-yl)-thieno[3,2-c]
pyridine-6-carboxamide;
N-(2-azabicyclo[2.2.1]hept-5-yl)-thieno[3,2-c]pyridine-6-
carboxamide;
N-(2-azabicyclo[2.2.1]hept-6-yl)-thieno[3,2-c]pyridine-6-
carboxamide;
N-(1-(6-methyl)-azabicyclo[2.2.2]oct-3-yl)-1H-pyrrolo[2,
3-c]pyridine-5-carboxamide;
N-(2-azabicyclo[2.2.1]hept-5-yl)-1H-pyrrolo[2,3-c]
pyridine-5-carboxamide;
N-(2-azabicyclo[2.2.1]hept-6-yl)-1H-pyrrolo[2,3-c]
pyridine-5-carboxamide;
N-(1-(6-methyl)-azabicyclo[2.2.2]oct-3-yl)-1-methyl-1H-
pyrrolo[2,3-c]pyridine-5-carboxamide;
N-(2-azabicyclo[2.2.1]hept-5-yl)-1-methyl-1H-pyrrolo[2,3-
c]pyridine-5-carboxamide;
N-(2-azabicyclo[2.2.1]hept-6-yl)-1-methyl-1H-pyrrolo[2,3-
c]pyridine-5-carboxamide;
N-(1-(6-methyl)-azabicyclo[2.2.2]oct-3-yl)-3-bromofuro[2,
3-c]pyridine-5-carboxamide;
N-(2-azabicyclo[2.2.1]hept-5-yl)-3-bromofuro[2,3-c]
pyridine-5-carboxamide;
N-(2-azabicyclo[2.2.1]hept-6-yl)-3-bromofuro[2,3-c]
pyridine-5-carboxamide;
N-(1-(6-methyl)-azabicyclo[2.2.2]oct-3-yl)-3-chlorofuro[2,
3-c]pyridine-5-carboxamide;
N-(2-azabicyclo[2.2.1]hept-5-yl)-3-chlorofuro[2,3-c]
pyridine-5-carboxamide; or
N-(2-azabicyclo[2.2.1]hept-6-yl)-3-chlorofuro[2,3-c]
pyridine-5-carboxamide.

The compound of Formula I, where the compound is any one or more or combination of the following as the free base, or pharmaceutally acceptable salt thereof as a pure enantiomer or racemic mixture thereof:

N-[1-(6-methyl)-azabicyclo[2.2.2]oct-3-yl]-2-ethynylfuro
[3,2-c]pyridine-6-carboxamide;
N-[1-(6-methyl)-azabicyclo[2.2.2]oct-3-yl]-2-prop-1-
ynylfuro[3,2-c]pyridine-6-carboxamide;
N-[1-(6-methyl)-azabicyclo[2.2.2]oct-3-yl]-2-cyanofuro[3,
2-c]pyridine-6-carboxamide;
N-[1-(6-methyl)-azabicyclo[2.2.2]oct-3-yl]-2-fluorofuro[3,
2-c]pyridine-6-carboxamide;
N-[1-(6-methyl)-azabicyclo[2.2.2]oct-3-yl]-2-chlorofuro[3,
2-c]pyridine-6-carboxamide;
N-[1-(6-methyl)-azabicyclo[2.2.2]oct-3-yl]-2-bromofuro[3,
2-c]pyridine-6-carboxamide;
N-[1-(6-methyl)-azabicyclo[2.2.2]oct-3-yl]-2-iodofuro[3,2-
c]pyridine-6-carboxamide;
N-[1-(6-methyl)-azabicyclo[2.2.2]oct-3-yl]-2-
trifluoromethylfuro[3,2-c]pyridine-6-carboxamide;
2-(acetylamino)-N-[1-(6-methyl)-azabicyclo[2.2.2]oct-3-yl]
furo[3,2-c]pyridine-6-carboxamide;
N-[1-(6-methyl)-azabicyclo[2.2.2]oct-3-yl]-2-(pyrrolidin-1-
yl)furo[3,2-c]pyridine -6-carboxamide;
N-[1-(6-methyl)-azabicyclo[2.2.2]oct-3-yl]-2-
[dimethylamino]furo[3,2-c]pyridine-6-carboxamide;
N-6-[1-(6-methyl)-azabicyclo[2.2.2]oct-3-yl]furo[3,2-c]
pyridine-2,6-dicarboxamide;
2-acetyl-N-[1-(6-methyl)-azabicyclo[2.2.2]oct-3-yl]furo[3,
2-c]pyridine-6-carboxamide;
methyl 6-{[1-(6-methyl)-azabicyclo[2.2.2]oct-3-ylamino]
carbonyl}furo[3,2-c]pyridine-2-carboxylate;
N-[1-(6-methyl)-azabicyclo[2.2.2]oct-3-yl]-3-vinylfuro[2,
3-c]pyridine-5-carboxamide;
N-[1-(6-methyl)-azabicyclo[2.2.2]oct-3-yl]-3-ethynylfuro
[2,3-c]pyridine-5-carboxamide;
N-[1-(6-methyl)-azabicyclo[2.2.2]oct-3-yl]-3-prop-1-
ynylfuro[2,3-c]pyridine-5-carboxamide;
N-[1-(6-methyl)-azabicyclo[2.2.2]oct-3-yl]-3-cyanofuro[2,
3-c]pyridine-5-carboxamide;
N-[1-(6-methyl)-azabicyclo[2.2.2]oct-3-yl]-3-fluorofuro[2,
3-c]pyridine-5-carboxamide;
N-[1-(6-methyl)-azabicyclo[2.2.2]oct-3-yl]-3-iodofuro[2,3-
c]pyridine-5-carboxamide;
N-[1-(6-methyl)-azabicyclo[2.2.2]oct-3-yl]-3-
trifluoromethylfuro[2,3-c]pyridine-5-carboxamide;
3-(acetylamino)-N-[1-(6-methyl)-azabicyclo[2.2.2]oct-3-yl]
furo[2,3-c]pyridine-5-carboxamide;
N-[1-(6-methyl)-azabicyclo[2.2.2]oct-3-yl]-3-(pyrrolidin-1-
yl)furo[2,3-c]pyridine-5-carboxamide;
N-[1-(6-methyl)-azabicyclo[2.2.2]oct-3-yl]-3-
[dimethylamino]furo[2,3-c]pyridine-5-carboxamide;
N-5-[1-(6-methyl)-azabicyclo[2.2.2]oct-3-yl]furo[2,3-c]
pyridine-3,5-dicarboxamide;
N-[1-(6-methyl)-azabicyclo[2.2.2]oct-3-yl]-3-formylfuro[2,
3-c]pyridine-5-carboxamide;
3-acetyl-N-[1-(6-methyl)-azabicyclo[2.2.2]oct-3-yl]furo[2,
3-c]pyridine-5-carboxamide;
methyl 5-{[1-(6-methyl)-azabicyclo[2.2.2]oct-3-ylamino]
carbonyl}furo[2,3-c]pyridine-3-carboxylate;
N-(2-azabicyclo[2.2.1]hept-5-yl)-2-ethynylfuro[3,2-c]
pyridine-6-carboxamide;
N-(2-azabicyclo[2.2.1]hept-5-yl)-2-prop-1-ynylfuro[3,2-c]
pyridine-6-carboxamide;
N-(2-azabicyclo[2.2.1]hept-5-yl)-2-cyanofuro[3,2-c]
pyridine-6-carboxamide;
N-(2-azabicyclo[2.2.1]hept-5-yl)-2-fluorofuro[3,2-c]
pyridine-6-carboxamide;
N-(2-azabicyclo[2.2.1]hept-5-yl)-2-chlorofuro[3,2-c]
pyridine-6-carboxamide;
N-(2-azabicyclo[2.2.1]hept-5-yl)-2-bromofuro[3,2-c]
pyridine-6-carboxamide;
N-(2-azabicyclo[2.2.1]hept-5-yl)-2-iodofuro[3,2-c]
pyridine-6-carboxamide;
N-(2-azabicyclo[2.2.1]hept-5-yl)-2-trifluoromethylfuro[3,
2-c]pyridine-6-carboxamide;
2-(acetylamino)-N-(2-azabicyclo[2.2.1]hept-5-yl)furo[3,2-
c]pyridine-6-carboxamide;
N-(2-azabicyclo[2.2.1]hept-5-yl)-2-(pyrrolidin-1-yl)furo[3,
2-c]pyridine-6-carboxamide;
N-(2-azabicyclo[2.2.1]hept-5-yl)-2-[dimethylamino]furo[3,
2-c]pyridine-6-carboxamide;

N-6-[1-(6-methyl)-azabicyclo[2.2.2]oct-3-yl]furo[3,2-c]pyridine-2,6-dicarboxamide;
2-acetyl-N-(2-azabicyclo[2.2.1]hept-5-yl)furo[3,2-c]pyridine-6-carboxamide;
methyl 6-[(2-azabicyclo[2.2.1]hept-5-ylamino)carbonyl]furo[3,2-c]pyridine-2-carboxylate;
N-(2-azabicyclo[2.2.1]hept-5-yl)-3-vinylfuro[2,3-c]pyridine-5-carboxamide;
N-(2-azabicyclo[2.2.1]hept-5-yl)-3-ethynylfuro[2,3-c]pyridine-5-carboxamide;
N-(2-azabicyclo[2.2.1]hept-5-yl)-3-prop-1-ynylfuro[2,3-c]pyridine-5-carboxamide;
N-(2-azabicyclo[2.2.1]hept-5-yl)-3-cyanofuro[2,3-c]pyridine-5-carboxamide;
N-(2-azabicyclo[2.2.1]hept-5-yl)-3-fluorofuro[2,3-c]pyridine-5-carboxamide;
N-(2-azabicyclo[2.2.1]hept-5-yl)-3-iodofuro[2,3-c]pyridine-5-carboxamide;
N-(2-azabicyclo[2.2.1]hept-5-yl)-3-trifluoromethylfuro[2,3-c]pyridine-5-carboxamide;
3-(acetylamino)-N-(2-azabicyclo[2.2.1]hept-5-yl)furo[2,3-c]pyridine-5-carboxamide;
N-(2-azabicyclo[2.2.1]hept-5-yl)-3-(pyrrolidin-1-yl)furo[2,3-c]pyridine-5-carboxamide;
N-(2-azabicyclo[2.2.1]hept-5-yl)-3-[dimethylamino]furo[2,3-c]pyridine-5-carboxamide;
N-5-[1-(6-methyl)-azabicyclo[2.2.2]oct-3-yl]furo[2,3-c]pyridine-3,5-dicarboxamide;
N-(2-azabicyclo[2.2.1]hept-5-yl)-3-formylfuro[2,3-c]pyridine-5-carboxamide;
3-acetyl-N-(2-azabicyclo[2.2.1]hept-5-yl)furo[2,3-c]pyridine-5-carboxamide;
methyl 5-[(2-azabicyclo[2.2.1]hept-5-ylamino)carbonyl]furo[2,3-c]pyridine-3-carboxylate;
N-(2-azabicyclo[2.2.1]hept-6-yl)-2-ethynylfuro[3,2-c]pyridine-6-carboxamide;
N-(2-azabicyclo[2.2.1]hept-6-yl)-2-prop-1-ynylfuro[3,2-c]pyridine-6-carboxamide;
N-(2-azabicyclo[2.2.1]hept-6-yl)-2-cyanofuro[3,2-c]pyridine-6-carboxamide;
N-(2-azabicyclo[2.2.1]hept-6-yl)-2-fluorofuro[3,2-c]pyridine-6-carboxamide;
N-(2-azabicyclo[2.2.1]hept-6-yl)-2-chlorofuro[3,2-c]pyridine-6-carboxamide;
N-(2-azabicyclo[2.2.1]hept-6-yl)-2-bromofuro[3,2-c]pyridine-6-carboxamide;
N-(2-azabicyclo[2.2.1]hept-6-yl)-2-iodofuro[3,2-c]pyridine-6-carboxamide;
N-(2-azabicyclo[2.2.1]hept-6-yl)-2-trifluoromethylfuro[3,2-c]pyridine-6-carboxamide;
2-(acetylamino)-N-(2-azabicyclo[2.2.1]hept-6-yl)furo[3,2-c]pyridine-6-carboxamide;
N-(2-azabicyclo[2.2.1]hept-6-yl)-2-(pyrrolidin-1-yl)furo[3,2-c]pyridine-6-carboxamide;
N-(2-azabicyclo[2.2.1]hept-6-yl)-2-[dimethylamino]furo[3,2-c]pyridine-6-carboxamide;
N-6-[1-(6-methyl)-azabicyclo[2.2.2]oct-3-yl]furo[3,2-c]pyridine-2,6-dicarboxamide;
2-acetyl-N-(2-azabicyclo[2.2.1]hept-6-yl)furo[3,2-c]pyridine-6-carboxamide;
methyl 6-[2-azabicyclo[2.2.1]hept-6-ylamino)carbonyl]furo[3,2-c]pyridine-2-carboxylate;
N-(2-azabicyclo[2.2.1]hept-6-yl)-3-vinylfuro[2,3-c]pyridine-5-carboxamide;
N-(2-azabicyclo[2.2.1]hept-6-yl)-3-ethynylfuro[2,3-c]pyridine-5-carboxamide;
N-(2-azabicyclo[2.2.1]hept-6-yl)-3-prop-1-ynylfuro[2,3-c]pyridine-5-carboxamide;
N-(2-azabicyclo[2.2.1]hept-6-yl)-3-cyanofuro[2,3-c]pyridine-5-carboxamide;
N-(2-azabicyclo[2.2.1]hept-6-yl)-3-fluorofuro[2,3-c]pyridine-5-carboxamide;
N-(2-azabicyclo[2.2.1]hept-6-yl)-3-iodofuro[2,3-c]pyridine-5-carboxamide;
N-(2-azabicyclo[2.2.1]hept-6-yl)-3-trifluoromethylfuro[2,3-c]pyridine-5-carboxamide;
3-(acetylamino)-N-(2-azabicyclo[2.2.1]hept-6-yl)furo[2,3-c]pyridine-5-carboxamide;
N-(2-azabicyclo[2.2.1]hept-6-yl)-3-(pyrrolidin-1-yl)furo[2,3-c]pyridine-5-carboxamide;
N-(2-azabicyclo[2.2.1]hept-6-yl)-3-[dimethylamino]furo[2,3-c]pyridine-5-carboxamide;
N-5-[1-(6-methyl)-azabicyclo[2.2.2]oct-3-yl]furo[2,3-c]pyridine-3,5-dicarboxamide;
N-(2-azabicyclo[2.2.1]hept-6-yl)-3-formylfuro[2,3-c]pyridine-5-carboxamide;
3-acetyl-N-(2-azabicyclo[2.2.1]hept-6-yl)furo[2,3-c]pyridine-5-carboxamide; or
methyl 5-[2-azabicyclo[2.2.1]hept-6-ylamino)carbonyl]furo[2,3-c]pyridine-3-carboxylate.

The compound of Formula I, where the compound is any one or more or combination of the following as the free base, or pharmaceutally acceptable salt thereof as a pure enantiomer or racemic mixture thereof:
N-(1-azabicyclo[2.2.1]hept-3-yl)thieno[3,4-c]pyridine-6-carboxamide;
N-(1-(6-methyl)-azabicyclo[2.2.1]hept-3-yl)thieno[3,4-c]pyridine-6-carboxamide;
N-((3R,5R)-1-azabicyclo[3.2.1]oct-3-yl)thieno[3,4-c]pyridine-6-carboxamide; or
N-(1-azabicyclo[3.2.2]non-3-yl)thieno[3,4-c]pyridine-6-carboxamide.

The compound of Formula I, where the compound is any one or more or combination of the following as the free base, or pharmaceutally acceptable salt thereof as a pure enantiomer or racemic mixture thereof:
N-(1-(6-methyl)-azabicyclo[2.2.2]oct-3-yl)thieno[3,4-c]pyridine-6-carboxamide;
N-(2-azabicyclo[2.2.1]hept-5-yl)thieno[3,4-c]pyridine-6-carboxamide; or
N-(2-azabicyclo[2.2.1]hept-6-yl)thieno[3,4-c]pyridine-6-carboxamide.

The compound of Formula I, where the compound is any one or more or combination of the following as the free base, or pharmaceutally acceptable salt thereof as a pure enantiomer or racemic mixture thereof:
N-(1-azabicyclo[2.2.1]hept-3-yl)-benzothieno[3,2-c]pyridine-3-carboxamide;
N-(1-(6-methyl)-azabicyclo[2.2.1]hept-3-yl)-benzothieno[3,2-c]pyridine-3-carboxamide;
N-((3R,5R)-1-azabicyclo[3.2.1]oct-3-yl)-benzothieno[3,2-c]pyridine-3-carboxamide;
N-(1-azabicyclo[3.2.2]non-3-yl)-benzothieno[3,2-c]pyridine-3-carboxamide;
N-[exo-4(S)-1-azabicyclo[2.2.1]hept-3-yl][1]benzofuro[2,3-c]pyridine-3-carboxamide; or
N-[exo-4(S)-1-azabicyclo[2.2.1]hept-3-yl][1]benzothieno[2,3-c]pyridine-3-carboxamide.

The compound of Formula I, where the compound is any one or more or combination of the following as the free base, or pharmaceutally acceptable salt thereof as a pure enantiomer or racemic mixture thereof:

N-(1-(6-methyl)-azabicyclo[2.2.2]oct-3-yl)-benzothieno[3,2-c]pyridine-3-carboxamide;

N-(2-azabicyclo[2.2.1]hept-5-yl)-benzothieno[3,2-c]pyridine-3-carboxamide; or

N-(2-azabicyclo[2.2.1]hept-6-yl)-benzothieno[3,2-c]pyridine-3-carboxamide.

A further embodiment of the present invention includes the compounds of the present invention, pharmaceutical compositions containing the active compounds as the free base or as a pharmaceutically acceptable salt and a pharmaceutically acceptable carrier, and methods to treat the identified diseases.

In another aspect, the invention includes treating a mammal suffering from schizophrenia or psychosis by administering compounds of Formula I in conjunction with antipsychotic drugs (also called anti-psychotic agents). The compounds of the present invention and the antipsychotic drugs can be administered simultaneously or at separate intervals. When administered simultaneously the compounds of the present invention and the antipsychotic drugs can be incorporated into a single pharmaceutical composition. Alternatively, two separate compositions, i.e., one containing compounds of the present invention and the other containing antipsychotic drugs, can be administered simultaneously.

A further embodiment of the present invention provides a method comprising administering a therapeutically effective amount of a compound of the present invention or a pharmaceutical composition contains said compound to the mammal.

The present invention also includes a pharmaceutical composition comprising a compound of Formula I or a pharmaceutically acceptable salt thereof and a pharmaceutically acceptable excipient. The pharmaceutical composition is administered rectally, topically, orally, sublingually, or parenterally for a therapeutically effective interval. The pharmaceutical composition is administered to deliver a compound of the present invention in an amount of from about 0.001 to about 100 mg/kg of body weight of said mammal per day. The pharmaceutical composition is also administered to deliver a compound of the present invention in an amount of from about 0.1 to about 50 mg/kg of body weight of said mammal per day.

A pharmaceutical composition comprising a compound of Formula I or a pharmaceutically acceptable salt thereof, an anti-psychotic agent, and a pharmaceutically acceptable excipient. The pharmaceutical composition is administered to independently administer said compound and said agent rectally, topically, orally, sublingually, or parenterally for a therapeutically effective interval.

The pharmaceutical composition is administered to deliver a compound of the present invention in an amount of from about 0.001 to about 100 mg/kg of body weight of said mammal per day. The pharmaceutical composition is also administered to deliver a compound of the present invention in an amount of from about 0.1 to about 50 mg/kg of body weight of said mammal per day.

The present invention also includes a use of a compound according to Formula I or pharmaceutically acceptable salt thereof for the preparation of a medicament for treating a disease or condition, wherein the mammal would receive symptomatic relief from the administration of a therapeutically effective amount of α7 nicotinic acetylcholine receptor agonist.

The present invention also includes a use of a compound according to Formula I or pharmaceutically acceptable salt thereof for the preparation of a medicament for treating a disease or condition, wherein the mammal would receive symptomatic relief from the administration of a therapeutically effective amount of α7 nicotinic acetylcholine receptor agonist, wherein the disease, or condition is any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

The present invention also includes a method for treating a disease or condition in a mammal in need thereof, wherein the mammal would receive symptomatic relief from the administration of an α7 nicotinic acetylcholine receptor agonist comprising administering to the mammal a therapeutically effective amount of a compound according to Formula I or pharmaceutically acceptable salt thereof.

The present invention also includes a method for treating a disease or condition in a mammal in need thereof comprising administering to the mammal a therapeutically effective amount of a compound according to Formula I or pharmaceutically acceptable salt thereof, wherein the disease or condition is any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

The compounds of Formula I (Azabicyclo is I) have optically active centers on the quinuclidine ring. The compounds of the present invention include quinuclidines with the 3R configuration and also includes racemic mixtures, the separate stereoisomers, and compositions of varying degrees of stereochemical purity. For example, and not by limitation, compounds of Formula I include compounds with stereospecificity including:

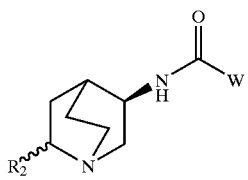

The compounds of Formula I (Azabicyclo is II) have optically active center(s) on the [2.2.1]azabicyclic ring at C3 and C4. The scope of this invention includes racemic mixtures of varying degrees of stereochemical purities, the separate stereoisomers, and compositions of varying degrees of stereochemical purities of Formula I being endo-4S, endo-4R, exo-4S, exo-4R:

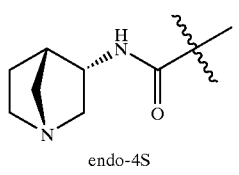
endo-4S

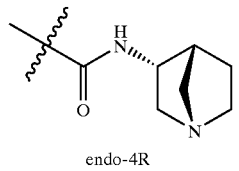
endo-4R

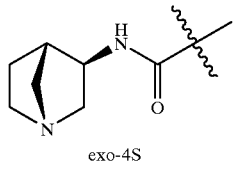
exo-4S

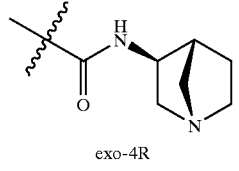
exo-4R

The endo isomer is the isomer where the non-hydrogen substituent at C3 of the [2.2.1]azabicyclic compound is projected toward the larger of the two remaining bridges.

The exo isomer is the isomer where the non-hydrogen substituent at C3 of the [2.2.1]azabicyclic compound is projected toward the smaller of the two remaining bridges. Thus, there can be four separate isomers: exo-4(R), exo-4(S), endo-4(R), and endo-4(S).

The compounds of Formula I (Azabicyclo III) have optically active center(s) on the [2.2.1]azabicyclic ring at C1, C4 and C5. The scope of this invention includes racemic mixtures of varying degrees of stereochemical purities, the separate stereoisomers, and compositions of varying degrees of stereochemical purities of Formula I being (1R,4R,5S), (1R,4R,5R), (1S,4S,5R), (1S,4S,5S):

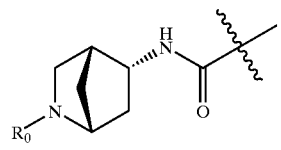
endo-1R,4R,5R

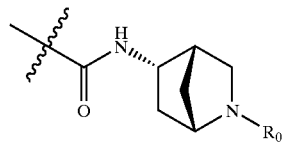
endo-1S,4S,5S

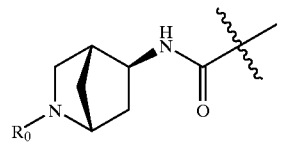
exo-1R,4R,5S

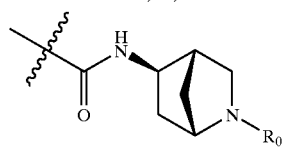
exo-1S,4S,5R

The endo isomer is the isomer where the non-hydrogen substituent at C5 of the [2.2.1]azabicyclic compound is projected toward the larger of the two remaining bridges.

The exo isomer is the isomer where the non-hydrogen substituent at C5 of the [2.2.1]azabicyclic compound is projected toward the smaller of the two remaining bridges. Thus, there can be four separate isomers: exo-(1R,4R,5S), exo-(1S,4S,5R), endo-(1S,4S,5S), endo-(1R,4R,5R).

The compounds of Formula I (Azabicyclo IV) have optically active center(s) on the [2.2.1]azabicyclic ring at C1, C4 and C6. The scope of this invention includes racemic mixtures of varying degrees of stereochemical purities, the separate stereoisomers, and compositions of varying degrees of stereochemical purities of Formula I being exo-(1S,4R,6S), exo-(1R,4S,6R), endo-(1S,4R,6R), and endo-(1R,4S,6S):

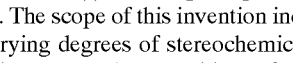
endo-1R,4S,6S

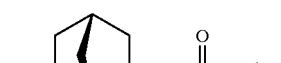
endo-1S,4R,6R

exo-1R,4S,6R

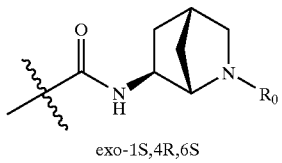

exo-1S,4R,6S

The endo isomer is the isomer where the non-hydrogen substituent at C6 of the [2.2.1]azabicyclic compound is projected toward the larger of the two remaining bridges. The exo isomer is the isomer where the non-hydrogen substituent at C6 of the [2.2.1]azabicyclic compound is projected toward the smaller of the two remaining bridges. Thus, there can be four separate isomers: exo-(1S,4R,6S), exo-(1R,4S,6R), endo-(1S,4R,6R), and endo-(1R,4S,6S).

The compounds of Formula I (Azabicyclo is V) have optically active center(s) on the [3.2.1]azabicyclic ring at C3 and C5. The scope of this invention includes racemic mixtures of varying degrees of stereochemical purities, the separate stereoisomers, and compositions of varying degrees of stereochemical purities of Formula I being endo-3S,5R, endo-3R,5S, exo-3R,5R, exo-3S,5S:

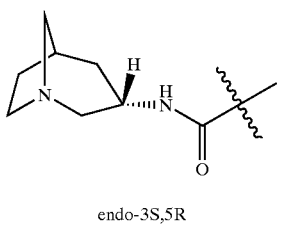

endo-3S,5R

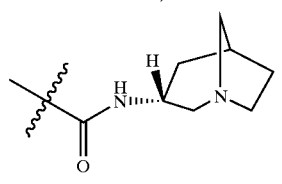

endo-3R,5S

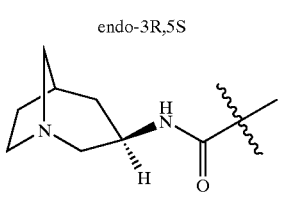

exo-3R,5R

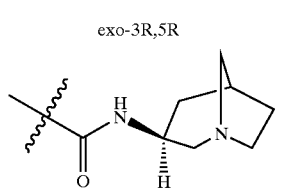

exo-3S,5S

The compounds of Formula I (Azabicyclo is VI) have optically active centers on the [3.2.2]azabicyclic ring with one center being at C3 when $R_2$ is absent. The scope of this invention includes racemic mixtures of varying degrees of stereochemical purities, the separate stereoisomers, and compositions of varying degrees of stereochemical purities of Formula I being 3(S) and 3(R):

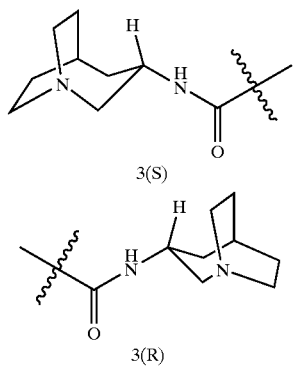

3(S)

3(R)

The compounds of the present invention having the specified stereochemistry have different levels of activity and that for a given set of values for the variable substituents one isomer may be preferred over the other isomers. Although it is desirable that the stereochemical purity be as high as possible, absolute purity is not required. This invention involves racemic mixtures and compositions of varying degrees of stereochemical purities when the Azabicyclo is substituted with only the amide/thioamide or is substituted with substituents in addition to the amide/thioamide, e.g., $R_2$ is alkyl. When racemic mixtures and compositions are referenced, it is meant racemic mixtures and compositions of varying degrees of stereochemical purities. It is preferred to carry out stereoselective syntheses and/or to subject the reaction product to appropriate purification steps so as to produce substantially enantiomerically pure materials. Suitable stereoselective synthetic procedures for producing enantiomerically pure materials are well known in the art, as are procedures for purifying racemic mixtures into enantiomerically pure fractions.

Stereoselective syntheses and/or subjecting the reaction product to appropriate purification steps produces substantially enantiomerically pure materials. Suitable stereoselective synthetic procedures for producing enantiomerically pure materials are well known in the art, as are procedures for purifying racemic mixtures into enantiomerically pure fractions.

Another embodiment of the compounds of Formula I includes any one or more or combination of the following configurations for compounds:

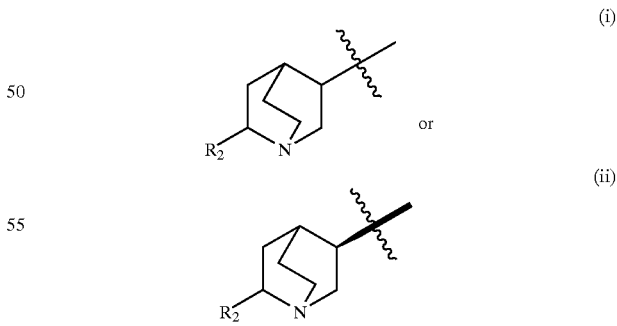

where (i) the compound is a racemic mixture, or
(ii) the compound has the R stereochemistry at C-3 as discussed herein and stereochemistry is unspecified at C-6.

Another embodiment of compounds of Formula I includes any one or more or combination of the following configurations for compounds:

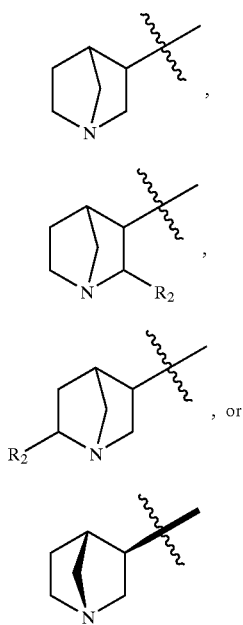

where (i) $k_2$ is 0 ($R_2$ is absent);
(ii) $R_2$ is alkyl, halogenated alkyl, substituted alkyl, cycloalkyl, or aryl;
(iii) $R_2$ is alkyl, halogenated alkyl, substituted alkyl, cycloalkyl, or aryl; or
(iv) the 2.2.1 moiety has the exo-4(S) stereochemistry as discussed herein.

Another embodiment of compounds of Formula I includes any one or more or combination of the following configurations for compounds:

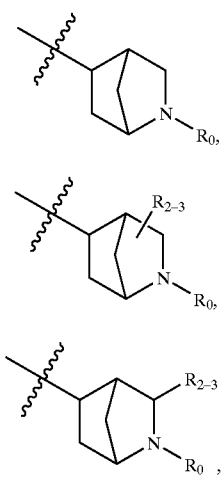

where (i) $R_{2-3}$ is H;
(ii) $R_{2-3}$ is F, Cl, Br, I, alkyl, halogenated alkyl, substituted alkyl, cycloalkyl, or aryl; or
(iii) $R_{2-3}$ is alkyl, halogenated alkyl, substituted alkyl, cycloalkyl, or aryl.

Another embodiment of compounds of Formula I includes any one or more or combination of the following configurations for compounds:

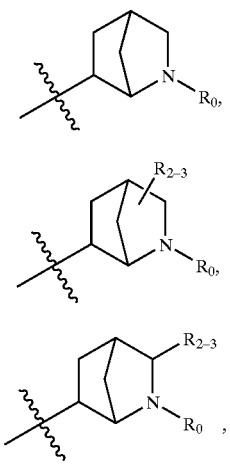

where (i) $R_{2-3}$ is H;
(ii) $R_{2-3}$ is F, Cl, Br, I, alkyl, halogenated alkyl, substituted alkyl, cycloalkyl, or aryl; or
(iii) $R_{2-3}$ is alkyl, halogenated alkyl, substituted alkyl, cycloalkyl, or aryl.

Another embodiment of compounds of Formula I includes any one or more or combination of the following configurations for compounds:

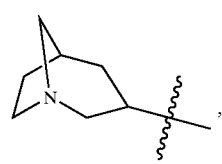

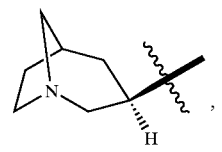

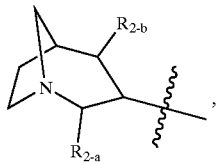

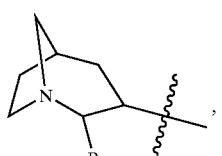

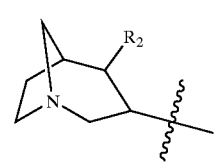

where (i) $k_5$ is 0 ($R_2$ is absent);
(ii) $R_2$ is absent and where the Azabicyclo has the stereochemistry of 3R, 5R;

(iii) $k_5$ is 2, where $R_{2\text{-}a}$ is alkyl, halogenated alkyl, substituted alkyl, cycloalkyl, or aryl, and where $R_{2\text{-}b}$ is F, Cl, Br, I, alkyl, halogenated alkyl, substituted alkyl, cycloalkyl, or aryl;

(iv) $k_5$ is 1, where $R_2$ is alkyl, halogenated alkyl, substituted alkyl, cycloalkyl, or aryl; or (v) $k_5$ is 1, where $R_2$ is F, Cl, Br, I, alkyl, halogenated alkyl, substituted alkyl, cycloalkyl, or aryl.

Another embodiment of compounds of Formula I includes any one or more or combination of the following configurations for compounds:

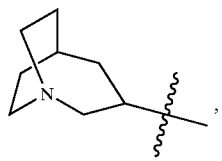 (i)

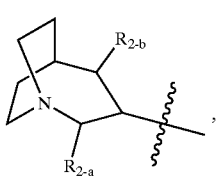 (ii)

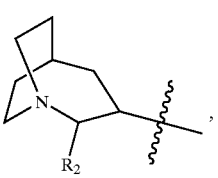 (iii)

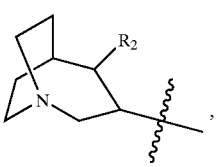 (iv)

where (i) $k_6$ is 0 ($R_2$ is absent);

(ii) $k_6$ is 2, where each $R_{2\text{-}a}$ is alkyl, halogenated alkyl, substituted alkyl, cycloalkyl, or aryl and where each $R_{2\text{-}b}$ is F, Cl, Br, I, alkyl, halogenated alkyl, substituted alkyl, cycloalkyl, or aryl;

(iii) $k_6$ is 1, where $R_2$ is alkyl, halogenated alkyl, substituted alkyl, cycloalkyl, or aryl; or (iv) $k_6$ is 1, where $R_2$ is F, Cl, Br, I, alkyl, halogenated alkyl, substituted alkyl, cycloalkyl, or aryl.

Further aspects and embodiments of the invention may become apparent to those skilled in the art from a review of the following detailed description, taken in conjunction with the examples and the appended claims. While the invention is susceptible of embodiments in various forms, described hereafter are specific embodiments of the invention with the understanding that the present disclosure is intended as illustrative, and is not intended to limit the invention to the specific embodiments described herein.

DETAILED DESCRIPTION OF THE INVENTION

Surprisingly, we have found that compounds of Formula I:

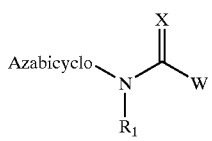

Formula I wherein Azabicyclo is

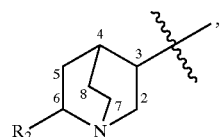 I

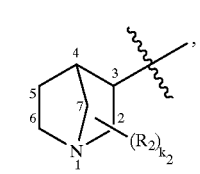 II

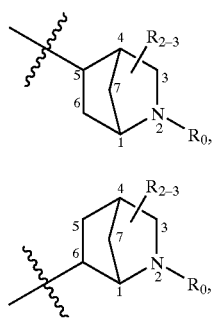 III

IV

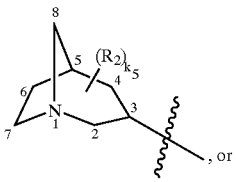 V

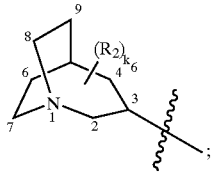, or

VI

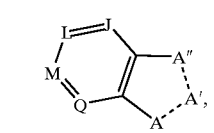;

W is (a)

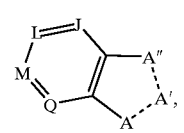

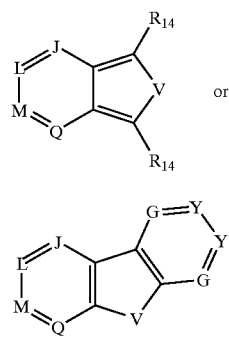

provided that the bond between the —C(=X)— group and the W group may be attached at any available carbon atom within the W group as provided in $R_3$, $R_6$, and $R_{15}$;

X is O, or S;

$R_0$ is H, lower alkyl, substituted lower alkyl, or halogenated lower alkyl;

Lower alkyl is both straight- and branched-chain moieties having 1–4 carbon atoms;

Halogenated lower alkyl is lower alkyl having 1 to (2n+1) substituent(s) independently selected from F, Cl, Br, or I where n is the maximum number of carbon atoms in the moiety;

Substituted lower alkyl is lower alkyl having 0–3 substituents independently selected from F, Cl, Br, or I and further having 1 substituent selected from —CN, —NO$_2$, —OR$_{10}$, —SR$_{10}$, —NR$_1$OR$_{10}$, —C(O)R$_{10}$, —C(O)OR$_{10}$, —C(S)R$_{10}$, —C(O)N(R$_{10}$)$_2$, —NR$_{10}$C(O)N(R$_{10}$)$_2$, —NR$_{10}$C(O)R$_{10}$, —S(O)R$_{10}$, —S(O)$_2$R$_{10}$, —OS(O)$_2$R$_{10}$, —S(O)$_2$NR$_{10}$R$_{10}$, —NR$_{10}$S(O)$_2$R$_{10}$ phenyl, or phenyl having 1 substituent selected from $R_{18}$ and further having 0–3 substituents independently selected from F, Cl, Br, or I;

Each $R_1$ is H, alkyl, cycloalkyl, halogenated alkyl, substituted phenyl, or substituted naphthyl;

Alkyl is both straight- and branched-chain moieties having from 1–6 carbon atoms;

Halogenated alkyl is an alkyl moiety having from 1–6 carbon atoms and having 1 to (2n+1) substituent(s) independently selected from F, Cl, Br, or I, where n is the maximum number of carbon atoms in the moiety;

Cycloalkyl is a cyclic alkyl moiety having from 3–6 carbon atoms;

Substituted phenyl is a phenyl either having 1–4 substituents independently selected from F, Cl, Br, or I, or having 1 substituent selected from $R_{12}$ and 0–3 substituents independently selected from F, Cl, Br, or I;

Substituted naphthyl is a naphthalene moiety either having 1–4 substituents independently selected from F, Cl, Br, or 1, or having 1 substituent selected from $R_{12}$ and 0–3 substituents independently selected from F, Cl, Br, or I, where the substitution can be independently on either only one ring or both rings of said naphthalene moiety;

Each $R_2$ is alkyl, halogenated alkyl, substituted alkyl, cycloalkyl, aryl, F, Cl, Br, I, or $R_2$ is absent provided that $k_2$, $k_5$, or $k_6$ is 0;

$R_{2-3}$ is H, alkyl, substituted alkyl, halogenated alkyl, F, Cl, Br, or I;

Substituted alkyl is an alkyl moiety from 1–6 carbon atoms and having 0–3 substituents independently selected from F, Cl, Br, or I, and further having 1 substituent selected from $R_7$, $R_9$, —CN, —NO$_2$, —OR$_{10}$, —SR$_{10}$, —NR$_{10}$R$_{10}$, —C(O)R$_{10}$, —C(O)OR$_{10}$, —C(S)R$_{10}$, —C(O)N(R$_{10}$)$_2$, —NR$_1$C(O)N(R$_{10}$)$_2$, —NR$_{10}$C(O)R$_{10}$, —S(O)R$_{10}$, —S(O)$_2$R$_{10}$, —OS(O)$_2$R$_{10}$, —S(O)$_2$NR$_{10}$R$_{10}$, —NR$_{10}$S(O)$_2$R$_{10}$, phenyl, or phenyl having 1 substituent selected from $R_{18}$ and further having 0–3 substituents independently selected from F, Cl, Br, or I;

$k_2$ is 0 or 1;

$k_5$ and $k_6$ are independently 0, 1, or 2;

A - - - A' - - - A" is N(R$_4$)—C(R$_3$)=C(R$_3$), N=C(R$_3$)—C(R$_{15}$)$_2$, C(R$_3$)=C(R$_3$)—N(R$_4$), C(R$_3$)$_2$—N(R$_4$)—C(R$_3$)$_2$, C(R$_{15}$)$_2$—C(R$_3$)=N,N(R$_4$)—C(R$_3$)$_2$—C(R$_3$)$_2$, C(R$_3$)$_2$—C(R$_3$)$_2$—N(R$_4$), O—C(R$_3$)—C(R$_3$), O—C(R$_3$)$_2$—C(R$_3$)$_2$—O—C(R$_3$)$_2$, C(R$_3$)=C(R$_3$)—O, C(R$_3$)$_2$—C(R$_3$)$_2$—O, S—C(R$_3$)=C(R$_3$), S—C(R$_3$)$_2$—C(R$_3$)$_2$, C(R$_3$)$_2$—S—C(R$_3$)$_2$, C(R$_3$)—C(R$_3$)—S, or C(R$_3$)$_2$—C(R$_3$)$_2$—S;

Each $R_3$ is independently a bond to the core molecule provided that only one $R_3$ and no $R_6$ or $R_{15}$ is also said bond, H, alkyl, substituted alkyl, halogenated alkyl, alkenyl, substituted alkenyl, halogenated alkenyl, alkynyl, substituted alkynyl, halogenated alkynyl, —CN, —NO$_2$, F, Br, Cl, I, —OR$_{19}$, —C(O)N(R$_{10}$)$_2$, —N(R$_{10}$)$_2$, —SR$_{19}$, —S(O)$_2$R$_{19}$, —C(O)R$_{19}$, —CO$_2$R$_{19}$, aryl, $R_7$, or $R_9$;

Aryl is phenyl, substituted phenyl, naphthyl, or substituted naphthyl;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n−1) substituent(s) independently selected from F, Cl, Br, or I, where n is the maximum number of carbon atoms in the moiety;

Substituted alkenyl is an unsaturated alkenyl moiety having from 2–6 carbon atoms and having 0–3 substituents independently selected from F, or Cl, and further having 1 substituent selected from $R_7$, $R_9$, —CN, —NO$_2$, —OR$_{10}$, —SR$_{10}$, —NR$_{10}$R$_{10}$, —C(O)R$_{10}$, —C(O)OR$_{10}$, —C(S)R$_{10}$, —C(O)N(R$_{10}$)$_2$, —NR$_{10}$C(O)N(R$_{10}$)$_2$, —NR$_{10}$R$_{10}$, —S(O)R$_{10}$, —S(O)$_2$R$_{10}$, —OS(O)$_2$R$_{10}$, —S(O)$_2$NR$_{10}$R$_{10}$, —NR$_{10}$S(O)$_2$R$_{10}$, phenyl, or phenyl having 1 substituent selected from $R_{18}$ and further having 0–3 substituents independently selected from F, Cl, Br, or I;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n−3) substituent(s) independently selected from F, Cl, Br, or I, where n is the maximum number of carbon atoms in the moiety;

Substituted alkynyl is an unsaturated alkynyl moiety having from 3–6 carbon atoms and having 0–3 substituents independently selected from F, or Cl, and further having 1 substituent selected from $R_7$, $R_9$, —CN, —NO$_2$, —OR$_{10}$, —SR$_{10}$, —NR$_{10}$R$_{10}$, —C(O)R$_{10}$, —C(O)OR$_{10}$, —C(S)R$_{10}$, —C(O)N(R$_{10}$)$_2$, —NR$_1$OC(O)N(R$_{10}$)$_2$, —NR$_{10}$C(O)R$_{10}$, —S(O)R$_{10}$, —S(O)$_2$R$_{10}$, —OS(O)$_2$R$_{10}$, —S(O)$_2$NR$_{10}$R$_{10}$, —NR$_{10}$S(O)$_2$R$_{10}$, phenyl, or phenyl having 1 substituent selected from $R_{18}$ and further having 0–3 substituents independently selected from F, Cl, Br, or I;

Halogenated cycloalkyl is a cyclic moiety having from 3–6 carbon atoms and having 1–4 substituents independently selected from F, or Cl;

Substituted cycloalkyl is a cyclic moiety having from 3–6 carbon atoms and having 0–3 substituents independently selected from F, or Cl, and further having 1 substituent selected from $R_7$, $R_9$, —CN, —NO$_2$, —OR$_{10}$, —SR$_{10}$, —NR$_{10}$R$_{10}$, —C(O)R$_{10}$, —C(O)OR$_{10}$, —C(S)R$_{10}$, —C(O)N(R$_{10}$)$_2$, —NR$_1$OC(O)N(R$_{10}$)$_2$, —NR$_1$OC(O)R$_{10}$, —S(O)R$_{10}$, —S(O)$_2$R$_{10}$, —OS(O)$_2$R$_{10}$, —S(O)$_2$NR$_{10}$R$_{10}$, —NR$_{10}$S(O)$_2$R$_{10}$, phenyl, or phenyl having 1 substituent selected from $R_{18}$ and further having 0–3 substituents independently selected from F, Cl, Br, or I;

Heterocycloalkyl is a cyclic moiety having 4–7 atoms with 1–2 atoms within the ring being —S—, —N(R$_{17}$)—, or —O—;

Halogenated heterocycloalkyl is a cyclic moiety having from 4–7 atoms with 1–2 atoms within the ring being —S—, —N(R$_{17}$)—, or —O—, and having 1–4 substituents independently selected from F, or Cl;

Substituted heterocycloalkyl is a cyclic moiety having from 4–7 atoms with 1–2 atoms within the ring being —S—, —N(R$_{17}$)—, or —O— and having 0–3 substituents independently selected from F, or Cl, and further having 1 substituent selected from $R_7$, $R_9$, —CN, —NO$_2$, —OR$_{10}$, —SR$_{10}$, —NR$_{10}$R$_{10}$, —C(O)R$_{10}$, —C(O)OR$_{10}$, —C(S)R$_{10}$, —C(O)N(R$_{10}$)$_2$, —NR$_{10}$C(O)N(R$_{10}$)$_2$, —NR$_{10}$C(O)R$_{10}$, —S(O)R$_{10}$, —S(O)$_2$R$_{10}$, —OS(O)$_2$R$_{10}$, —S(O)$_2$NR$_{10}$R$_{10}$, —NR$_1$OS(O)$_2$R$_0$, phenyl, or phenyl having 1 substituent selected from $R_{18}$ and further having 0–3 substituents independently selected from F, Cl, Br, or I;

J, L, M, and Q are N or C(R$_6$) provided that only one of J, L, M, or Q, is N and the others are C(R$_6$), further provided that when the core molecule is attached to the pyridinyl moiety at M, Q is C(H), and further provided that there is only one attachment to the core molecule;

G and Y are C(R$_6$), provided that when the molecule is attached to the phenyl moiety at Y, G is CH;

$R_4$ is H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, or $R_9$;

Each $R_5$ is independently H, lower alkyl, or lower alkenyl;

Lower alkenyl is straight- and branched-chain moieties having from 2–4 carbon atoms and having at least one carbon-carbon double bond;

Each $R_6$ is independently H, F, Br, I, Cl, —CN, —CF$_3$, —OR$_5$, —SR$_5$, —N(R$_5$)$_2$, or a bond to the core molecule provided that only one $R_6$ and no $R_3$ or $R_{15}$ is said bond;

V is selected from O, S, or N(R$_4$);

$R_7$ is 5-membered heteroaromatic mono-cyclic moieties containing within the ring 1–3 heteroatoms independently selected from the group consisting of =N—, —N(R$_{17}$)—, —O—, and —S—, and having 0–1 substituent selected from $R_{18}$ and further having 0–3 substituents independently selected from F, Cl, Br, or I, or $R_7$ is 9-membered fused-ring moieties having a 6-membered ring fused to a 5-membered ring including the formula

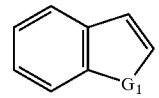

wherein $G_1$ is O, S, or NR$_{17}$,

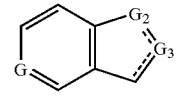

wherein $G_1$ is O, S or NR$_{17}$,
wherein G is C(R$_{16}$) or N, and each $G_2$ and $G_3$ are independently selected from C(R$_{16}$)$_2$, C(R$_{16}$), O, S, N, and N(R$_{18}$), provided that both $G_2$ and $G_3$ are not simultaneously O, simultaneously S, or simultaneously O and S, or

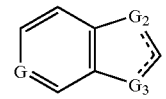

wherein G is C(R$_{16}$) or N, and each $G_2$ and $G_3$ are independently selected from C(R$_{16}$)$_2$, C(R$_{16}$), O, S, N, and N(R$_{17}$), each 9-membered fused-ring moiety having 0–1 substituent selected from $R_{18}$ and further having 0–3 substituent(s) independently selected from F, Cl, Br, or I, wherein the $R_7$ moiety attaches to other substituents as defined in formula I at any position on either ring as valency allows;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from $R_{18}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{18}$ and 0–3 substituent(s) independently selected from F, Cl, Br, or I, and having a bond directly or indirectly attached to the core molecule where valency allows;

Each $R_{10}$ is independently H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_1$ is independently H, alkyl, cycloalkyl, heterocycloalkyl, halogenated alkyl, halogenated cycloalkyl, or halogenated heterocycloalkyl;

$R_{12}$ is —NO$_2$, —CN, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —C(O)NR$_{11}$R$_{11}$, —NR$_{11}$C(O)R$_{11}$, —S(O)$_2$NR$_{11}$R$_{11}$, or —NR$_{11}$S(O)$_2$R$_{11}$;

$R_{13}$ is —CN, —CF$_3$, —NO$_2$, —OR$_{11}$, —SR$_{11}$, —NR$_{11}$R$_{11}$, —C(O)R$_{11}$, —C(O)NR$_{11}$R$_{11}$, —NR$_{11}$C(O)R$_{11}$, —S(O)$_2$NR$_{11}$R$_{11}$, or —NR$_{11}$S(O)$_2$R$_{11}$;

Each $R_{14}$ is H, alkyl, substituted alkyl, halogenated alkyl, alkenyl, substituted alkenyl, halogenated alkenyl, alkynyl, substituted alkynyl, halogenated alkynyl, F, Br, Cl, I, —CN, —NO$_2$, —OR$_{19}$, —C(O)N(R$_{10}$)$_2$, —N(R$_{10}$)$_2$, —SR$_9$, —S(O)$_2$R$_{19}$, —C(O)R$_{19}$, —CO$_2$R$_{19}$, aryl, R$_7$ or R$_9$;

Each $R_{15}$ is independently alkyl, substituted alkyl, halogenated alkyl, alkenyl, substituted alkenyl, halogenated alkenyl, alkynyl, substituted alkynyl, halogenated alkynyl, F, Br, Cl, I, —CN, —NO$_2$, —OR$_{19}$, —C(O)N(R$_{10}$)$_2$, —N(R$_{10}$)$_2$, —SR$_{19}$, —CO$_2$R$_{19}$, aryl, R$_7$, R$_9$, or a bond to the core molecule provided that only one R$_{15}$ and no R$_6$ or R$_3$ is said bond;

Each $R_{16}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, F, Cl, Br, I, —NO$_2$, —CN, —OR$_{11}$, —SR$_{11}$, —NR$_{11}$R$_{11}$, —C(O)R$_{11}$, —C(O)NR$_{11}$ R$_{11}$, —NR$_{11}$C(O)R$_{11}$, —S(O)$_2$NR$_{11}$R$_{11}$, —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$,—NO$_2$, —C(O)NR$_{11}$R$_{11}$,—CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

$R_{17}$ is H, alkyl, halogenated alkyl, substituted alkyl, cycloalkyl, halogenated cycloalkyl, substituted cycloalkyl, phenyl, —SO$_2$R$_8$, or phenyl having 1 substituent selected from R$_{18}$ and further having 0–3 substituents independently selected from F, Cl, Br, or I;

$R_{18}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —NO$_2$, alkyl substituted with 1–4 substituent(s) independently selected from F, Cl, Br, I, or R$_{13}$, cycloalkyl substituted with 1–4 substituent(s) independently selected from F, Cl, Br, I, or R$_{13}$, or heterocycloalkyl substituted with 1–4 substituent(s) independently selected from F, Cl, Br, I, or R$_{13}$;

$R_{19}$ is H, alkyl, cycloalkyl, substituted alkyl, halogenated alkyl, substituted phenyl, or substituted naphthyl;

or pharmaceutical composition, pharmaceutically acceptable salt, racemic mixture, or pure enantiomer thereof useful to treat any one of or combination of cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependant drug cessation, Gilles de la Tourette's Syndrome, glaucoma, neurodegeneration associated with glaucoma, or symptoms associated with pain.

In another aspect, the invention includes methods of treating a mammal suffering from schizophrenia or psychosis by administering compounds of Formula I in conjunction with antipsychotic drugs (also called antipsychotic agents). The compounds of Formula I and the antipsychotic drugs can be administered simultaneously or at separate intervals. When administered simultaneously the compounds of Formula I and the antipsychotic drugs can be incorporated into a single pharmaceutical composition. Alternatively, two separate compositions, i.e., one containing compounds of Formula I and the other containing antipsychotic drugs, can be administered simultaneously.

The present invention also includes the compounds of the present invention, pharmaceutical compositions containing the active compounds, and methods to treat the identified diseases.

Abbreviations which are well known to one of ordinary skill in the art may be used (e.g., "Ph" for phenyl, "Me" for methyl, "Et" for ethyl, "h" for hour or hours, "min" for minute or minutes, and "rt" for room temperature).

All temperatures are in degrees Centigrade.

Room temperature is within the range of 15–25 degrees Celsius.

AChR refers to acetylcholine receptor.

Pre-senile dementia is also known as mild cognitive impairment. nAChR refers to nicotinic acetylcholine receptor.

5HT$_3$R refers to the serotonin-type 3 receptor.

α-btx refers to α-bungarotoxin.

FLIPR refers to a device marketed by Molecular Devices, Inc. designed to precisely measure cellular fluorescence in a high throughput whole-cell assay. (Schroeder et. al., *J. Biomolecular Screening*, 1(2), p 75–80, 1996).

TLC refers to thin-layer chromatography.

HPLC refers to high pressure liquid chromatography.

MeOH refers to methanol.

EtOH refers to ethanol.

IPA refers to isopropyl alcohol.

THF refers to tetrahydrofuran.

DMSO refers to dimethylsulfoxide.

DMF refers to dimethylformamide.

EtOAc refers to ethyl acetate.

Na$_2$SO$_4$ refers to sodium sulfate.

K$_2$CO$_3$ refers to potassium carbonate.

MgSO$_4$ refers to magnesium sulfate.

When Na$_2$SO$_4$, K$_2$CO$_3$, or MgSO$_4$ is used as a drying agent, it is anhydrous.

TMS refers to tetramethylsilane.

TEA refers to triethylamine.

DIEA refers to N,N-diisopropylethylamine.

MLA refers to methyllycaconitine.

Ether refers to diethyl ether.

HATU refers to O-(7-azabenzotriazol-1-yl)-N,N,N',N'-tetramethyluronium hexafluorophosphate.

DBU refers to 1,8-diazabicyclo[5.4.0]undec-7-ene.

DPPA refers to diphenylphosphoryl azide. 50% saturated 1:1 NaCl/NaHCO$_3$ means a solution made by making a solution of 1:1 saturated NaCl/NaHCO₃ and adding an equal volume of water.

CH₃SO₂Cl refers to methanesulfonyl chloride.

Halogen is F, Cl, Br, or I.

Non-inclusive examples of heteroaryl compounds that fall within the definition of $R_7$ and $R_9$ include, but are not limited to, thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, furopyridinyl, pyrrolopyridinyl, or thienopyridinyl. All isomeric forms of the non-inclusive named moieties are included, e.g., benzofuranyl includes 1-benzofuran-2-yl, 1-benzofuran-3-yl, 1-benzofuran-4-yl, 1-benzofuran-5-yl, 1-benzofuran-6-yl, 1-benzofuran-7-yl, 2-benzofuran-1-yl, 2-benzofuran-2-yl, 2-benzofuran-3-yl, 2-benzofuran-4-yl, or 2-benzofuran-5-yl. The non-inclusive examples of $R_7$ and $R_9$ may be substituted as allowed within the respective definition of $R_7$ and $R_9$ as valency allows. One of ordinary skill in the art can identify the allowed substitution by comparing the non-inclusive examples with the respective definitions of $R_7$ and $R_9$.

Non-inclusive examples of heterocycloalkyl include, but are not limited to, tetrahydrofurano, tetrahydropyrano, morpholino, pyrrolidino, piperidino, piperazine, azetidino, azetidinono, oxindolo, dihydroimidazolo, pyrrolidino, or isoxazolinyl.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$ alkyl refers to alkyl of one to six carbon atoms.

The core molecule is Azabicyclo-N($R_1$)—C(=X)—:

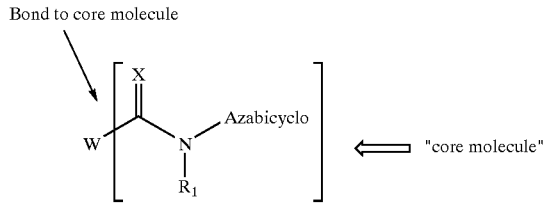

Some of the amines described herein require the use of an amine-protecting group to ensure functionalization of the desired nitrogen. One of ordinary skill in the art would appreciate where, within the synthetic scheme to use said protecting group. Amino protecting group includes, but is not limited to, carbobenzyloxy (CBz), tert butoxy carbonyl (BOC) and the like. Examples of other suitable amino protecting groups are known to person skilled in the art and can be found in "Protective Groups in Organic synthesis," 3rd Edition, authored by Theodora Greene and Peter Wuts.

Mammal denotes human and other mammals.

Brine refers to an aqueous saturated sodium chloride solution.

Equ means molar equivalents.

IR refers to infrared spectroscopy.

Lv refers to leaving groups within a molecule, including Cl, OMe, OEt, or mixed anhydride.

Parr refers to the name of the company who sells the jars used for conducting reactions under pressure.

PSI means pound per square inch.

NMR refers to nuclear (proton) magnetic resonance spectroscopy, chemical shifts are reported in ppm (δ) downfield from TMS.

MS refers to mass spectrometry expressed as m/e or mass/charge unit. HRMS refers to high resolution mass spectrometry expressed as m/e or mass/charge unit. M+H⁺ refers to the positive ion of a parent plus a hydrogen atom. M−H⁻ refers to the negative ion of a parent minus a hydrogen atom. M+Na⁺ refers to the positive ion of a parent plus a sodium atom. M+K⁺ refers to the positive ion of a parent plus a potassium atom. EI refers to electron impact. ESI refers to electrospray ionization. CI refers to chemical ionization. FAB refers to fast atom bombardment.

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The amount of therapeutically effective compound(s) that is administered and the dosage regimen for treating a disease condition with the compounds and/or compositions of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of Formula I. The pharmaceutical compositions may contain active ingredient in the range of about 0.001–100 mg/kg/day for an adult, preferably in the range of about 0.1–50 mg/kg/day for an adult. A total daily dose of about 1–1000 mg of active ingredient may be appropriate for an adult. The daily dose can be administered in one to four doses per day.

In addition to the compound(s) of Formula I, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, EtOH, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the γ-aminobutyric acid type A receptor. Like the other members of this receptor superfamily, the $5HT_3R$ exhibits a large degree of sequence homology with α7 nAChR but functionally the two ligand-gated ion channels are very different. For example, α7 nAChR is rapidly inactivated, is highly permeable to calcium and is activated by acetylcholine and nicotine. On the other hand, $5HT_3R$ is inactivated slowly, is relatively impermeable to calcium and is activated by serotonin. These experiments suggest that the α7 nAChR and $5HT_3R$ proteins have some degree of homology, but function very differently. Indeed the pharmacology of the channels is very different. For example, Ondansetron, a highly selective $5HT_3R$ antagonist, has little activity at the α7 nAChR. The converse is also true. For example, GTS-21, a highly selective α7 nAChR agonist, has little activity at the $5HT_3R$. α7 nAChR is a ligand-gated $Ca^{++}$ channel formed by a homopentamer of α7 subunits. Previous studies have established that α-bungarotoxin (α-btx) binds selectively to this homopetameric, α7 nAChR subtype, and that α7 nAChR has a high affinity binding site for both α-btx and methyllycaconitine (MLA). α7 nAChR is expressed at high levels in the hippocampus, ventral tegmental area and ascending cholinergic projections from nucleus basilis to thalamocortical areas. α7 nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E. D., *Psychopharmacology*, 108:417–31, 1992; Levin, E. D. and Simon B. B., *Psychopharmacology*, 138:217–30, 1998). For example, it is well known that nicotine increases cognition and attention in humans. ABT-418, a compound that activates α4β2 and α7 nAChR, improves cognition and attention in clinical trials of Alzheimer's disease and attention-deficit disorders (Potter, A. et. al., *Psychopharmacology (Berl).*, 142(4):334–42, March 1999; Wilens, T. E. et. al., *Am. J. Psychiatry*, 156(12):1931–7, December 1999). It is also clear that nicotine and selective but weak α7 nAChR agonists increase cognition and attention in rodents and non-human primates.

Schizophrenia is a complex multifactorial illness caused by genetic and non-genetic risk factors that produce a constellation of positive and negative symptoms. The positive symptoms include delusions and hallucinations and the negative symptoms include deficits in affect, attention, cognition and information processing. No single biological element has emerged as a dominant pathogenic factor in this disease. Indeed, it is likely that schizophrenia is a syndrome that is produced by the combination of many low penetrance risk factors. Pharmacological studies established that dopamine receptor antagonists are efficacious in treating the overt psychotic features (positive symptoms) of schizophrenia such as hallucinations and delusions. Clozapine, an "a typical" antipsychotic drug, is novel because it is effective in treating both the positive and some of the negative symptoms of this disease. Clozapine's utility as a drug is greatly limited because continued use leads to an increased risk of agranulocytosis and seizure. No other antipsychotic drug is effective in treating the negative symptoms of schizophrenia. This is significant because the restoration of cognitive functioning is the best predictor of a successful clinical and functional outcome of schizophrenic patients (Green, M. F., *Am J Psychiatry*, 153:321–30, 1996). By extension, it is clear that better drugs are needed to treat the cognitive disorders of schizophrenia in order to restore a better state of mental health to patients with this disorder.

One aspect of the cognitive deficit of schizophrenia can be measured by using the auditory event-related potential (P50) test of sensory gating. In this test, electroencephalographic (EEG) recordings of neuronal activity of the hippocampus are used to measure the subject's response to a series of auditory "clicks" (Adler, L. E. et. al., *Biol. Psychiatry*, 46:8–18, 1999). Normal individuals respond to the first click with greater degree than to the second click. In general, schizophrenics and schizotypal patients respond to both clicks nearly the same (Cullum, C. M. et. al., *Schizophr. Res.*, 10:131–41, 1993). These data reflect a schizophrenic's inability to "filter" or ignore unimportant information. The sensory gating deficit appears to be one of the key pathological features of this disease (Cadenhead, K. S. et. al., *Am. J. Psychiatry*, 157:55–9, 2000). Multiple studies show that nicotine normalizes the sensory deficit of schizophrenia (Adler, L. E. et. al., *Am. J. Psychiatry*, 150:1856–61, 1993). Pharmacological studies indicate that nicotine's effect on sensory gating is via the α7 nAChR (Adler, L. E. et. al., *Schizophr. Bull.*, 24:189–202, 1998). Indeed, the biochemical data indicate that schizophrenics have 50% fewer of α7 nAChR receptors in the hippocampus, thus giving a rationale to partial loss of α7 nAChR functionality (Freedman, R. et. al., *Biol. Psychiatry*, 38:22–33, 1995). Interestingly, genetic data indicate that a polymorphism in the promoter region of the α7 nAChR gene is strongly associated with the sensory gating deficit in schizophrenia (Freedman, R. et. al., *Proc. Nat'l Acad. Sci. USA*, 94(2):587–92, 1997; Myles-Worsley, M. et. al., *Am. J. Med. Genet*, 88(5):544–50, 1999). To date, no mutation in the coding region of the α7 nAChR has been identified. Thus, schizophrenics express the same α7 nAChR as non-schizophrenics.

Selective α7 nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of α7 nAChR and 5HT$_3$R. To conduct such an assay, one uses cell lines that expressed functional forms of the α7 nAChR using the α7/5-HT$_3$ channel as the drug target and cell lines that expressed functional 5HT$_3$R. In both cases, the ligand-gated ion channel was expressed in SH-EP1 cells. Both ion channels can produce robust signal in the FLIPR assay.

The compounds of the present invention are α7 nAChR agonists and may be used to treat a wide variety of diseases. For example, they may be used in treating schizophrenia, or psychosis.

Schizophrenia is a disease having multiple aspects. Currently available drugs are generally aimed at controlling the positive aspects of schizophrenia, such as delusions. One drug, Clozapine, is aimed at a broader spectrum of symptoms associated with schizophrenia. This drug has many side effects and is thus not suitable for many patients. Thus, there is a need for a drug to treat the cognitive and attention deficits associated with schizophrenia. Similarly, there is a need for a drug to treat the cognitive and attention deficits associated with schizoaffective disorders, or similar symptoms found in the relatives of schizophrenic patients.

Psychosis is a mental disorder characterized by gross impairment in the patient's perception of reality. The patient may suffer from delusions, and hallucinations, and may be incoherent in speech. His behavior may be agitated and is often incomprehensible to those around him. In the past, the term psychosis has been applied to many conditions that do not meet the stricter definition given above. For example, mood disorders were named as psychoses.

There are a variety of antipsychotic drugs. The conventional antipsychotic drugs include Chlorpromazine, Fluphenazine, Haloperidol, Loxapine, Mesoridazine, Molindone, Perphenazine, Pimozide, Thioridazine, Thiothixene, and Trifluoperazine. These drugs all have an affinity for the dopamine 2 receptor.

These conventional antipsychotic drugs have several side effects, including sedation, weight gain, tremors, elevated prolactin levels, akathisia (motor restlessness), dystonia and muscle stiffness. These drugs may also cause tardive dyskinesia. Unfortunately, only about 70% of patients with schizophrenia respond to conventional antipsychotic drugs. For these patients, a typical antipsychotic drugs are available.

Atypical antipsychotic drugs generally are able to alleviate positive symptoms of psychosis while also improving negative symptoms of the psychosis to a greater degree than conventional antipsychotics. These drugs may improve neurocognitive deficits. Extrapyramidal (motor) side effects are not as likely to occur with the a typical antipsychotic drugs, and thus, these a typical antipsychotic drugs have a lower risk of producing tardive dyskinesia. Finally these a typical antipsychotic drugs cause little or no elevation of prolactin. Unfortunately, these drugs are not free of side effects. Although these drugs each produce different side effects, as a group the side effects include: agranulocytosis; increased risk of seizures, weight gain, somnolence, dizziness, tachycardia, decreased ejaculatory volume, and mild prolongation of QTc interval.

In a combination therapy to treat multiple symptoms of diseases such as schizophrenia, the compounds of Formula I and the anti-psychotic drugs can be administered simultaneously or at separate intervals. When administered simultaneously the compounds of Formula I and the anti-psychotic drugs can be incorporated into a single pharmaceutical composition, e.g., a pharmaceutical combination therapy composition. Alternatively, two separate compositions, i.e., one containing compounds of Formula I and the other containing anti-psychotic drugs, can be administered simultaneously. Examples of anti-psychotic drugs, in addition to those listed above, include, but are not limited to, Thorazine, Mellaril, Trilafon, Navane, Stelazine, Permitil, Prolixin, Risperdal, Zyprexa, Seroquel, ZELDOX, Acetophenazine, Carphenazine, Chlorprothixene, Droperidol, Loxapine, Mesoridazine, Molindone, Ondansetron, Pimozide, Prochlorperazine, and Promazine.

A pharmaceutical combination therapy composition can include therapeutically effective amounts of the compounds of Formula I and a therapeutically effective amount of anti-psychotic drugs. These compositions may be formulated with common excipients, diluents or carriers, and compressed into tablets, or formulated elixirs or solutions for convenient oral administration or administered by intramuscular intravenous routes. The compounds can be administered rectally, topically, orally, sublingually, or parenterally and maybe formulated as sustained relief dosage forms and the like.

When separately administered, therapeutically effective amounts of compositions containing compounds of Formula I and anti-psychotic drugs are administered on a different schedule. One may be administered before the other as long as the time between the two administrations falls within a therapeutically effective interval. A therapeutically effective interval is a period of time beginning when one of either (a) the compounds of Formula I, or (b) the anti-psychotic drugs is administered to a human and ending at the limit of the beneficial effect in the treatment of schizophrenia or psychosis of the combination of (a) and (b). The methods of administration of the compounds of Formula I and the anti-psychotic drugs may vary. Thus, either agent or both agents may be administered rectally, topically, orally, sublingually, or parenterally.

As discussed, the compounds of the present invention are α7 nAChR agonists. Therefore, as another aspect of the present invention, the compounds of the present invention may be used to treat a variety of diseases including cognitive and attention deficit symptoms of Alzheimer's, neurodegeneration associated with diseases such as Alzheimer's disease, pre-senile dementia (also known as mild cognitive impairment), and senile dementia.

Alzheimer's disease has many aspects, including cognitive and attention deficits. Currently, these deficits are treated with cholinesterase inhibitors. These inhibitors slow the break down of acetylcholine, and thereby provide a general nonspecific increase in the activity of the cholinergic nervous system. Since the drugs are nonspecific, they have a wide variety of side effects. Thus, there is a need for a drug that stimulates a portion of the cholinergic pathways and thereby provides improvement in the cognitive and attention deficits associated with Alzheimer's disease without the side effects created by nonspecific stimulation of the cholinergic pathways.

Neurodegeneration is a common problem associated with diseases such as Alzheimer's disease. While the current drugs treat some of the symptoms of this disease, they do not control the underlying pathology of the disease. Accordingly, it would be desirable to provide a drug that can slow the progress of Alzheimer's disease.

Pre-senile dementia (mild cognitive impairment) concerns memory impairment rather than attention deficit problems and otherwise unimpaired cognitive functioning. Mild cognitive impairment is distinguished from senile dementia in that mild cognitive impairment involves a more persistent and troublesome problem of memory loss for the age of the patient. There currently is no medication specifically identified for treatment of mild cognitive impairment, due somewhat to the newness of identifying the disease. Therefore, there is a need for a drug to treat the memory problems associated with mild cognitive impairment.

Senile dementia is not a single disease state. However, the conditions classified under this name frequently include cognitive and attention deficits. Generally, these deficits are not treated. Accordingly, there is a need for a drug that provides improvement in the cognitive and attention deficits associated with senile dementia.

As discussed, the compounds of the present invention are $\alpha 7$ nAChR agonists. Therefore, yet other diseases to be treated with compounds of the present invention include treating the cognitive and attention deficits as well as the neurodegeneration associated with any one or more or combination of the following: attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulimia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

Attention deficit disorder is generally treated with methylphenidate, an amphetamine-like molecule that has some potential for abuse. Accordingly, it would be desirable to provide a drug that treats attention deficit disorder while having fewer side effects than the currently used drug.

Attention deficit hyperactivity disorder, otherwise known as ADHD, is a neurobehavioral disorder affecting 3–5% of all American children. ADHD concerns cognitive alone or both cognitive and behavioral actions by interfering with a person's ability to stay on a task and to exercise age-appropriate inhibition. Several types of ADHD exist: a predominantly inattentive subtype, a predominantly hyperactive-impulsive subtype, and a combined subtype. Treatment may include medications such as methylphenidate, dextroamphetamine, or pemoline, which act to decrease impulsivity and hyperactivity and to increase attention. No "cure" for ADHD currently exists. Children with the disorder seldom outgrow it; therefore, there is a need for appropriate medicaments.

Depression is a mood disorder of varying lengths of normally several months to more than two years and of varying degrees of feelings involving sadness, despair, and discouragement. The heterocyclic antidepressants (HCA's) are currently the largest class of antidepressants, but monoamine oxidase inhibitors (MAOI's) are used in particular types of depression. Common side effects from HCA's are sedation and weight gain. In elderly patients with organic brain disease, the side effects from HCA's can also include seizures and behavioral symptoms. The main side effects from using MAOI's occur from dietary and drug interactions. Therefore, agents with fewer side effects would be useful.

Anxiety disorders (disorders with prominent anxiety or phobic avoidance), represent an area of umet medical needs in the treatment of psychiatric illness. See Diagnostic & Statistical Manual of Mental Disorders, IV (1994), pp 393–394, for various disease forms of anxiety.

General anxiety disorder (GAD) occurs when a person worries about things such as family, health, or work when there is no reason to worry and is unable not to worry. About 3 to 4% of the U.S. population has GAD during the course of a year. GAD most often strikes people in childhood or adolescence, but can begin in adulthood, too. It affects women more often than men. Currently, treatment involves cognitive-behavioral therapy, relaxation techniques, and biofeedback to control muscle tension and medications such as benzodiazepines, imipramine, and buspirone. These drugs are effective but all have side-effect liabilities. Therefore, there is a need of a pharmaceutical agent to address the symptoms with fewer side effects.

Anxiety also includes post-traumatic stress disorder (PTSD), which is a form of anxiety triggered by memories of a traumatic event that directly affected the patient or that the patient may have witnessed. The disorder commonly affects survivors of traumatic events including sexual assault, physical assault, war, torture, natural disasters, an automobile accident, an airplane crash, a hostage situation, or a death camp. The affliction also can affect rescue workers at an airplane crash or a mass shooting, someone who witnessed a tragic accident or someone who has unexpectedly lost a loved one. Treatment for PTSD includes cognitive-behavioral therapy, group psychotherapy, and medications such as Clonazepam, Lorazepam and selective serotonin-reuptake inhibitors such as Fluoxetine, Sertraline, Paroxetine, Citalopram and Fluvoxamine. These medications help control anxiety as well as depression. Various forms of exposure therapy (such as systemic desensitization and imaginal flooding) have all been used with PTSD patients. Exposure treatment for PTSD involves repeated reliving of the trauma, under controlled conditions, with the aim of facilitating the processing of the trauma. Therefore, there is a need for better pharmaceutical agents to treat post traumatic stress disorder.

Mood and affective disorders fall within a large group of diseases, including monopolar depression and bi-polar mood disorder. These diseases are treated with three major classes of compounds. The first group is the heterocyclic antidepressant (HCA's). This group includes the well-known tricyclic antidepressants. The second group of compounds used to treat mood disorders is the monoamine oxidase inhibitors (MAOI's) that are used in particular types of diseases. The third drug is lithium. Common side effects from HCA's are sedation and weight gain. In elderly patients with organic brain disease, the side effects of HCA's can also include seizures and behavioral symptoms. The main side effects from using MAOI's occur from dietary and drug interactions. Benign side effects from the use of lithium include, but are not limited to, weight gain, nausea, diarrhea, polyuria, polydipsia, and tremor. Toxic side effects from lithium can include persistent headache, mental confusion, and may reach seizures and cardiac arrhythmias. Therefore, agents with less side effects or interactions with food or other medications would be useful.

Borderline personality disorder, although not as well known as bipolar disorder, is more common. People having borderline personality disorder suffer from a disorder of emotion regulation. Pharmaceutical agents are used to treat specific symptoms, such as depression or thinking distortions.

Acquired immune deficiency syndrome (AIDS) results from an infection with the human immunodeficiency virus (HIV). This virus attacks selected cells and impairs the proper function of the immune, nervous, and other systems. HIV infection can cause other problems such as, but not limited to, difficulties in thinking, otherwise known as AIDS dementia complex. Therefore, there is a need to drugs to relieve the confusion and mental decline of persons with AIDS.

Amyotrophic lateral sclerosis, also known as Lou Gehrig's disease, belongs to a class of disorders known as motor neuron diseases wherein specific nerve cells in the brain and spinal cord gradually degenerate to negatively affect the control of voluntary movement. Currently, there is no cure for amyotrophic lateral sclerosis although patients may receive treatment from some of their symptoms and although Riluzole has been shown to prolong the survival of patients. Therefore, there is a need for a pharmaceutical agent to treat this disease.

Traumatic brain injury occurs when the brain is damaged from a sudden physical assault on the head. Symptoms of the traumatic brain injury include confusion and other cognitive problems. Therefore, there is a need to address the symptoms of confusion and other cognitive problems.

Brain tumors are abnormal growths of tissue found inside of the skull. Symptoms of brain tumors include behavioral and cognitive problems. Surgery, radiation, and chemotherapy are used to treat the tumor, but other agents are necessary to address associated symptoms. Therefore, there is a need to address the symptoms of behavioral and cognitive problems.

Persons with Down's syndrome have in all or at least some of their cells an extra, critical portion of the number 21 chromosome. Adults who have Down's syndrome are known to be at risk for Alzheimer-type dementia. Currently, there is no proven treatment for Down's syndrome. Therefore, there is a need to address the dementia associated with Down's syndrome.

Genetically programmed degeneration of neurons in certain areas of the brain cause Huntington's disease. Early symptoms of Huntington's disease include mood swings, or trouble learning new things or remembering a fact. Most drugs used to treat the symptoms of Huntington's disease have side effects such as fatigue, restlessness, or hyperexcitability. Currently, there is no treatment to stop or reverse the progression of Huntington's disease. Therefore, there is a need of a pharmaceutical agent to address the symptoms with fewer side effects.

Dementia with Lewy Bodies is a neurodegenerative disorder involving abnormal structures known as Lewy bodies found in certain areas of the brain. Symptoms of dementia with Lewy bodies include, but are not limited to, fluctuating cognitive impairment with episodic delirium. Currently, treatment concerns addressing the parkinsonian and psychiatric symptoms. However, medicine to control tremors or loss of muscle movement may actually accentuate the underlying disease of dementia with Lewy bodies. Therefore, there is a need of a pharmaceutical agent to treat dementia with Lewy bodies.

Parkinson's disease is a neurological disorder characterized by tremor, hypokinesia, and muscular rigidity. Currently, there is no treatment to stop the progression of the disease. Therefore, there is a need of a pharmaceutical agent to address Parkinson's.

Tardive dyskinesia is associated with the use of conventional antipsychotic drugs. This disease is characterized by involuntary movements most often manifested by puckering of the lips and tongue and/or writhing of the arms or legs. The incidence of tardive dyskinesia is about 5% per year of drug exposure among patients taking conventional antipsychotic drugs. In about 2% of persons with the disease, tardive dyskinesia is severely disfiguring. Currently, there is no generalized treatment for tardive dyskinesia. Furthermore, the removal of the effect-causing drugs is not always an option due to underlying problems. Therefore, there is a need for a pharmaceutical agent to address the symptoms of tardive dyskinesia.

Pick's disease results from a slowly progressive deterioration of social skills and changes in personality with the resulting symptoms being impairment of intellect, memory, and language. Common symptoms include memory loss, lack of spontaneity, difficulty in thinking or concentrating, and speech disturbances. Currently, there is no specific treatment or cure for Pick's disease but some symptoms can be treated with cholinergic and serotonin-boosting antidepressants. In addition, antipsychotic medications may alleviate symptoms in FTD patients who are experiencing delusions or hallucinations. Therefore, there is a need for a pharmaceutical agent to treat the progressive deterioration of social skills and changes in personality and to address the symptoms with fewer side effects.

Dysregulation of food intake associated with eating disease, including bulemia nervosa and anorexia nervosa, involve neurophysiological pathways. Anorexia nervosa is hard to treat due to patients not entering or remaining in after entering programs. Currently, there is no effective treatment for persons suffering from severe anorexia nervosa. Cognitive behavioral therapy has helped patients suffering from bulemia nervosa; however, the response rate is only about 50% and current treatment does not adequately address emotional regulation. Therefore, there is a need for pharmaceutical agents to address neurophysiological problems underlying diseases of dysregulation of food intake.

Cigarette smoking has been recognized as a major public health problem for a long time. However, in spite of the public awareness of health hazard, the smoking habit remains extraordinarily persistent and difficult to break. There are many treatment methods available, and yet people continue to smoke. Administration of nicotine transdermally, or in a chewing gum base is common treatments. However, nicotine has a large number of actions in the body, and thus can have many side effects. It is clear that there is both a need and a demand of long standing for a convenient and relatively easy method for aiding smokers in reducing or eliminating cigarette consumption. A drug that could selectively stimulate only certain of the nicotinic receptors would be useful in smoke cessation programs.

Smoke cessation programs may involve oral dosing of the drug of choice. The drug may be in the form of tablets. However, it is preferred to administer the daily dose over the waking hours, by administration of a series of incremental doses during the day. The preferred method of such administration is a slowly dissolving lozenge, troche, or chewing gum, in which the drug is dispersed. Another drug in treating nicotine addiction is Zyban. This is not a nicotine replacement, as are the gum and patch. Rather, this works on other areas of the brain, and its effectiveness is to help control nicotine craving or thoughts about cigarette use in people trying to quit. Zyban is not very effective and effective drugs are needed to assist smokers in their desire to stop smoking. These drugs may be administered transdermally through the use of skin patches. In certain cases, the drugs may be administered by subcutaneous injection, especially if sustained release formulations are used.

Drug use and dependence is a complex phenomenon, which cannot be encapsulated within a single definition. Different drugs have different effects, and therefore different types of dependence. Drug dependence has two basic causes, that is, tolerance and physical dependence. Tolerance exists when the user must take progressively larger doses to produce the effect originally achieved with smaller doses. Physical dependence exists when the user has developed a state of physiologic adaptation to a drug, and there is a withdrawal (abstinence) syndrome when the drug is no longer taken. A withdrawal syndrome can occur either when the drug is discontinued or when an antagonist displaces the drug from its binding site on cell receptors, thereby counteracting its effect. Drug dependence does not always require physical dependence.

In addition drug dependence often involves psychological dependence, that is, a feeling of pleasure or satisfaction when taking the drug. These feelings lead the user to repeat the drug experience or to avoid the displeasure of being deprived of the drug. Drugs that produce strong physical dependence, such as nicotine, heroin and alcohol are often abused, and the pattern of dependence is difficult to break. Drugs that produce dependence act on the CNS and generally reduce anxiety and tension; produce elation, euphoria, or other pleasurable mood changes; provide the user feelings of increased mental and physical ability; or alter sensory perception in some pleasurable manner. Among the drugs that are commonly abused are ethyl alcohol, opioids, anxiolytics, hypnotics, cannabis (marijuana), cocaine, amphetamines, and hallucinogens. The current treatment for drug-addicted people often involves a combination of behavioral therapies and medications. Medications, such as methadone or LAAM (levo-alpha-acetyl-methadol), are effective in suppressing the withdrawal symptoms and drug craving associated with narcotic addiction, thus reducing illicit drug use and improving the chances of the individual remaining in treatment. The primary medically assisted withdrawal method for narcotic addiction is to switch the patient to a comparable drug that produces milder withdrawal symptoms, and then gradually taper off the substitute medication. The medication used most often is methadone, taken orally once a day. Patients are started on the lowest dose that prevents the more severe signs of withdrawal and then the dose is gradually reduced. Substitutes can be used also for withdrawal from sedatives. Patients can be switched to long-acting sedatives, such as diazepam or phenobarbital, which are then gradually reduced.

Gilles de la Tourette's Syndrome is an inherited neurological disorder. The disorder is characterized by uncontrollable vocal sounds called tics and involuntary movements. The symptoms generally manifest in an individual before the person is 18 years of age. The movement disorder may begin with simple tics that progress to multiple complex tics, including respiratory and vocal ones. Vocal tics may begin as grunting or barking noises and evolve into compulsive utterances. Coprolalia (involuntary scatologic utterances) occurs in 50% of patients. Severe tics and coprolalia may be physically and socially disabling. Tics tend to be more complex than myoclonus, but less flowing than choreic movements, from which they must be differentiated. The patient may voluntarily suppress them for seconds or minutes.

Currently simple tics are often treated with benzodiazepines. For simple and complex tics, Clonidine may be used. Long-term use of Clonidine does not cause tardive dyskinesia; its limiting adverse effect is hypotension. In more severe cases, antipsychotics, such as Haloperidol may be required, but side effects of dysphoria, parkinsonism, akathisia, and tardive dyskinesia may limit use of such antipsychotics. There is a need for safe and effective methods for treating this syndrome.

Age-related macular degeneration (AMD) is a common eye disease of the macula which is a tiny area in the retina that helps produce sharp, central vision required for "straight ahead" activities that include reading and driving. Persons with AMD lose their clear, central vision. AMD takes two forms: wet and dry. In dry AMD, there is a slow breakdown of light-sensing cells in the macula. There currently is no cure for dry AMD. In wet AMD, new, fragile blood vessels growing beneath the macula as dry AMD worsens and these vessels often leak blood and fluid to cause rapid damage to the macula quickly leading to the loss of central vision. Laser surgery can treat some cases of wet AMD. Therefore, there is a need of a pharmaceutical agent to address AMD.

Glaucoma is within a group of diseases occurs from an increase in intraocular pressure causing pathological changes in the optical disk and negatively affects the field of vision. Medicaments to treat glaucoma either decrease the amount of fluid entering the eye or increase drainage of fluids from the eye in order to decrease intraocular pressure. However, current drugs have drawbacks such as not working over time or causing side effects so the eye-care professional has to either prescribe other drugs or modify the prescription of the drug being used. There is a need for safe and effective methods for treating problems manifesting into glaucoma.

Ischemic periods in glaucoma cause release of excitotoxic amino acids and stimulate inducible form of nitric oxide synthase (iNOS) leading to neurodegeneration. Alpha 7 nicotinic agonists may stimulate the release of inhibitory amino acids such as GABA which will dampen hyperexcitablity. Alpha 7 nicotinic agonists are also directly neuroprotective on neuronal cell bodies. Thus alpha 7 nicotinic agonists have the potential to be neuroprotective in glaucoma.

Persons afflicted with pain often have what is referred to as the "terrible triad" of suffering from the pain, resulting in sleeplessness and sadness, all of which are hard on the afflicted individual and that individual's family. Pain can manifest itself in various forms, including, but not limited to, headaches of all severity, back pain, neurogenic, and pain from other ailments such as arthritis and cancer from its existence or from therapy to irradicate it. Pain can be either chronic (persistent pain for months or years) or acute (short-lived, immediate pain to inform the person of possible injury and need of treatment). Persons suffering from pain respond differently to individual therapies with varying degrees of success. There is a need for safe and effective methods for treating pain.

Finally, the compounds of the present invention may be used in combination therapy with typical and a typical anti-psychotic drugs (also called an anti-psychotic agent). All compounds within the present invention are useful for and may also be used in combination with each other to prepare pharmaceutical compositions. Such combination therapy lowers the effective dose of the anti-psychotic drug and thereby reduces the side effects of the anti-psychotic drugs. Some typical anti-psychotic drugs that may be used in the practice of the invention include Haldol. Some a typical anti-psychotic drugs include Ziprasidone, Olanzapine, Resperidone, and Quetiapine.

Compounds of Formula I can be prepared as shown in Scheme 1. The key step in the preparation of this class of compounds is the coupling of an azabicyclic moiety with the requisite acid chloride (Lv=Cl), mixed anhydride (e.g., Lv=diphenyl phosphoryl, bis(2-oxo-3-oxazolidinyl) phosphinyl, or acyloxy of the general formula of O—C (O)—R$_{Lv}$, where R$_{Lv}$ includes phenyl or t-butyl), or carboxylic acid (Lv=OH) in the presence of an activating reagent. Suitable activating reagents are well known in the art, for examples see Kiso, Y., Yajima, H. "Peptides" pp. 39–91, San Diego, Calif., Academic Press, (1995), and include, but are not limited to, agents such as carbodiimides, phosphonium and uronium salts (such as HATU).

Scheme 1

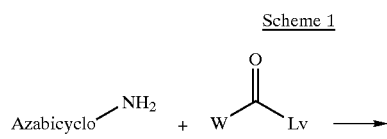

-continued

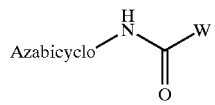

Generally, the acid is activated using HATU or is converted to the acyl azide by using DPPA. The appropriate Azabicyclo-amine is added to a solution of the appropriate activated acid or azide to give the desired final compounds. Or, the acid is converted into a mixed anhydride by treatment with bis (2-oxo-3-oxazolidinyl) phosphinic chloride in the presence of TEA with $CH_2Cl_2$ or $CHCl_3$ as the solvent. The resulting anhydride solution is directly reacted with the appropriate amine added neat or using DMF or aqueous DMF as solvent. In some cases, the ester (Lv being OMe or OEt) may be reacted directly with the amine in refluxing methanol or ethanol to give the compounds of Formula I.

There are several methods by which the amine precursor for Azabicyclo I can be obtained. Certain 6-substituted-[2.2.2]-3-amines are known in the art. The preparation of compounds of Azabicyclo I is described in *Acta Pol. Pharm.* 179–85 (1981). Alternatively, the 6-substituted-[2.2.2]-3-amine can be prepared by reduction of an oxime or an imine of the corresponding 6-substituted-3-quinuclidinone by methods known to one of ordinary skill in the art (see *J. Labelled Compds. Radiopharm.*, 53–60 (1995), *J. Med. Chem.* 988–995, (1998), *Synth. Commun.* 1895–1911 (1992), *Synth. Commun.* 2009–2015 (1996)). Alternatively, the 6-substituted-[2.2.2]-3-amine can be prepared from a 6-substituted-3-hydroxyquinuclidine by Mitsunobu reaction followed by deprotection as described in *Synth. Commun.* 1895–1911 (1995). Alternatively, the 6-substituted-[2.2.2]-3-amine can be prepared by conversion of a 6-substituted-3-hydroxyquinuclidine into the corresponding mesylate or tosylate, followed by displacement with sodium azide and reduction as described in *J. Med. Chem.* 587–593 (1975).

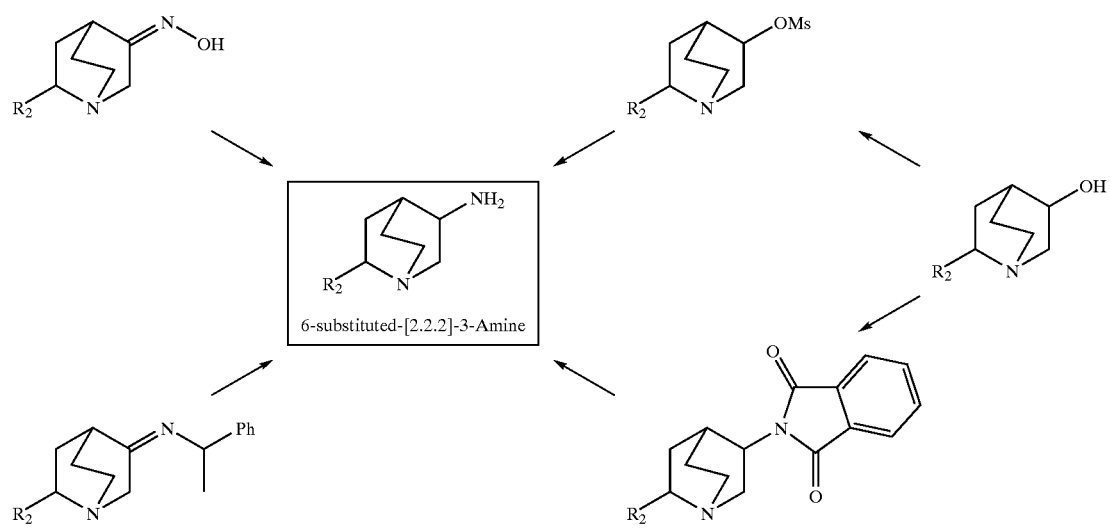

The oximes can be prepared by treatment of the 3-quinuclidinones with hydroxylamine hydrochloride in the presence of base. The imines can be prepared by treatment of the 3-quinuclidinones with a primary amine under dehydrating conditions. The 3-hydroxyquinuclidines can be prepared by reduction of the 3-quinuclidinones. The 6-substituted-3-quinuclidinones can be prepared by known procedures (see *J. Gen. Chem. Russia* 3791–3795, (1963), *J. Chem. Soc. Perkin Trans. I* 409–420 (1991), *J. Org. Chem.* 3982–3996 (2000)).

One of ordinary skill in the art will recognize that the methods described for the reaction of the unsubstituted 3-amino-1-azabicyclo[2.2.1]heptane (Azabicyclo II where $R_2$ is absent) are equally applicable to substituted compounds ($R_2$ is present and is other than H). The compounds where $R_2$ is other than H can be prepared from appropriately substituted nitro alcohols using procedures described in *Tetrahedron* (1997), 53, p. 11121 as shown below. Methods to synthesize nitro alcohols are well known in the art (see *J. Am. Chem. Soc.* (1947), 69, p 2608). The scheme below is a modification of the synthesis of exo-3-amino-1-azabicyclo [2.2.1]heptane as the bis(hydro para-toluenesulfonate) salt, described in detail herein, to show how to obtain these amine precursors. The desired salt can be made using standard procedures.

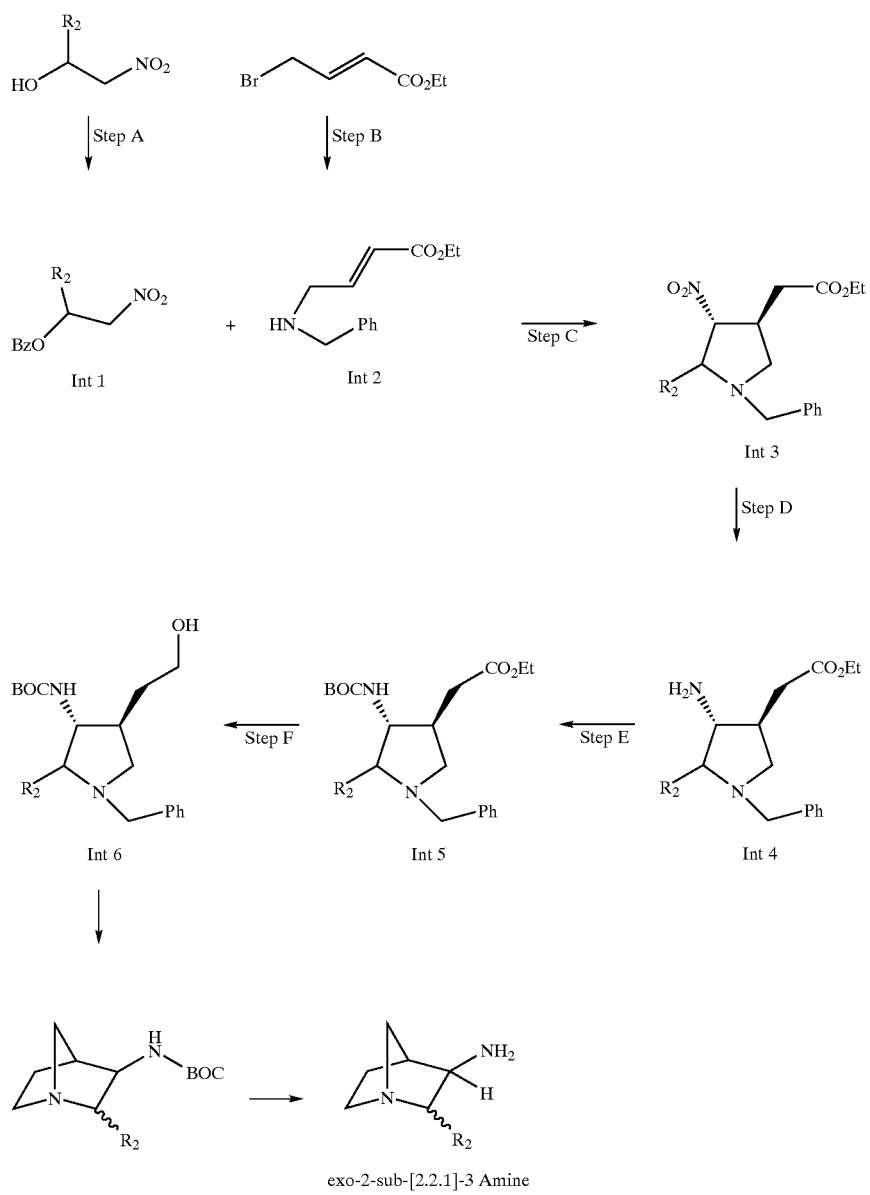

exo-2-sub-[2.2.1]-3 Amine

Compounds for Azabicyclo II where $R_2$ is other than H can also be prepared by modification of intermediates described in the synthesis of exo-3-amino-1-azabicyclo [2.2.1]heptane as the bis(hydro para-toluenesulfonate)salt, described in detail herein. For example, Int 6 can be oxidized to the aldehyde and treated with an organometallic reagent to provide Int 20 using procedures described in *Tetrahedron* (1999), 55, p 13899. Int 20 can be converted into the amine using methods described for the synthesis of exo-3-amino-1-azabicyclo[2.2.1]heptane as the bis(hydro para-toluenesulfonate) salt. Once the amine is obtained, the desired salt can be made using standard procedures.

-continued

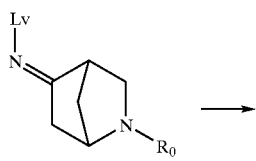

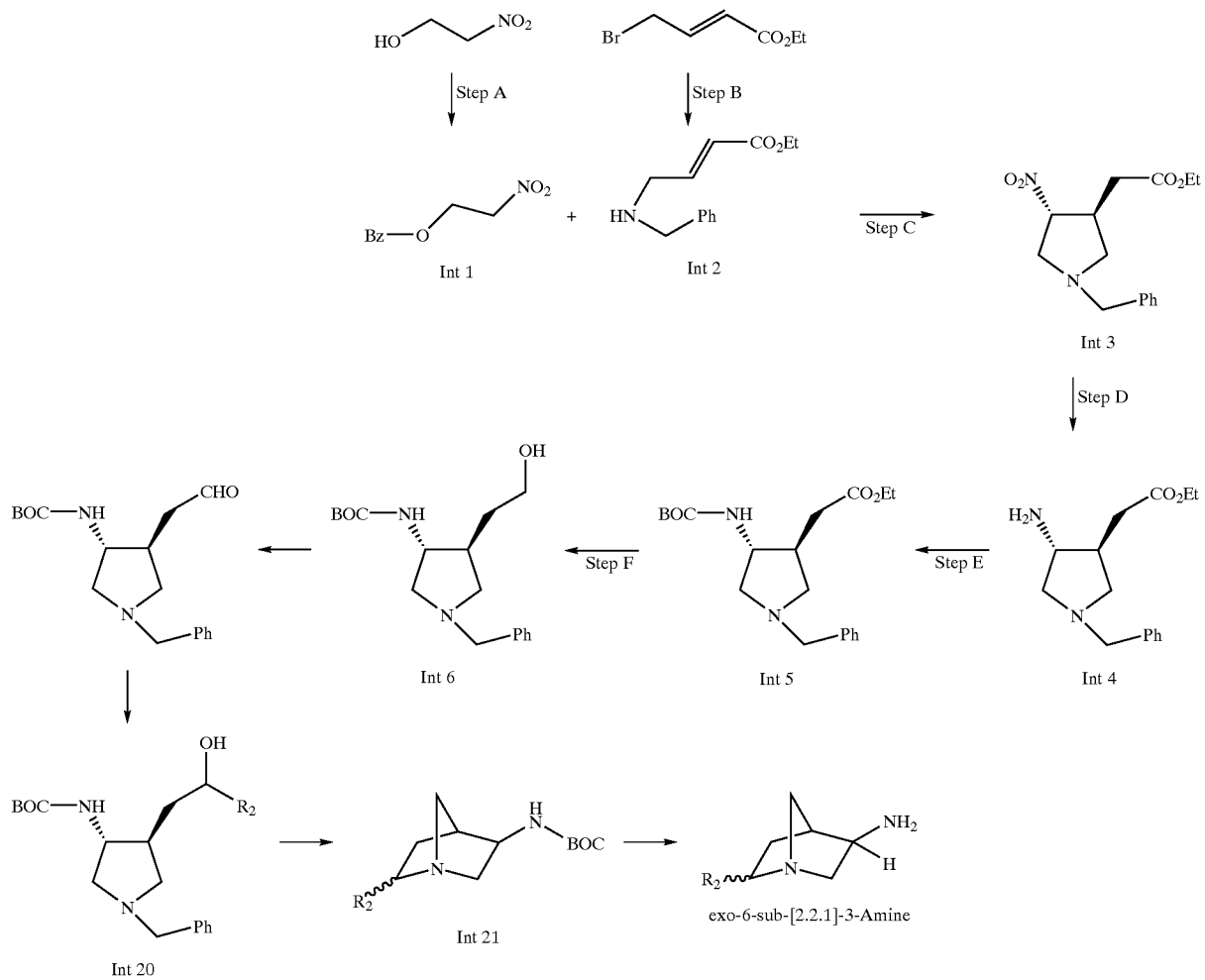

The schemes used are for making exo-3-amino-1-azabicyclo [2.2.1]heptane. However, the modifications discussed are applicable to make the endo isomer also.

N-(2-azabicyclo[2.2.1]hept)-5-amine and 6-amine

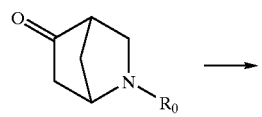

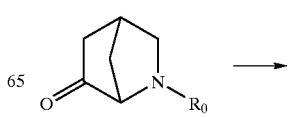

-continued

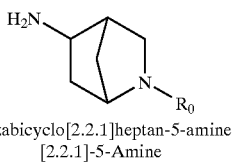

2-azabicyclo[2.2.1]heptan-5-amine
[2.2.1]-5-Amine

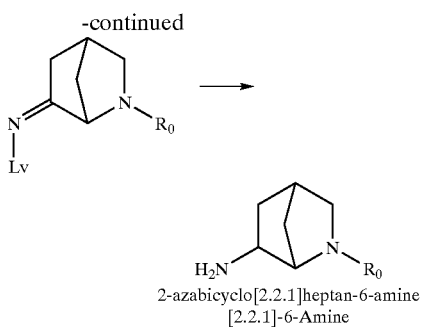

2-azabicyclo[2.2.1]heptan-6-amine
[2.2.1]-6-Amine where Lv can be —CH₂Ph, —CH(Me)Ph, —OH, —OMe, or —OCH₂Ph.

The respective amine precursors for Azabicyclo III and Azabicyclo IV can be prepared by reduction of an oxime or an imine of the corresponding N-2-azabicyclo[2.2.1]-heptanone by methods known to one skilled in the art (see *J. Labelled Compds. Radiopharm.,* 53–60 (1995), *J. Med. Chem.* 988–995, (1998), *Synth. Commun.* 1895–1911 (1992), *Synth. Commun.* 2009–2015 (1996)). The oximes can be prepared by treatment of the N-2-azabicyclo[2.2.1] heptanones with hydroxylamine hydrochloride in the presence of a base. The imines can be prepared by treatment of the N-2-azabicyclo[2.2.1]-heptanones with a primary amine under dehydrating conditions. The N-2-azabicyclo[2.2.1] heptanones can be prepared by known procedures (see *Tet. Lett.* 1419–1422 (1999), *J. Med. Chem.* 2184–2191 (1992), *J. Med. Chem.* 706–720 (2000), *J. Org. Chem.,* 4602–4616 (1995)).

One of ordinary skill in the art will also recognize that the methods described for the reaction of the unsubstituted 1-azabicyclo[3.2.1]octan-3-amine or 1-azabicyclo[3.2.2] nonan-3-amine ($R_2$ is absent) are equally applicable to substituted compounds ($R_2$ is other than H) (Azabicyclo is V and VI, respectively). The $R_2$ substituent may be introduced as known to one skilled in the art through standard alkylation chemistry. Exposure of 1-azabicyclo[3.2.1]octan-3-one or 1-azabicyclo[3.2.2]nonan-3-one to a hindered base such as LDA (lithium diisopropylamide) in a solvent such as THF or ether between 0° C. to –78° C. followed by the addition of an alkylating agent ($R_2$Lv, where Lv=Cl, Br, I, OTs, etc.) will, after being allowed to warm to about 0° C. to rt followed by an aqueous workup, provide the desired compound as a mixture of isomers. Chromatographic resolution (flash, HPLC, or chiral HPLC) will provided the desired purified alkylated ketones. From there, formation of the oxime and subsequent reduction will provide the desired stereoisomers.

Thioamides can be prepared from the requisite thioester by direct displacement of the thioester with an aminoazabicyclic compound. The thioester can be prepared as described in *J. Organometallic Chem.,* 95–98 (1987). One of ordinary skill in the art would quickly identify that said compounds could also be prepared directly from the amides exemplified herein by direct treatment with a reagent such and Lawesson's reagent (see Lawesson et. al. in *Bull. Soc. Chim. Belg.,* 229 (1978)) or $P_4S_{10}$ (see *Chem. Rev.,* 45 (1961)). Alternatively one can react a dithiocarboxylic ester with the corresponding amino-azabicyclo compound to form the same thioamide.

Preparation of the Amines

Synthesis of Exo-3-amino-1-azabicyclo[2.2.1] heptane as the bis(hydro para-toluenesulfonate) salt

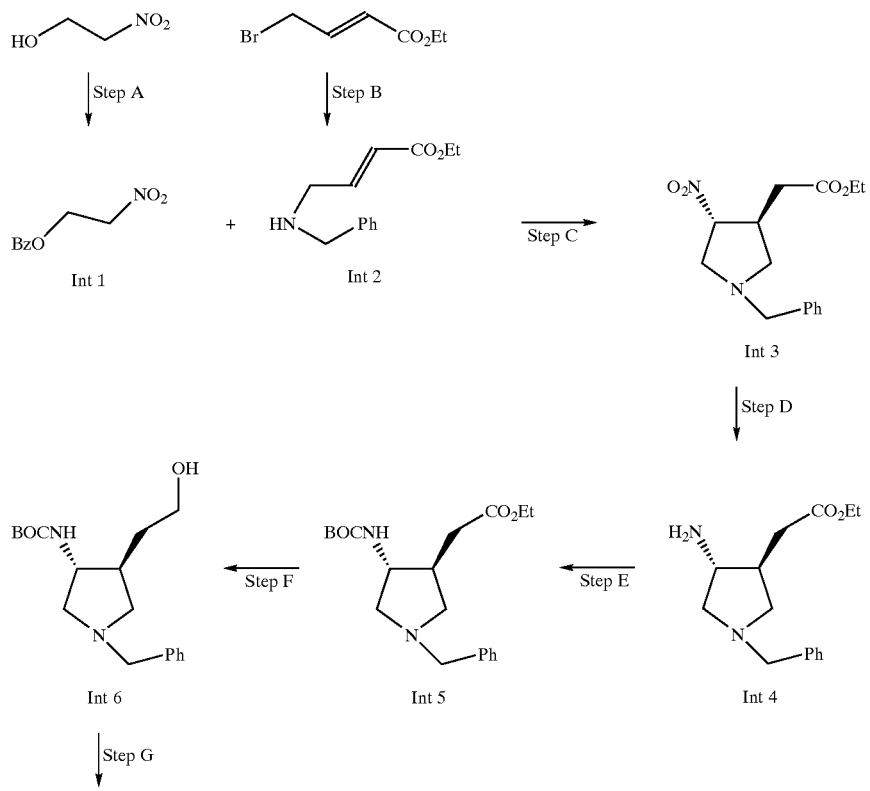

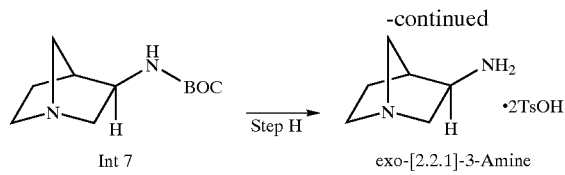

Int 7 → Step H → exo-[2.2.1]-3-Amine

Step A. Preparation of 2-(benzoyloxy)-1-nitroethane (Int 1)

Benzoyl chloride (14.9 mL, 128 mmol) is added to a stirred solution of nitroethanol (9.2 mL, 128 mmol) in dry benzene (120 mL). The solution is refluxed for 24 hr and then concentrated in vacuo. The crude product is purified by flash chromatography on silica gel. Elution with hexanes-EtOAc (80:20) affords Int 1 as a white solid (68% yield): $^1$H NMR (CDCl$_3$) δ 8.0, 7.6, 7.4, 4.9, 4.8.

Step B. Preparation of Ethyl E-4-(benzylamino)-2-butenoate (Int 2)

Ethyl E-4-bromo-2-butenoate (10 mL, 56 mmol, tech grade) is added to a stirred solution of benzylamine (16 mL, 146 mmol) in CH$_2$Cl$_2$ (200 mL) at rt. The reaction mixture stirs for 15 min, and is diluted with ether (1 L). The mixture is washed with saturated aqueous NaHCO$_3$ solution (3×) and water, dried over Na$_2$SO$_4$, filtered and concentrated in vacuo. The residue is purified by flash chromatography on silica gel. Elution with hexanes-EtOAc (70:30) affords Int 2 as a clear oil (62% yield): $^1$H NMR (CDCl$_3$) δ 7.4–7.2, 7.0, 6.0, 4.2, 3.8, 3.4, 2.1–1.8, 1.3.

Step C. Preparation of Trans-4-nitro-1-(phenylmethyl)-3-pyrrolidineacetic Acid Ethyl Ester (Int 3)

A solution of Int 1 (6.81 g, 34.9 mmol) and Int 2 (7.65 g, 34.9 mmol) in EtOH (70 mL) stirs at rt for 15 h and is then concentrated in vacuo. The residue is diluted with ether (100 mL) and saturated aqueous NaHCO$_3$ solution (100 mL). The organic layer is separated and dried over Na$_2$SO$_4$, filtered and concentrated in vacuo. The crude product is purified by flash chromatography on silica gel. Elution with hexanes-EtOAc (85:15) affords Int 3 as a clear oil (76% yield): $^1$H NMR (CDCl$_3$) δ 7.4–7.3, 4.8–4.7, 4.1, 3.8–3.6, 3.3–3.0, 2.7–2.6, 2.4–2.3, 1.2.

Step D. Preparation of Trans-4-amino-1-(phenylmethyl)-3-pyrrolidineacetic Acid Ethyl Ester (Int 4)

A mixture of Int 3 (3.28 g, 11.2 mmol) and RaNi (1.5 g) in EtOH (100 mL) is placed in a Parr bottle and hydrogenated for 4 h under an atmosphere of hydrogen (46 psi) at rt. The mixture is filtered through a pad of Celite, and the solvent is removed in vacuo to afford Int 4 as a clear oil (100% yield): $^1$H NMR (300 MHz, CDCl$_3$) δ 7.3–7.2, 4.1, 3.6, 3.2, 3.0–2.9, 2.8, 2.8–2.6, 2.6–2.4, 2.30–2.2, 1.2.

Step E. Preparation of Trans-4-(1,1-dimethylethoxycarbonylamido)-1-(phenylmethyl)-3-pyrrolidineacetic Acid Ethyl Ester (Int 5)

Di-tert-butyldicarbonate (3.67 g, 16.8 mmol) is added to a stirred solution of Int 4 (2.94 g, 11.2 mmol) in CH$_2$Cl$_2$ (30 mL) cooled in an ice bath. The reaction is allowed to warm to rt and stirred overnight. The mixture is concentrated in vacuo. The crude product is purified by flash chromatography on silica gel. Elution with hexanes-EtOAc (80:20) affords Int 5 as a white solid (77% yield): $^1$H NMR (300 MHz, CDCl$_3$) δ 7.4–7.2, 5.1–4.9, 4.1, 4.0–3.8, 3.6, 3.2–3.0, 2.8–2.6, 2.5–2.4, 2.3–2.1, 1.4, 1.3.

Step F. Preparation of Trans (tert-butoxycarbonylamino)-4-(2-hydroxyethyl)-1-(N-phenylmethyl) pyrrolidine (Int 6)

LiAlH$_4$ powder (627 mg, 16.5 mmol) is added in small portions to a stirred solution of Int 5 (3.0 g, 8.3 mmol) in anhydrous THF (125 mL) in a −5° C. bath. The mixture is stirred for 20 min in a −5° C. bath, then quenched by the sequential addition of water (0.6 mL), 15% (w/v) aqueous NaOH (0.6 mL) and water (1.8 mL). Excess anhydrous K$_2$CO$_3$ is added, and the mixture is stirred for 1 h, then filtered. The filtrate is concentrated in vacuo. The residue is purified by flash chromatography on silica gel. Elution with EtOAc affords Int 6 as a white solid (94% yield): $^1$H NMR (CDCl$_3$) δ 7.4–7.3, 5.3–5.2, 4.1–4.0, 3.9–3.7, 3.3–3.2, 2.8–2.7, 2.3–2.1, 1.7, 1.5.

Int 6 is a racemic mixture that can be resolved via chromatography using a Diacel chiral pack AD column. From the two enantiomers thus obtained, the (+)-enantiomer, $[\alpha]^{25}_D$+35 (c 1.0, MeOH), gives rise to the corresponding enantiomerically pure exo-4-S final compounds, whereas the (−)-enantiomer, $[\alpha]^{25}_D$−34 (c 0.98, MeOH), gives rise to enantiomerically pure exo-4-R final compounds making non-critical changes of the methods provided herein.

Step G. Preparation of Exo 3-(tert-butoxycarbonylamino)-1-azabicyclo[2.2.]heptane (Int 7)

TEA (8.0 g, 78.9 mml) is added to a stirred solution of Int 6 (2.5 g, 7.8 mmol) in CH$_2$Cl$_2$ (50 mL), and the reaction is cooled in an ice-water bath. CH$_3$SO$_2$Cl (5.5 g, 47.8 mmol) is then added dropwise, and the mixture is stirred for 10 min in an ice-water bath. The resulting yellow mixture is diluted with saturated aqueous NaHCO$_3$ solution, extracted with CH$_2$Cl$_2$ several times until no product remains in the aqueous layer by TLC. The organic layers are combined, washed with brine, dried over Na$_2$SO$_4$ and concentrated in vacuo. The residue is dissolved in EtOH (85 mL) and is heated to reflux for 16 h. The reaction mixture is allowed to cool to rt, transferred to a Parr bottle and treated with 10% Pd/C catalyst (1.25 g). The bottle is placed under an atmosphere of hydrogen (53 psi) for 16 h. The mixture is filtered through Celite, and fresh catalyst (10% Pd/C, 1.25 g) is added. Hydrogenolysis continues overnight. The process is repeated three more times until the hydrogenolysis is complete. The final mixture is filtered through Celite and concentrated in vacuo. The residue is purified by flash chromatography on silica gel. Elution with CHCl$_3$—MeOH—NH$_4$OH (90:9.5:0.5) affords Int 7 as a white solid (46% yield): $^1$H NMR (CDCl$_3$) δ 5.6–5.5, 3.8–3.7, 3.3–3.2, 2.8–2.7, 2.0–1.8, 1.7–1.5, 1.5.

Step H. Preparation of Exo-3-amino-1-azabicyclo[2.2.1]heptane bis(hydro-para-toluenesulfonate)

Para-toluenesulfonic acid monohydrate (1.46 g, 7.68 mmol) is added to a stirred solution of Int 7 (770 mg, 3.63 mmol) in EtOH (50 mL). The reaction mixture is heated to reflux for 10 h, followed by cooling to rt. The precipitate is collected by vacuum filtration and washed with cold EtOH to give exo-[2.2.1]-3-Amine (as a racemix mixture) as a white solid (84% yield): $^1$H NMR (CD$_3$OD) δ 7.7, 7.3, 3.9–3.7, 3.7–3.3, 3.2, 2.4, 2.3–2.2, 1.9–1.8. The corresponding amines can be obtained by using the resolved Int 6 to give exo-(4R)-[2.2.1]-3-Amine and exo-(4S)-[2.2.1]-3-Amine.

Synthesis of Endo-3-amino-1-azabicyclo[2.2.1]
heptane as the bis(hydro para-toluenesulfonate) salt

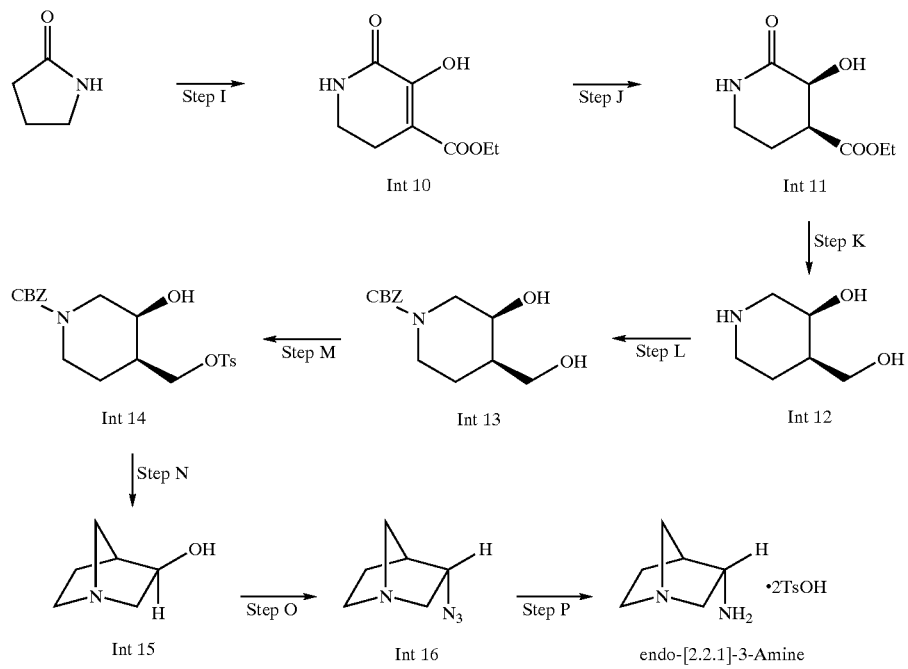

Step I. Preparation of Ethyl 5-hydroxy-6-oxo-1,2,3,6-tetrahydropyridine-4-carboxylate (Int 10)

Absolute EtOH (92.0 mL, 1.58 mol) is added to a mechanically stirred suspension of potassium ethoxide (33.2 g, 395 mmol) in dry toluene (0.470 L). When the mixture is homogeneous, 2-pyrrolidinone (33.6 g, 395 mmol) is added, and then a solution of diethyl oxalate (53.1 mL, 390 mmol) in toluene (98 mL) is added via an addition funnel. After complete addition, toluene (118 mL) and EtOH (78 mL) is added sequentially. The mixture is heated to reflux for 18 h. The mixture is cooled to rt and aqueous HCl (150 mL of a 6.0 M solution) is added. The mixture is mechanically stirred for 15 min. The aqueous layer is extracted with $CH_2Cl_2$, and the combined organic layers are dried over $MgSO_4$, filtered and concentrated in vacuo to a yellow residue. The residue is recrystallized from EtOAc to afford Int 10 as a yellow solid (38% yield): $^1$H NMR ($CDCl_3$) δ 11.4, 7.4, 4.3, 3.4, 2.6, 1.3.

Step J. Preparation of Ethyl cis-3-hydroxy-2-oxopiperidine-4-carboxylate (Int 11)

A mixture of Int 10 (15 g, 81 mmol) and 5% rhodium on carbon (2.0 g) in glacial acetic acid is placed under an atmosphere of hydrogen (52 psi). The mixture is shaken for 72 h. The mixture is filtered through Celite, and the filtrate is concentrated in vacuo to afford Int 11 as a white solid (98% yield): $^1$H NMR ($CDCl_3$) δ 6.3, 4.2, 4.0–3.8, 3.4, 3.3–3.2, 2.2, 1.3.

Step K. Preparation of Cis-4-(hydroxymethyl)piperidin-3-ol (Int 12)

Int 11 (3.7 g, 19.9 mmol) as a solid is added in small portions to a stirred solution of $LiAlH_4$ in THF (80 mL of a 1.0 M solution) in an ice-water bath. The mixture is warmed to rt, and then the reaction is heated to reflux for 48 h. The mixture is cooled in an ice-water bath before water (3.0 mL, 170 mmol) is added dropwise, followed by the sequential addition of NaOH (3.0 mL of a 15% (w/v) solution) and water (9.0 mL, 500 mmol). Excess $K_2CO_3$ is added, and the mixture is stirred vigorously for 15 min. The mixture is filtered, and the filtrate is concentrated in vacuo to afford Int 12 as a yellow powder (70% yield): $^1$H NMR (DMSO-$d_6$) δ 4.3, 4.1, 3.7, 3.5–3.2, 2.9–2.7, 2.5–2.3, 1.5, 1.3.

Step L. Preparation of Benzyl Cis-3-hydroxy-4-(hydroxymethyl)piperidine-1-carboxylate (Int 13)

N-(benzyloxy carbonyloxy)succinimide (3.04 g, 12.2 mmol) is added to a stirred solution of Int 12 (1.6 g, 12.2 mmol) in saturated aqueous $NaHCO_3$ (15 mL) at rt. The mixture is stirred at rt for 18 h. The organic and aqueous layers are separated. The aqueous layer is extracted with ether (3×). The combined organic layers are dried over anhydrous $K_2CO_3$, filtered and concentrated in vacuo to afford Int 13 as a yellow oil (99% yield): $^1$H NMR ($CDCl_3$) δ 7.4–7.3, 5.2, 4.3, 4.1, 3.8–3.7, 3.0–2.8, 2.1, 1.9–1.7, 1.4.

Step M. Preparation of Benzyl Cis-3-hydroxy-4-[(4-methylphenyl)sulfonyl oxymethyl]piperidine-1-carboxylate (Int 14)

Para-toluenesulfonyl chloride (1.0 g, 5.3 mmol) is added to a stirred solution of Int 13 (3.6 g, 5.3 mmol) in pyridine (10 mL) in a −15° C. bath. The mixture is stirred for 4 h, followed by addition of HCl (4.5 mL of a 6.0 M solution). $CH_2Cl_2$ (5 mL) is added. The organic and aqueous layers are separated. The aqueous layer is extracted with $CH_2Cl_2$. The combined organic layers are washed with brine, dried over $MgSO_4$, filtered and concentrated in vacuo to afford Int 14 as a colorless oil (78% yield): $^1$H NMR ($CDCl_3$) δ 7.8, 7.4–7.2, 5.1, 4.3–4.2, 4.1, 3.9–3.8, 2.9–2.7, 2.4, 1.9, 1.6–1.3.

Step N. Preparation of Exo-1-azabicyclo[2.2.1]heptan-3-ol (Int 15)

A mixture of Int 14 (3.6 g, 8.6 mmol) and 10% Pd/C catalyst (500 mg) in EtOH (50 mL) is placed under an atmosphere of hydrogen. The mixture is shaken for 16 h. The mixture is filtered through Celite. Solid $NaHCO_3$ (1.1 g, 13 mmol) is added to the filtrate, and the mixture is heated in an oil bath at 50° C. for 5 h. The solvent is removed in vacuo. The residue is dissolved in saturated aqueous $K_2CO_3$ solution. Continuous extraction of the aqueous layer using a liquid-liquid extraction apparatus (18 h), followed by drying the organic layer over anhydrous $K_2CO_3$ and removal of the solvent in vacuo affords Int 15 as a white solid (91% yield): $^1$H NMR δ 3.8, 3.0–2.8, 2.6–2.5, 2.4–2.3, 1.7, 1.1.

Step O. Preparation of Endo-3-azido-1-azabicyclo[2.2.1]heptane (Int 16)

To a mixture of Int 15 (1.0 g, 8.9 mmol) and triphenyl phosphine (3.0 g, 11.5 mmol) in toluene-THF (50 mL, 3:2) in an ice-water bath are added sequentially a solution of hydrazoic acid in toluene (15 mL of ca. 2 M solution) and a solution of diethyl azadicarboxylate (1.8 mL, 11.5 mmol) in toluene (20 mL). The mixture is allowed to warm to rt and stir for 18 h. The mixture is extracted with aqueous 1.0M HCl solution. The aqueous layer is extracted with EtOAc, and the combined organic layers are discarded. The pH of the aqueous layer is adjusted to 9 with 50% aqueous NaOH solution. The aqueous layer is extracted with $CH_2Cl_2$ (3×), and the combined organic layers are washed with brine, dried over $Na_2SO_4$, filtered and concentrated in vacuo. The crude product is purified by flash chromatography on silica gel. Elution with $CHCl_3$-MeOH—$NH_4OH$ (92:7:1) affords Int 16 as a colorless oil (41% yield): $^1$H NMR ($CDCl_3$) δ 4.1, 3.2, 2.8, 2.7–2.5, 2.2, 1.9, 1.5.

Step P. Preparation of Endo-3-amino-1-azabicyclo[2.2.1]heptane bis(hydro-para-toluenesulfonate)

A mixture of Int 16 (250 mg, 1.8 mmol) and 10% Pd/C catalyst (12 mg) in EtOH (10 mL) is placed under an atmosphere of hydrogen (15 psi). The mixture is stirred for 1 h at rt. The mixture is filtered through Celite, and the filtrate is concentrated in vacuo. The residue is dissolved in EtOH (10 mL) and para-toluenesulfonic acid monohydrate (690 mg, 3.7 mmol) is added. The mixture is stirred for 30 min, and the precipitate is filtered. The precipitate is washed sequentially with cold EtOH and ether. The precipitate is dried in vacuo to afford endo-[2.2.1]-3-Amine as a white solid (85% yield): $^1$H NMR ($CD_3OD$) δ 7.7, 7.3, 4.2, 3.9, 3.6–3.4, 3.3–3.2, 2.4, 2.3, 2.1.

Preparation of the 3.2.1-Amine

The exo- and endo-1-azabicyclo[3.2.1]octan-3-amines are prepared from 1-azabicyclic[3.2.1]octan-3-one (Thill, B. P., Aaron, H. S., *J. Org. Chem.*, 4376–4380 (1968)) according to the general procedure as discussed in Lewin, A. H., et al., *J. Med. Chem.*, 988–995 (1998).

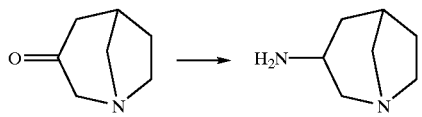

Exo-1-Azabicyclo[3.2.1]octan-3-amine dihydrochloride (exo-[3.2.1]-Amine)

A mixture of 1-azabicyclo[3.2.1]octan-3-one hydrochloride (2.80 g, 17.3 mmol), ethanol (25 mL), and hydroxylamine hydrochloride (1.56 g, 22.4 mmol) is treated with sodium acetate trihydrate (7.07 g, 51.2 mmol). The mixture is stirred for 3 h and evaporated in vacuo. The residue is diluted with $CH_2Cl_2$, treated with charcoal, filtered and evaporated. The resulting material is taken up in 1-propanol (45 mL) and heated in a 100° C. oil bath. The solution is treated with sodium metal (6.4 g in portions). Heating is continued for 3 h and the mixture cooled to rt. Water is added carefully and the organic layer is extracted, dried ($MgSO_4$), filtered, acidified with MeOH/HCl(g), and evaporated. 2-Propanol is added and the resulting solid is filtered and dried in vacuo to give exo-[3.2.1]-Amine in 49% yield. MS for $C_7H_{14}N_2$.$(HCl)_2$ (ESI) $(M+H)^+$ m/z=127.

Endo-1-Azabicyclo [3.2.1]octan-3-amine dihydrochloride (endo-[3.2.1]-Amine)

A mixture of 1-azabicyclo[3.2.1]octan-3-one hydrochloride (2.80 g, 17.3 mmol), ethanol (25 mL), and hydroxylamine hydrochloride (1.56 g, 22.4 mmol) is treated with sodium acetate trihydrate (7.07 g, 51.2 mmol). The mixture is stirred for 3 h and evaporated in vacuo. The residue is diluted with $CH_2Cl_2$, treated with charcoal, filtered and evaporated. The resulting oxime (3.1 mmol) is treated with acetic acid (30 mL) and hydrogenated at 50 psi over $PtO_2$ (50 mg) for 12 h. The mixture is then filtered and evaporated. The residue is taken up in a minimal amount of water (6 mL) and the pH is adjusted to >12 using solid NaOH. The mixture is then extracted with ethyl acetate (4×25 mL), dried over $MgSO_4$, filtered, treated with ethereal HCl, and evaporated to give endo-[3.2.1]-Amine.

1-Azabicyclo[3.2.1]octan-3-amine

Preparation of the 3R,5R-[3.2.1]-Amine

This amine can also be prepared according to the following method:

(3S)-1-[(S)-1-Phenethyl]-5-oxo-3-pyrrolidine-carboxylic Acid

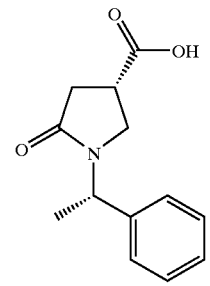

According to the literature procedure (Nielsen et al. J. Med. Chem 1990, 70–77), a mixture of itaconic acid (123.17 g, 946.7 mmol) and (S)-(−)-α-methyl benzylamine (122.0 mL, 946.4 mmol) are heated (neat) in a 160° C. oil bath for 4 h. Upon cooling, MeOH (~200 mL) is added and the resulting solid collected by filtration. The solid is treated with EtOH (~700 mL) and warmed using a steam bath until ~450 mL solvent remained. After cooling to rt, the solid is collected and dried to afford 83.2 g as a crystalline solid: $[α]^{25}_D$=−80 (c 0.97, DMSO). $^1$H NMR (400 MHz, DMSO-$d_6$) δ 12.66, 7.20–7.40, 5.23, 3.40–3.55, 3.10–3.25, 2.40–2.65, 1.45; MS (EI) m/z 233 $(M^+)$.

(3S)-1-[(S)-1-Phenethyl]-3-(hydroxymethyl)pyrrolidine

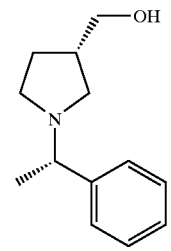

A suspension (3S)-1-[(S)-1-phenethyl]-5-oxo-3-pyrrolidine-carboxylic acid (82.30 g, 352.8 mmol) in $Et_2O$ (200 mL) is added in small portions to a slurry of $LiAlH_4$ (17.41 g, 458.6 mmol) in $Et_2O$ (700 mL). The mixture begins to reflux during the addition. The addition funnel containing the suspension is rinsed with $Et_2O$ (2×50 mL), and the mixture is heated in a 50° C. oil bath for an additional 2 h and first allowed to cool to rt and then further cooled using an ice bath. The mixture is carefully treated with H$_2$O (62 mL). The resulting precipitate is filtered, rinsed with Et$_2$O, and discarded. The filtrate is concentrated to a yellow oil. When EtOAc is added to the oil, a solid began to form. Hexane is then added, and the mixture is filtered and the solid is dried to afford 43.3 g. $[\alpha]^{25}_D$=−71 (c 0.94, CHCl$_3$); $^1$H NMR (400 MHz, CDCl$_3$) δ 7.20–7.45, 3.60–3.70, 3.40–3.60, 3.19, 3.05–3.15, 2.35–2.55, 2.25–2.35, 1.95–2.10, 1.75–1.90, 1.42; HRMS (FAB) calcd for C$_{13}$H$_{19}$NO (MH$^+$) 206.1545, found 206.1532.

(3R)-1-[(S)-1-Phenethyl]-3-(cyanomethyl)pyrrolidine

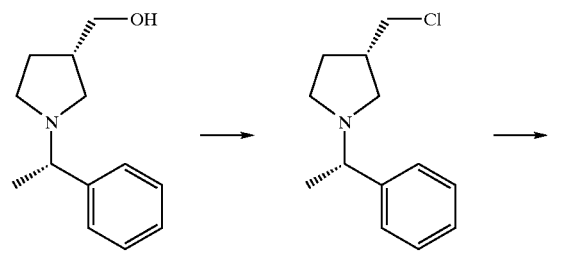

A solution of (3S)-1-[(S)-1-phenethyl]-3-(hydroxymethyl)pyrrolidine (42.75 g, 208.23 mmol) in chloroform (350 mL) is heated to reflux under N$_2$. The solution is treated with a solution of thionyl chloride (41.8 mL, 573 mmol) in chloroform (40 mL) dropwise over 45 min. The mixture is stirred for an additional 30 min, is cooled and concentrated. The residue is diluted with H$_2$O (~200 mL), 1 N NaOH is added until a pH ~8 (pH paper). A small portion (~50 mL) of sat. NaHCO$_3$ is added and the basic mixture is extracted with EtOAc (3×400 mL), washed with brine, dried over MgSO$_4$, filtered and concentrated to give 46.51 g of (3S)-1-[(S)-1-phenethyl]-3-(chloromethyl)pyrrolidine: MS (ESI+) m/z 224.2 (MH$^+$). The chloride (46.35 g, 208.0 mmol) is transferred to a flask, DMSO (200 mL) is added, and the solution is treated with NaCN (17.84 g, 363.9 mmol). The mixture is heated under N$_2$ in a 100° C. oil bath overnight and is cooled. The brown mixture is poured into H$_2$O (300 mL) and is extracted with EtOAc (1000 mL in portions). The combined organic layer is washed with H$_2$O (6×~50 mL), brine (~100 mL), dried (MgSO$_4$), filtered and concentrated to give 40.61 g of an oil: $^1$H NMR (400 MHz, CDCl$_3$) δ 7.20–7.40, 3.26, 2.70–2.85, 2.40–2.60, 2.27, 2.10–2.20, 1.50–1.70, 1.41; MS (ESI+) for m/z 215.2 (M+H$^+$).

(3R)-Methyl 1-[(S)-1-phenylethyl]pyrrolidine-3-acetate

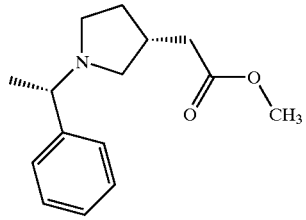

Acetyl chloride (270 mL, 3.8 mol) is carefully added to a flask containing chilled (0° C.) methanol (1100 mL). After the addition is complete, the acidic solution is stirred for 45 min (0° C.) and then (3R)-1-[(S)-1-phenethyl]-3-(cyanomethyl)pyrrolidine (40.50 g, 189.0 mmol) in methanol (200 mL) is added. The ice bath is removed and the mixture is stirred for 100 h at rt. The resulting suspension is concentrated. Water (~600 mL) is added, the mixture stirred for 45 min and then the pH is adjusted (made basic) through the addition of 700 mL sat. aq. NaHCO$_3$. The mixture is extracted with EtOAc (3×300 mL). The combined organic layers are washed with brine, dried (MgSO$_4$), filtered through celite and concentrated to give 36.86 g as an oil: $^1$H NMR (400 MHz, CDCl$_3$) δ 7.20–7.40, 3.69, 3.30–3.40, 2.85–2.95, 2.40–2.70, 2.00–2.20, 1.10–1.65; MS (ESI+) m/z 248.2 (M+H$^+$).

(5R)-1-Azabicyclo[3.2.1]octan-3-one Hydrochloride

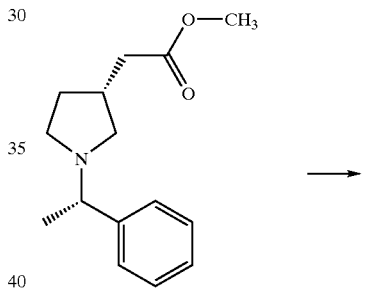

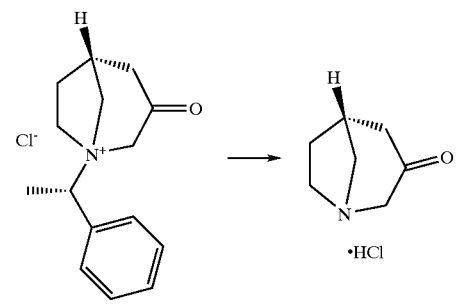

A solution of (3R)-methyl 1-[(S)-1-phenylethyl] pyrrolidine-3-acetate (25.72 g, 104.0 mmol) in THF (265 mL) is cooled under N$_2$ in a CO$_2$/acetone bath. Next, ICH$_2$Cl (22.7 mL, 312.0 mmol) is added, and the mixture stirred for 30 min. A solution of 2.0M lithium diisopropylamide (heptane/THF/ethylbenzene, 156 mL, 312 mmol) is added slowly over 30 min. The internal temperature reached a maximum of −40° C. during this addition. After 1 h, sat. NH$_4$Cl (100 mL) is added and the mixture is allowed to warm to rt. The organic layer is separated, dried (MgSO$_4$), filtered and concentrated. The resulting foam is chromatographed (300 g SiO$_2$, CHCl$_3$—MeOH—NH$_4$OH (89:10:1)

followed by CHCl₃—MeOH (3:1). The product fractions are pooled and concentrated to afford (5R)-3-oxo-1-[(1S)-1-phenylethyl]-1-azoniabicyclo[3.2.1]octane chloride (10.12 g) as a foam (MS (ESI+) m/z 230.1 (M+H⁺). This foam (10.1 g, 38 mmol) is taken up in MeOH (500 mL), 10% Pd(C) (3.0 g) added and the mixture is hydrogenated (45 psi) overnight. The mixture is filtered and re-subjected to the reduction conditions (9.1 g, 10% Pd/C, 50 psi). After 5 h, TLC indicates the consumption of the (5R)-3-oxo-1-[(1S)-1-phenylethyl]-1-azoniabicyclo[3.2.1]octane chloride. The mixture is filtered, concentrated and triturated (minimal iPrOH) to give 3.73 g in two crops, as a solid: $[\alpha]^{25}_D$=33 (c 0.97, DMSO); HRMS (FAB) calcd for $C_7H_{11}NO$ (M+H⁺) 126.0919, found 126.0937.

fully quenched through the dropwise addition of H₂O (100 mL). Saturated aq. NaCl (20 mL) is added, and the layers are separated. The organic layer is dried (MgSO₄), filtered, treated with freshly prepared MeOH/HCl, and concentrated. The resulting solid is triturated with 30 mL EtOH, filtered and dried in vaccuo to afford 3.51 g as a white solid: $[\alpha]^{25}_D$=−3 (c 0.94, DMSO); ¹H NMR (400 MHz, DMSO-d₆) δ 3.60–3.80, 2.95–3.10, 2.65–2.75, 1.90–2.15, 1.70–1.90; HRMS (FAB) calcd for $C_7H_{14}N_2$ (M+H⁺) 127.1235, found 127.1235.

Preparation of 1-azabicyclo[3.2.2]nonan-3-amine bis(4-methylbenzenesulfonate) ([3.2.2]-Amine)

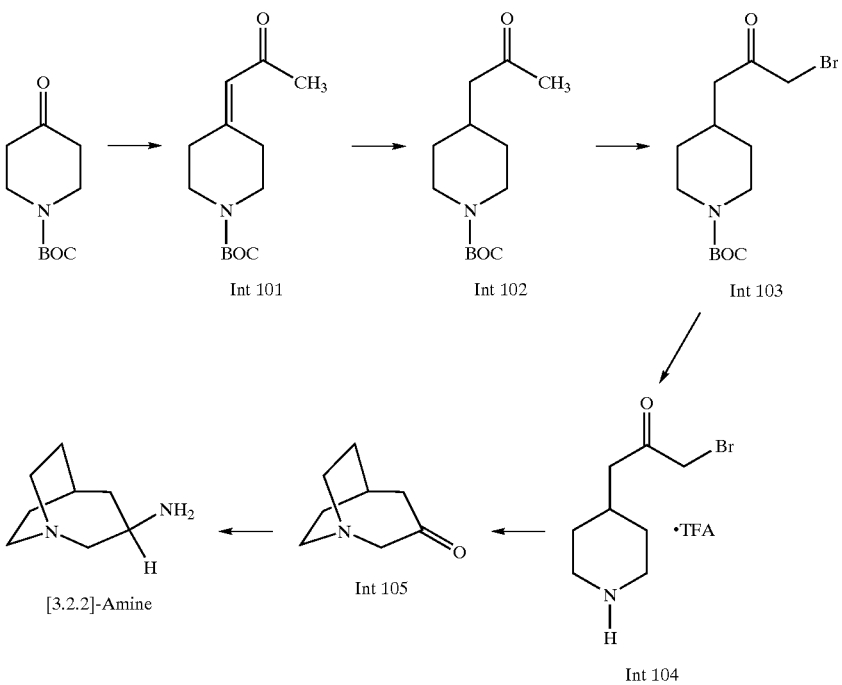

(3R,5R)-1-azabicyclo[3.2.1]octan-3-amine dihydrochloride

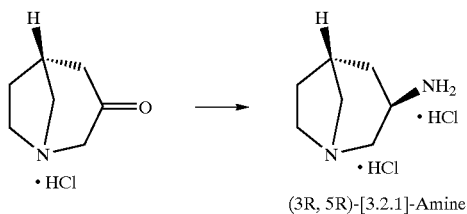

(3R, 5R)-[3.2.1]-Amine

To a flask containing (5R)-1-azabicyclo[3.2.1]octan-3-one hydrochloride (3.64 g, 22.6 mmol), hydroxylamine hydrochloride (2.04 g, 29.4 mmol), and ethanol (130 mL) is added sodium acetate trihydrate (9.23 g, 67.8 mmol). The mixture stirred for 3 h and is filtered and concentrated. The resulting white solid is taken up in n-propanol (100 mL) and sodium (~13.6 g, 618 mmol) is added in 20–25 portions. The reaction spontaneously begins to reflux, and the reaction is heated in an oil bath (100° C.). The addition is complete in ~20 min and the mixture solidifies after ~40 min. The oil bath is removed and n-propanol (2×25 mL) is added dissolving the remaining sodium metal. The mixture is care- Preparation of tert-butyl 4-(2-oxopropylidene)piperidine-1-carboxylate (Int 101)

Sodium hydride (60% oil dispersion, 2.01 g, 50.2 mmol) is washed with pentane (3×) and suspended in dry THF (40 mL). The solution is cooled to 0° C. before diethyl (2-oxopropyl)phosphonate (9.75 g, 50.2 mmol) is added dropwise. After complete addition, the solution is warmed to rt and stirred for 30 min. tert-Butyl 4-oxo-1-piperidinecarboxylate (5.0 g, 25.1 mmol) is added in portions over 10 min, followed by stirring at rt for 2 h. A saturated aqueous solution of ammonium chloride is added, followed by dilution with ether. The organic layer is extracted with water. The organic layer is dried over anhydrous MgSO₄, filtered and concentrated to a yellow oil. The crude product is purified by flash chromatography on silica gel. Elution with hexanes-ether (60:40) gave 4.5 g (75%) of Int 101 as a white solid: ¹H NMR (CDCl₃) δ 6.2, 3.5, 3.4, 2.9, 2.3, 2.2, 1.5.

Preparation of tert-butyl 4-(2-oxopropyl)piperidine-1-carboxylate (Int 102)

A mixture of Int 101 (4.5 g, 19 mmol) and 10% palladium on activated carbon (450 mg) in EtOH (150 mL) is placed in a Parr bottle and hydrogenated for 5 h at 50 psi. The mixture is filtered through Celite, and the filtrate is concentrated in vacuo to afford 4.3 g (94%) of Int 102 as a clear oil: ¹H NMR (CDCl₃) δ 4.1, 2.8, 2.4, 2.2, 2.0, 1.7, 1.5, 1.1.

Preparation of tert-butyl 4-(3-bromo-2-oxopropyl)piperidine-1-carboxylate (Int 103)

To a stirred solution lithium hexamethyldisilylamide in THF (20.0 mL, 1.0 M) in a −78° C. bath is added chlorotrimethylsilane (11.0 mL, 86.4 mmol) dropwise. The mixture is stirred at −78° C. for 20 min, followed by addition of Int 102 (3.21 g, 13.3 mmol) in a solution of THF (50 mL) dropwise. After complete addition, the mixture is stirred at −78° C. for 30 min. The mixture is warmed to 0° C. in an ice-water bath and phenyltrimethylammonium tribromide (5.25 g, 14.0 mmol) is added. The mixture is stirred in an ice-bath for 30 min, followed by the addition of water and ether. The aqueous layer is washed with ether, and the combined organic layers were washed with saturated aqueous sodium thiosulfate solution. The organic layer is dried over anhydrous MgSO$_4$, filtered and concentrated in vacuo to afford a yellow oil. The crude product is purified by flash chromatography on silica gel. Elution with hexanes-ether (60:40) gave 2.2 g (52%) of Int 103 as a lt. yellow oil: $^1$H NMR (CDCl$_3$) δ 4.2–4.1, 3.9, 2.8, 2.7, 2.6, 2.1–2.0, 1.7, 1.5, 1.2–1.1.2.

Preparation of 1-bromo-3-piperidin-4-ylacetone trifluoroacetate (Int 104)

To a stirred solution of Int 103 (2.2 g, 6.9 mmol) in CH$_2$Cl$_2$ (30 mL) in an ice-water bath is added trifluoroacetic acid (10 mL, 130 mmol). The mixture is stirred at 0° C. for 30 min. The volatiles were removed in vacuo to afford 2.0 g (87%) of Int 104 as a yellow residue: MS (ESI) for C$_8$H$_{15}$BrNO [M+H] m/e 220.

Preparation of 1-azabicyclo[3.2.2]nonan-3-one (Int 105)

To a stirred solution of DIEA (13 mL) in acetoniltrile (680 mL) at reflux temperature is added a solution of Int 104 (2.0 g, 6.0 mmol) in acetonitrile (125 mL) over a 4 h period via syringe pump. The mixture is kept at reflux temperature overnight. The mixture is concentrated in vacuo and the remaining residue is partitioned between a saturated aqueous K$_2$CO$_3$ solution and CHCl$_3$—MeOH (90:10). The aqueous layer is extracted with CHCl$_3$—MeOH (90:10), and the combined organic layers were dried over MgSO$_4$, filtered and concentrated in vacuo to a brown oil. The crude product is purified by flash chromatography on silica gel. Elution with CHCl$_3$—MeOH—NH$_4$OH (95:4.5:0.5) gave 600 mg (72%) of Int 105 as a clear solid: $^1$H NMR (CDCl$_3$) δ 3.7, 3.3–3.2, 3.1–3.0, 2.7, 2.3, 2.0–1.8.

To a stirred mixture of Int 105 (330 mg, 2.4 mmol) and sodium acetate.trihydrate (670 mg, 4.8 mmol) in EtOH (6.0 mL) is added hydroxylamine.hydrochloride (200 mg, 2.8 mmol). The mixture is stirred at rt for 10 h. The mixture is filtered and the filtrate is concentrated in vacuo to a yellow solid. To a solution of the solid (350 mg, 2.3 mmol) in n-propanol (30 mL) at reflux temperature is added sodium metal (2.0 g, 87 mmol) in small portions over 30 min. Heating at reflux is continued for 2 h. The solution is cooled to rt and brine is added. The mixture is extracted with n-propanol, and the combined organic layers are concentrated in vacuo. The residue is taken up in CHCl$_3$ and the remaining solids were filtered. The filtrate is dried over anhydrous MgSO$_4$, filtered and concentrated in vacuo to a clear solid. To a stirred solution of the solid (320 mg, 2.3 mmol) in EtOH (4 mL) is added p-toluenesulfonic acid monohydrate (875 mg, 4.6 mmol). The solution is warmed in a water bath to 45° C. for 30 min, followed by concentration of the solvent to afford 710 mg (62%) of [3.2.2]-Amine as a white solid: $^1$H NMR (CD$_3$OD) δ 7.7, 7.3, 4.1–3.9, 3.6–3.4, 2.6–2.5, 2.4, 2.2–2.1, 2.1–2.0, 1.9.

Resolution of Stereoisomers

The amine can be coupled to form the appropriate amides or thioamides as a racemic mixture. The racemic mixture can then be resolved by chromatography using chiral columns or chiral HPLC, techniques widely known in the art, to provide the requisite resolved enantiomers 3(R) and 3(S) of said amides or thioamides.

The following examples are provided as examples and are not intended to limit the scope of this invention to only those provided examples and named compounds. Also, the salts made in the examples are only exemplary and are not intended to limit the invention. Any pharmaceutically acceptable salt can be made by one of ordinary skill in the art. Further, the naming of specific stereoisomers is for exemplification and the lack of naming of specific stereoisomers is for simplification, and neither nomenclature method is intended to limit in anyway the scope of the invention. The invention includes the following examples in pure stereoisomeric form at all optically active centers or as racemic mixtures.

Furthermore, the examples provided are carried out using a specific amine as indicated in the examples. However, any disclosed amine could be used making non-critical changes but starting with the appropriate amine. Therefore, the stereospecificity of the resulting compound is not drawn and may not be stated. But, the scope of this invention includes the different stereoisomers as described herein as well as racemic mixtures.

Coupling the Amine with the Requisite Acid

EXAMPLE 1(i)

Exo-4(S)-N-(1-azabicyclo[2.2.1]hept-3-yl)furo[2,3-c]pyridine-5-carboxamide.fumarate

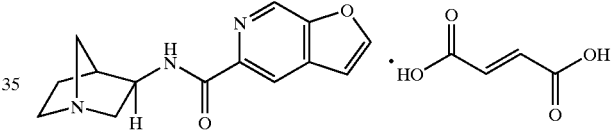

2-Chloro-3-pyridinol (20.0 g, 0.154 mole), NaHCO$_3$ (19.5 g, 0.232 mole, 1.5 equ), and 150 mL of water are placed in a flask. The flask is placed in an oil bath at 90° C., and after 5 min, 37% aqueous formaldehyde (40.5 mL, 0.541 mole, 3.5 equ) is added in six unequal doses in the following order: 12 mL, 3×8 mL, then 2.2 mL all at 90-min intervals and then the final 2.3 mL after the reaction stirs for 15 h at 90° C. The reaction is stirred at 90° C. for another 4 h and then cooled by placing the flask in an ice bath. The pH of the reaction is then adjusted to 1 using 6N HCl. The reaction is stirred for 1.5 h in an ice bath allowing an undesired solid to form. The undesired solid is removed by filtration, and the filtrate is extracted seven times with EtOAc. The combined organic extracts are concentrated in vacuo, toluene is added to the flask and removed in vacuo to azeotrope water, and then CH$_2$Cl$_2$ is added and removed in vacuo to obtain 2-chloro-6-(hydroxymethyl)-3-pyridinol (C1) as a pale yellow solid (81% yield) sufficiently pure for subsequent reaction. MS (EI) for C$_6$H$_6$ClNO$_2$, m/z: 159 (M)$^+$.

C1 (11.6 g, 72.7 mmol) and NaHCO$_3$ (18.3 g, 218 mmol) are added to 200 mL H$_2$O. The mixture is stirred until homogeneous, the flask is placed in an ice bath, iodine (19.4 g, 76.3 mmol) is added, and the reaction is stirred over the weekend at rt. The pH of the mixture is adjusted to 3 with 2N NaHSO$_4$, and the mixture is extracted with 4×50 mL EtOAc. The combined organic layer is dried over MgSO$_4$, is filtered, and the filtrate is concentrated in vacuo to a yellow solid. The crude solid is washed with EtOAc to provide 2-chloro-6-(hydroxymethyl)-4-iodo-3-pyridinol (C2) as an off-white solid (62% yield), and the filtrate is concentrated to a small volume and is chromatographed over 250 g silica gel (230–400 mesh) eluting with 2.5:4.5:4:0.1 EtOAc/$CH_2Cl_2$/hexane/acetic acid to afford additional pure C2 (12% yield). MS (EI) for $C_6H_5ClINO_2$, m/z: 285(M)$^+$.

C2 (13.9 g, 48.6 mmol) is combined with trimethylsilylacetylene (9.6 mL, 68 mmol), bis(triphenylphosphine) palladium dichloride (1.02 g, 1.46 mmol) and cuprous iodide (139 mg, 0.73 mmol) in 80 mL $CHCl_3$/40 mL THF under $N_2$. TEA (21 mL, 151 mmol) is added, and the reaction is stirred 3 h at rt and is diluted with 200 mL $CHCl_3$. The mixture is washed with 2×150 mL 5% HCl and the combined aqueous layers are extracted with 2×50 mL $CHCl_3$. The combined organic layer is washed with 100 mL 50% saturated NaCl, is dried over $MgSO_4$, and concentrated in vacuo to an amber oil. The crude material is chromatographed over 350 g silica gel (230–400 mesh), eluting with 35% EtOAc/hexane to afford 2-chloro-6-(hydroxymethyl)-4-[(trimethylsilyl)ethynyl]-3-pyridinol (C3) as a golden solid (92% yield). MS (EI) for $C_{11}H_{14}ClNO_2Si$, m/z: 255 (M)$^+$.

C3 (7.9 g, 31.2 mmol) and cuprous iodide (297 mg, 1.6 mmol) in 60 mL EtOH/60 mL TEA are added to a flask. The reaction is placed in an oil bath at 70° C. for 3.5 h, is cooled to rt, and concentrated in vacuo. The residue is partitioned between 100 mL 5% HCl and $CH_2Cl_2$ (4×50 mL). The combined organic layer is dried over $MgSO_4$, filtered, and concentrated in vacuo to give 6.5 g of a crude amber solid. The crude material is chromatographed over 300 g silica gel (230–400 mesh) eluting with 30–40% EtOAc/hexane. Two sets of fractions with two different desired compounds are identified by TLC/UV. The two compounds eluted separately. The early-eluting pool of fractions is combined and concentrated to afford [7-chloro-2-(trimethylsilyl)furo[2,3-c]pyridin-5-yl]methanol (C5) as a white solid (46% yield). The later-eluting pool of fractions is combined and concentrated to provide (7-chlorofuro[2,3-c]pyridin-5-yl)methanol (C4) as a white solid (27% yield). MS (EI) for $C_8H_6ClNO_2$, m/z: 183 (M)$^+$ for C4. HRMS (FAB) calculated for $C_{11}H_{14}ClNO_2Si$ m/z: 255.0482, found 255.0481 for C5.

C5 (1.05 g, 4.1 mmol) and 10% Pd/C catalyst (1.05 g) are placed in 20 mL absolute EtOH. Cyclohexene (4 mL, 40.1 mmol) is added, and the reaction is refluxed for 2.5 h, and then filtered through celite. The filter cake is washed with 1:1 EtOH/$CH_2Cl_2$, and the filtrate is concentrated to a pale yellow solid. The residue is partitioned between 40 mL saturated $NaHCO_3$ and extracted with $CH_2Cl_2$ (4×20 mL). The combined organic layer is dried over $MgSO_4$, filtered, and then concentrated in vacuo to a pale oil (1.04 g). The pale oil is chromatographed over 50 g silica gel (230–400 mesh) eluting with 50–70% EtOAc/hexane to afford 5-hydroxymethyl-2-trimethylsilyl-furo[2,3-c]pyridine (C14) as a white solid (90% yield). MS (EI) for $C_{11}H_{15}NO_2Si$, m/z: 221(M)$^+$.

C14 (770 mg, 3.48 mmol) is dissolved in 10 mL MeOH. 2N NaOH (3 mL, 6 mmol) is added, and the reaction is stirred for 1.5 h at rt. The solution is concentrated in vacuo to a residue. Water (20 mL) is added to the residue and extracted with 4×10 mL $CH_2Cl_2$. The combined organic layer is dried over anhydrous $K_2CO_3$, filtered, and concentrated in vacuo to afford furo[2,3-c]pyridin-5-yl methanol (C16) as a white solid (90% yield). Analysis calculated for $C_8H_7NO_2$: C, 64.42; H, 4.73; N, 9.39. Found: C, 64.60; H, 4.56; N, 9.44.

Oxalyl chloride (685 µL, 7.8 mmol) is dissolved in 30 mL $CH_2Cl_2$ in a dry flask under $N_2$. The flask is placed in a dry-ice/acetone bath, DMSO (1.11 mL, 15.6 mmol) in 5 mL $CH_2Cl_2$ is added drop-wise, and the mixture is stirred for 20 min. C16 (1.0 g, 6.7 mmol) in 10 mL $CH_2Cl_2$ is added, and the reaction is stirred 30 min at −78° C. TEA (4.7 mL, 33.5 mmol) is added, the reaction is allowed to warm to rt, is stirred 1 h, and washed with 25 mL saturated $NaHCO_3$. The organic layer is dried over anhydrous $K_2CO_3$, filtered, and concentrated in vacuo to an orange solid. The crude material is chromatographed over 50 g silica gel (230–400 mesh) eluting with 33% EtOAc/hexane to provide furo[2,3-c]pyridine-5-carbaldehyde (C17) as a white solid (86% yield). MS (EI) for $C_8H_5NO_2$, m/z: 147 (M)$^+$.

C17 (850 mg, 5.8 mmol) is dissolved in 10 mL DMSO. $KH_2PO_4$ (221 mg, 1.6 mmol) in 3 mL $H_2O$ is added and then $NaClO_2$ (920 mg, 8.2 mmol) in 7 mL $H_2O$ is added, and the reaction is stirred 3 h at rt. The reaction is diluted with 25 mL water, the pH is adjusted to 10 with 2N NaOH, and the mixture is extracted with 3×20 mL ether. The combined ether layer is discarded. The pH of the aqueous layer is adjusted to 3.5 with 10% aqueous HCl and is extracted with 13×10 mL 10% MeOH/$CH_2Cl_2$. The MeOH/$CH_2Cl_2$ organic layer is dried over anhydrous $Na_2SO_4$, filtered, and concentrated in vacuo to a pale oil. The residual DMSO is removed under a stream of $N_2$ at rt to provide a white paste. The paste is dissolved in MeOH and concentrated to dryness. The white solid is washed with ether and dried to afford crude furo[2,3-c]pyridine-5-carboxylic acid (C18) (94% yield). MS (ESI) for $C_8H_5NO_3$, 162.8 (M−H)$^-$.

Step 1a. Preparation of the Carboxamide

To a stirred solution of furo[2,3-c]pyridine-5-carboxylic acid (C18) (294 mg, 1.80 mmol) in dry THF-DMF (12 mL, 5:1) is added DIEA (956 µL, 5.49 mmol), followed by exo-(4S)-[2.2.1]-3-Amine (747 mg, 1.64 mmol). The solution is cooled with an ice bath before HATU (684 mg, 1.80 mmol) is added. The solution is allowed to warm to rt and stir for 16 h. The solvent is removed in vacuo, and the remaining residue is partitioned between saturated aqueous $K_2CO_3$ solution and 9:1 $CHCl_3$—MeOH. The aqueous layer was extracted with 9:1 $CHCl_3$-MeOH, and the combined organic layers are washed with brine, dried over $MgSO_4$, filtered and concentrated in vacuo to afford the desired carboxamide as a light yellow solid (420 mg, 100%): MS for $C_{14}H_{16}N_3O_2$ (ESI) m/e 258 (M+H).

Step 1b. Preparation of the Fumarate Salt

To a stirred solution of the product from Step 1a (200 mg, 0.78 mmol) in acetone (5 mL) is added a hot solution of fumaric acid (90 mg, 0.78 mmol) in IPA (2 mL). The mixture is stirred for 30 min in a 50° C. water bath. The solvents are removed in vacuo and the remaining residue is dissolved in acetone (5 mL). The mixture is stirred overnight at rt. The solid precipitate is collected by filtration and washed with acetone. The solid is dried in vacuo overnight to give 156 mg (54%) of Example 1(i) as a white solid: $^1$H NMR (CD$_3$OD) δ 8.9, 8.5, 8.1, 7.1, 6.7, 4.3, 3.7, 3.6, 3.4, 3.3, 3.2, 3.1, 2.2, 1.9.

EXAMPLE 1(i-b)

Exo-4(R)—N-(1-azabicyclo[2.2.1]hept-3-yl)furo[2,3-c]pyridine-5-carboxamide, using exo-(4R)-[2.2.1]-3-Amine: $^1$H NMR (400 MHz, MeOH-d$_4$) δ 8.9, 8.5, 8.1, 7.1, 6.7, 4.3, 3.7, 3.6, 3.4, 3.3, 3.2, 3.1, 2.2, 1.9.

EXAMPLE 1(i-c)

Exo-(racemic)-N-(1-azabicyclo[2.2.1]hept-3-yl)furo[2,3-c]pyridine-5-carboxamide, using exo-[2.2.1]-3-Amine EXAMPLE 1(i-d)

(+)-N-[endo-1-azabicyclo[2.2.1]hept-3-yl]furo[2,3-c]pyridine-5-carboxamide and

EXAMPLE 1(i-e)

(−)-N-[endo-1-azabicyclo[2.2.1]hept-3-yl]furo[2,3-c] pyridine-5-carboxamide:

To a stirred solution of furo[2,3-c]pyridine-5-carboxylic acid (400 mg, 0.877 mmol) in anhydrous DMF (10 mL) are added DIEA (626 μL, 3.59 mmol) and endo-[2.2.1]-3-Amine (175 mg, 0.877 mmol). The mixture is cooled to 0° C. in an ice bath, and HATU (333 mg, 0.877 mmol) is added in one portion. The reaction mixture is allowed to warm to rt and stir overnight. The solvent is removed in vacuo, and the residue is partitioned between saturated aqueous $K_2CO_3$ solution and $CHCl_3$. The aqueous layer is extracted with $CHCl_3$ (2×). The combined organic layers are washed with brine, dried over $Na_2SO_4$, filtered and concentrated in vacuo to give 230 mg solid. The racemic mixture is resolved via chromatography using a Chiralcel OJ column. The amides are converted to their fumarate salt forms as described in Step 1b. The (+)-enantiomer ($[\alpha]^{25}_D$ 31 (c 0.28, MeOH)) gives rise to Example 1-d, and the (−)-enantiomer ($[\alpha]^{25}_D$ −31 (c 0.30, MeOH)) gives rise to Example 1-e. For Example 1-d: $^1$H NMR (400 MHz, $CD_3OD$) δ 8.94, 8.46, 8.14, 7.13, 6.71, 4.75–4.70, 3.86–3.79, 3.48–3.42, 3.28–3.21, 2.21–2.03.

EXAMPLE 1(i-f)

N-(1-(6-methyl)-azabicyclo[2.2.1]hept-3-yl)furo[2,3-c] pyridine-5-carboxamide: This example can be prepared according to the coupling procedures discussed herein.

EXAMPLE 1(ii)

N-(1-(6-methyl)-azabicyclo[2.2.2]oct-3-yl)furo[2,3-c] pyridine-5-carboxamide: This example can be prepared according to the coupling procedures discussed herein.

EXAMPLE 1(iii)

N-(2-azabicyclo[2.2.1]hept-5-yl)furo[2,3-c]pyridine-5-carboxamide: This example can be prepared according to the coupling procedures discussed herein.

EXAMPLE 1(iv)

N-(2-azabicyclo[2.2.1]hept-6-yl)furo[2,3-c]pyridine-5-carboxamide: This example can be prepared according to the coupling procedures discussed herein.

EXAMPLE 1(v)

N-((3R,5R)-1-azabicyclo[3.2.1]oct-3-yl)furo[2,3-c] pyridine-5-carboxamide: Yield from coupling is 70%. HRMS (FAB) calcd for $C_{15}H_{17}N_3O_2$ (MH$^+$) 272.1399, found 272.1413.

EXAMPLE 1(vi)

N-(1-azabicyclo[3.2.2]non-3-yl)furo[2,3-c]pyridine-5-carboxamide.fumarate: Example 1(vi) is obtained as a white solid: $^1$H NMR ($CD_3OD$) δ 8.9, 8.4, 8.1, 7.1, 6.7, 4.8–4.7, 3.8, 3.7–3.6, 3.5–3.3, 2.4, 2.2–2.0.

EXAMPLE 2(i)

N-[(exo-1-azabicyclo[2.2.1]hept-3-yl]furo[3,2-c] pyridine-6-carboxamide:

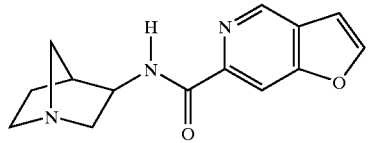

3-Bromofuran (8.99 mL, 100.0 mmol) is dissolved in DMF (8.5 mL), cooled to 0° C., treated dropwise with $POCl_3$ (9.79 mL, 105.0 mmol), stirred for 1 h at RT and then heated to 80° C. for 2 h. The mixture is cooled to RT, poured over ice (1 kg) and neutralized to pH 9 with solid $K_2CO_3$. The mixture is stirred for 1 h, extracted with $Et_2O$ (3×500 mL), dried over $K_2CO_3$ and concentrated to a dark brown oil. The crude material is chromatographed over 600 g slurry-packed silica gel, eluting with 6% EtOAc/hexane (4 L), 8% EtOAc/hexane (2 L), 10% EtOAc/hexane (1 L), and finally 20% EtOAc/hexane. The appropriate fractions are combined and concentrated in vacuo to afford 14.22 g (81%) of 3-bromo-2-furaldehyde as a yellow oil. MS (EI) m/z: 174 (M$^+$). 3-Bromo-2-furaldehyde (14.22 g, 81.3 mmol) is combined with ethylene glycol (6.55 mL, 117.4 mmol) and para-toluene sulfonic acid monohydrate (772 mg, 4.06 mmol) in benzene (200 mL) and heated to reflux with a Dean-Stark trap for 5 h. Additional ethylene glycol (1.64 mL, 29.41 mmol) and benzene (150 mL) are added and the solution is heated for an additional 2 h. The mixture is cooled to RT, treated with saturated $NaHCO_3$ and stirred for 0.5 h. The layers are separated and the organics are dried over $Na_2SO_4$ and concentrated to a brown oil (18.8 g). The crude material is chromatographed over 700 g slurry-packed silica gel, eluting with 15% EtOAc/hexane. The appropriate fractions are combined and concentrated in vacuo to afford 16.45 g (92%) of 2-(3-bromo-2-furyl)-1,3-dioxolane as a yellow-orange oil. MS (EI) m/z: 218 (M$^+$).

2-(3-Bromo-2-furyl)-1,3-dioxolane (438 mg, 2.0 mmol) is dissolved in $Et_2O$ (5 mL) in a dry flask under nitrogen, cooled to −78° C., treated dropwise with tert-butyllithium (2.59 mL, 4.4 mmol) and stirred for 1 h. DMF (178 μL, 2.3 mmol) in $Et_2O$ (2 mL) is added dropwise, the mixture stirred for 4 h at −78° C., then treated with oxalic acid dihydrate (504 mg, 4.0 mmol) followed by water (2 mL). The cooling bath is removed and the mixture allowed to warm to RT over 1 h. The mixture is diluted with water (20 mL) and EtOAc (20 mL), the layers are separated and the aqueous layer extracted with EtOAc (1×20 mL). The organics are dried over $Na_2SO_4$ and concentrated to a yellow oil. The crude material is chromatographed over 12 g slurry-packed silica gel, eluting with 15% EtOAc/hexane. The appropriate fractions are combined and concentrated in vacuo to afford 228 mg (68%) of 2-(1,3-dioxolan-2-yl)-3-furaldehyde as a pale yellow oil. MS (EI) m/z: 168 (M$^+$). 2-(1,3-Dioxolan-2-yl)-3-furaldehyde (2.91 g, 17.31 mmol) is combined with formic acid (17 mL, 451 mmol) and water (4.25 mL) and stirred at RT for 18 h. The mixture is slowly transferred into a solution of $NaHCO_3$ (45 g, 541 mmol) in water (600 mL), then stirred for 0.5 h. EtOAc (200 mL) is added, the layers separated and the aqueous layer extracted with EtOAc (2×200 mL). The combined organics are dried over $Na_2SO_4$ and concentrated to a yellow oil (3.28 g). The crude material is chromatographed over 90 g slurry-packed silica gel, eluting with 20% EtOAc/hexane. The appropriate fractions are combined and concentrated to afford 2.45 g of furan-2, 3-dicarbaldehyde slightly contaminated with ethylene glycol diformate as a yellow oil. $^1$H NMR (CDCl$_3$): δ 7.00 (d, J=2 Hz, 1H), 7.67 (d, J=2 Hz, 1H), 10.07 (s, 1 H), 10.49 (s, 1 H) ppm.

Methyl (acetylamino)(dimethoxyphosphoryl)acetate (2.34 g, 9.8 mmol) is dissolved in CHCl$_3$ (40 mL), treated with DBU (1.46 mL, 9.8 mmol), stirred for 5 min then added dropwise to a 0° C. solution of furan-2,3-dicarbaldehyde (1.65 g, 8.9 mmol) in CHCl$_3$ (80 mL). The mixture is stirred for 2.5 h as the cooling bath expires then 5.5 h at RT and finally 24 h at 50° C. The mixture is concentrated in vacuo to a yellow oily-solid (6.66 g). The crude material is chromatographed over a standard 100 g slurry-packed silica gel, eluting with 65% EtOAc/hexane. The appropriate fractions are combined and concentrated in vacuo to afford 1.30 g (82%) of methyl furo[3,2-c]pyridine-6-carboxylate as a yellow solid. MS (EI) m/z: 177 (M$^+$).

Methyl furo[3,2-c]pyridine-6-carboxylate (1.55 g, 8.74 mmol) is dissolved in MeOH (30 mL) and H$_2$O (15 mL), treated with 3 N NaOH (6.4 mL) and stirred at RT for 7 h. The mixture is concentrated to dryness, dissolved in H$_2$O (10 mL) and acidified to pH 2 with concentrated HCl. The solution is concentrated to dryness, suspended in a smaller amount of water (7 mL) and the resulting solid collected via filtration (lot A). The filtrate is concentrated, triturated with water (3 mL) and the resulting solid collected via filtration (lot B). The filtrate from lot B is concentrated and carried on without further purification as an acid/salt mixture (lot C). Both lots A and B are dried in a vacuum oven at 50° C. for 18 h to afford 690 mg (48%) for lot A and 591 mg (42%) for lot B of furo[3,2-c]pyridine-6-carboxylic acid as yellow solids. MS (CI) m/z: 164 (M+H$^+$).

Examples 2(i), 2(i-a), 2(ii), 2(iii), 2(iv), and 2(vi) can be prepared according to the coupling procedures described herein, making non-critical changes.

EXAMPLE 2(i-a)

N-(1-(6-methyl)-azabicyclo[2.2.1]hept-3-yl)furo[3,2-c]pyridine-6-carboxamide.

EXAMPLE 2(i)

N-(1-(6-methyl)-azabicyclo[2.2.2]oct-3-yl)furo[3,2-c]pyridine-6-carboxamide.

EXAMPLE 2(iii)

N-(2-azabicyclo[2.2.1]hept-5-yl)furo[3,2-c]pyridine-6-carboxamide.

EXAMPLE 2(iv)

N-(2-azabicyclo[2.2.1]hept-6-yl)furo[3,2-c]pyridine-6-carboxamide.

EXAMPLE 2(v)

N-((3R,5R)-1-azabicyclo[3.2.1]oct-3-yl)furo[3,2-c]pyridine-6-carboxamide: Yield for coupling is 94%. $^1$H NMR (400 MHz, CD$_3$OD) δ 9.30, 8.75–8.80, 8.35–8.45, 7.35–7.45, 4.65–4.80, 3.25–3.80, 2.85–2.95, 2.30–2.45, 2.10–2.25, 1.95–2.10.

EXAMPLE 2(vi)

N-(1-azabicyclo[3.2.2]non-3-yl)furo[3,2-c]pyridine-6-carboxamide.

EXAMPLE 3(i)

N-(1-azabicyclo[2.2.1]-hept-3-yl)-2,3-dihydrofuro[2,3-c]pyridine-5-carboxamide:

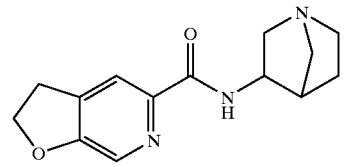

Oxalyl chloride (3.1 mL, 35 mmol) is dissolved in 200 mL CH$_2$Cl$_2$ in a dried flask under N$_2$. The flask is placed in a dry-ice/acetone bath at −78° C., DMSO (4.95 mL, 70 mmol) in 10 mL CH$_2$Cl$_2$ is added drop-wise, and the mixture is stirred for 20 min. (7-Chlorofuro[2,3-c]pyridin-5-yl)methanol (C4) (5.5 g, 30 mmol) in 10 mL CH$_2$Cl$_2$ is added, and the reaction is stirred 30 min at −78° C. TEA (21.3 mL, 153 mmol) is then added. The reaction is stirred 30 min in the dry-ice/acetone bath, an ice bath replaces the dry-ice/acetone bath, and the reaction is stirred 1 h and is washed with 100 mL 1:1 saturated NaCl/NaHCO$_3$. The organic layer is dried over anhydrous K$_2$CO$_3$, filtered, and concentrated in vacuo to afford 7-chlorofuro[2,3-c]pyridine-5-carbaldehyde (C6) as a pale yellow solid (97% yield). MS (EI) for C$_8$H$_4$ClNO$_2$ m/z: 181 (M)$^+$.

C6 (3.0 g, 16.5 mmol) is dissolved in 40 mL DMSO. KH$_2$PO$_4$ (561 mg, 4.1 mmol) in 6.5 mL H$_2$O is added and then NaClO$_2$ (2.6 g, 23.1 mmol) in 24 mL H$_2$O is added, and the reaction is stirred overnight at rt. The reaction is diluted with 200 mL H$_2$O, the pH is adjusted to 9 with 2N NaOH, and any remaining aldehyde is extracted into 3×50 mL ether. The pH of the aqueous layer is adjusted to 3 with 10% aqueous HCl and is extracted with 4×50 mL EtOAc. The combined organic layer is dried over MgSO$_4$, filtered, and concentrated in vacuo to a white solid. The solid is washed with ether and dried to afford 7-chlorofuro[2,3-c]pyridine-5-carboxylic acid (C7) (55% yield). MS (CI) for C$_8$H$_4$ClNO$_3$, m/z: 198 (M+H).

C7 (980 mg, 4.98 mmol) is dissolved in 75 mL MeOH containing 500 mg 20% palladium hydroxide on carbon in a 250 mL Parr shaker bottle. The reaction mixture is hydrogenated at 20 PSI for 24 h. The catalyst is removed by filtration and the filtrate is concentrated in vacuo to a white solid. The solid is dissolved in MeOH and is loaded onto 20 mL Dowex 50W-X2 ion exchange resin (hydrogen form) which had been prewashed with MeOH. The column is eluted with 50 mL MeOH followed by 150 mL 5% TEA in MeOH to afford 2,3-dihydrofuro[2,3-c]pyridine-5-carboxylic acid (C8) (74% yield). HRMS (FAB) calculated for C$_8$H$_7$NO$_3$+H: 166.0504, found 166.0498 (M+H).

Example 3(i-a) can be prepared according to the coupling procedures discussed herein using C8.

The following examples can be prepared according to the coupling procedures discussed herein:

EXAMPLE 3(i-a)

N-(1-(6-methyl)-azabicyclo[2.2.1]hept-3-yl)-2,3-dihydrofuro[2,3-c]pyridine-5-carboxamide.

EXAMPLE 3(ii)

N-(1-(6-methyl)-azabicyclo[2.2.2]oct-3-yl)-2,3-dihydrofuro[2,3-c]pyridine-5-carboxamide.

EXAMPLE 3(iii)

N-(2-azabicyclo[2.2.1]hept-5-yl)-2,3-dihydrofuro[2,3-c]pyridine-5-carboxamide.

EXAMPLE 3(iv)

N-(2-azabicyclo[2.2.1]hept-6-yl)-2,3-dihydrofuro[2,3-c]pyridine-5-carboxamide.

EXAMPLE 3(v)

N-((3R,5R)-1-azabicyclo[3.2.1]oct-3-yl)-2,3-dihydrofuro[2,3-c]pyridine-5-carboxamide.

EXAMPLE 3(vi)

N-(1-azabicyclo[3.2.2]non-3-yl)-2,3-dihydrofuro[2,3-c]pyridine-5-carboxamide.

EXAMPLE 4(i)

N-(1-azabicyclo[2.2.1]hept-3-yl)-7-chlorofuro[2,3-c]pyridine-5-carboxamide:

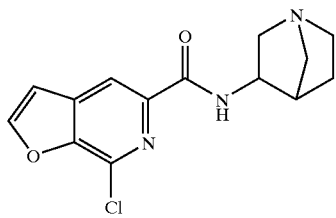

Example 4(i) can be obtained by coupling either the exo-[2.2.1]-3-Amine or endo-[2.2.1]-3-Amine with 7-chlorofuro[2,3-c]pyridine-5-carboxylic acid (C7).

The following examples can be prepared according to the coupling procedures discussed herein:

EXAMPLE 4(i-a)

N-(1-(6-methyl)-azabicyclo[2.2.1]hept-3-yl)-7-chlorofuro[2,3-c]pyridine-5-carboxamide.

EXAMPLE 4(ii)

N-(1-(6-methyl)-azabicyclo[2.2.2]oct-3-yl)-7-chlorofuro[2,3-c]pyridine-5-carboxamide.

EXAMPLE 4(iii)

N-(2-azabicyclo[2.2.1]hept-5-yl)-7-chlorofuro[2,3-c]pyridine-5-carboxamide.

EXAMPLE 4(iv)

N-(2-azabicyclo[2.2.1]hept-6-yl)-7-chlorofuro[2,3-c]pyridine-5-carboxamide.

EXAMPLE 4(v)

N-((3R,5R)-1-azabicyclo[3.2.1]oct-3-yl)-7-chlorofuro[2,3-c]pyridine-5-carboxamide.

EXAMPLE 5(i)

N-(1-azabicyclo[2.2.1]hept-3-yl)-3,3-dimethyl-2,3-dihydrofuro[2,3-c]pyridine-5-carboxamide:

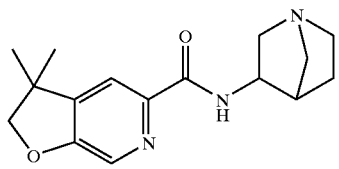

2-Chloro-6-(hydroxymethyl)-4-iodo-3-pyridinol (C2) (6.3 g, 22 mmol) is dissolved in 30 mL DMF in a dry flask under $N_2$. The flask is placed in an ice bath, and 60% sodium hydride in mineral oil (880 mg, 22 mmol) is added. The reaction is stirred 30 min while the flask is kept in an ice bath. The ice bath is removed for 30 min and then the flask is placed back into the ice bath to cool the reaction. 3-Bromo-2-methylpropene (23.1 mmol) is added, and the reaction is stirred overnight at rt. The reaction is diluted with 150 mL EtOAc and is washed with 4×50 mL 50% saturated 1:1 NaCl/NaHCO$_3$. The organic layer is dried over anhydrous Na$_2$SO$_4$, filtered, and then concentrated in vacuo to a pale oil which is crystallized from hexanes to afford (6-chloro-4-iodo-5-[(2-methyl-2-propenyl)oxy]-2-pyridinyl)methanol (C19) (86% yield). HRMS (FAB) calculated for $C_{10}H_{11}C_{11}NO_2$+H: 339.9603, found 339.9604 (M+H).

C19 (6.3 g, 18.9 mmol), sodium formate (1.49 g, 21.8 mmol), TEA (8 mL, 57.2 mmol), palladium acetate (202 mg, 0.9 mmol) and tetra (n-butyl)ammonium chloride (5.25 g, 18.9 mmol) are added to 30 mL DMF in a dry flask under $N_2$. The reaction is warmed to 60° C. for 5 h, is poured into 150 mL EtOAc, and is washed with 4×50 mL 50% saturated 1:1 NaCl/NaHCO$_3$. The organic layer is dried over anhydrous Na$_2$SO$_4$, filtered, and concentrated in vacuo to a pale oil. The crude material is chromatographed over 40 g silica gel (Biotage), eluting with 30% EtOAc/hexane to afford (7-chloro-3,3-dimethyl-2,3-dihydrofuro[2,3-c]pyridin-5-yl)methanol (C20) (54% yield). MS (EI) for $C_{10}H_{12}ClNO_2$, m/z: 213 (M)$^+$.

C20 (2.11 g, 9.9 mmol) and 600 mg 10% Pd/C catalyst are placed in 30 mL EtOH in a 250 mL Parr shaker bottle. 2N NaOH (5 mL, 10 mmol) is then added and the mixture is hydrogenated at 20 PSI for 2.5 h. The catalyst is removed by filtration, and the filtrate is concentrated in vacuo to an aqueous residue. Saturated NaHCO$_3$ (20 mL) is added to the residue and extracted with 4×20 mL CH$_2$Cl$_2$. The combined organic layer is dried over anhydrous K$_2$CO$_3$, filtered, and concentrated in vacuo to afford (3,3-dimethyl-2,3-dihydrofuro[2,3-c]pyridin-5-yl)methanol (C21) (92% yield). MS (EI) for $C_{10}H_{13}NO_2$, m/z: 179 (M)$^+$.

Oxalyl chloride (869 μL, 9.9 mmol) is dissolved in 50 mL CH$_2$Cl$_2$ in a dry flask under $N_2$. The flask is placed in a dry-ice/acetone bath at −78° C., DMSO (1.41 mL, 19.8 mmol) in 5 mL CH$_2$Cl$_2$ is added drop-wise, and the mixture is stirred for 20 min. C21 (1.53 g, 8.5 mmol) in 5 mL CH$_2$Cl$_2$ is then added, and the reaction is stirred 30 min at −78° C. TEA (5.9 mL, 42.5 mmol) is added and the reaction is stirred 20 min at −78° C. The dry-ice/acetone bath is removed, the reaction is stirred 1 h, and the reaction is washed with 25 mL saturated NaHCO$_3$. The organic layer is dried over anhydrous K$_2$CO$_3$, filtered, and then concentrated in vacuo to an orange solid. The crude material is chromatographed over 40 g silica gel (Biotage) eluting with 25% EtOAc/hexane to afford 3,3-dimethyl-2,3-dihydrofuro[2,3-c]pyridine-5-carbaldehyde (C22) (92% yield). MS (EI) for $C_{10}H_{11}NO_2$, m/z: 177 (M)$^+$.

C22 (1.35 g, 7.62 mmol) is dissolved in 40 mL THF, 20 mL t-butanol, and 20 mL $H_2O$. $KH_2PO_4$ (3.11 g, 22.9 mmol) and $NaClO_2$ (2.58 g, 22.9 mmol) are added, and the reaction is stirred over the weekend at rt. The reaction is concentrated in vacuo to a residue. The residue is partitioned between 20 mL water and $CH_2Cl_2$ (2×50 mL). The combined organic layer is dried over anhydrous $Na_2SO_4$, filtered, and then concentrated in vacuo to afford crude 3,3-dimethyl-2,3-dihydrofuro[2,3-c]pyridine-5-carboxylic acid (C23) (99% yield). HRMS (FAB) calculated for $C_{10}H_{11}NO_3$+H: 194.0817, found 194.0808 (M+H).

Example 5(i) can be obtained by coupling C23 with either the exo-[2.2.1]-3-Amine or the endo-[2.2.1]-3-Amine using the coupling procedures discussed herein.

The following examples can be prepared according to the coupling procedures discussed herein:

EXAMPLE 5(i-a)

N-(1-(6-methyl)-azabicyclo[2.2.1]hept-3-yl)-3,3-dimethyl-2,3-dihydrofuro[2,3-c]pyridine-5-carboxamide.

EXAMPLE 5(ii)

N-(1-(6-methyl)-azabicyclo[2.2.2]oct-3-yl)-3,3-dimethyl-2,3-dihydrofuro[2,3-c]pyridine-5-carboxamide.

EXAMPLE 5(iii)

N-(2-azabicyclo[2.2.1]hept-5-yl)-3,3-dimethyl-2,3-dihydrofuro[2,3-c]pyridine-5-carboxamide.

EXAMPLE 5(iv)

N-(2-azabicyclo[2.2.1]hept-6-yl)-3,3-dimethyl-2,3-dihydrofuro[2,3-c]pyridine-5-carboxamide.

EXAMPLE 5(v)

N-((3R,5R)-1-azabicyclo[3.2.1]oct-3-yl)-3,3-dimethyl-2,3-dihydrofuro[2,3-c]pyridine-5-carboxamide.

EXAMPLE 6(i)

N-(1-azabicyclo[2.2.1]hept-3-yl)-2-methylfuro[2,3-c]pyridine-5-carboxamide:

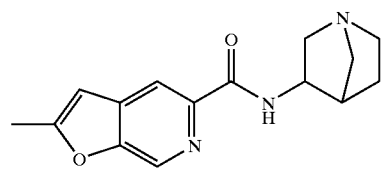

2-Chloro-6-(hydroxymethyl)-4-iodo-3-pyridinol (C2) (4.6 g, 16 mmol), propargyl trimethylsilane (2 g, 17.8 mmol), bis(triphenylphosphine)palladium dichloride (156 mg, 0.21 mmol), cuprous iodide (122 mg, 0.64 mmol), and piperidine (3.52 mL, 26.6 mmol) are added to 25 mL DMF in a dry flask under $N_2$. The mixture is warmed to 45° C. for 7 h, is stirred overnight at rt, and is diluted with 150 mL EtOAc. The mixture is washed with 4×50 mL 50% saturated 1:1 NaCl/NaHCO$_3$. The organic layer is dried over anhydrous $Na_2SO_4$, filtered, and then concentrated in vacuo to an amber oil. The crude material is chromatographed over 40 g silica gel (230–400 mesh) eluting with 35% EtOAc/hexane to afford (7-chloro-2-methylfuro[2,3-c]pyridin-5-yl)methanol (C24) (44% yield). MS (CI) for $C_9H_8ClNO_2$, m/z: 198 (M+H).

C24 (2.0 g, 10.8 mmol) is added to 500 mg 10% Pd/C catalyst in 25 mL EtOH in a 250 mL Parr shaker bottle. 2N NaOH (6 mL, 12 mmol) is added, and the reaction is hydrogenated at 20 PSI for 6 h. The catalyst is removed by filtration, and the filtrate is concentrated in vacuo to an aqueous residue. The residue is partitioned between 50 mL 50% saturated NaCl and 30 mL $CH_2Cl_2$. The organic layer is dried over anhydrous $K_2CO_3$, filtered, and then concentrated in vacuo to afford (2-methylfuro[2,3-c]pyridin-5-yl)methanol (C25) (77% yield). MS (CI) for $C_9H_9NO_2$, m/z: 164 (M+H).

Oxalyl chloride (784 μL, 8.9 mmol) is dissolved in 25 mL $CH_2Cl_2$ in a dry flask under $N_2$. The flask is placed in a dry-ice/acetone bath at −78° C., and DMSO (1.26 mL, 17.8 mmol) in 5 mL $CH_2Cl_2$ is added. The mixture is stirred for 20 min and C25 (1.53 g, 8.5 mmol) in 5 mL $CH_2Cl_2$ is added. The reaction is stirred 1 h, TEA (5.9 mL, 42.5 mmol) is added, and the reaction is stirred 30 min at −78° C. The flask is placed in an ice bath, and the reaction is stirred 1 h. The reaction is washed with 50 mL saturated NaHCO$_3$. The organic layer is dried over anhydrous $K_2CO_3$, filtered, and then concentrated in vacuo to a tan solid. The crude material is chromatographed over 40 g silica gel (Biotage) eluting with 25% EtOAc/hexane to afford 2-methylfuro[2,3-c]pyridine-5-carbaldehyde (C26) (99% yield). MS (EI) for $C_9H_7NO_2$, m/z: 161 (M)$^+$.

C26 (1.15 g, 7.1 mmol) is dissolved in 40 mL THF, 20 mL t-butanol, and 20 mL $H_2O$. 2-Methyl-2-butene (6.5 mL, 57.4 mmol) is added, and then $KH_2PO_4$ (3.11 g, 22.9 mmol) and $NaClO_2$ (2.58 g, 22.9 mmol) are added. The reaction is stirred 6 h at rt. The reaction is concentrated in vacuo. Water (20 ml) is added to the residue, a white solid remained. The white solid is collected, washed with water and then with ether, and is dried to afford 2-methylfuro[2,3-c]pyridine-5-carboxylic acid (C27) (70% yield). MS (EI) for $C_9H_7NO_3$, m/z: 177 (M)$^+$.

Example 6(i) can be obtained by coupling either exo-[2.2.1]-3-Amine or endo-[2.2.1]-3-Amine with C27.

The examples can be prepared according to the coupling procedures discussed herein:

EXAMPLE 6(1-a)

N-(1-(6-methyl)-azabicyclo[2.2.1]hept-3-yl)-2-methylfuro[2,3-c]pyridine-5-carboxamide.

EXAMPLE 6(ii)

N-(1-(6-methyl)-azabicyclo[2.2.2]oct-3-yl)-2-methylfuro[2,3-c]pyridine-5-carboxamide.

EXAMPLE 6(iii)

N-(2-azabicyclo[2.2.1]hept-5-yl)-2-methylfuro[2,3-c]pyridine-5-carboxamide.

EXAMPLE 6(iv)

N-(2-azabicyclo[2.2.1]hept-6-yl)-2-methylfuro[2,3-c]pyridine-5-carboxamide.

EXAMPLE 6(v)

N-((3R,5R)-1-azabicyclo[3.2.1]oct-3-yl)-2-methylfuro[2,3-c]pyridine-5-carboxamide.

EXAMPLE 7(i)

Exo-4(S)-N-(1-azabicyclo[2.2.1]hept-3-yl)-3-methylfuro[2,3-c]pyridine-5-carboxamide.furmate:

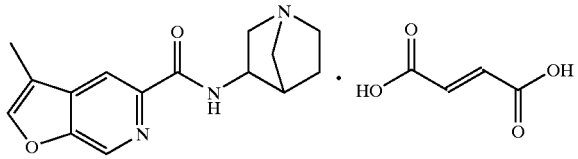

2-Chloro-6-(hydroxymethyl)-4-iodo-3-pyridinol (C2) (7.14 g, 25.0 mmol) is dissolved in DMF (50 mL) in a dry flask under $N_2$, sodium hydride (60% dispersion in mineral oil) (1.0 g, 25.0 mmol) is added, and the reaction is stirred for 1 h at rt. Allyl bromide (2.38 mL, 27.5 mmol) is added, and the reaction mixture is stirred 48 h at rt. The mixture is diluted with EtOAc (50 mL) and washed 4×25 mL of a 50% saturated solution of 1:1 NaCl/NaHCO$_3$. The organic layer is dried over MgSO$_4$, filtered and concentrated in vacuo to a white solid. The solid is washed with hexane and dried to afford 3-(allyloxy)-2-chloro-6-(hydroxymethyl)-4-iodopyridine (C50) as a white solid (68% yield). MS (EI) for $C_9H_9ClINO_2$, m/z: 325 (M)$^+$.

C50 (5.51 g, 16.9 mmol) is suspended in benzene (30 mL) in a dry flask under $N_2$. Azo(bis)isobutyryl nitrile (289 mg, 1.8 mmol) is added, the mixture is rapidly heated to reflux, and tributyltin hydride (4.91 mL, 18.2 mmol) in benzene (10 mL) is added. The solution is refluxed for 1.5 h, allowed to cool to rt and concentrated in vacuo. The resulting residue is chromatographed over 125 g slurry-packed silica gel, eluting with a gradient of EtOAc/hexane (20%–60%) to afford (7-chloro-3-methyl-2,3-dihydrofuro[2,3-c]pyridin-5-yl)methanol (C51) as a white solid (89% yield). MS (ESI) for $C_9H_{10}ClNO_2$+H, m/z: 200.1 (M+H).

C51 (3.00 g, 15.0 mmol) is added to 20% palladium hydroxide on carbon (800 mg) and 2N NaOH (9.2 mL, 18.2 mmol) in a Parr shaker bottle. The mixture is hydrogenated at 20 PSI for 3 h, is filtered through celite and concentrated in vacuo to a residue. The resulting residue is partitioned between $H_2O$ (50 mL) and $CH_2Cl_2$ (4×30 mL). The combined organic layer is dried over MgSO$_4$, filtered, and concentrated to a colorless oil which solidified upon standing to afford 2.50 g (greater than 100% yield) of (3-methyl-2,3-dihydrofuro[2,3-c]pyridin-5-yl)methanol (C52) as a white crystalline solid. MS (EI) for $C_9H_{11}NO_2$, m/z: 165 (M)$^+$.

C52 (2.48 g, 15.03 mmol) is dissolved in pyridine (15 mL), and acetic anhydride (4.18 mL, 45.09 mmol) is added and stirred for 16 h at rt under $N_2$. The reaction is concentrated in vacuo, and the residue is diluted with EtOAc (75 mL), washed with 50% saturated NaHCO$_3$ (4×30 mL), and dried over MgSO$_4$. The organic layer is filtered and concentrated in vacuo to afford (3-methyl-2,3-dihydrofuro[2,3-c]pyridin-5-yl)methyl acetate (C53) as a colorless oil (92% yield). MS (EI) for $C_{11}H_{13}NO_3$, m/z: 207 (M)$^+$.

C53 (2.85 g, 13.8 mmol) is dissolved in dioxane (100 mL), 2,3,5,6-tertachlorobenzoquinone (3.72 g, 15.1 mmol) is added, and the reaction is heated to reflux for 17 h. The reaction is concentrated in vacuo. The resulting brown solid is washed with 1:1 EtOAc/ether (50 mL), and the insoluble material filtered off. The filtrate is concentrated to a brown solid, dissolved in MEOH (50 mL), treated with 2N NaOH (16 mL, 32 mmol), and stirred at rt for 1 h. The mixture is concentrated to dryness, dissolved in 1N NaOH (75 mL), and extracted with $CH_2Cl_2$ (4×50 mL). The combined organic layer is dried over $K_2CO_3$, filtered, and concentrated to a white solid (2.0 g). The crude material is adsorbed onto silica gel (4 g) and chromatographed over a standard 40 g Biotage column, eluting with 90% EtOAc/hexane to afford (3-methylfuro[2,3-c]pyridin-5-yl)methanol (C54) as a white solid (84% yield). MS (EI) for $C_9H_9NO_2$, m/z: 163 (M)$^+$.

Oxalyl chloride (1.16 mL, 13.2 mmol) is added to $CH_2Cl_2$ (30 mL) in a dry flask under $N_2$ and in a dry-ice/acetone bath at −78° C. DMSO (18.80 mL, 26.5 mmol) is slowly added. The solution is stirred for 20 min, and C54 (1.88 g, 11.5 mmol) is added. The mixture is stirred for 1 h at −78° C., then 30 min at 0–5° C. The material is washed with saturated NaHCO$_3$ (75 mL), dried over $K_2CO_3$, filtered, and concentrated in vacuo to a yellow solid (3.23 g). The crude material is adsorbed onto silica gel (6 g) and chromatographed over a standard 40 g Biotage column, eluting with 25% EtOAc/hexane to afford 3-methylfuro[2,3-c]pyridine-5-carbaldehyde (C55) as a white solid (72% yield). MS (EI) for $C_9H_7NO_2$, m/z: 161 (M)$^+$.

C55 (1.33 g, 8.28 mmol) is dissolved in THF (50 mL), tert-butylalcohol (25 mL) and $H_2O$ (25 mL), under $N_2$, and NaClO$_2$ (2.81 g, 24.84 mmol) and KH$_2$PO$_4$ (2.25 g, 16.56 mmol) are added. The reaction mixture is stirred overnight at rt, concentrated to dryness, dissolved in 50% saturated brine (60 mL) and extracted with ether (3×). TLC of extracts indicates acid as well as residual aldehyde, so the organic and aqueous layers are combined and basified to pH 10 with NH$_4$OH. The layers are separated and the residual aldehyde extracted with additional ether. The aqueous layer is acidified to pH 3 with concentrated HCl, then extracted with $CH_2Cl_2$ (4×). Large amounts of acid remained in the aqueous layer, so the aqueous layer is concentrated to dryness. The solid is triturated with CHCl$_3$ (4×), and then 10% MeOH/$CH_2Cl_2$ (4×) to extract much of the acid into the supernatant. The combined organic layer is dried over Na$_2$SO$_4$, filtered, and concentrated to a tan solid (1.69 g, greater than 100% isolated yield). The solid is diluted with CHCl$_3$ and is heated to reflux for 3 h. The flask is removed from heat, allowed to cool slightly, then filtered. The filtrate is concentrated to a tan solid (1.02 g). The solid is triturated with ether, filtered and dried to afford 3-methylfuro[2,3-c]pyridine-5-carboxylic acid (C56) as a light tan solid (51% yield). MS (CI) for $C_9H_7NO_3$, m/z: 178 (M+H).

Example 7(i) is obtained by coupling exo-(4S)-[2.2.1]-3-Amine with C56, followed by fumarate salt formation as outlined in Steps 1a and 1b, respectively, to afford Example 7(i) in 77% yield. MS for $C_{15}H_{18}N_3O_2$ (ESI) m/e 272 (M+H).

EXAMPLE 7(i-a)

N-(1-(6-methyl)-azabicyclo[2.2.1]hept-3-yl)-3-methylfuro[2,3-c]pyridine-5-carboxamide: This example can be prepared according to the coupling procedures discussed herein.

EXAMPLE 7(ii)

N-(1-(6-methyl)-azabicyclo[2.2.2]oct-3-yl)-3-methylfuro[2,3-c]pyridine-5-carboxamide: This example can be prepared according to the coupling procedures discussed herein.

EXAMPLE 7(iii)

N-(2-azabicyclo[2.2.1]hept-5-yl)-3-methylfuro[2,3-c]pyridine-5-carboxamide: This example can be prepared according to the coupling procedures discussed herein.

EXAMPLE 7(iv)

N-(2-azabicyclo[2.2.1]hept-6-yl)-3-methylfuro[2,3-c]pyridine-5-carboxamide: This example can be prepared according to the coupling procedures discussed herein.

EXAMPLE 7(v)

(exo)-N-[1-Azabicyclo[3.2.1]oct-3-yl]-3-methylfuro[2,3-c]pyridine-5-carboxamide dihydrochloride.

A mixture of exo-[3.2.1]-Amine (0.199 g, 1.00 mmol), C56 (0.177 g, 1.00 mmol), THF (15 mL), DIEA (0.53 mL, 3.02 mmol), and DMF (4 mL) is cooled in an ice bath and treated with HATU (0.380 g, 1.00 mmol). The mixture warmed to ambient temperature and is evaporated. The residue is diluted with $CHCl_3$ and washed with aqueous NaOH (1N). The organic layer is dried ($MgSO_4$), filtered, evaporated, and the resulting oil purified by flash column chromatography (1:7:90; conc. $NH_4OH$—MeOH—$CHCl_3$). The bis-hydrocloride salt is formed and triturated with 2-propanol/acetone to yield the desired product (0.110 g, 30%). MS for $C_{16}H_{19}N_3O_2$+H (ESI) (M+H)$^+$ m/z=286.

EXAMPLE 8(i)

Exo-4(S)-N-(1-azabicyclo[2.2.1]hept-3-yl)-3-ethylfuro[2,3-c]pyridine-5-carboxamide.furmate:

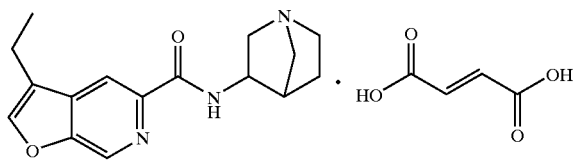

Starting with 1-chloro-2-butene and 2-chloro-6-(hydroxymethyl)-4-iodo-3-pyridinol (C2), the corresponding 3-ethylfuro[2,3-c]pyridine-5-carboxylic acid (C60) was prepared. HRMS (FAB) calculated for $C_{10}H_9NO_3$+H: 192.0661, found 192.0659 (M+H). Example 8 is obtained by coupling exo-4(S)-[2.2.1]-3-Amine with C60 followed by fumarate salt formation as described in Steps 1a and 1b, respectively, to give Example 8(i) in 87% yield. MS for $C_{16}H_{20}N_3O_2$ (ESI) m/e 286 (M+H).

The following examples can be prepared according to the coupling procedures discussed herein:

EXAMPLE 8(i-a)

N-(1-(6-methyl)-azabicyclo[2.2.1]hept-3-yl)-3-ethylfuro[2,3-c]pyridine-5-carboxamide.

EXAMPLE 8(ii)

N-(1-(6-methyl)-azabicyclo[2.2.2]oct-3-yl)-3-ethylfuro[2,3-c]pyridine-5-carboxamide.

EXAMPLE 8(iii)

N-(2-azabicyclo[2.2.1]hept-5-yl)-3-ethylfuro[2,3-c]pyridine-5-carboxamide.

EXAMPLE 8(iv)

N-(2-azabicyclo[2.2.1]hept-6-yl)-3-ethylfuro[2,3-c]pyridine-5-carboxamide.

EXAMPLE 8(v)

N-((3R,5R)-1-azabicyclo[3.2.1]oct-3-yl)-3-ethylfuro[2,3-c]pyridine-5-carboxamide.

EXAMPLE 10(i)

N-(1-azabicyclo[2.2.1]hept-3-yl)-furo[2,3-b]pyridine-2-carboxamide:

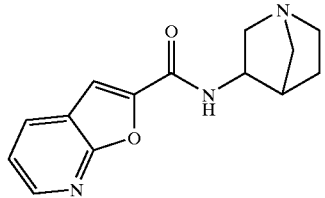

Ethyl glycolate (35.5 mL, 375 mmol) is slowly added (over 20 minutes) to a slurry of NaOH (15.8 g, 394 mmol) in 1,2-dimethoxyethane (400 mL) under $N_2$ with the flask being in an ice bath. The mixture is allowed to warm to rt, is stirred for 30 min, and ethyl 2-chloronicotinate (27.84 g, 150 mmol) in 1,2-dimethoxyethane (50 mL) is added over 10 minutes. The reaction is warmed to 65° C. for 15 h in an oil bath. The mixture is concentrated to dryness, the residue is dissolved in $H_2O$ (500 mL), washed with hexane (500 mL), acidified to pH 3 with 5% HCl, and extracted with $CHCl_3$ (4×400 mL). The combined organic layer is dried over $MgSO_4$, filtered, and concentrated to a yellow solid. The solid is suspended in ether (200 mL) and heated on a steam bath until concentrated to a volume of 40 mL. The material is allowed to crystallize overnight, then filtered to afford ethyl 3-hydroxyfuro[2,3-b]pyridine-2-carboxylate (C40) as a pale orange solid (41% yield). Additional material is obtained by concentrating the filtrate. Recrystallization in ether a second time afforded (C40) as a pale yellow solid (7.3% yield). MS (EI) for $C_{10}H_9NO_4$, m/z: 207 (M)$^+$.

C40 (207 mg, 1.0 mmol) is added to TEA (139 μL, 1.0 mmol) in $CH_2Cl_2$ (5 mL) at rt and 2-[N,N-bis(trifluoromethylsulfonyl)amino]-5-chloropyridine (393 mg, 1.0 mmol) is added. The solution is stirred for 1 h at rt, diluted with EtOAc (25 mL) and washed with 50% saturated brine (2×15 mL). The organic layer is dried over $Na_2SO_4$, filtered, and concentrated to a yellow oil which solidified upon standing. The crude material is adsorbed onto silica gel (1.2 g) and chromatographed over 25 g slurry-packed silica gel, eluting with 20% EtOAc/hexane to afford ethyl 3-([(trifluoromethyl)sulfonyl]oxy)furo[2,3-b]pyridine-2-carboxylate (C41) as a white crystalline solid (98% yield). Analysis calculated for $C_{11}H_8F_3NO_6S$: C, 38.94; H, 2.38; N, 4.13, found: C, 38.84; H, 2.29; N, 4.11.

C41 (1.36 g, 4.0 mmol) is added to 10% Pd/C catalyst (68 mg) and $NaHCO_3$ (336 mg, 4.0 mmol) in EtOH (100 mL)/$H_2O$ (5 mL) in a 250 mL Parr shaker bottle. The mixture is hydrogenated at 10 PSI for 5 h, filtered and concentrated to a residue. The residue is partitioned between 50% saturated $NaHCO_3$ (80 mL) and EtOAc (80 mL). The organic layer is dried over $Na_2SO_4$, filtered, and concentrated in vacuo to a colorless oil which solidified upon standing (793 mg). The crude material is chromatographed over 40 g slurry-packed silica gel, eluting with 25% EtOAc/hexane to afford ethyl furo[2,3-b]pyridine-2-carboxylate (C42) as a white solid (90% yield). MS (EI) for $C_{10}H_9NO_3$, m/z: 191 (M)$^+$.

C42 (758 mg, 3.96 mmol) is dissolved in MeOH (20 mL) and lithium hydroxide monohydrate (366 mg, 8.7 mmol) in 6 mL $H_2O$ is added under $N_2$. The reaction is stirred at rt for 2 h, concentrated to near-dryness, diluted with $H_2O$ (5 mL) and acidified to pH 3 with 10% HCl. The resulting solid is collected by filtration, washed with additional water and dried to afford furo[2,3-b]pyridine-2-carboxylic acid (C43) as a white solid (97% yield). MS (EI) for $C_8H_5NO_3$, m/z: 163 (M)+.

Example 10(i) can be obtained by coupling either exo-[2.2.1]-3-Amine or endo-[2.2.1]-3-Amine with C43.

The following examples can be prepared according to the coupling procedures discussed herein:

EXAMPLE 10(i-a)

N-(1-(6-methyl)-azabicyclo[2.2.1]hept-3-yl)-furo[2,3-b]pyridine-2-carboxamide.

EXAMPLE 10(ii)

N-(1-(6-methyl)-azabicyclo[2.2.2]oct-3-yl)-furo[2,3-b]pyridine-2-carboxamide.

EXAMPLE 10(iii)

N-(2-azabicyclo[2.2.1]hept-5-yl)-furo[2,3-b]pyridine-2-carboxamide.

EXAMPLE 10(iv)

N-(2-azabicyclo[2.2.1]hept-6-yl)-furo[2,3-b]pyridine-2-carboxamide.

EXAMPLE 10(v)

N-((3R,5R)-1-azabicyclo[3.2.1]oct-3-yl)-furo[2,3-b]pyridine-2-carboxamide.

EXAMPLE 10(vi)

N-(1-azabicyclo[3.2.2]non-3-yl)-furo[2,3-b]pyridine-2-carboxamide.

EXAMPLE 11(i)

Exo-4(S)-N-(1-azabicyclo[2.2.1]hept-3-yl)-3-isopropylfuro[2,3-c]pyridine-5-carboxamide.fumarate:

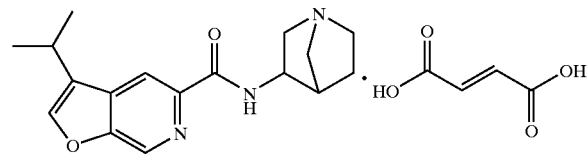

Using the method used to make the acid for Example 7(i) with non-critical changes 3-isopropylfuro[2,3-c]pyridine-5-carboxylic acid (C70) is made starting with 1-chloro-3-methyl-2-butene and 2-chloro-6-(hydroxymethyl)-4-iodo-3-pyridinol (C2). HRMS (FAB) calculated for $C_{11}H_{11}NO_3$+H: 206.0817, found 206.0817 (M+H)+.

Example 11(i) is obtained by coupling exo-(4S)-[2.2.1]-3-Amine with C70, followed by fumarate salt formation as outlined in Steps 1a and 1b, respectively, to give Example 11(i) in 89% yield. MS for $C_{17}H_{22}N_3O_2$ (ESI) m/e: 300 (M+H).

The following examples can be prepared according to the coupling procedures discussed herein:

EXAMPLE 11(i-a)

N-(1-(6-methyl)-azabicyclo[2.2.1]hept-3-yl)-3-isopropylfuro[2,3-c]pyridine-5-carboxamide.

EXAMPLE 11(ii)

N-(1-(6-methyl)-azabicyclo[2.2.2]oct-3-yl)-3-isopropylfuro[2,3-c]pyridine-5-carboxamide.

EXAMPLE 11(iii)

N-(2-azabicyclo[2.2.1]hept-5-yl)-3-isopropylfuro[2,3-c]pyridine-5-carboxamide.

EXAMPLE 11(iv)

N-(2-azabicyclo[2.2.1]hept-6-yl)-3-isopropylfuro[2,3-c]pyridine-5-carboxamide.

EXAMPLE 11(v)

N-((3R,5R)-1-azabicyclo[3.2.1]oct-3-yl)-3-isopropylfuro[2,3-c]pyridine-5-carboxamide.

EXAMPLE 12(i)

N-(1-azabicyclo[2.2.1]hept-3-yl)-7-(methylsulfanyl)furo[2,3-c]pyridine-5-carboxamide:

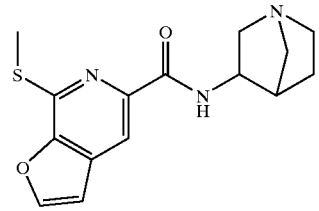

Example 12(i) can be obtained by adding Example 4(i) (0.72 mmol) and sodium thiomethoxide (0.79 mmol) to DMF (3 mL) and stirring until Example 4(i) is not present by TLC. The reaction mixture can then be diluted with MeOH and loaded onto a column of AG 50W-X2 resin (hydrogen form), rinsing with MeOH, and eluting the product with approximately 5% TEA/MeOH solution onto a column of AMBER-JET 4400 OH resin. The crude material can be further purified by chromatography over slurry-packed silica gel, eluting with approximately 0.5% $NH_4OH$/8% MeOH/$CH_2Cl_2$.

The following examples can be prepared according to the coupling procedures discussed herein:

EXAMPLE 12(-a)

N-(1-(6-methyl)-azabicyclo[2.2.1]hept-3-yl)-7-(methylsulfanyl)furo[2,3-c]pyridine-5-carboxamide.

EXAMPLE 12(ii)

N-(1-(6-methyl)-azabicyclo[2.2.2]oct-3-yl)-7-(methylsulfanyl)furo[2,3-c]pyridine-5-carboxamide.

EXAMPLE 12(iii)

N-(2-azabicyclo[2.2.1]hept-5-yl)-7-(methylsulfanyl)furo[2,3-c]pyridine-5-carboxamide.

EXAMPLE 12(iv)

N-(2-azabicyclo[2.2.1]hept-6-yl)-7-(methylsulfanyl)furo[2,3-c]pyridine-5-carboxamide.

EXAMPLE 12(v)

N-((3R,5R)-1-azabicyclo[3.2.1]oct-3-yl)-7-(methylsulfanyl)furo[2,3-c]pyridine-5-carboxamide.

EXAMPLE 13(i)

N-(1-azabicyclo[2.2.1]hept-3-yl)-thieno[2,3-b]pyridine-2-carboxamide:

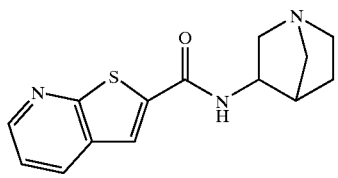

THF (200 mL) in a dry flask under $N_2$ is chilled by placing the flask in a dry-ice/acetone bath at −78° C. Butyllithium (125 mL, 200 mmol) is added drop-wise, followed by the drop-wise addition of iodobenzene (11.19 mL, 100 mmol) in THF (10 mL). The solution is allowed to stir for 30 min at −78° C. Diisopropylamine (0.70 mL, 5 mmol) in THF (3 mL) and 2-chloropyridine (9.46 mL, 100 mmol) in THF (30 mL) are added successively in a drop-wise manner, and the solution is stirred for 1 h at −40° C. Formyl piperidine (11.1 mL, 100 mmol) in THF (25 mL) is added drop-wise, and the solution is stirred for 1 h at −40° C. The reaction is quenched with 40 mL 6N HCl, diluted with 250 mL ether, and a small amount of sodium thiosulfate solution is added to remove the iodine color. The solution is neutralized with saturated $NaHCO_3$, filtered, and extracted with ether (3×150 mL). The combined organic layer is dried over $Na_2SO_4$, filtered, and concentrated in vacuo. The crude material is chromatographed over 600 g slurry-packed silica, eluting with 20% EtOAc/hexane to afford 2-chloronicotinaldehyde (C90) as a pale orange solid (54% yield). MS (EI) for $C_6H_4ClNO$, m/z: 141 (M)$^+$.

C90 (1.41 g, 10.01 mmol) is dissolved in DMF (10 mL) and $H_2O$ (1 mL) under $N_2$. $K_2CO_3$ (1.56 g, 11.27 mmol) and methyl thioglycolate (1.00 mL, 11.25 mmol) are added portionwise. The reaction is stirred at 35° C. for 24 h, quenched with cold $H_2O$ (75 mL), and placed in an ice bath to enhance precipitation. The precipitate is isolated by filtration, affording methyl-thieno[2,3-b]pyridine-2-carboxylate (C101) as an orange powder (40% yield). MS (EI) for $C_9H_7NO_2S$, m/z: 193 (M)$^+$.

C101 (0.700 g, 3.63 mmol) is dissolved in MeOH (15 mL) and 3 mL $H_2O$. 2N NaOH (1.82 mL, 3.63 mmol) is added drop-wise, and the reaction is stirred at rt for 24 h. The reaction is concentrated in vacuo, and $H_2O$ (40 mL) is added to dissolve the residue. The resulting solution is acidified to pH 4 using concentrated HCl, and the precipitate is isolated by filtration, yielding thieno[2,3-b]pyridine-2-carboxylic acid (C102) as a white powder (85% yield). MS (EI) for $C_8H_5NO_2S$, m/z: 179 (M)$^+$.

Example 13(i) can be obtained by coupling either exo-[2.2.1]-3-Amine or endo-[2.2.1]-3-Amine with C102.

The following examples can be prepared according to the coupling procedures discussed herein:

EXAMPLE 13(i-a)

N-(1-(6-methyl)-azabicyclo[2.2.1]hept-3-yl)-thieno[2,3-b]pyridine-2-carboxamide.

EXAMPLE 13(ii)

N-(1-(6-methyl)-azabicyclo[2.2.2]oct-3-yl)-thieno[2,3-b]pyridine-2-carboxamide.

EXAMPLE 13(iii)

N-(2-azabicyclo[2.2.1]hept-5-yl)-thieno[2,3-b]pyridine-2-carboxamide.

EXAMPLE 13(iv)

N-(2-azabicyclo[2.2.1]hept-6-yl)-thieno[2,3-b]pyridine-2-carboxamide.

EXAMPLE 13(v)

N-((3R,5R)-1-azabicyclo[3.2.1]oct-3-yl)-thieno[2,3-b]pyridine-2-carboxamide.

EXAMPLE 13(vi)

N-(1-azabicyclo[3.2.2]non-3-yl)-thieno[2,3-b]pyridine-2-carboxamide.

EXAMPLE 14(i)

N-(1-azabicyclo[2.2.1]hept-3-yl)-thieno[2,3-b]pyridine-5-carboxamide:

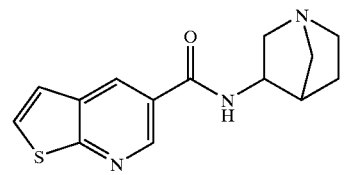

2-Nitrothiophene (33.76 g, 261.4 mmol) is suspended in concentrated HCl (175 mL) and heated to 50° C. Stannous chloride (118.05 g, 523.2 mmol) is added portionwise, maintaining the reaction temperature between 45–50° C. with an ice bath, that is removed after the addition. The solution is allowed to cool slowly to 30° C. over an hour. The solution is then cooled in an ice bath and filtered. The cake is washed with concentrated HCl (20 mL), dried in a stream of air, and washed with ether (50 mL) to afford the hexachlorostannate salt of 2-aminothiophene as a brown solid (26% yield).

3,3-Dimethyl-2-formyl propionitrile sodium (3.33 g, 20.2 mmol) can readily be prepared from the method described by Bertz, S. H., et al., *J. Org. Chem.*, 47, 2216–2217 (1982). 3,3-Dimethyl-2-formyl propionitrile sodium is dissolved in MeOH (40 mL), and concentrated HCl (4 mL) and the hexachlorostannate salt of 2-aminothiophene (10.04 g, 19.1 mmol) in MeOH (130 mL) is slowly added drop-wise to the mixture. Following addition, the mixture is heated to reflux in an oil bath (80° C.) for 4 h, and then MeOH (10 mL) and concentrated HCl (10 mL) are added. The reaction continued refluxing for another 20 h. The solution is cooled to rt, and the reaction is concentrated in vacuo. The purple residue is dissolved in $H_2O$ (60 mL), and the slurry is filtered. The cake is pulverized and stirred vigorously with 5% MeOH/$CHCl_3$ (105 mL) while heating to 55° C. The mixture is cooled and filtered, and the organic layer is concentrated to a green oil. The crude material is chromatographed over 130 g slurry-packed silica, eluting with 30% EtOAc/hexane to afford thieno[2,3-b]pyridine-5-carbonitrile (C105) as a pale yellow solid (24% yield). HRMS (FAB) calculated for $C_8H_4N_2S+$ H: 161.0173, found 161.0173 (M+H).

NaOH (0.138 g, 3.45 mmol) is added to a solution of C105 (0.503 g, 3.14 mmol) dissolved in 70% EtOH/$H_2O$ (12 mL). The mixture is heated to reflux at 100° C. for 3 h. The reaction is concentrated in vacuo, and the residue is dissolved in $H_2O$ (8 mL) and neutralized with concentrated HCl. The slurry is filtered and rinsed with ether. An initial NMR of the isolated material indicates the presence of the carboxamide intermediate, so the material is suspended in 1M NaOH (6 mL) and stirred overnight. Water (10 mL) is added, the solution is extracted with ether (3×10 mL), and the mixture is neutralized with concentrated HCl. The slurry is filtered and rinsed with ether, affording of thieno[2,3-b]pyridine-5-carboxylic acid (C106) as an off-white solid (48% yield). MS (EI) for $C_8H_5NO_2S$, m/z: 179 (M)$^+$.

Example 14(i) can be obtained by coupling either exo-[2.2.1]-3-Amine or endo-[2.2.1]-3-Amine with C106.

The following examples can be prepared according to the coupling procedures discussed herein:

EXAMPLE 14(i-a)

N-(1-(6-methyl)-azabicyclo[2.2.1]hept-3-yl)-thieno[2,3-b]pyridine-5-carboxamide.

EXAMPLE 14(ii)

N-(1-(6-methyl)-azabicyclo[2.2.2]oct-3-yl)-thieno[2,3-b]pyridine-5-carboxamide.

EXAMPLE 14(iii)

N-(2-azabicyclo[2.2.1]hept-5-yl)-thieno[2,3-b]pyridine-5-carboxamide.

EXAMPLE 14(iv)

N-(2-azabicyclo[2.2.1]hept-6-yl)-thieno[2,3-b]pyridine-5-carboxamide.

EXAMPLE 14(v)

N-((3R,5R)-1-azabicyclo[3.2.1]oct-3-yl)thieno[2,3-b]pyridine-5-carboxamide.

EXAMPLE 14(vi)

N-(1-azabicyclo[3.2.2]non-3-yl)-thieno[2,3-b]pyridine-5-carboxamide.

EXAMPLE 15(i)

N-(1-azabicyclo[2.2.1]hept-3-yl)-thieno[2,3-b]pyridine-6-carboxamide:

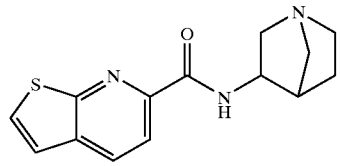

2-Nitrothiophene (12.9 g, 99.9 mmol) is dissolved in concentrated HCl (200 mL) and stirred vigorously at 30° C. Granular tin (25 g, 210 mmol) is slowly added portionwise. When the tin is completely dissolved, zinc chloride (6.1 g, 44.7 mmol) in EtOH (70 mL) is added drop-wise, the mixture is heated to 85° C., and malondialdehyde diethyl acetal (24 mL, 100 mmol) in EtOH (30 mL) is added. The solution continued stirring at 85° C. for 1 h, and is quenched by pouring over ice (100 g). The mixture is adjusted to pH 10 with NH$_4$OH, and the resulting slurry is carefully filtered through celite overnight. The liquor is extracted with CHCl$_3$ (3×300 mL), and the combined organic layer is dried over MgSO$_4$, filtered, and concentrated to a brown oil. The crude material is chromatographed over 250 g slurry-packed silica, eluting with 35% EtOAc/hexane to give thieno[2,3-b]pyridine (C110) as an orange oil (26% yield). MS (EI) for $C_7H_5NS$, m/z: 135 (M)$^+$.

C110 (3.47 g, 25.7 mmol) is dissolved in acetic acid (12 mL) and heated to 85° C. 30% Hydrogen peroxide (9 mL) is added drop-wise and the solution is allowed to stir overnight. The reaction is allowed to cool to rt and quenched with paraformaldehyde until a peroxide test proved negative using starch-iodine paper. The solution is diluted with H$_2$O (100 mL) and neutralized with NaHCO$_3$, then extracted repeatedly with CHCl$_3$ (12×80 mL, 6×50 mL). The combined organic layer is dried over Na$_2$SO$_4$, filtered, and concentrated to a brown solid. The crude material is chromatographed over 70 g slurry-packed silica eluting with 3.5% MeOH/CH$_2$Cl$_2$ to afford thieno[2,3-b]pyridine-7-oxide (C111) as a pale yellow solid (22% yield). MS (EI) for $C_7H_5NOS$ m/z: 151 (M)$^+$.

A 0.5M solution of C111 (5 mL, 2.5 mmol) in CH$_2$Cl$_2$ is diluted with 8 mL of CH$_2$Cl$_2$ under N$_2$. Dimethyl carbamyl chloride (0.27 mL, 2.9 mmol) is added drop-wise, followed by the addition of trimethylsilyl cyanide (0.388 mL, 2.9 mmol) via syringe. The reaction is allowed to stir for 9 days and is quenched with 10% K$_2$CO$_3$ (10 mL). The layers are allowed to separate, the organic layer is isolated and dried over K$_2$CO$_3$, filtered, and concentrated to a brown solid. The crude material is chromatographed over 25 g slurry-packed silica, eluting with 35% EtOAc/hexane to afford thieno[2,3-b]pyridine-6-carbonitrile (C112) as a pale yellow solid (100% yield). Analysis calculated for $C_8H_4N_2S$: C, 59.98; H, 2.52; N, 17.49, found: C, 59.91; H, 2.57; N, 17.43.

NaOH (398 mg, 9.95 mmol) is added portionwise to a solution of C112 (674 mg, 4.2 mmol) in 70% EtOH/H$_2$O (20 mL). The solution is heated to reflux at 100° C. for 24 h, and the reaction is concentrated in vacuo. The residue is dissolved in H$_2$O (15 mL) and washed with ether (3×10 mL). Concentrated HCl is used to adjust the pH to 3.5, creating a precipitate. The slurry is filtered, giving thieno[2,3-b]pyridine-6-carboxylic acid (C113) as a white solid (45% yield). MS (EI) for $C_8H_5NO_2S$, m/z: 179(M)$^+$.

Example 15(i) can be obtained by coupling either exo-[2.2.1]-3-Amine or endo-[2.2.1]-3-Amine with C113.

The following examples can be prepared according to the coupling procedures discussed herein:

EXAMPLE 15(i-a)

N-(1-(6-methyl)-azabicyclo[2.2.1]hept-3-yl)-thieno[2,3-b]pyridine-6-carboxamide.

EXAMPLE 15(ii)

N-(1-(6-methyl)-azabicyclo[2.2.2]oct-3-yl)-thieno[2,3-b]pyridine-6-carboxamide.

EXAMPLE 15(iii)

N-(2-azabicyclo[2.2.1]hept-5-yl)-thieno[2,3-b]pyridine-6-carboxamide.

EXAMPLE 15(iv)

N-(2-azabicyclo[2.2.1]hept-6-yl)-thieno[2,3-b]pyridine-6-carboxamide.

EXAMPLE 15(v)

N-((3R,5R)-1-azabicyclo[3.2.1]oct-3-yl)-thieno[2,3-b]pyridine-6-carboxamide.

EXAMPLE 15(vi)

N-(1-azabicyclo[3.2.2]non-3-yl)-thieno[2,3-b]pyridine-6-carboxamide.

EXAMPLE 16(i)

N-(1-azabicyclo[2.2.1]hept-3-yl)-thieno[2,3-c]pyridine-2-carboxamide:

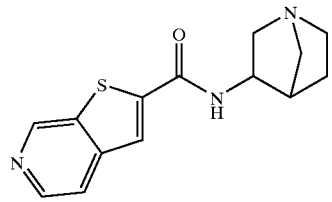

THF (200 mL) is chilled to −70° C. in a dry flask under $N_2$, and N-butyllithium (24.4 mL, 55.0 mmol) is added drop-wise. The reaction is placed in an ice bath and DIA (7.71 mL, 55.0 mmol) in THF (20 mL) is added drop-wise. The solution is again chilled to −70° C., and 3-chloropyridine (4.75 mL, 50.0 mmol) in THF (20 mL) is added drop-wise. The reaction is allowed to stir for 4 h at −70° C. and ethyl formate (4.44 mL, 55.0 mmol) in THF (20 mL) is added. The reaction is stirred for an additional 3 h at −70° C. and quenched with $H_2O$ (500 mL). The layers are allowed to separate, and the aqueous layer is extracted with EtOAc (3×250 mL). The combined organic layer is dried over $MgSO_4$, filtered, and concentrated to a dark brown solid. The crude material is chromatographed over 250 g slurry-packed silica, eluting with 50% EtOAc/hexane to give 3-chloroisonicotinaldehyde (C120) as an off-white solid (55% yield). MS (EI) for $C_6H_4ClNO$, m/z: 141 (M)$^+$.

C120 (2.12 g, 14.9 mmol) is dissolved in DMF (75 mL) with a small amount of $H_2O$ (7.5 mL). Methyl thioglycolate (1.67 mL, 18.7 mmol) and $K_2CO_3$ (2.59 g, 18.7 mmol) are added portionwise, and the mixture is stirred at 45° C. for 24 h. The reaction is quenched with cold $H_2O$ (200 mL) and extracted with EtOAc (3×150 mL). The combined organic layer is washed with 50% NaCl solution (3×150 mL), dried over $MgSO_4$, filtered, and concentrated to an orange solid. The crude material is chromatographed over 40 g slurry-packed silica, eluting with 50% EtOAc/hexane to afford ethyl thieno[2,3-c]pyridine-2-carboxylate (C121) as a pale yellow solid (22% yield).

C121 (577 mg, 2.99 mmol) is combined with 2M NaOH (1.5 mL, 3.0 mmol) in MeOH (15 mL) and $H_2O$ (1.5 mL). The reaction is stirred at rt for 24 h. The reaction is concentrated in vacuo and the residue is dissolved in $H_2O$ (75 mL). Concentrated HCl is used to acidify the solution to pH 3. The slurry is filtered, washed with $H_2O$ and ether, and dried, affording thieno[2,3-c]pyridine-2-carboxylic acid (C122) as an off-white solid (38% yield). HRMS (FAB) calculated for $C_8H_5NO_2S+H$: 180.0119, found 180.0119 (M+H).

Example 16(i) can be obtained by coupling either exo-[2.2.1]-3-Amine or endo-[2.2.1]-3-Amine with C122.

The following examples can be prepared according to the coupling procedures discussed herein:

EXAMPLE 16(i-a)

N-(1-(6-methyl)-azabicyclo[2.2.1]hept-3-yl)-thieno[2,3-c]pyridine-2-carboxamide.

EXAMPLE 16(ii)

N-(1-(6-methyl)-azabicyclo[2.2.2]oct-3-yl)-thieno[2,3-c]pyridine-2-carboxamide.

EXAMPLE 16(iii)

N-(2-azabicyclo[2.2.1]hept-5-yl)-thieno[2,3-c]pyridine-2-carboxamide.

EXAMPLE 16(iv)

N-(2-azabicyclo[2.2.1]hept-6-yl)-thieno[2,3-c]pyridine-2-carboxamide.

EXAMPLE 16(v)

N-((3R,5R)-1-azabicyclo[3.2.1]oct-3-yl)-thieno[2,3-c]pyridine-2-carboxamide.

EXAMPLE 16(vi)

N-(1-azabicyclo[3.2.2]non-3-yl)-thieno[2,3-c]pyridine-2-carboxamide.

EXAMPLE 17(i)

N-(1-azabicyclo[2.2.1]hept-3-yl)-thieno[3,2-b]pyridine-2-carboxamide:

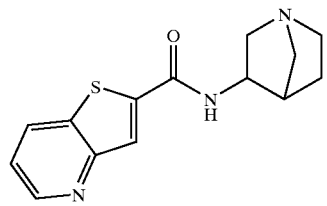

3-Chloropyridine (9.5 mL. 99.9 mmol) is dissolved in acetic acid (35 mL) and heated to 98° C. 30% Hydrogen peroxide (28 mL) is added drop-wise, and the reaction stirred for 5 h at 98° C. The reaction is cooled and paraformaldehyde is added so that a negative peroxide test is achieved using starch-iodine paper. The solution is concentrated in vacuo and the crude paste is chromatographed over 600 g slurry-packed silica eluting with 4 L of 2% MeOH/$CH_2Cl_2$, 2 L of 4% MeOH/$CH_2Cl_2$, and finally 1 L of 10% MeOH/$CH_2Cl_2$ to afford 3-chloropyridine 1-oxide (C125) as a pale oil (100% yield).

A 2M solution of C125 (10 mL, 20 mmol) is combined with an additional 90 mL of $CH_2Cl_2$. Dimethylcarbamoyl chloride (2.03 mL, 22.0 mmol) is added drop-wise, followed by the addition of trimethyl silylcyanide (2.93 mL, 22.0 mmol) via syringe. The reaction is stirred at rt for 10 days and is quenched with 10% $K_2CO_3$ (100 mL). The layers are allowed to separate, and the organic layer is dried over $K_2CO_3$, filtered, and concentrated to an orange solid. The crude material is chromatographed over 160 g slurry-packed silica eluting with 40% EtOAc/hexane to yield 3-chloropyridine-2-carbonitrile (C126) as a white solid (59% yield). MS (EI) for $C_6H_3ClN_2$, m/z: 138 (M)$^+$.

C126 (1.01 g, 7.29 mmol) and $K_2CO_3$ (1.10 g, 7.96 mmol) are added to DMF (10 mL) and $H_2O$ (1 mL). Methyl thioglycolate (0.709 mL, 7.93 mmol) is added drop-wise, and the solution is heated to 40° C. and stirred for 3 h. The reaction is quenched with cold $H_2O$ (70 mL) and placed on ice to enhance precipitation. The slurry is filtered and the cake is dissolved in $CHCl_3$. This organic solution is dried over $MgSO_4$, filtered, and concentrated, affording methyl 3-aminothieno[3,2-b]pyridine-2-carboxylate (C127) as a yellow solid (84% yield). HRMS (FAB) calculated for $C_9H_8N_2O_2S+H$: 209.0385, found 209.0383 (M+H).

C127 (0.919 g, 4.42 mmol) is dissolved in 50% hypophosphorous acid (35 mL) and chilled in an ice bath. Sodium nitrite (0.61 g, 8.84 mmol) is dissolved in a minimal amount of $H_2O$ and added drop-wise to the previous solution, and the reaction is stirred for 3 h in an ice bath. 3M NaOH is used to adjust the pH to 7.9, and the solution is extracted with EtOAc (3×100 mL). The combined organic layer is dried over MgSO$_4$, filtered, and concentrated to afford methyl thieno[3,2-b]pyridine-2-carboxylate (C128) as a yellow solid (44% yield). MS (EI) for C$_9$H$_7$NO$_2$S, m/z: 193 (M)$^+$.

2M NaOH (0.8 mL, 1.6 mmol) and C128 (300 mg, 1.55 mmol) are added to MeOH (8 mL) and H$_2$O (1 mL) and is stirred for 24 h. The reaction is concentrated in vacuo, and the residue is dissolved with H$_2$O (5 mL). 5% HCl is used to adjust the pH to 3.5, creating a precipitate. The slurry is filtered and washed with ether, affording thieno[3,2-b] pyridine-2-carboxylic acid (C129) as a brown solid (67% yield). HRMS (FAB) calculated for C$_8$H$_5$NO$_2$S+H: 180.0119, found 180.0121 (M+H).

Example 17(i) can be obtained by coupling either exo-[2.2.1]-3-Amine or endo-[2.2.1]-3-Amine with C129.

The following examples can be prepared according to the coupling procedures discussed herein:

EXAMPLE 17(i-a)

N-(1-(6-methyl)-azabicyclo[2.2.1]hept-3-yl)-thieno[3,2-b]pyridine-2-carboxamide.

EXAMPLE 17(ii)

N-(1-(6-methyl)-azabicyclo[2.2.2]oct-3-yl)-thieno[3,2-b]pyridine-2-carboxamide.

EXAMPLE 17(iii)

N-(2-azabicyclo[2.2.1]hept-5-yl)-thieno[3,2-b]pyridine-2-carboxamide.

EXAMPLE 17(iv)

N-(2-azabicyclo[2.2.1]hept-6-yl)-thieno[3,2-b]pyridine-2-carboxamide.

EXAMPLE 17(v)

N-((3R,5R)-1-azabicyclo[3.2.1]oct-3-yl)-thieno[3,2-b]pyridine-2-carboxamide.

EXAMPLE 17(vi)

N-(1-azabicyclo[3.2.2]non-3-yl)-thieno[3,2-b]pyridine-2-carboxamide.

EXAMPLE 18(i)

N-(1-azabicyclo[2.2.1]hept-3-yl)-thieno[3,2-b]pyridine-5-carboxamide:

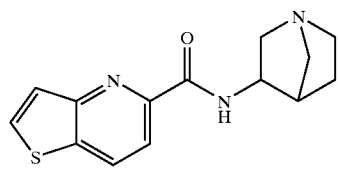

Example 18(i) can be obtained by coupling either exo-[2.2.1]-3-Amine or endo-[2.2.1]-3-Amine with commercially-available thieno[3,2-b]pyridine-5-carboxylic acid.

The following examples can be prepared according to the coupling procedures discussed herein:

EXAMPLE 18(i-a)

N-(1-(6-methyl)-azabicyclo[2.2.1]hept-3-yl)-thieno[3,2-b]pyridine-5-carboxamide.

EXAMPLE 18(ii)

N-(1-(6-methyl)-azabicyclo[2.2.2]oct-3-yl)-thieno[3,2-b]pyridine-5-carboxamide.

EXAMPLE 18(iii)

N-(2-azabicyclo[2.2.1]hept-5-yl)-thieno[3,2-b]pyridine-5-carboxamide.

EXAMPLE 18(iv)

N-(2-azabicyclo[2.2.1]hept-6-yl)-thieno[3,2-b]pyridine-5-carboxamide.

EXAMPLE 18(v)

N-((3R,5R)-1-azabicyclo[3.2.1]oct-3-yl)-thieno[3,2-b]pyridine-5-carboxamide.

EXAMPLE 18(vi)

N-(1-azabicyclo[3.2.2]non-3-yl)-thieno[3,2-b]pyridine-5-carboxamide.

EXAMPLE 19(i)

N-(1-azabicyclo[2.2.1]hept-3-yl)-thieno[3,2-b]pyridine-6-carboxamide:

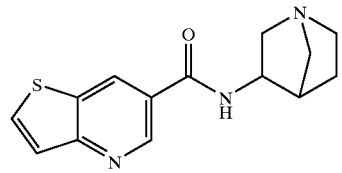

Methyl 3-aminothiophene-2-carboxylate (1.52 g, 9.68 mmol) is dissolved in 2M NaOH (10 mL, 20 mmol) and heated to reflux in a 115° C. oil bath for 30 min. The mixture is cooled to rt, placed in an ice bath, and carefully acidified with concentrated HCl. The slurry is filtered and rinsed with H$_2$O (25 mL). The cake is then dissolved in acetone (50 mL), dried over MgSO$_4$, filtered, and concentrated to a thick paste. The crude material is dissolved in 1-propanol (25 mL), and oxalic acid (0.90 g, 10.0 mmol) is added portionwise. The mixture is heated at 38° C. for 45 min, cooled to rt, and diluted with ether. The precipitate is isolated via filtration, and washed with ether, affording 3-aminothiophene oxalate (C135) as a fluffy white solid (70% yield). HRMS (FAB) calculated for C$_4$H$_5$NS+H: 100.0221, found 100.0229 (M+H).

3,3-Dimethyl-2-formyl propionitrile sodium (5.38 g, 32.6 mmol) is dissolved in MeOH (60 mL) with concentrated HCl (6 mL). C135 (6.16 g, 32.6 mmol) is suspended in MeOH (200 mL) and added drop-wise to the acidic solution. The mixture is heated to reflux at 80° C. for 5 h when an additional 20 mL concentrated HCl and 20 mL H$_2$O are added; the mixture continues refluxing for another 12 h. The mixture is concentrated in vacuo, and the residue is dissolved with cold H$_2$O (100 mL). The resulting precipitate is filtered off and dried, giving thieno[3,2-b]pyridine-6-carbonitrile (C136) as a brown solid (44% yield). HRMS (FAB) calculated for C$_8$H$_4$N$_2$S+H: 161.0173, found 161.0170 (M+H).

C136 (1.99 g, 12.5 mmol) is dissolved in 70% EtOH/H$_2$O (20 mL), and NaOH (0.52 g, 13.0 mmol) is added portionwise. The mixture is heated at 100° C. for 15 h and then allowed to cool to rt. The mixture is concentrated in vacuo.

The residue is dissolved in cold H$_2$O (30 mL), and the solution is rinsed with ether (3×10 mL). The pH is adjusted to 3.5 with concentrated HCl to precipitate the desired product that is removed by filtration to give thieno[3,2-b] pyridine-6-carboxylic acid (C137) as a tan solid (77% yield). HRMS (FAB) calculated for C$_8$H$_5$NO$_2$S+H: 180.0119, found 180.0118 (M+H).

Example 19(i) can be obtained by coupling either exo-[2.2.1]-3-Amine or endo-[2.2.1]-3-Amine with C137.

The following examples can be prepared according to the coupling procedures discussed herein:

EXAMPLE 19(i)

N-(1-(6-methyl)-azabicyclo[2.2.1]hept-3-yl)-thieno[3,2-b]pyridine-6-carboxamide.

EXAMPLE 19(ii)

N-(1-(6-methyl)-azabicyclo[2.2.2]oct-3-yl)-thieno[3,2-b]pyridine-6-carboxamide.

EXAMPLE 19(iii)

N-(2-azabicyclo[2.2.1]hept-5-yl)-thieno[3,2-b]pyridine-6-carboxamide.

EXAMPLE 19(iv)

N-(2-azabicyclo[2.2.1]hept-6-yl)-thieno[3,2-b]pyridine-6-carboxamide.

EXAMPLE 19(v)

N-((3R,5R)-1-azabicyclo[3.2.1]oct-3-yl)-thieno[3,2-b]pyridine-6-carboxamide.

EXAMPLE 19(vi)

N-(1-azabicyclo[3.2.2]non-3-yl)-thieno[3,2-b]pyridine-6-carboxamide.

EXAMPLE 20(i)

N-(1-azabicyclo[2.2.1]hept-3-yl)-thieno[3,2-c]pyridine-2-carboxamide:

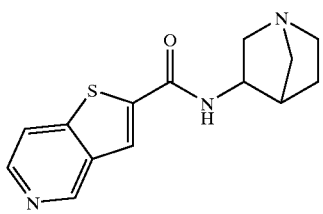

4-Chloropyridine hydrochloride (15 g, 99.9 mmol) is free-based by stirring in 1000 mL 1:1 saturated NaHCO$_3$/ether for 1 h. The layers are allowed to separate, the aqueous layer is extracted with ether (2×175 mL), and the combined organic layer is dried over MgSO$_4$, filtered, and concentrated to an oil. THF (300 mL) is chilled to −70° C. in a dry flask. N-butyllithium (105.1 mL, 168.2 mmol) is added drop-wise, and the mixture is placed in an ice bath. Diisopropylamine (23.6 mL. 168.4 mmol) in THF (50 mL) is added drop-wise, the yellow solution is stirred for 30 min, and the reaction is cooled to −70° C. The free-based 4-chloropyridine oil (9.55 g, 84.1 mmol) is dissolved in THF (50 mL) and added drop-wise to the chilled yellow solution, that turned dark red after the addition. The reaction is stirred at −70° C. for 2 h. Ethyl formate (13.6 mL, 168.3 mmol) in THF (25 mL) is then added drop-wise to the dark solution at −70° C. After 2 hours, the reaction is warmed to −10° C. and quenched with water (450 mL). The layers are allowed to separate, and the aqueous layer is extracted with ether (3×200 mL). The combined organic layer is dried over MgSO$_4$, filtered, and concentrated in vacuo to an oil. The crude material is chromatographed over 320 g slurry-packed silica eluting with 30% EtOAc/hexane to afford 4-chloropyridine-3-carboxaldehyde (C140) an orange oil which solidified under vacuum to an orange solid (21% yield).

C140 (2.53 g, 17.9 mmol) is dissolved in DMF (20 mL) and H$_2$O (2 mL). K$_2$CO$_3$ (2.97 g, 21.5 mmol) and methyl thioglycolate (1.92 mL, 21.5 mmol) are added portionwise. The reaction is stirred at 45° C. for 24 h, then quenched with cold H$_2$O (100 mL), and the flask is placed on ice to enhance precipitation. The precipitate is isolated by filtration and dried, affording methyl thieno[3,2-c]pyridine-2-carboxylate (C141) as a white solid (92% yield). MS (EI) for C$_9$H$_7$NO$_2$S, m/z: 193 (M)$^+$.

C141 (2.65 g, 13.7 mmol) is dissolved in MeOH (70 mL) and H$_2$O (5 mL). 2N NaOH (6.86 mL, 13.7 mmol) is added drop-wise, and the reaction is stirred at rt for 24 h. The reaction is concentrated in vacuo, and H$_2$O (150 mL) is added to dissolve the residue. The resulting salt solution is acidified to pH 3.5 using concentrated HCl, and the precipitate is isolated by filtration and dried, affording thieno[3,2-c]pyridine-2-carboxylic acid (C142) as a white powder (57% yield). HRMS (FAB) calculated for C$_8$H$_5$NO$_2$S+H: 180.0119, found 180.0124 (M+H).

Example 20(i) can be obtained by coupling either exo-[2.2.1]-3-Amine or endo-[2.2.1]-3-Amine with C142.

The following examples can be prepared according to the coupling procedures discussed herein:

EXAMPLE 20(i-a)

N-(1-(6-methyl)-azabicyclo[2.2.1]hept-3-yl)-thieno[3,2-c]pyridine-2-carboxamide.

EXAMPLE 20(ii)

N-(1-(6-methyl)-azabicyclo[2.2.2]oct-3-yl)-thieno[3,2-c]pyridine-2-carboxamide.

EXAMPLE 20(iii)

N-(2-azabicyclo[2.2.1]hept-5-yl)-thieno[3,2-c]pyridine-2-carboxamide.

EXAMPLE 20(iv)

N-(2-azabicyclo[2.2.1]hept-6-yl)-thieno[3,2-c]pyridine-2-carboxamide.

EXAMPLE 20(v)

N-(2-azabicyclo[2.2.1]hept-6-yl)-thieno[3,2-c]pyridine-2-carboxamide.

EXAMPLE 20(vi)

N-(2-azabicyclo[2.2.1]hept-6-yl)-thieno[3,2-c]pyridine-2-carboxamide.

EXAMPLE 21(i)

Exo-4(S)-N-(1-azabicyclo[2.2.1]hept-3-yl)-thieno[2,3-c]pyridine-5-carboxamide.fumarate:

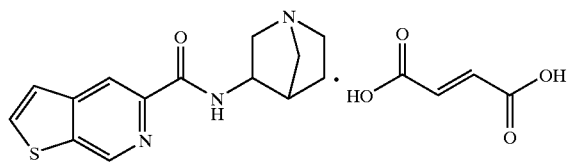

Glyoxylic acid monohydrate (20.3 g, 221 mmol) and benzyl carbamate (30.6 g, 202 mmol) are added to ether (200 mL). The solution is allowed to stir for 24 h at rt. The resulting thick precipitate is filtered, and the residue is washed with ether, affording ([(benzyloxy)carbonyl]amino)(hydroxy)acetic acid (C150) as a white solid (47% yield). MS (CI) for $C_{10}H_{11}NO_5$+H m/z: 226 (M+H).

C150 (11.6 g, 51.5 mmol) is dissolved in absolute MeOH (120 mL) and chilled in an ice bath. Concentrated sulfuric acid (2.0 mL) is carefully added dropwise. The ice bath is allowed to expire as the solution stirred for 2 days. The reaction is quenched by pouring onto a mixture of 500 g ice with saturated $NaHCO_3$ solution (400 mL). The solution is extracted with EtOAc (3×300 mL), and the combined organic layer is dried over $MgSO_4$, filtered, and concentrated to a pale oil that crystallized upon standing, giving methyl([(benzyloxy)carbonyl]amino)(methoxy)acetate (C151) as a white solid (94% yield). Analysis calculated for $C_{12}H_{15}NO_5$: C, 56.91; H, 5.97; N, 5.53, found: C, 56.99; H, 6.02; N, 5.60.

C151 (11.76 g, 46.4 mmol) is dissolved in toluene (50 mL) under $N_2$ and heated to 70° C. Phosphorous trichloride (23.2 mL, 46.4 mmol) is added drop-wise via syringe, and the solution is stirred for 18 h at 70° C. Trimethyl phosphite (5.47 mL, 46.4 mmol) is then added drop-wise, and stirring continued for an additional 2 h at 70° C. The mixture is concentrated in vacuo to an oil, and the crude material is dissolved in EtOAc (100 mL) and washed with saturated $NaHCO_3$ (3×50 mL). The organic layer is dried over $Na_2SO_4$, filtered, and concentrated to a volume of 30 mL. This remaining solution is stirred vigorously while hexane is added until a precipitate formed. The precipitated solid is removed by filtration, affording methyl ([(benzyloxy)carbonyl]amino)(dimethoxyphosphoryl)acetate (C152) as a white solid (84% yield). MS (EI) for $C_{13}H_{18}NO_7P$, m/z: 331 (M)$^+$.

C152 (12.65 g, 38.2 mmol) and acetic anhydride (9.02 mL, 95.5 mmol) in MeOH (100 mL) were added to a Parr flask. The solution is hydrogenated with 10% Pd/C catalyst (0.640 g) at 45 PSI for 3 h. The catalyst is filtered off, and the filtrate is concentrated in vacuo to an oil. The oil is placed under reduced pressure and solidified as the reduced pressure is applied. The white residue is dissolved in a small amount of EtOAc and stirred vigorously while pentane is added until a precipitate began to form. The precipitate is removed by filtration to give methyl (acetylamino)(dimethoxyphosphoryl)acetate (C153) as a white powder (87% yield). MS (CI) for $C_7H_{14}NO_6P$, m/z: 240 (M+H).

2,3-Thiophene dicarboxaldehyde (1.40 g, 9.99 mmol) is dissolved in $CH_2Cl_2$ (100 mL) and the flask is placed in an ice bath. C152 (2.63 g, 11.0 mmol) is dissolved in $CH_2Cl_2$ (50 mL), 1,8-diazabicyclo[5.4.0]undec-7-ene (1.65 mL, 11.0 mmol) is added, and this solution is added drop-wise to the chilled thiophene solution. The reaction mixture is stirred for 1 h while the flask is in an ice bath and then over night at rt. The reaction is concentrated in vacuo, and the crude material is chromatographed over 300 g slurry-packed silica eluting with 50% EtOAc/hexane. The fractions were collected in two different groups to obtain the desired compounds. Each group of fractions is combined and concentrated separately. The first group of fractions affords methyl thieno[2,3-c]pyridine-5-carboxylate (C154) as a white solid (41% yield), and the second group of fractions affords methyl thieno[3,2-c]pyridine-6-carboxylate (C155) as a yellow solid (38% yield). MS (EI) for C154 for $C_9H_7NO_2S$, m/z: 193 (M)$^+$. MS (EI) for C155 for $C_9H_7NO_2S$, m/z: 193 (M)$^+$.

C154 (736 mg, 3.8 mmol) is dissolved in MeOH (16 mL) with water (2 mL). 2M NaOH (2.0 mL, 4.0 mmol) is added drop-wise and the solution stirred at rt. After 2 days (complete disappearance of ester by TLC), the reaction is concentrated in vacuo. The residue is dissolved in $H_2O$ (12 mL), and the pH is adjusted to 3.5 with 10% HCl. The precipitated solid is removed by filtration, and the solid is rinsed with ether, affording thieno[2,3-c]pyridine-5-carboxylic acid (C156) as a white solid (58% yield). HRMS (FAB) calculated for $C_8H_5NO_2S$+H: 180.0119, found 180.0123 (M+H).

Coupling exo-(4S)-[2.2.1]-3-Amine with C156, followed by fumarate salt formation as described in Steps 1a and 1b, respectively, gives Example 21(i) in 84% yield. MS for $C_{14}H_{16}N_3OS$ (ESI) m/e: 274 (M+H).

EXAMPLE 21(i-a)

N-(1-(6-methyl)-azabicyclo[2.2.1]hept-3-yl)-thieno[2,3-c]pyridine-5-carboxamide: This example can be prepared according to the coupling procedures discussed herein.

EXAMPLE 21(ii)

N-(1-(6-methyl)-azabicyclo[2.2.2]oct-3-yl)-thieno[2,3-c]pyridine-5-carboxamide: This example can be prepared according to the coupling procedures discussed herein.

EXAMPLE 21(iii)

N-(2-azabicyclo[2.2.1]hept-5-yl)-thieno[2,3-c]pyridine-5-carboxamide: This example can be prepared according to the coupling procedures discussed herein.

EXAMPLE 21(iv)

N-(2-azabicyclo[2.2.1]hept-6-yl)-thieno[2,3-c]pyridine-5-carboxamide: This example can be prepared according to the coupling procedures discussed herein.

EXAMPLE 21(v)

N-((3R,5R)-1-azabicyclo[3.2.1]oct-3-yl)-thieno[2,3-c]pyridine-5-carboxamide: Yield from coupling is 66%. MS (EI) m/z 287 (M$^+$).

EXAMPLE 21(vi)

N-(1-azabicyclo[3.2.2]non-3-yl)-thieno[2,3-c]pyridine-5-carboxamide: This example can be prepared according to the coupling procedures discussed herein.

EXAMPLE 22(i)

Exo-4(S)-N-(1-azabicyclo[2.2.1]hept-3-yl)-thieno[3,2-c]pyridine-6-carboxamide.fumarate:

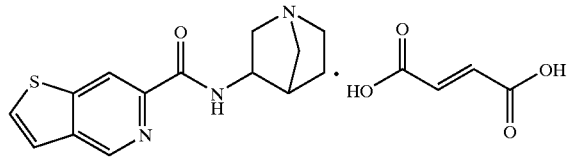

Methyl thieno[3,2-c]pyridine-6-carboxylate (C155) (678 mg, 3.5 mmol) is dissolved in MeOH (16 mL) and H$_2$O (2 mL). 2M NaOH (1.8 mL, 3.6 mmol) is added drop-wise, and the solution stirred at rt. After 2 days (complete disappearance of ester by TLC), the solution is concentrated in vacuo. The residue is dissolved in H$_2$O (12 mL), and the pH is adjusted to 3.5 with 10% HCl. The precipitated solid is removed by filtration, and the solid is rinsed with ether, affording thieno[3,2-c]pyridine-6-carboxylic acid (C160) as a white solid (43% yield). HRMS (FAB) calculated for C$_8$H$_5$NO$_2$S+H: 180.0119, found 180.0123 (M+H).

Example 22 is obtained by coupling exo-(4S)-[2.2.1]-3-Amine with C160, followed by fumarate salt formation as described in Steps 1a and 1b, respectively, to give Example 22(i) in 77% yield. MS for C$_{14}$H$_{16}$N$_3$SO (ESI) m/e: 274 (M+H).

EXAMPLE 22(i-a)

N-(1-(6-methyl)-azabicyclo[2.2.1]hept-3-yl)-thieno[3,2-c]pyridine-6-carboxamide: This example can be prepared according to the coupling procedures discussed herein.

EXAMPLE 22(ii)

N-(1-(6-methyl)-azabicyclo[2.2.2]oct-3-yl)-thieno[3,2-c]pyridine-6-carboxamide: This example can be prepared according to the coupling procedures discussed herein.

EXAMPLE 22(iii)

N-(2-azabicyclo[2.2.1]hept-5-yl)-thieno[3,2-c]pyridine-6-carboxamide: This example can be prepared according to the coupling procedures discussed herein.

EXAMPLE 22(iv)

N-(2-azabicyclo[2.2.1]hept-6-yl)-thieno[3,2-c]pyridine-6-carboxamide: This example can be prepared according to the coupling procedures discussed herein.

EXAMPLE 22(v)

N-((3R,5R)-1-azabicyclo[3.2.1]oct-3-yl)-thieno[3,2-c]pyridine-6-carboxamide: Example 22(v) is made by coupling C160 with exo-[3.2.1]-Amine using the coupling procedures described herein. Yield for coupling is 58%. MS (EI) m/z 287 (M$^+$).

EXAMPLE 22(vi)

N-(1-azabicyclo[3.2.2]non-3-yl)-thieno[3,2-c]pyridine-6-carboxamide: This example can be prepared according to the coupling procedures discussed herein.

EXAMPLE 23(i)

N-(1-azabicyclo[2.2.1]hept-3-yl)-1H-pyrrolo[2,3-c]pyridine-5-carboxamide:

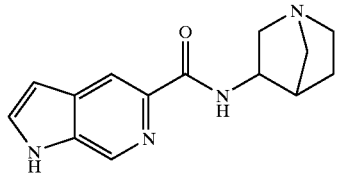

2,4-Lutidine (51.4 mL, 0.445 mole) is added drop-wise to 250 mL fuming sulfuric acid in a flask under N$_2$ in an ice bath. The solution is treated portionwise with potassium nitrate (89.9 g, 0.889 mole) over a 15 min period. The reaction is stirred 1 h in an ice bath, 2 h at rt, is gradually warmed in a 100° C. oil bath for 5 h, and then in a 130° C. oil bath for 4 h. The mixture is cooled, is poured into 1000 mL ice, and the mixture is neutralized with NaHCO$_3$ (1,100 g, 13.1 mole). The precipitated Na$_2$SO$_4$ is removed by filtration, the solid is washed with 500 mL H$_2$O and the filtrate is extracted with 4×500 mL ether. The combined organic layer is dried over MgSO$_4$ and is concentrated in vacuo to a yellow oil (50 g). The crude oil is distilled under vacuum to provide three fractions: 16 g recovered 2,4-lutidine (85° C.), 16 g 2,4-dimethyl-3-nitro-pyridine (C169) contaminated with 25% 2,4-dimethyl-5-nitro-pyridine (135–145° C.), and 16 g 2,4-dimethyl-5-nitro-pyridine (C170) contaminated with 2,4-dimethyl-3-nitropyridine (145–153° C.). $^1$H NMR of C169 (CDCl$_3$) δ 2.33, 2.54, 7.10, 8.43 ppm. $^1$H NMR of C170 (CDCl$_3$) δ 2.61, 2.62, 7.16, 9.05 ppm.

C170/C169 (75:25) (5.64 g, 37 mmol) is combined with benzeneselenic anhydride (8.2 g, 22.8 mmol) in 300 mL dioxane in a flask under N$_2$. The reaction is warmed to reflux for 10 h, is cooled, and is concentrated to a dark yellow oil. The oil is chromatographed over 250 g silica gel (230–400 mesh) eluting with 15% EtOAc/hexane to afford 2-formyl-4-methyl-5-nitropyridine (C171) (66% yield). HRMS (EI) calculated for C$_7$H$_6$N$_2$O$_3$: 166.0378, found 166.0383 (M$^+$).

C171 (1.15 g, 6.9 mmol), p-toluene sulfonic acid (41 mg, 0.22 mmol), and ethylene glycol (1.41 mL, 25 mmol) are added to 25 mL toluene in a flask equipped with a Dean-Starke trap. The reaction is warmed to reflux for 2 h, is cooled to rt, and is concentrated in vacuo to an oily residue. The crude oil is chromatographed over 40 g silica gel (Biotage), eluting with 20% EtOAc/hexane to afford 2-(1,3-dioxolan-2-yl)-4-methyl-5-nitropyridine (C172) (90% yield). MS (EI) for C$_9$H$_{10}$N$_2$O$_4$, m/z: 210 (M)$^+$.

C172 (1.3 g, 6.2 mmol) and DMF dimethyl acetal (1.12 mL, 8.4 mmol) are added to 15 mL DMF under N$_2$. The reaction is warmed to 90° C. for 3 h, is cooled, and the reaction is concentrated in vacuo. The residue is combined with 1.25 g 5% Pd/BaSO$_4$ in 20 mL EtOH in a 250 mL Parr shaker bottle and the mixture is hydrogenated at ambient pressure until uptake ceased. The catalyst is removed by filtration, and the filtrate is combined with 500 mg 10% Pd/C catalyst in a 250 mL Parr shaker bottle. The mixture is hydrogenated at ambient pressure for 1 h. No additional hydrogen uptake is observed. The catalyst is removed by filtration, and the filtrate is concentrated in vacuo to a tan solid. The crude material is chromatographed over 50 g silica gel (230–400 mesh), eluting with 7% MeOH/CH$_2$Cl$_2$. The appropriate fractions are combined and concentrated to afford 5-(1,3-dioxolan-2-yl)-1H-pyrrolo[2,3-c]pyridine (C173) (69%yield). MS for C$_{10}$H$_{10}$N$_2$O$_2$, (EI) m/z: 190 (M)$^+$.

C173 (800 mg, 4.21 mmol) is dissolved in 44 mL 10% aqueous acetonitrile. p-Toluene sulfonic acid (630 mg, 3.3 mmol) is added, and the mixture is heated to reflux for 5 h. The mixture is cooled to rt, is concentrated in vacuo, and the resultant residue is diluted with 15 mL saturated $NaHCO_3$. A pale yellow solid is collected, washed with water, and is dried to afford 1H-pyrrolo[2,3-c]pyridine-5-carbaldehyde (C174) (81% yield). HRMS (FAB) calculated for $C_8H_6N_2O+H$: 147.0558, found 147.0564 (M+H).

C174 (500 mg, 3.42 mmol) is dissolved in 1.5 mL formic acid. The solution is cooled in an ice bath, 30% aqueous hydrogen peroxide (722 µL, 6.8 mmol) is added drop-wise, and the reaction is stirred 1 h in an ice bath, and allowed to stand overnight at 5° C. The mixture is diluted with $H_2O$, the solid is collected, washed with $H_2O$ and is dried to give 522 mg of an off-white solid. The formate salt is added to 7 mL $H_2O$, 3 mL 2N NaOH is added, and the pH is adjusted to 3 with 5% aqueous HCl. The precipitate is collected and is dried to afford 1H-pyrrolo[2,3-c]pyridine-5-carboxylic acid (C176) (67% yield). HRMS (FAB) calculated for $C_8H_6N_2O_2+H$: 163.0508, found 163.0507 (M+H).

Example 23(i) can be obtained by coupling either exo-[2.2.1]-3-Amine or endo-[2.2.1]-3-Amine with C176.

The following examples can be prepared according to the coupling procedures discussed herein:

EXAMPLE 23(i-a)

N-(1-(6-methyl)-azabicyclo[2.2.1]hept-3-yl)-1H-pyrrolo[2,3-c]pyridine-5-carboxamide.

EXAMPLE 23(ii)

N-(1-(6-methyl)-azabicyclo[2.2.2]oct-3-yl)-1H-pyrrolo[2,3-c]pyridine-5-carboxamide.

EXAMPLE 23(iii)

N-(2-azabicyclo[2.2.1]hept-5-yl)-1H-pyrrolo[2,3-c]pyridine-5-carboxamide.

EXAMPLE 23(iv)

N-(2-azabicyclo[2.2.1]hept-6-yl)-1H-pyrrolo[2,3-c]pyridine-5-carboxamide.

EXAMPLE 23(v)

N-((3R,5R)-1-azabicyclo[3.2.1]oct-3-yl)-1H-pyrrolo[2,3-c]pyridine-5-carboxamide.

EXAMPLE 23(vi)

N-(1-azabicyclo[3.2.2]non-3-yl)-1H-pyrrolo[2,3-c]pyridine-5-carboxamide.

EXAMPLE 24(i)

N-(1-azabicyclo[2.2.1]hept-3-yl)-1-methyl-1H-pyrrolo[2,3-c]pyridine-5-carboxamide:

5-(1,3-Dioxolan-2-yl)-1H-pyrrolo[2,3-c]pyridine (C173) (1.05 g, 5.52 mmol) is dissolved in 20 mL THF in a dried flask under $N_2$. 60% Sodium hydride (243 mg, 6.07 mmol) is added, the reaction is stirred 30 min, methyl iodide (360 µL, 5.8 mmol) is added, and the reaction is stirred overnight at rt. The reaction is concentrated in vacuo and the residue is partitioned between 10 mL saturated NaCl and $CH_2Cl_2$ (4×10 mL). The combined organic layer is dried over anhydrous $K_2CO_3$ and is concentrated in vacuo to a tan paste. The crude material is chromatographed over 50 g silica gel (230–400 mesh) eluting with 5% $MeOH/CH_2Cl_2$. The appropriate fractions are combined and concentrated to afford 5-(1,3-dioxolan-2-yl)-1-methyl-1H-pyrrolo[2,3-c]pyridine (C175) (86% yield). HRMS (FAB) calculated for $C_{11}H_{12}N_2O_2+H$: 205.0977, found 205.0983.

C175 (920 mg, 4.5 mmol) is dissolved in 25 mL 10% aqueous acetonitrile in a flask. p-Toluene sulfonic acid (630 mg, 3.3 mmol) is added, and the mixture is heated to 90° C. for 8 h. The mixture is cooled to rt, concentrated in vacuo, and the residue is partitioned between 15 mL saturated $NaHCO_3$ and $CH_2Cl_2$ (4×10 mL). The combined organic layer is dried over anhydrous $K_2CO_3$ and is concentrated in vacuo to afford 1-methyl-pyrrolo[2,3-c]pyridine-5-carbaldehyde (C177) (99% yield). HRMS (FAB) calculated for $C_9H_8N_2O+H$: 161.0715, found 161.0711.

C177 (690 mg, 4.3 mmol) is dissolved in 2 mL formic acid. The solution is cooled in an ice bath, 30% aqueous hydrogen peroxide (970 mL, 8.6 mmol) is added drop-wise, and the reaction is stirred 1 h in an ice bath, and allowed to stand overnight at 5° C. The mixture is concentrated to dryness, is suspended in $H_2O$, and the pH is adjusted to 7 with 2N NaOH. The mixture is concentrated to dryness, is dissolved in MeOH, and is passed over 15 mL 50W-X2 ion exchange resin (hydrogen form) eluting with 200 mL MeOH followed by 200 mL 5% $Et_3N/MeOH$. The basic wash is concentrated to dryness to afford 1-methyl-pyrrolo[2,3-c]pyridine-5-carboxylic acid (C178) (78% yield). HRMS (FAB) calculated for $C_9H_8N_2O_2+H$: 177.0664, found 177.0672 (M+H).

Example 24(i) can be obtained by coupling either exo-[2.2.1]-3-Amine or endo-[2.2.1]-3-Amine with C178.

The following examples can be prepared according to the coupling procedures discussed herein:

EXAMPLE 24(i-a)

N-(1-(6-methyl)-azabicyclo[2.2.1]hept-3-yl)-1-methyl-1H-pyrrolo[2,3-c]pyridine-5-carboxamide.

EXAMPLE 24(ii)

N-(1-(6-methyl)-azabicyclo[2.2.2]oct-3-yl)-1-methyl-1H-pyrrolo[2,3-c]pyridine-5-carboxamide.

EXAMPLE 24(iii)

N-(2-azabicyclo[2.2.1]hept-5-yl)-1-methyl-1H-pyrrolo[2,3-c]pyridine-5-carboxamide.

EXAMPLE 24(iv)

N-(2-azabicyclo[2.2.1]hept-6-yl)-1-methyl-1H-pyrrolo[2,3-c]pyridine-5-carboxamide.

EXAMPLE 24(v)

N-((3R,5R)-1-azabicyclo[3.2.1]oct-3-yl)-1-methyl-1H-pyrrolo[2,3-c]pyridine-5-carboxamide.

EXAMPLE 25(i)

N-(exo-(4S)-1-azabicyclo[2.2.1]hept-3-yl)-3-bromofuro[2,3-c]pyridine-5-carboxamide.1.5fumarate

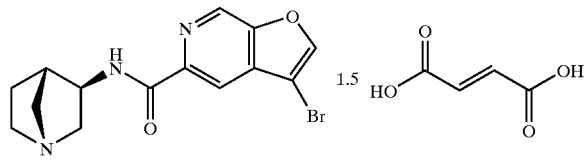

Furo[2,3-c]pyridin-5-ylmethyl acetate (5.17 g, 27.05 mmol) is dissolved in $CH_2Cl_2$ (130 mL), layered with saturated $NaHCO_3$ (220 mL), treated with $Br_2$ (8.36 mL, 162.3 mmol) and stirred very slowly for 4.5 h at rt. The mixture is stirred vigorously for 30 min, is diluted with $CH_2Cl_2$ (100 mL) and the layers separated. The aqueous layer is extracted with $CH_2Cl_2$ (2×100 mL) and the combined organics are concentrated to a small volume under a stream of nitrogen. The solution is diluted with EtOH (200 mL), treated with $K_2CO_3$ (22.13 g, 160.1 mmol) and stirred for 2.5 days at rt. The mixture is concentrated to dryness, partitioned between 50% saturated NaCl (200 mL) and $CH_2Cl_2$ (5×200 mL), dried over $Na_2SO_4$ and concentrated in vacuo to a yellow solid (6.07 g). The crude material is adsorbed onto silica gel (12 g) and chromatographed over 250 g slurry-packed silica gel, eluting with a gradient of 50% EtOAc/hexane to 100% EtOAc. The appropriate fractions are combined and concentrated in vacuo to afford 5.02 g (81%) of (3-bromofuro[2,3-c]pyridin-5-yl)methanol as a white solid. MS (EI) m/z: 227 ($M^+$).

Oxalyl chloride (1.77 mL, 20.1 mmol) is combined with $CH_2Cl_2$ (60 mL) in a dried flask under nitrogen, cooled to −78° C., treated dropwise with DMSO (2.86 mL, 40.25 mmol) and stirred for 20 min. The cooled solution is treated drop-wise with a solution of (3-bromofuro[2,3-c]pyridin-5-yl)methanol (4.0 mg, 17.5 mmol) in THF (50 mL), stirred for 1 h, then treated drop-wise with $Et_3N$ (12.2 mL, 87.5 mmol). The mixture is stirred for 30 min at −78° C., then 30 min at 0° C. The mixture is washed with saturated $NaHCO_3$ (120 mL) and the organics dried over $K_2CO_3$ and concentrated in vacuo to a dark yellow solid (3.91 g). The crude material is chromatographed over 150 g slurry-packed silica gel, eluting with 30% EtOAc/hexane. The appropriate fractions are combined and concentrated in vacuo to afford 3.93 g (99%) of 3-bromofuro[2,3-c]pyridine-5-carbaldehyde as a white solid. MS (EI) m/z: 225 ($M^+$).

3-Bromofuro[2,3-c]pyridine-5-carbaldehyde (3.26 g, 14.42 mmol) is dissolved in THF (100 mL)/t-BuOH (50 mL)/$H_2O$ (50 mL), treated with a single portion of $NaOCl_2$ (4.89 g, 43.3 mmol) and $KH_2PO_4$ (3.92 g, 28.8 mmol) and stirred at rt for 18 h. The white solid is collected via filtration and the filtrate is concentrated in vacuo to dryness. The residue is suspended in water (25 mL), acidified to pH 2 with concentrated HCl and the resulting solid collected via filtration. The collected solids are dried in a vacuum oven at 50° C. for 18 h and combined to afford 3.52 g (99%) of 3-bromofuro[2,3-c]pyridine-5-carboxylic acid as a white solid. MS (EI) m/z: 241 ($M^+$).

To a stirred suspension of 3-bromofuro[2,3-c]pyridine-5-carboxylic acid (182 mg, 0.75 mmol) in DMF (10 mL) are added DIEA (400 μL, 2.30 mmol) and exo-4(S)-[2.2.1]-3-Amine (343 mg, 0.75 mmol). The mixture is cooled in an ice bath to 0° C., and HATU (286 mg, 0.75 mmol) is added in one portion. The reaction mixture is allowed to warm to rt and stir overnight. The solvent is removed in vacuo, and the residue is partitioned between saturated aqueous $K_2CO_3$ solution and chloroform-methanol (95:5). The aqueous layer is extracted with chloroform (3×). The combined organic layers are washed with brine, dried over $Na_2SO_4$, filtered and concentrated in vacuo to give 50 mg (20%) of the amide as a white solid.

To a stirred solution of the above amide (50 mg, 0.15 mmol) in MeOH (5 mL) is added a solution of fumaric acid (66 mg, 0.35 mmol) in MeOH (5 mL). The solvent is removed in vacuo, and the remaining residue is diluted with acetone (5 mL). The mixture is stirred overnight at rt. The solid precipitate is collected by filtration, washed with ether, and dried in vacuo overnight to give 53 mg (70%) of Example 25(i) as a white solid: $^1$H NMR (400 MHz, $CD_3OD$) δ 8.97, 8.36, 8.31, 6.72, 4.35–4.34, 3.78–3.72, 3.55–3.36, 3.28–3.25, 3.09, 2.25–2.17, 1.92–1.85.

The following examples can be prepared according to the coupling procedures discussed herein:

EXAMPLE 25(i-a)

N-(1-(6-methyl)-azabicyclo[2.2.1]hept-3-yl)-3-bromofuro[2,3-c]pyridine-5-carboxamide.

EXAMPLE 25(ii)

N-(1-(6-methyl)-azabicyclo[2.2.2]oct-3-yl)-3-bromofuro[2,3-c]pyridine-5-carboxamide.

EXAMPLE 25(iii)

N-(2-azabicyclo[2.2.1]hept-5-yl)-3-bromofuro[2,3-c]pyridine-5-carboxamide.

EXAMPLE 25(iv)

N-(2-azabicyclo[2.2.1]hept-6-yl)-3-bromofuro[2,3-c]pyridine-5-carboxamide.

EXAMPLE 25(v)

N-((3R,5R)-1-azabicyclo[3.2.1]oct-3-yl)-3-bromofuro[2,3-c]pyridine-5-carboxamide.

EXAMPLE 26(i)

N-[exo-(4S)-1-azabicyclo[2.2.1]hept-3-yl]-3-chlorofuro[2,3-c]pyridine-5-carboxamide.fumarate:

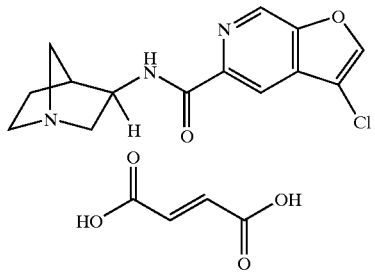

Furo[2,3-c]pyridin-5-ylmethanol (7.70 g, 51.63 mmol) is dissolved in pyridine (45 mL), treated with acetic anhydride (14.36 mL, 154.9 mmol) and stirred for 18 h at rt. The pyridine is removed in vaeuo and the resulting residue dissolved in EtOAc (200 mL), washed with 50% saturated sodium bicarbonate (4×90 mL), dried over $MgSO_4$ and concentrated in vacuo to afford 9.32 g (94%) of furo[2,3-c]pyridin-5-ylmethyl acetate as a yellow oil. MS (EI) m/z: 191 ($M^+$), 277, 148, 119, 118, 86, 84, 77, 63, 51, 50.

Furo[2,3-c]pyridin-5-ylmethyl acetate (956 mg, 5 mmol) is dissolved in $CH_2Cl_2$ (40 mL) and cooled to 0° C. Chlorine gas is bubbled through the solution for 15 min, the cooling bath is immediately removed and the mixture stirred for 2 h. The mixture is re-cooled to 0° C., saturated with chlorine gas, the cooling bath removed and the solution warmed to rt. The solution is layered with saturated $NaHCO_3$ (20 mL), stirred gently for 2 h then stirred vigorously for 15 min. The mixture is diluted with saturated $NaHCO_3$ (50 mL), extracted with $CH_2Cl_2$ (1×40 mL then 1×20 mL), dried over $K_2CO_3$ and concentrated to a volume of 20 mL under a stream of nitrogen. The solution is diluted with EtOH (35 mL), treated with $K_2CO_3$ (4.09 g, 29.6 mmol) and stirred for 18 h at rt. Water (7 mL) is added and the mixture stirred for 2 days. The mixture is concentrated to dryness, partitioned between 50% saturated NaCl (50 mL) and $CH_2Cl_2$ (4×50 mL), dried over $K_2CO_3$ and concentrated in vacuo to a brown solid (833 mg). The crude material is chromatographed over a standard 40 g Biotage column, eluting with 50% EtOAc/hexane. The appropriate fractions are combined and concentrated to afford 624 mg (68%) of (3-chlorofuro[2,3-c]pyridin-5-yl)methanol as a yellow oil. $^1$H NMR (DMSO-$d_6$): δ 4.69, 5.56, 7.69, 8.55, 8.93 ppm.

Oxalyl chloride (231 μL, 2.6 mmol) is combined with $CH_2Cl_2$ (10 mL), cooled to −78° C., treated dropwise with DMSO (373 μL, 5.3 mmol) and stirred for 20 min. The cooled solution is treated dropwise with a solution of (3-chlorofuro[2,3-c]pyridin-5-yl)methanol (420 mg, 2.3 mmol) in THF (5 mL)/$CH_2Cl_2$ (5 mL), stirred for 1 h, then treated dropwise with $Et_3N$ (1.59 mL, 11.45 mmol). The mixture is stirred for 30 min at −78° C., then 30 min at 0° C. The mixture is washed with saturated $NaHCO_3$ (20 mL) and the organics dried over $K_2CO_3$ and concentrated in vacuo to a yellow solid (410 mg). The crude material is chromatographed over 20 g slurry-packed silica gel, eluting with 15% EtOAc/hexane. The appropriate fractions are combined and concentrated in vacuo to afford 322 mg (77%) of 3-chlorofuro[2,3-c]pyridine-5-carbaldehyde as a white solid. $^1$H NMR ($CDCl_3$): δ 7.89, 8.33, 9.02, 10.18 ppm. 3-Chlorofuro[2,3-c]pyridine-5-carbaldehyde (317 mg, 1.74 mmol) is dissolved in THF (10 mL)/t-BuOH (5 mL)/$H_2O$ (5 mL), treated with a single portion of sodium chlorite (592 mg, 5.24 mmol) and $KH_2PO_4$ (473 mg, 3.48 mmol) and stirred at rt for 18 h. The reaction mixture is concentrated in vacuo to dryness, suspended in water (10 mL), acidified to pH 3.5 with concentrated HCl and stirred at rt for 2 h. The resulting solid is filtered, washed with water and dried in a vacuum oven at 40° C. for 18 h to afford 364 mg of 3-chlorofuro[2,3-c]pyridine-5-carboxylic acid as a white solid. MS (EI) m/z: 197 ($M^+$).

To a stirred solution of 3-chlorofuro[2,3-c]pyridine-5-carboxylic acid (99 mg, 0.5 mmol) in anhydrous DMF (10 mL) are added DIEA (265 μL, 1.52 mmol) and exo-4(S)-[2.2.1]-3-Amine (228 mg, 0.5 mmol). The mixture is cooled in an acetone/icewater bath to −5° C., and HATU (190 mg, 0.5 mmol) is added in one portion. The reaction mixture is allowed to warm to rt and stir overnight. The solvent is removed in vacuo, and the residue is partitioned between saturated aqueous $K_2CO_3$ solution and chloroform. The aqueous layer is extracted with chloroform (2×). The combined organic layers are washed with brine, dried over $Na_2SO_4$, filtered and concentrated in vacuo to give the amide as a white solid (125 mg, 85%).

To a stirred solution of the above amide (125 mg, 0.43 mmol) in acetone (5 mL) is added a warm solution of fumaric acid (49.7 mg, 0.43 mmol) in isopropanol (5 mL). The mixture is warmed to 50° C. for 10 min. The solvents are removed in vacuo, and the remaining residue is diluted with acetone (5 mL). The mixture is stirred overnight at rt. The solid is collected by filtration, washed with acetone, and dried under high vacuum overnight to give 152 mg (87%) of Example 26(i) as a white solid: $^1$H NMR (400 MHz, $CD_3OD$) δ 8.98, 8.42, 8.32, 6.71, 4.32–4.29, 3.73–3.68, 3.50–3.35, 3.26–3.20, 3.07, 2.22–2.13, 1.89–1.81.

The following examples can be prepared according to the coupling procedures discussed herein:

EXAMPLE 26(i-a)

N-(1-(6-methyl)-azabicyclo[2.2.1]hept-3-yl)-3-chlorofuro[2,3-c]pyridine-5-carboxamide.

EXAMPLE 26(ii)

N-(1-(6-methyl)-azabicyclo[2.2.2]oct-3-yl)-3-chlorofuro[2,3-c]pyridine-5-carboxamide.

EXAMPLE 26(iii)

N-(2-azabicyclo[2.2.1]hept-5-yl)-3-chlorofuro[2,3-c]pyridine-5-carboxamide.

EXAMPLE 26(iv)

N-(2-azabicyclo[2.2.1]hept-6-yl)-3-chlorofuro[2,3-c]pyridine-5-carboxamide.

EXAMPLE 26(v)

N-((3R,5R)-1-azabicyclo[3.2.1]oct-3-yl)-3-chlorofuro[2,3-c]pyridine-5-carboxamide.

EXAMPLE 27(i)

N-(1-azabicyclo[2.2.1]hept-3-yl)-benzothieno[3,2-c]pyridine-3-carboxamide:

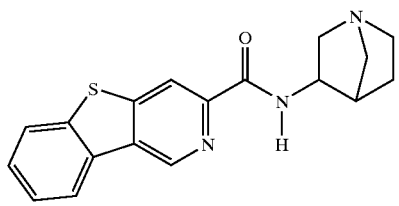

N-butyl lithium (150.6 ml, 241 mmol) is added dropwise to ether (100 ml) at −20° C. under $N_2$. 3-Bromothianaphthene (10.5 ml, 80.3 mmol) is dissolved in ether (50 ml) and also added dropwise to the chilled solution, stirring cold for 0.5 h. DMF (16.3 ml, 210 mmol) is dissolved in ether (75 ml) and added dropwise, and the solution stirred an additional 15 h at −20° C. The reaction is quenched onto ice (300 g) in 10% $H_2SO_4$ (200 ml) and stirred until both layers turn yellow in color. The resulting slurry is filtered, and the cake is allowed to dry in the air stream, affording 1-benzothiophene-2,3-dicarbaldehyde (C180) as a yellow solid (60% yield). HRMS (FAB) calculated for $C_{10}H_6O_2S+H$: 191.0167, found 191.0172 (M+H).

1-Benzothiophene-2,3-dicarbaldehyde (C180) (1.91 g, 10.0 mmol) is dissolved in $CH_2Cl_2$ (100 ml) and chilled in an ice bath. Methyl (acetylamino)(dimethoxyphosphoryl)acetate (C152) (2.63 g, 11.0 mmol) is dissolved in $CH_2Cl_2$ (50 ml) and added to 1,8-diazabicyclo[5.4.0]undec-7-ene (1.65 ml, 11.0 mmol), stirring for 5 minutes. This solution is added dropwise to the chilled thiophene solution. The reaction mixture is stirred in the ice bath for 1 h and then over night at rt. The reaction is concentrated in vacuo and the crude material is chromatographed over 500 g slurry-packed silica eluting with 50% ethyl acetate/hexane to afford methyl benzothieno[3,2-c]pyridine-3-carboxylate (C 181) as a white solid (73% yield). MS for $C_{13}H_9NO_2S$, (EI) m/z: 243 (M)⁺.

C181 (1.43 g, 5.87 mmol) is dissolved in MeOH (25 ml) with $H_2O$ (3 ml). 2M NaOH (3.0 ml, 6.0 mmol) is added dropwise and the solution stirred at rt. After 4 days (complete disappearance of ester by TLC), the reaction is concentrated in vacuo. The residue is dissolved in $H_2O$ (5 ml) and the pH is adjusted to 3 with 10% HCl. The solution is stirred over night before precipitation is complete. The slurry is filtered and the cake is rinsed with ether, giving a 100% yield of benzothieno[3,2-c]pyridine-3-carboxylic acid (C182) as a white solid. HRMS (FAB) calculated for $C_{12}H_7NO_2S+H$ 230.0276, found 230.0275 (M+H).

Example 27(i) can be obtained by coupling either exo-[2.2.1]-3-Amine or endo-[2.2.1]-3-Amine with (C182).

The following examples can be prepared according to the coupling procedures discussed herein:

EXAMPLE 27(i-a)

N-(1-(6-methyl)-azabicyclo[2.2.1]hept-3-yl)-benzothieno[3,2-c]pyridine-3-carboxamide.

EXAMPLE 27(ii)

N-(1-(6-methyl)-azabicyclo[2.2.2]oct-3-yl)-benzothieno[3,2-c]pyridine-3-carboxamide.

EXAMPLE 27(iii)

N-(2-azabicyclo[2.2.1]hept-5-yl)-benzothieno[3,2-c]pyridine-3-carboxamide.

EXAMPLE 27(iv)

N-(2-azabicyclo[2.2.1]hept-6-yl)-benzothieno[3,2-c]pyridine-3-carboxamide.

EXAMPLE 27(v)

N-((3R,5R)-1-azabicyclo[3.2.1]oct-3-yl)-benzothieno[3,2-c]pyridine-3-carboxamide.

EXAMPLE 27(vi)

N-(1-azabicyclo[3.2.2]non-3-yl)-benzothieno[3,2-c]pyridine-3-carboxamide.

EXAMPLE 28(i)

N-(1-azabicyclo[2.2.1]hept-3-yl)thieno[3,4-c]pyridine-6-carboxamide:

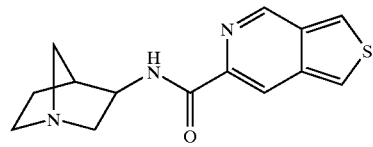

3,4-Dibromothiophene (12.5 ml, 113 mmol) is combined with CuCN (30.4 g, 339 mmol) in DMF (40 ml) in a dry flask under nitrogen utilizing an over-head stirrer. The reaction is allowed to reflux at 180° C. for 5 h. The dark mixture is then poured into a solution of $FeCl_3$ (113.6 g, 700 mmol) in 1.7M HCl (200 ml) and heated at 65° C. for 0.5 h, again using the over-head stirrer. The reaction is cooled to rt and extracted with $CH_2Cl_2$ (7×300 ml). Each extract is washed individually with 200 ml each 6M HCl (2×), water, saturated $NaHCO_3$, and water. The organics are then combined, dried over $MgSO_4$, filtered, and concentrated, affording 10.49 g (69%) of 3,4-dicyanothiophene as a fluffy tan solid. HRMS (EI) calcd for $C_6H_2N_2S$: 133.9939, found 133.9929 (M⁺).

3,4-Dicyanothiophene (5.0 g, 37.2 mmol) is suspended in benzene (150 ml) in a dry flask under nitrogen utilizing an over-head stirrer. Diisobutyl aluminum hydride (1.0M in toluene) (82.0 ml, 82.0 mmol) is added dropwise, and the reaction stirred at rt for 2 h. The reaction is then carefully quenched with MeOH (5 ml) and poured onto 30% $H_2SO_4$ (60 ml) with ice (200 g). The slurry is stirred until all lumps are dissolved, and the layers are allowed to separate. The aqueous layer is extracted with $Et_2O$ (4×200 ml), and the combined organics are dried over $MgSO_4$, filtered, and adsorbed onto silica. The crude material is chromatographed over 225 g slurry-packed silica, eluting with 40% EtOAc/hexane. The appropriate fractions are combined and concentrated to afford 1.88 g (36%) of 3,4-thiophene dicarboxaldehyde as a pale yellow solid. MS (EI) m/z: 140 (M⁺).

3,4-Thiophene dicarboxaldehyde (1.0 g, 7.13 mmol) is dissolved in $CH_2Cl_2$ (40 ml) and chilled to 0° C. Methyl (acetylamino)(dimethoxyphosphoryl)acetate (1.88 g, 7.85 mmol) is dissolved in $CH_2Cl_2$ (30 ml) and combined with DBU (1.1 ml, 7.85 mmol). This solution is added dropwise to the chilled thiophene solution after stirring for 5 min. The reaction mixture is stirred at 0° C. for 1 h and then overnight at rt. The volatiles are removed in vacuo and the crude material is chromatographed over 68 g slurry-packed silica eluting with 70% EtOAc/hexane. The appropriate fractions are combined and concentrated to yield 2.09 g of the carbinol intermediate as a white foam. The intermediate is dissolved in $CHCl_3$ (50 ml) and treated with DBU (1.32 ml, 8.8 mmol) and trifluoracetic anhydride (1.24 ml, 8.8 mmol) in a drop-wise fashion. The reaction is stirred overnight at rt and is then quenched with saturated $NaHCO_3$ solution (50 ml). The layers are separated, and the aqueous layer is extracted with $CHCl_3$ (2×50 ml). The combined organics are dried over $MgSO_4$, filtered, and concentrated to a yellow oil. This oil is chromatographed over 50 g slurry-packed silica, eluting with 90% EtOAc/hexane. The appropriate fractions are combined and concentrated to afford 1.2 g (88%) of methyl thieno[3,4-c]pyridine-6-carboxylate as a yellow solid. MS (EI) m/z: 193 ($M^+$).

Methyl thieno[3,4-c]pyridine-6-carboxylate (250 mg, 1.3 mmol) is dissolved in MeOH (7 ml) and water (1 ml). 2M NaOH (0.72 ml, 1.43 mmol) is added drop-wise. The reaction is stirred overnight at rt and is monitored by TLC. The volatiles are removed in vacuo and the residue is dissolved in water (2 ml). 10% HCl is used to adjust the pH to 3, and the reaction again stirred overnight at rt. The aqueous solution is extracted repeatedly with EtOAc (20×10 ml). The combined organics are dried over $MgSO_4$, filtered, and concentrated to a yellow solid. The amount of isolated product via extraction is minimal (67 mg), so the aqueous layer is concentrated and found to contain the majority of product. Extraction of the solid aqueous residue with EtOAc provided 225 mg (97%) of thieno[3,4-c]pyridine-6-carboxylic acid as a yellow solid. MS (EI) m/z: 179 ($M^+$).

Example 28(i) can be obtained by coupling either exo-[2.2.1]-3-Amine or endo-[2.2.1]-3-Amine with thieno[3,4-c]pyridine-6-carboxylic acid using procedures discussed herein.

The following examples can be prepared according to the coupling procedures discussed herein:

EXAMPLE 28(i-a)

N-(1-(6-methyl)-azabicyclo[2.2.1]hept-3-yl)thieno[3,4-c]pyridine-6-carboxamide.

EXAMPLE 28(ii)

N-(1-(6-methyl)-azabicyclo[2.2.2]oct-3-yl)thieno[3,4-c]pyridine-6-carboxamide.

EXAMPLE 28(iii)

N-(2-azabicyclo[2.2.1]hept-5-yl)thieno[3,4-c]pyridine-6-carboxamide.

EXAMPLE 28(iv)

N-(2-azabicyclo[2.2.1]hept-6-yl)thieno[3,4-c]pyridine-6-carboxamide.

EXAMPLE 28(v)

N-((3R,5R)-1-azabicyclo[3.2.1]oct-3-yl)thieno[3,4-c]pyridine-6-carboxamide.

EXAMPLE 28(vi)

N-(1-azabicyclo[3.2.2]non-3-yl)thieno[3,4-c]pyridine-6-carboxamide.

Materials and Methods for Determining α7 nAChR Agonist Activity
Cell-based Assay for Measuring the $EC_{50}$ of α7 nAChR Agonists
Construction and Expression of the α7-$5HT_3$ Receptor The cDNA encoding the N-terminal 201 amino acids from the human α7 nAChR that contain the ligand binding domain of the ion channel was fused to the cDNA encoding the pore forming region of the mouse $5HT_3$ receptor as described by Eisele J L, et al., Chimaeric nicotinic-serotonergic receptor combines distinct ligand binding and channel specificities, Nature (1993), December 2;366(6454):479–83, and modified by Groppi, et al., WO 00/73431. The chimeric α7-$5HT_3$ ion channel was inserted into pGS 175 and pGS 179 which contain the resistance genes for G-418 and hygromycin B, respectively. Both plasmids were simultaneously transfected into SH-EP1 cells and cell lines were selected that were resistant to both G-418 and hyrgromycin B. Cell lines expressing the chimeric ion channel were identified by their ability to bind fluorescent α-bungarotoxin on their cell surface. The cells with the highest amount of fluorescent α-bungarotoxin binding were isolated using a Fluorescent Activated Cell Sorter (FACS). Cell lines that stably expressed the chimeric α7-$5HT_3$ were identified by measuring fluorescent α-bungarotoxin binding after growing the cells in minimal essential medium containing nonessential amino acids supplemented with 10% fetal bovine serum, L-glutamine, 100 units/ml penicillin/streptomycin, 250 ng/mg fungizone, 400 μg/ml hygromycin B, and 400 μg/ml G-418 at 37° C. with 6% $CO_2$ in a standard mammalian cell incubator for at least 4 weeks in continuous culture.

Assay of the Activity of the Chimeric α7-$5HT_3$ Receptor

To assay the activity of the α7-$5HT_3$ ion channel, cells expressing the channel were plated into each well of either a 96 or 384 well dish (Corning #3614) and grown to confluence prior to assay. On the day of the assay, the cells were loaded with a 1:1 mixture of 2 mM Calcium Green 1, AM (Molecular Probes) dissolved in anhydrous DMSO and 20% pluronic F-127 (Molecular Probes). This solution was added directly to the growth media of each well to achieve a final concentration 2 μM. The cells were incubated with the dye for 60 min at 37° C. and then washed with a modified version of Earle's balanced salt solution (MMEBSS) as described in WO 00/73431. The ion conditions of the MMEBSS was adjusted to maximize the flux of calcium ion through the chimeric α7-$5HT_3$ ion channel as described in WO 00/73431. The activity of compounds on the chimeric α7-$5HT_3$ ion channel was analyzed on FLIPR. The instrument was set up with an excitation wavelength of 488 nanometers using 500 milliwatts of power. Fluorescent emission was measured above 525 nanometers with an appropriate F-stop to maintain a maximal signal to noise ratio. Agonist activity of each compound was measured by directly adding the compound to cells expressing the chimeric α7-$5HT_3$ ion channel and measuring the resulting increase in intracellular calcium that is caused by the agonist-induced activation of the chimeric ion channel. The assay is quantitative such that concentration-dependent increase in intracelluar calcium is measured as concentration-dependent change in Calcium Green fluorescence. The effective concentration needed for a compound to cause a 50% maximal increase in intracellular calcium is termed the $EC_{50}$. The following examples were tested and have $EC_{50}$ values from about 40 nM to about 1200 nM: Example 1(i), Example 1(i-b), Example 1(i-d), Example 1(v), Example 1(vi), Example 2(v), Example 7(i), Example 7(v), Example 8(i), Example 11(i), Example 21(i), Example 21(v), Example 22(i), Example 22(v), Example 25(i), and Example 26(i).

Binding Constants

Another way for measuring α7 nAChR agonist activity is to determine binding constants of a potential agonist in a competition binding assay. For α7 nAChR agonists, there is good correlation between functional $EC_{50}$ values using the chimeric α7-5HT$_3$ ion channel as a drug target and binding affinity of compounds to the endogenous α7 nAChR.

Membrane Preparation

Male Sprague-Dawley rats (300–350 g) are sacrificed by decapitation and the brains (whole brain minus cerebellum) are dissected quickly, weighed and homogenized in 9 volumes/g wet weight of ice-cold 0.32 M sucrose using a rotating pestle on setting 50 (10 up and down strokes). The homogenate is centrifuged at 1,000×g for 10 minutes at 4° C. The supernatant is collected and centrifuged at 20,000×g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at rt and diluted with Kreb's −20 mM Hepes buffer pH 7.0 (at rt) containing 4.16 mM NaHCO$_3$, 0.44 mM KH$_2$PO$_4$, 127 mM NaCl, 5.36 mM KCl, 1.26 mM CaCl$_2$, and 0.98 mM MgCl$_2$, so that 25–150 μg protein are added per test tube. Proteins are determined by the Bradford method (Bradford, M. M., *Anal. Biochem.*, 72, 248–254, 1976) using bovine serum albumin as the standard.

Binding Assay

For saturation studies, 0.4 mL homogenate are added to test tubes containing buffer and various concentrations of radioligand, and are incubated in a final volume of 0.5 mL for 1 hour at 25° C. Nonspecific binding was determined in tissues incubated in parallel in the presence of 0.05 mls MLA for a final concentration of 1 μM, added before the radioligand. In competition studies, drugs are added in increasing concentrations to the test tubes before addition of 0.05 mls [$^3$H]-MLA for a final concentration 3.0 to 4.0 nM. The incubations are terminated by rapid vacuum filtration through Whatman GF/B glass filter paper mounted on a 48 well Brandel cell harvester. Filters are pre-soaked in 50 mM Tris HCl pH 7.0–0.05% polyethylenimine. The filters are rapidly washed two times with 5 mL aliquots of cold 0.9% saline and then counted for radioactivity by liquid scintillation spectrometry.

Data Analysis

In competition binding studies, the inhibition constant (Ki) was calculated from the concentration dependent inhibition of [3H]-MLA binding obtained from non-linear regression fitting program according to the Cheng-Prusoff equation (Cheng, Y. C. and Prussoff, W. H., *Biochem. Pharmacol.*, 22, p. 3099–3108, 1973). Hill coefficients were obtained using non-linear regression (GraphPad Prism sigmoidal dose-response with variable slope).

What is claimed:

1. A compound selected from the group consisting of

Exo-4(S)-N-(1-azabicyclo[2.2.1]hept-3-yl)furo[2,3-c]pyridine-5-carboxamide;
Exo-4(R)-N-(1-azabicyclo[2.2.1]hept-3-yl)furo[2,3-c]pyridine-5-carboxamide;
Exo-N-(1-azabicyclo[2.2.1]hept-3-yl)furo[2,3-c]pyridine-5-carboxamide;
(+)-N-[endo-1-azabicyclo[2.2.1]hept-3-yl]furo[2,3-c]pyridine-5-carboxamide;
(−)-N-[endo-1-azabicyclo[2.2.1]hept-3-yl]furo[2,3-c]pyridine-5-carboxamide;
N-(1-(6-methyl)-azabicyclo[2.2.1]hept-3-yl)furo[2,3-c]pyridine-5-carboxamide;
N-((3R,5R)-1-azabicyclo[3.2.1]oct-3-yl)furo[2,3-c]pyridine-5-carboxamide;
N-(1-azabicyclo[3.2.2]non-3-yl)furo[2,3-c]pyridine-5-carboxamide;
N-[(exo)-azabicyclo[2.2.1]hept-3-yl]furo[3,2-c]pyridine-6-carboxamide;
N-(1-(6-methyl)-azabicyclo[2.2.1]hept-3-yl)furo[3,2-c]pyridine-6-carboxamide;
N-((3R,5R)-1-azabicyclo[3.2.1]oct-3-yl)furo[3,2-c]pyridine-6-carboxamide;
N-(1-azabicyclo[3.2.2]non-3-yl)furo[3,2-c]pyridine-6-carboxamide;
N-(1-azabicyclo[2.2.1]-hept-3-yl)-2,3-dihydrofuro[2,3-c]pyridine-5-carboxamide;
N-(1-(6-methyl)-azabicyclo[2.2.1]hept-3-yl)-2,3-dihydrofuro[2,3-c]pyridine-5-carboxamide;
N-((3R,5R)-1-azabicyclo[3.2.1]oct-3-yl)-2,3-dihydrofuro[2,3-c]pyridine-5-carboxamide;
N-(1-azabicyclo[3.2.2]non-3-yl)-2,3-dihydrofuro[2,3-c]pyridine-5-carboxamide;
N-(1-azabicyclo[2.2.1]hept-3-yl)-7-chlorofuro[2,3-c]pyridine-5-carboxamide;
N-(1-(6-methyl)-azabicyclo[2.2.1 ]hept-3-yl)-7-chlorofuro[2,3-c]pyridine-5-carboxamide;
N-((3R,5R)-1-azabicyclo[3.2.1]oct-3-yl)-7-chlorofuro[2,3-c]pyridine-5-carboxamide;
N-(1-azabicyclo[2.2.1]hept-3-yl)-3,3-dimethyl-2,3-dihydrofuro[2,3-c]pyridine-5-carboxamide;
N-(1-(6-methyl)-azabicyclo[2.2.1]hept-3-yl)-3,3-dimethyl-2,3-dihydrofuro[2,3-c]pyridine-5-carboxamide;
N-((3R,5R)-1-azabicyclo[3.2.1]oct-3-yl)-3,3-dimethyl-2,3-dihydrofuro[2,3-c]pyridine-5-carboxamide;
N-(1-azabicyclo[2.2.1]hept-3-yl)-2-methylfuro[2,3-c]pyridine-5-carboxamide;
N-(1-(6-methyl)-azabicyclo[2.2.1]hept-3-yl)-2-methylfuro[2,3-c]pyridine-5-carboxamide;
N-((3R,5R)-1-azabicyclo[3.2.1]oct-3-yl)-2-methylfuro[2,3-c]pyridine-5-carboxamide;
Exo-4(S)-N-(1-azabicyclo[2.2.1]hept-3-yl)-3-methylfuro[2,3-c]pyridine-5-carboxamide;
N-(1-(6-methyl)-azabicyclo[2.2.1]hept-3-yl)-3-methylfuro[2,3-c]pyridine-5-carboxamide;
(exo)-N-[1-Azabicyclo[3.2.1]oct-3-yl]-3-methylfuro[2,3-c]pyridine-5-carboxamide;
(3R,5R)-N-[1-azabicyclo[3.2.1]oct-3-yl]-3-methylfuro[2,3-c]pyridine-5-carboxamide;
Exo-4(S)-N-(1-azabicyclo[2.2.1]hept-3-yl)-3-ethylfuro[2,3-c]pyridine-5-carboxamide;
N-(1-(6-methyl)-azabicyclo[2.2.1]hept-3-yl)-3-ethylfuro[2,3-c]pyridine-5-carboxamide;
N-((3R,5R)-1-azabicyclo[3.2.1]oct-3-yl)-3-ethylfuro[2,3-c]pyridine-5-carboxamide;
N-(1-azabicyclo[2.2.1]hept-3-yl)-furo[2,3-b]pyridine-2-carboxamide;
N-(1-(6-methyl)-azabicyclo[2.2.1]hept-3-yl)-furo[2,3-b]pyridine-2-carboxamide;
N-((3R,5R)-1-azabicyclo[3.2.1]oct-3-yl)-furo[2,3-b]pyridine-2-carboxamide;
N-(1-azabicyclo[3.2.2]non-3-yl)-furo[2,3-b]pyridine-2-carboxamide;
Exo-4(S)-N-(1-azabicyclo[2.2.1]hept-3-yl)-3-isopropylfuro[2,3-c]pyridine-5-carboxamide;
N-(1-(6-methyl)-azabicyclo[2.2.1]hept-3-yl)-3-isopropylfuro[2,3-c]pyridine-5-carboxamide;
N-((3R,5R)-1-azabicyclo[3.2.1]oct-3-yl)-3-isopropylfuro[2,3-c]pyridine-5-carboxamide;
N-(1-azabicyclo[2.2.1]hept-3-yl)-7-(methylsulfanyl)furo[2,3-c]pyridine-5-carboxamide;
N-(1-(6-methyl)-azabicyclo[2.2.1]hept-3-yl)-7-(methylsulfanyl)furo[2,3-c]pyridine-5-carboxamide;
N-((3R,5R)-1-azabicyclo[3.2.1]oct-3-yl)-7-(methylsulfanyl)furo[2,3-c]pyridine-5-carboxamide;
N-(1-azabicyclo[2.2.1]hept-3-yl)-thieno[2,3-b]pyridine-2-carboxamide;

N-(1-(6-methyl)-azabicyclo[2.2.1]hept-3-yl)-thieno[2,3-b]
    pyridine-2-carboxamide;
N-((3R,5R)-1-azabicyclo[3.2.1]oct-3-yl)-thieno[2,3-b]
    pyridine-2-carboxamide;
N-(1-azabicyclo[3.2.2]non-3-yl)-thieno[2,3-b]pyridine-2-
    carboxamide;
N-(1-azabicyclo[2.2.1]hept-3-yl)-thieno[2,3-b]pyridine-5-
    carboxamide;
N-(1-(6-methyl)-azabicyclo[2.2.1]hept-3-yl)-thieno[2,3-b]
    pyridine-5-carboxamide;
N-((3R,5R)-1-azabicyclo[3.2.1]oct-3-yl)thieno[2,3-b]
    pyridine-5-carboxamide;
N-(1-azabicyclo[3.2.2]non-3-yl)-thieno[2,3-b]pyridine-5-
    carboxamide;
N-(1-azabicyclo[2.2.1]hept-3-yl)-thieno[2,3-b]pyridine-6-
    carboxamide;
N-(1-(6-methyl)-azabicyclo[2.2.1]hept-3-yl)-thieno[2,3-b]
    pyridine-6-carboxamide;
N-((3R,5R)-1-azabicyclo[3.2.1]oct-3-yl)-thieno[2,3-b]
    pyridine-6-carboxamide;
N-(1-azabicyclo[3.2.2]non-3-yl)-thieno[2,3-b]pyridine-6-
    carboxamide;
N-(1-azabicyclo[2.2.1]hept-3-yl)-thieno[2,3-c]pyridine-2-
    carboxamide;
N-(1-(6-methyl)-azabicyclo[2.2.1]hept-3-yl)-thieno[2,3-c]
    pyridine-2-carboxamide;
N-((3R,5R)-1-azabicyclo[3.2.1]oct-3-yl)-thieno[2,3-c]
    pyridine-2-carboxamide;
N-(1-azabicyclo[3.2.2]non-3-yl)-thieno[2,3-c]pyridine-2-
    carboxamide;
N-(1-azabicyclo[2.2.1]hept-3-yl)-thieno[3,2-b]pyridine-2-
    carboxamide;
N-(1-(6-methyl)-azabicyclo[2.2.1]hept-3-yl)-thieno[3,2-b]
    pyridine-2-carboxamide;
N-((3R,5R)-1-azabicyclo[3.2.1]oct-3-yl)-thieno[3,2-b]
    pyridine-2-carboxamide;
N-(1-azabicyclo[3.2.2]non-3-yl)-thieno[3,2-b]pyridine-2-
    carboxamide;
N-(1-azabicyclo[2.2.1]hept-3-yl)-thieno[3,2-b]pyridine-5-
    carboxamide;
N-(1-(6-methyl)-azabicyclo[2.2.1]hept-3-yl)-thieno[3,2-b]
    pyridine-5-carboxamide;
N-((3R,5R)-1-azabicyclo[3.2.1]oct-3-yl)-thieno[3,2-b]
    pyridine-5-carboxamide;
N-(1-azabicyclo[3.2.2]non-3-yl)-thieno[3,2-b]pyridine-5-
    carboxamide;
N-(1-azabicyclo[2.2.1]hept-3-yl)-thieno[3,2-b]pyridine-6-
    carboxamide;
N-(1-(6-methyl)-azabicyclo[2.2.1]hept-3-yl)-thieno[3,2-b]
    pyridine-6-carboxamide;
N-((3R,5R)-1-azabicyclo[3.2.1]oct-3-yl)-thieno[3,2-b]
    pyridine-6-carboxamide;
N-(1-azabicyclo[3.2.2]non-3-yl)-thieno[3,2-b]pyridine-6-
    carboxamide;
N-(1-azabicyclo[2.2.1]hept-3-yl)-thieno[3,2-c]pyridine-2-
    carboxamide;
N-(1-(6-methyl)-azabicyclo[2.2.1]hept-3-yl)-thieno[3,2-b]
    pyridine-2-carboxamide;
N-(2-azabicyclo[2.2.1]hept-6-yl)-thieno[3,2-c]pyridine-2-
    carboxamide;
N-(2-azabicyclo[2.2.1]hept-6-yl)-thieno[3,2-c]pyridine-2-
    carboxamide;
Exo-4(S)-N-(1-azabicyclo[2.2.1]hept-3-yl)-thieno[2,3-c]
    pyridine-5-carboxamide;
N-(1-(6-methyl)-azabicyclo[2.2.1]hept-3-yl)-thieno[2,3-c]
    pyridine-5-carboxamide;
N-((3R,5R)-1-azabicyclo[3.2.1]oct-3-yl)-thieno[2,3-c]
    pyridine-5-carboxamide;
N-(1-azabicyclo[3.2.2]non-3-yl)-thieno[2,3-c]pyridine-5-
    carboxamide;
Exo-4(S)-N-(1-azabicyclo[2.2.1]hept-3-yl)-thieno[3,2-c]
    pyridine-6-carboxamide;
N-(1-(6-methyl)-azabicyclo[2.2.1]hept-3-yl)-thieno[3,2-c]
    pyridine-6-carboxamide;
N-((3R,5R)-1-azabicyclo[3.2.1]oct-3-yl)-thieno[3,2-c]
    pyridine-6-carboxamide;
N-(1-azabicyclo[3.2.2]non-3-yl)-thieno[3,2-c]pyridine-6-
    carboxamide;
N-(1-azabicyclo[2.2.1]hept-3-yl)-1H-pyrrolo[2,3-c]
    pyridine-5-carboxamide;
N-(1-(6-methyl)-azabicyclo[2.2.1]hept-3-yl)-1H-pyrrolo[2,
    3-c]pyridine-5-carboxamide;
N-((3R,5R)-1-azabicyclo[3.2.1]oct-3-yl)-1H-pyrrolo[2,3-c]
    pyridine-5-carboxamide;
N-(1-azabicyclo[3.2.2]non-3-yl)-1H-pyrrolo[2,3-c]
    pyridine-5-carboxamide;
N-(1-azabicyclo[2.2.1]hept-3-yl)-1-methyl-1H-pyrrolo[2,3-
    c]pyridine-5-carboxamide;
N-(1-(6-methyl)-azabicyclo[2.2.1]hept-3-yl)-1-methyl-1H-
    pyrrolo[2,3-c]pyridine-5-carboxamide;
N-((3R,5R)-1-azabicyclo[3.2.1]oct-3-yl)-1-methyl-1H-
    pyrrolo[2,3-c]pyridine-5-carboxamide;
N-(exo-(4S)-1-azabicyclo[2.2.1]hept-3-yl)-3-bromofuro[2,
    3-c]pyridine-5-carboxamide;
N-(1-(6-methyl)-azabicyclo[2.2.1]hept-3-yl)-3-bromofuro
    [2,3-c]pyridine-5-carboxamide;
N-((3R,5R)-1-azabicyclo[3.2.1]oct-3-yl)-3-bromofuro[2,3-
    c]pyridine-5-carboxamide;
N-[exo-(4S)-1-azabicyclo[2.2.1]hept-3-yl]-3-chlorofuro[2,
    3-c]pyridine-5-carboxamide;
N-(1-(6-methyl)-azabicyclo[2.2.1]hept-3-yl)-3-chlorofuro
    [2,3-c]pyridine-5-carboxamide; and
N-((3R,5R)-1-azabicyclo[3.2.1]oct-3-yl)-3-chlorofuro(2,3-
    c]pyridine-5-carboxamide;
or a pharmaceutically acceptable salt thereof, wherein the
compound is the pure enantiomer or a racemic mixture
thereof.

2. The compound of claim 1, wherein the compound is
Exo-4(S)-N-(1-azabicyclo[2.2.1]hept-3-yl)furo[2,3-c]
    pyridine-5-carboxamide;
N-(1-(6-methyl)-azabicyclo[2.2.1]hept-3-yl)furo[2,3-c]
    pyridine-5-carboxamide;
N-((3R,5R)-1-azabicyclo[3.2.1]oct-3-yl)furo[2,3-c]
    pyridine-5-carboxamide;
N-(1-azabicyclo[3.2.2]non-3-yl)furo[2,3-c]pyridine-5-
    carboxamide;
N-[(exo-(4S)-1-azabicyclo[2.2.1]hept-3-yl]furo[3,2-c]
    pyridine-6-carboxamide;
N-(1-(6-methyl)-azabicyclo[2.2.1]hept-3-yl)furo[3,2-c]
    pyridine-6-carboxamide;
N-((3R,5R)-1-azabicyclo[3.2.1]oct-3-yl)furo[3,2-c]
    pyridine-6-carboxamide;
N-(1-azabicyclo[3.2.2]non-3-yl)furo[3,2-c]pyridine-6-
    carboxamide;
N-(1-azabicyclo[2.2.1]hept-3-yl)-2-methylfuro[2,3-c]
    pyridine-5-carboxamide;
N-(1-(6-methyl)-azabicyclo[2.2.1]hept-3-yl)-2-methylfuro
    [2,3-c]pyridine-5-carboxamide;
N-((3R,5R)-1-azabicyclo[3.2.1]oct-3-yl)-2-methylfuro[2,3-
    c]pyridine-5-carboxamide;
Exo-4(S)-N-(1-azabicyclo[2.2.1]hept-3-yl)-3-methylfuro[2,
    3-c]pyridine-5-carboxamide;
N-(1-(6-methyl)-azabicyclo[2.2.1]hept-3-yl)-3-methylfuro
    [2,3-c]pyridine-5-carboxamide;
(exo)-N-[1-Azabicyclo[3.2.1]oct-3-yl]-3-methylfuro[2,3-c]
    pyridine-5-carboximide;

(3R,5R)-N-[1-azabicyclo[3.2.1]oct-3-yl]-3-methylfuro[2,3-c]pyridine-5-carboximide;
Exo-4(S)-N-(1-azabicyclo[2.2.1]hept-3-yl)-3-ethylfuro[2,3-c]pyridine-5-carboxamide;
N-(1-(6-methyl)-azabicyclo[2.2.1]hept-3-yl)-3-ethylfuro[2,3-c]pyridine-5-carboxamide;
N-((3R,5R)-1-azabicyclo[3.2.1]oct-3-yl)-3-ethylfuro[l2,3-c]pyridine-5-carboxamide;
N-(1-azabicyclo[2.2.1]hept-3-yl)-thieno[2,3-b]pyridine-5-carboxamide;
N-(1-(6-methyl)-azabicyclo[2.2.1]hept-3-yl)-thieno[2,3-b]pyridine-5-carboxamide;
N-((3R,5R)-1-azabicyclo[3.2.1]oct-3-yl)thieno[2,3-b]pyridine-5-carboxamide;
N-(1-azabicyclo[3.2.2]non-3-yl)-thieno[2,3-b]pyridine-5-carboxamide;
N-(1-azabicyclo[2.2.1]hept-3-yl)-thieno[2,3-b]pyridine-6-carboxamide;
N-(1-(6-methyl)-azabicyclo[2.2.1]hept-3-yl)-thieno[2,3-b]pyridine-6-carboxamide;
N-((3R,5R)-1-azabicyclo[3.2.1]oct-3-yl)-thieno[2,3-b]pyridine-6-carboxamide;
N-(1-azabicyclo[3.2.2]non-3-yl)-thieno[2,3-b]pyridine-6-carboxamide;
N-(1-azabicyclo[2.2.1]hept-3-yl)-thieno[3,2-b]pyridine-5-carboxamide;
N-(1-(6-methyl)-azabicyclo[2.2.1]hept-3-yl)-thieno[3,2-b]pyridine-5-carboxamide;
N-((3R,5R)-1-azabicyclo[3.2.1]oct-3-yl)-thieno[3,2-b]pyridine-5-carboxamide;
N-(1-azabicyclo[3.2.2]non-3-yl)-thieno[3,2-b]pyridine-5-carboxamide;
N-(1-azabicyclo[2.2.1]hept-3-yl)-thieno[3,2-b]pyridine-6-carboxamide;
N-(1-(6-methyl)-azabicyclo[2.2.1]hept-3-yl)-thieno[3,2-b]pyridine-6-carboxamide;
N-((3R,5R)-1-azabicyclo[3.2.1]oct-3-yl)-thieno[3,2-b]pyridine-6-carboxamide;
N-(1-azabicyclo[3.2.2]non-3-yl)-thieno[3,2-b]pyridine-6-carboxamide;
Exo-4(S)-N-(1-azabicyclo[2.2.1]hept-3-yl)-thieno[2,3-c]pyridine-5-carboxamide;
N-(1-(6-methyl)-azabicyclo[2.2.1]hept-3-yl)-thieno[2,3-c]pyridine-5-carboxamide;
N-((3R,5R)-1-azabicyclo[3.2.1]oct-3-yl)-thieno[2,3-c]pyridine-5-carboxamide;
N-(1-azabicyclo[3.2.2]non-3-yl)-thieno[2,3-c]pyridine-5-carboxamide;
Exo-4(S)-N-(1-azabicyclo[2.2.1]hept-3-yl)-thieno[3,2-c]pyridine-6-carboxamide;
N-(1-(6-methyl)-azabicyclo[2.2.1]hept-3-yl)-thieno[3,2-c]pyridine-6-carboxamide;
N-((3R,5R)-1-azabicyclo[3.2.1]oct-3-yl)-thieno[3,2-c]pyridine-6-carboxamide;
N-(1-azabicyclo[3.2.2]non-3-yl)-thieno[3,2-c]pyridine-6-carboxamide;
N-[exo-(4S)-1-azabicyclo[2.2.1]hept-3-yl]-3-chlorofuro[2,3-c pyridine-5-carboxamide;
N-(1-(6-methyl)-azabicyclo[2.2.1]hept-3-yl)-3-chlorofuro[2,3-c]pyridine-5-carboxamide;
N-((3R,5R)-1-azabicyclo[3.2.1]oct-3-yl)-3-chlorofuro[2,3-c]pyridine-5-carboxamide;
or a pharmaceutically acceptable salt thereof, wherein the compound is a racemic mixture or the pure enantiomer pure thereof.

3. A compound selected from the group consisting of
N-[exo-4(S)-1-azabicyclo[2.2.1]hept-3-yl]-2-vinylfuro[3,2-c]pyridine-6-carboxamide;
N-[exo-4(S)-1-azabicyclo[2.2.1]hept-3-yl]-2-ethynylfuro[3,2-c]pyridine-6-carboxamide;
N-[exo-4(S)-1-azabicyclo[2.2.1]hept-3-yl]-2-prop-1-ynylfuro[3,2-c]pyridine-6-carboxamide;
N-[exo-4(S)-1-azabicyclo[2.2.1]hept-3-yl]-2-(3-hydroxyprop-1-ynyl)furo[3,2-c]pyridine-6-carboxamide;
methyl 3-(6-{[exo-4(S)-1-azabicyclo[2.2.1]hept-3-ylamino]carbonyl}furo[3,2-c]pyridin-2-yl)prop-2-ynoate;
2-(3-amino-3-oxoprop-1-ynyl)-N-[exo-4(S)-1-azabicyclo[2.2.1]hept-3-yl]furo[3,2-c]pyridine-6-carboxamide;
N-[exo-4(S)-1-azabicyclo[2.2.1]hept-3-yl]-2-cyanofuro[3,2-c]pyridine-6-carboxamide;
N-[exo-4(S)-1-azabicyclo[2.2.1]hept-3-yl]-2-chlorofuro[3,2-c]pyridine-6-carboxamide;
N-[exo-4(S)-1-azabicyclo[2.2.1]hept-3-yl]-2-fluorofuro[3,2-c]pyridine-6-carboxamide;
N-[exo-4(S)-1-azabicyclo[2.2.1]hept-3-yl]-2-iodofuro[3,2-c]pyridine-6-carboxamide;
N-[exo-4(S)-1-azabicyclo[2.2.1]hept-3-yl]-2-trifluoromethylfuro[3,2-c]pyridine-6-carboxamide;
N-[exo-4(S)-1-azabicyclo[2.2.1]hept-3-yl]-2-(methylthio)furo[3,2-c]pyridine-6-carboxamide;
N-[exo-4(S)-1-azabicyclo[2.2.1]hept-3-yl]-2-(methylamino)furo[3,2-c]pyridine-6-carboxamide;
N-[exo-4(S)-1-azabicyclo[2.2.1]hept-3-yl]-2-(formylamino)furo[3,2-c]pyridine-6-carboxamide;
N-[exo-4(S)-1-azabicyclo[2.2.1]hept-3-yl]-2-(formyl(methyl)amino]furo[3,2-c]pyridine-6-carboxamide;
N-[exo-4(S)-1-azabicyclo[2.2.1]hept-3-yl]-2-[(trifluoroacetyl)amino]furo[3,2-c]pyridine-6-carboxamide;
N-6-[exo-4(S)-1-azabicyclo[2.2.1]hept-3-yl]furo[3,2-c]pyridine-2,6-dicarboxamide;
N-[exo-4(S)-1-azabicyclo[2.2.1]hept-3-yl]-2-formylfuro[3,2-c]pyridine-6-carboxamide;
N-[exo-4(S)-1-azabicyclo[2.2.1]hept-3-yl]-2-(trifluoroacetyl)furo[3,2-c]pyridine-6-carboxamide;
N-[exo-4(S)-1-azabicyclo[2.2.1]hept-3-yl]-2-(methylsulfonyl)furo[3,2-c]pyridine-6-carboxamide;
methyl 6-{[exo-4(S)-1-azabicyclo[2.2.1]hept-3-ylamino]carbonyl}furo[3,2-c]pyridine-2-carboxylate;
N-[exo-4(S)-1-azabicyclo[2.2.1]hept-3-yl]-2-vinylthieno[3,2-c]pyridine-6-carboxamide;
N-[exo-4(S)-1-azabicyclo[2.2.1]hept-3-yl]-2-ethynylthieno[3,2-c]pyridine-6-carboxamide;
N-[exo-4(S)-1-azabicyclo[2.2.1]hept-3-yl]-2-prop-1-ynyl)thieno[3,2-c]pyridine-6-carboxamide;
N-[exo-4(S)-1-azabicyclo[2.2.1]hept-3-yl]-2-(3-hydroxyprop-1-ynyl)thieno[3,2-c]pyridine-6-carboxamide;
methyl 3-(6-{[exo-4(S)-1-azabicyclo[2.2.1]hept-3-ylamino]carbonyl}thieno[3,2-c]pyridin-2-yl)prop-2-ynoate;
2-(3-amino-3-oxoprop-1-ynyl)-N-[exo-4(S)-1-azabicyclo[2.2.1]hept-3-yl]thieno[3,2-c]pyridine-6-carboxamide;
N-[exo-4(S)-1-azabicyclo[2.2.1]hept-3-yl]-2-cyanothieno[3,2-c]pyridine-6-carboxamide;
N-[exo-4(S)-1-azabicyclo[2.2.1]hept-3-yl]-2-chlorothieno[3,2-c]pyridine-6-carboxamide;
N-[exo-4(S)-1-azabicyclo[2.2.1]hept-3-yl]-2-fluorothieno[3,2-c]pyridine-6-carboxamide;
N-[exo-4(S)-1-azabicyclo[2.2.1]hept-3-yl]-2-iodothieno[3,2-c]pyridine-6-carboxamide;
N-[exo-4(S)-1-azabicyclo[2.2.1]hept-3-yl]-2-trifluoromethylthieno[3,2-c]pyridine-6-carboxamide;
N-[exo-4(S)-1-azabicyclo[2.2.1]hept-3-yl]-2-(methylthio)thieno[3,2-c]pyridine-6-carboxamide;
N-[exo-4(S)-1-azabicyclo[2.2.1]hept-3-yl]-2-(methylamino)thieno[3,2-c]pyridine-6-carboxamide;

N-[exo-4(S)-1-azabicyclo[2.2.1]hept-3-yl]-2-(formylamino)thieno[3,2-c]pyridine-6-carboxamide;
N-[exo-4(S)-1-azabicyclo[2.2.1]hept-3-yl]-2-[formyl(methyl)amino]thieno[3,2-c]pyridine-6-carboxamide;
N-[exo-4(S)-1-azabicyclo[2.2.1]hept-3-yl]-2-[(trifluoroacetyl)amino]thieno[3.2-c]pyridine-6-carboxamide;
N-[exo-4(S)-1-azabicyclo[2.2.1]hept-3-yl]-2-(cyclopropylamino)thieno[3,2-c]pyridine-6-carboxamide;
N-[exo-4(S)-1-azabicyclo[2.2.1]hept-3-yl]-2-[dimethylamino]thieno[3,2-c]pyridine-6-carboxamide;
N-6-[exo-4(S)-1-azabicyclo[2.2.1]hept-3-yl]thieno[3,2-c]pyridine-2,6-dicarboxamide;
N-[exo-4(S)-1-azabicyclo[2.2.1]hept-3-yl]-2-formylthieno[3,2-c]pyridine-6-carboxamide;
2-acetyl-N-[exo-4(S)-1-azabicyclo[2.2.1]hept-3-yl]thieno[3,2-c]pyridine-6-carboxamide;
N-[exo-4(S)-1-azabicyclo[2.2.1]hept-3-yl]-2-(trifluoroacetyl)thieno[3,2-c]pyridine-6-carboxamide;
N-[exo-4(S)-1-azabicyclo[2.2.1]hept-3-yl]-2-(methylsulfonyl)thieno[3,2-c]pyridine-6-carboxamide;
methyl 6-{[exo-4(S)-1-azabicyclo[2.2.1]hept-3-ylamino]carbonyl}thieno[3,2-c]pyridine-2-carboxylate
N-[exo-4(S)-1-azabicyclo[2.2.1]hept-3-yl]-3-vinylfuro[2,3-c]pyridine-5-carboxamide;
N-[exo-4(S)-1-azabicyclo[2.2.1]hept-3-yl]-3-ethynylfuro[2,3-c]pyridine-5-carboxamide;
N-[exo-4(S)-1-azabicyclo[2.2.1]hept-3-yl]-3-prop-1-ynylfuro[2,3-c]pyridine-5-carboxamide;
N-[exo-4(S)-1-azabicyclo[2.2.1]hept-3-yl]-3-(3-hydroxyprop-1-ynyl)furo[2,3-c]pyridine-5-carboxamide;
methyl 3-(5-{[exo-4(S)-1-azabicyclo[2.2.1]hept-3-ylamino]carbonyl}furo[2,3-c]pyridin-3-yl)prop-2-ynoate;
3-(3-amino-3-oxoprop-1-ynyl)-N-[exo-4(S)-1-azabicyclo[2.2.1]hept-3-yl]furo[2,3-c]pyridine-5-carboxamide;
N-[exo-4(S)-1-azabicyclo[2.2.1]hept-3-yl]-3-cyanofuro[2,3-c]pyridine-5-carboxamide;
N-[exo-4(S)-1-azabicyclo[2.2.1]hept-3-yl]-3-fluorofuro[2,3-c]pyridine-5-carboxamide;
N-[exo-4(S)-1-azabicyclo[2.2.1]hept-3-yl]-3-iodofuro[2,3-c]pyridine-5-carboxamide;
N-[exo-4(S)-1-azabicyclo[2.2.1]hept-3-yl)-3-trifluoromethylfuro[2,3-c]pyridine-5-carboxamide;
N-[exo-4(S)-1-azabicyclo[2.2.1]hept-3-yl]-3-(methylthio)furo[2,3-c]pyridine-5-carboxamide;
N-[exo-4(S)-1-azabicyclo[2.2.1]hept-3-yl]-3-(methylamino)furo[2,3-c]pyridine-5-carboxamide;
N-[exo-4(S)-1-azabicyclo[2.2.1]hept-3-yl]-3-(formylamino)furo[2,3-c]pyridine-5-carboxamide;
N-[exo-4(S)-1-azabicyclo[2.2.1]hept-3-yl]-3-[formyl(methyl)amino]furo[2,3-c]pyridine-5-carboxamide;
N-[exo-4(S)-1-azabicyclo[2.2.1]hept-3-yl]-3-[(trifluoroacetyl)amino]furo[2,3-c]pyridine-5-carboxamide;
N-[exo-4(S)-1-azabycyclo[2.2.1]hept-3-yl]-3-(cyclopropylamino)furo[2,3-c]pyridine-5-carboximide;
N-[exo-4(S)-1-azabicyclo[2.2.1]hept3-yl]-3[dimethylamino]furo[2,3-c]pyridine-5-carboxamide;
N-5-[exo-4(S)-1-azabicyclo[2.2.1]hept-3-yl]furo[2,3-c]pyridine-3,5-dicarboxamide;
N-[exo-4(S)-1-azabicyclo[2.2.1]hept-3-yl]-3-formylfuro[2,3-c]pyridine-5-carboxamide;
N-[exo-4(S)-1-azabicyclo[2.2.1]hept-3-yl]-3-(trifluoroacetyl)furo[2,3-c]pyridine-5-carboxamide;
N-[exo-4(S)-1-azabicyclo[2.2.1]hept-3-yl]-3-(methylsulfonyl)furo[2,3-c]pyridine-5-carboxamide;
methyl 5-{[exo-4(S)-1-azabicyclo[2.2.1]hept-3-ylamino]carbonyl}1furo[2,3-c]pyridine-3-carboxylate;
N-[exo-4(S)-1-azabicyclo[2.2.1]hept-3-yl]-3-vinylthieno[2,3-c]pyridine-5-carboxamide;
N-[exo-4(S)-1-azabicyclo[2.2.1]hept-3-yl]-3-ethynylthieno[2,3-c]pyridine-5-carboxamide;
N-[exo-4(S)-1-azabicyclo[2.2.1]hept-3-yl]-3-prop-1-ynylthieno[2,3-c]pyridine-5-carboxamide;
N-[exo-4(S)-1-azabicyclo[2.2.1]hept-3-yl]-3-(3-hydroxyprop-1-ynyl)thieno[2,3-c]pyridine-5-carboxamide;
methyl 3-(5-{[exo-4(S)-1-azabicyclo[2.2.1]hept-3-ylamino]carbonyl}thieno[2,3-c]pyridin-3-yl)prop-2-ynoate;
3-(3-amino-3-oxoprop-1-ynyl)-N-[exo-4(S)-1-azabicyclo[2.2.1]hept-3-yl]thieno[2,3-c]pyridine-5-carboxamide;
N-[exo-4(S)-1-azabicyclo[2.2.1]hept-3-yl]-3-cyanothieno[2,3-c]pyridine-5-carboxamide;
N-[exo-4(S)-1-azabicyclo[2.2.1]hept-3-yl]-3-chlorothieno[2,3-c]pyridine-5-carboxamide;
N-[exo-4(S)-1-azabicyclo[2.2.1]hept-3-yl]-3-fluorothieno[2,3-c]pyridine-5-carboxamide;
N-[exo-4(S)-1-azabicyclo[2.2.1]hept-3-yl]-3-iodothieno[2,3-c]pyridine-5-carboxamide;
N-[exo-4(S)-1-azabicyclo[2.2.1]hept-3-yl]-3-trifluoromethylthieno[2,3-c]pyridine-5-carboxamide;
N-[exo-4(S)-1-azabicyclo[2.2.1]hept-3-yl]-3-(methylthio)thieno[2,3-c]pyridine-5-carboxamide;
N-[exo-4(S)-1-azabicyclo[2.2.1]hept-3-yl]-3-(methylamino)thieno[2,3-c]pyridine-5-carboxamide;
N-[exo-4(S)-1-azabicyclo[2.2.1]hept-3-yl]-3-(formylamino)thieno[2,3-c]pyridine-5-carboxamide;
N-[exo-4(S)-1-azabicyclo[2.2.1]hept-3-yl]-3-[formyl(methyl)amino]thieno[2,3-c]pyridine-5-carboxamide;
N-[exo-4(S)-1-azabicyclo[2.2.1]hept-3-yl]-3-[(trifluoroacetyl)amino]thieno[2,3-c]pyridine-5-carboxamide;
N-[exo-4(S)-1-azabicyclo[2.2.1]hept-3-yl]-3-(cyclopropylamino)thieno[2,3-c]pyridine-5-carboxamide;
N-[exo-4(S)-1-azabicyclo[2.2.1]hept-3-yl]-3-[dimethylamino]thieno[2,3-c]pyridine-5-carboxamide;
N-5-[exo-4(S)-1-azabicyclo[2.2.1]hept-3-yl]1thieno[2,3-c]pyridine-3,5-dicarboxamide;
N-[exo-4(S)-1-azabicyclo[2.2.1]hept-3-yl]-3-formylthieno[2,3-c]pyridine-5-carboxamide;
N-[exo-4(S)-1-azabicyclo[2.2.1]hept-3-yl]-3-(trifluoroacetyl)thieno[2,3-c]pyridine-5-carboxamide;
N-[exo-4(S)-1-azabicyclo[2.2.1]hept-3-yl]-3-(methylsulfonyl)thieno[2,3-c]pyridine-5-carboxamide;
methyl 5-{[exo-4(S)-1-azabicyclo[2.2.1]hept-3-ylamino]carbonyl}thieno[2,3-c]pyridine-3-carboxylate;
N-[exo-4(S)-1-azabicyclo[2.2.1]hept-3-yl]-3-(phenylethynyl)furo[2,3-c]pyridine-5-carboxamide;
N-[exo-4(S)-1-azabicyclo[2.2.1]hept-3-yl]-3-(3,3,3-trifluoroprop-1-ynyl)furo[2,3-c]pyridine-5-carboxamide;
N-[exo-4(S)-1-azabicyclo[2.2.1]hept-3-yl]-3-(3,3-difluoroprop-1-ynyl)furo[2,3-c]pyridine-5-carboxamide;
N-[exo-4(S)-1-azabicyclo[2.2.1]hept-3-yl]-3-(phenylethynyl)thieno[2,3-c]pyridine-5-carboxamide;
N-[exo-4(S)-1-azabicyclo[2.2.1]hept-3-yl]-3-(3,3,3-trifluoroprop-1-ynyl)thieno[2,3-c]pyridine-5-carboxamide;
N-[exo-4(S)-1-azabicyclo[2.2.1]hept-3-yl]-3-(3,3-difluoroprop-1-ynyl)thieno[2,3-c]pyridine-5-carboxamide;
N-[exo-4(S)-1-azabicyclo[2.2.1]hept-3-yl]-2-(phenylethynyl)thieno[3,2-c]pyridine-5-carboxamide;

N-[exo-4(S)-1-azabicyclo[2.2.1]hept-3-yl]-2-(3,3,3-trifluoroprop-1-ynyl)thieno[3,2-c]pyridine-5-carboxamide;

N-[exo-4(S)-1-azabicyclo[2.2.1]hept-3-yl]-2-(3,3-difluoroprop-1-ynyl)thieno[3,2-c]pyridine-5-carboxamide;

N-((3R,5R)-1-azabicyclo[3.2.1]oct-3-yl)-2-methyl-furo[3,2-c]pyridine-6-carboxamide;

N-((3R,5R)-1-azabicyclo[3.2.1]oct-3-yl)-3-methyl-furo[3,2-c]pyridine-6-carboxamide;

N-((3R,5R)-1-azabicyclo[3.2.1]oct-3-yl)-2-ethyl-furo[3,2-c]pyridine-6-carboxamide;

N-((3R,5R)-1-azabicyclo[3.2.1]oct-3-yl)-3-ethyl-furo[3,2-c]pyridine-6-carboxamide;

N-((3R,5R)-1-azabicyclo[3.2.1]oct-3-yl)-4-methyl-furo[3,2-c]pyridine-6-carboxamide;

N-((3R,5R)-1-azabicyclo[3.2.1]oct-3-yl)-4-methylthio-furo[3,2-c]pyridine-6-carboxamide;

N-((3R,5R)-1-azabicyclo[3.2.1]oct-3-yl)-4-methoxy-furo[3,2-c]pyridine-6-carboxamide;

N-((3R,5R)-1-azabicyclo[3.2.1]oct-3-yl)-4-chloro-furo[3,2-c]pyridine-6-carboxamide;

N-((3R,5R)-1-azabicyclo[3.2.1]oct-3-yl)-2-vinylfuro[3,2-c]pyridine-6-carboxamide;

N-((3R,5R)-1-azabicyclo[3.2.1]oct-3-yl)-2-ethynylfuro[3,2-c]pyridine-6-carboxamide;

N-((3R,5R)-1-azabicyclo[3.2.1]oct-3-yl)-2-prop-1-ynylfuro[3,2-c]pyridine-6-carboxamide;

N-((3R,5R)-1-azabicyclo[3.2.1]oct-3-yl)-2-cyanofuro[3,2-c]pyridine-6-carboxamide;

N-((3R,5R)-1-azabicyclo[3.2.1]oct-3-yl)-3-ethynylfuro[3,2-c]pyridine-6-carboxamide;

N-((3R,5R)-1-azabicyclo[3.2.1]oct-3-yl)-3-prop-1-ynylfuro[3,2-c]pyridine-6-carboxamide;

N-((3R,5R)-1-azabicyclo[3.2.1]oct-3-yl)-3-cyanofuro[3,2-c]pyridine-6-carboxamide;

N-((3R,5R)-1-azabicyclo[3.2.1]oct-3-yl)-2-fluorofuro[3,2-c]pyridine-6-carboxamide;

N-((3R,5R)-1-azabicyclo[3.2.1]oct-3-yl)-2-chlorofuro[3,2-c]pyridine-6-carboxamide;

N-((3R,5R)-1-azabicyclo[3.2.1]oct-3-yl)-2-bromofuro[3,2-c]pyridine-6-carboxamide;

N-((3R,5R)-1-azabicyclo[3.2.1]oct-3-yl)-2-iodofuro[3,2-c]pyridine-6-carboxamide;

N-((3R,5R)-1-azabicyclo[3.2.1]oct-3-yl)-2-trifluoromethylfuro[3,2-c]pyridine-6-carboxamide;

N-((3R,5R)-1-azabicyclo[3.2.1]oct-3-yl)-3-trifluoromethylfuro[3,2-c]pyridine-6-carboxamide;

N-((3R,5R)-1-azabicyclo[3.2.1]oct-3-yl)-2-mercaptofuro[3,2-c]pyridine-6-carboxamide;

N-((3R,5R)-1-azabicyclo[3.2.1]oct-3-yl)-2-(methylthio)furo[3,2-c]pyridine-6-carboxamide;

N-((3R,5R)-1-azabicyclo[3.2.1]oct-3-yl)-2-(methylamino)furo[3,2-c]pyridine-6-carboxamide;

N-((3R,5R)-1-azabicyclo[3.2.1]oct-3-yl)-2-(formylamino)furo[3,2-c]pyridine-6-carboxamide;

2-(acetylamino)-N-((3R,5R)-1-azabicyclo[3.2.1]oct-3-yl)furo[3,2-c]pyridine-6-carboxamide;

2-(acetyl(methyl)amino)-N-((3R,5R)-1-azabicyclo[3.2.1]oct-3-yl)furo[3,2-c]pyridine-6-carboxamide;

N-((3R,5R)-1-azabicyclo[3.2.1]oct-3-yl)-2-[(trifluoroacetyl)amino]furo[3,2-c]pyridine-6-carboxamide;

N-((3R,5R)-1-azabicyclo[3.2.1]oct-3-yl)-2-(benzoylamino)furo[3,2-c]pyridine-6-carboxamide;

N-((3R,5R)-1-azabicyclo[3.2.1]oct-3-yl)-2-(diethylamino)furo[3,2-c]pyridine-6-carboxamide;

N-((3R,5R)-1-azabicyclo[3.2.1]oct-3-yl)-2-(diisopropylamino)furo[3,2-c]pyridine-6-carboxamide;

N-((3R,5R)-1-azabicyclo[3.2.1]oct-3-yl)-2-(pyrrolidin-1-yl)furo[3,2-c]pyridine-6-carboxamide;

N-((3R,5R)-1-azabicyclo[3.2.1]oct-3-yl)-2-(piperidin-1-yl)furo[3,2-c]pyridine-6-carboxamide;

N-((3R,5R)-1-azabicyclo[3.2.1]oct-3-yl)-2-(morpholin-4-yl)furo[3,2-c]pyridine-6-carboxamide;

N-((3R,5R)-1-azabicyclo[3.2.1]oct-3-yl)-2-(thiomorpholin-4yl)furo[3,2-c]pyridine-6-carboxamide;

N-((3R,5R)-1-azabicyclo[3.2.1]oct-3-yl)-2-(piperazin-1-yl)furo[3,2-c]pyridine-6-carboxamide;

N-((3R,5R)-1-azabicyclo[3.2.1]oct-3-yl)-2-(4-methylpiperazin-1-yl)furo[3,2-c]pyridine-6-carboxamide;

N-((3R,5R)-1-azabicyclo[3.2.1]oct-3-yl)-2-(cyclopropylamino)furo[3,2-c]pyridine-6-carboxamide;

N-((3R,5R)-1-azabicyclo[3.2.1]oct-3-yl)-2-[dimethylamino]furo[3,2-c]pyridine-6-carboxamide;

N-((3R,5R)-1-azabicyclo[3.2.1]oct-3-yl)-2-(pyrrolidin-1-ylcarbonyl)furo[3,2-c]pyridine-6-carboxamide;

N-((3R,5R)-1-azabicyclo[3.2.1]oct-3-yl)-2-(piperidin-1-ylcarbonyl)furo[3,2-c]pyridine-6-carboxamide;

N-((3R,5R)-1-azabicyclo[3.2.1]oct-3-yl)-2-(piperazin-1-ylcarbonyl)furo[3,2-c]pyridine-6-carboxamide;

N-((3R,5R)-1-azabicyclo[3.2.1]oct-3-yl)-2-[(4-methylpiperazin-1-yl)carbonyl]furo[3,2-c]pyridine-6-carboxamide;

N-((3R,5R)-1-azabicyclo[3.2.1]oct-3-yl)-2-(morpholin-4-ylcarbonyl)furo[3,2-c]pyridine-6-carboxamide;

N-((3R,5R)-1-azabicyclo[3.2.1]oct-3-yl)-2-(thiomorpholin-4-ylcarbonyl)furo[3,2-c]pyridine-6-carboxamide;

N-((3R,5R)-1-azabicyclo[3.2.1]oct-3-yl)-2-(aziridin-1-ylcarbonyl)furo[3,2-c]pyridine-6-carboxamide;

N-((3R,5R)-1-azabicyclo[3.2.1]oct-3-yl)-2-(azetidin-1-ylcarbonyl)furo[3,2-c]pyridine-6-carboxamide;

N-((3R,5R)-1-azabicyclo[3.2.1]oct-3-yl)-2-formylfuro[3,2-c]pyridine-6-carboxamide;

2-acetyl-N-((3R,5R)-1-azabicyclo[3.2.1]oct-3-yl)furo[3,2-c]pyridine-6-carboxamide;

N-((3R,5R)-1-azabicyclo[3.2.1]oct-3-yl)-2-(trifluoroacetyl)furo[3,2-c]pyridine-6-carboxamide;

N-((3R,5R)-1-azabicyclo[3.2.1]oct-3-yl)-2-[(phenyl)sulfonyl]furo[3,2-c]pyridine-6-carboxamide;

N-((3R,5R)-1-azabicyclo[3.2.1]oct-3-yl)-2-(methylsulfonyl)furo[3,2-c]pyridine-6-carboxamide;

N-((3R,5R)-1-azabicyclo[3.2.1]oct-3-yl)-4-methyl-thieno[3,2-c]pyridine-6-carboxamide;

N-((3R,5R)-1-azabicyclo[3.2.1]oct-3-yl)-4-methylthio-thieno[3,2-c]pyridine-6-carboxamide;

N-((3R,5R)-1-azabicyclo[3.2.1]oct-3-yl)-4-methoxy-thieno[3,2-c]pyridine-6-carboxamide;

N-((3R,5R)-1-azabicyclo[3.2.1]oct-3-yl)-4-chloro-thieno[3,2-c]pyridine-6-carboxamide;

N-((3R,5R)-1-azabicyclo[3.2.1]oct-3-yl)-2-vinylthieno[3,2-c]pyridine-6-carboxamide;

N-((3R,5R)-1-azabicyclo[3.2.1]oct-3-yl)-2-ethynylthieno[3,2-c]pyridine-6-carboxamide;

N-((3R,5R)-1-azabicyclo[3.2.1]oct-3-yl)-2-prop-1-ynylthieno[3,2-c]pyridine-6-carboxamide;

N-((3R,5R)-1-azabicyclo[3.2.1]oct-3-yl)-2-cyanothieno[3,2-c]pyridine-6-carboxamide;

N-((3R,5R)-1-azabicyclo[3.2.1]oct-3-yl)-2-fluorothieno[3,2-c]pyridine-6-carboxamide;

N-((3R,5R)-1-azabicyclo[3.2.1]oct-3-yl)-2-chlorothieno[3,2-c]pyridine-6-carboxamide;

N-((3R,5R)-1-azabicyclo[3.2.1]oct-3-yl)-2-bromothieno[3,2-c]pyridine-6-carboxamide;

N-((3R,5R)-1-azabicyclo[3.2.1]oct-3-yl)-2-iodothieno[3,2-c]pyridine-6-carboxamide;
N-((3R,5R)-1-azabicyclo[3.2.1]oct-3-yl)-2-trifluoromethylthieno[3,2-c]pyridine-6-carboxamide;
N-((3R,5R)-1-azabicyclo[3.2.1]oct-3-yl)-2-mercaptothieno[3,2-c]pyridine-6-carboxamide;
N-((3R,5R)-1-azabicyclo[3.2.1]oct-3-yl)-2-(methylthio)thieno[3,2-c]pyridine-6-carboxamide;
N-((3R,5R)-1-azabicyclo[3.2.1]oct-3-yl)-2-(methylamino)thieno[3,2-c]pyridine-6-carboxamide;
N-((3R,5R)-1-azabicyclo[3.2.1]oct-3-yl)-2-(formylamino)thieno[3,2-c]pyridine-6-carboxamide;
2-(acetylamino)-N-((3R,5R)-1-azabicyclo[3.2.1]oct-3-yl)thieno[3,2-c]pyridine-6-carboxamide;
2-(acetyl(methyl)amino)-N-((3R,5R)-1-azabicyclo[3.2.1]oct-3-yl)thieno[3,2-c]pyridine-6-carboxamide;
N-((3R,5R)-1-azabicyclo[3.2.1]oct-3-yl)-2-[(trifluoroacetyl)amino]thieno[3,2-c]pyridine-6-carboxamide;
N-((3R,5R)-1-azabicyclo[3.2.1]oct-3-yl)-2-(benzoylamino)thieno[3,2-c]pyridine-6-carboxamide;
N-((3R,5R)-1-azabicyclo[3.2.1]oct-3-yl)-2-(diethylamino)thieno[3,2-c]pyridine-6-carboxamide;
N-((3R,5R)-1-azabicyclo[3.2.1]oct-3-yl)-2-(diisopropylamino)thieno[3,2-c]pyridine-6-carboxamide;
N-((3R,5R)-1-azabicyclo[3.2.1]oct-3-yl)-2-(pyrrolidin-1-yl)thieno[3,2-c]pyridine-6-carboxamide;
N-((3R,5R)-1-azabicyclo[3.2.1]oct-3-yl)-2-(piperidin-1-yl)thieno[3,2-c]pyridine-6-carboxamide;
N-((3R,5R)-1-azabicyclo[3.2.1]oct-3-yl)-2-(morpholin-4-yl)thieno[3,2-c]pyridine-6-carboxamide;
N-((3R,5R)-1-azabicyclo[3.2.1]oct-3-yl)-2-(thiomorpholin-4yl)thieno[3,2-c]pyridine-6-carboxamide;
N-((3R,5R)-1-azabicyclo[3.2.1]oct-3-yl)-2-(piperazin-1-yl)thieno[3,2-c]pyridine-6-carboximide;
N-((3R,5R)-1-azabicyclo[3.2.1]oct-3-yl)-2-(4-methylpiperazin-1-yl)thieno[3,2-c]pyridine-6-carboximide;
N-((3R,5R)-1-azabicyclo[3.2.1]oct-3-yl)-2-(cyclopropylamino)thieno[3,2-c]pyridine-6-carboximide;
N-((3R,5R)-1-azabicyclo[3.2.1]oct-3-yl)-2-[dimethylamino]thieno[3,2-c]pyridine6-carboximide;
N-((3R,5R)-1-azabicyclo[3.2.1]oct-3-yl)-2-(pyrrolidin-1-ylcarbonyl)thieno[3,2-c]pyridine-6-carboxamide;
N-((3R,5R)-1-azabicyclo[3.2.1]oct-3-yl)-2-(piperidin-1-ylcarbonyl)thieno[3,2-c]pyridine-6-carboxamide;
N-((3R,5R)-1-azabicyclo[3.2.1]oct-3-yl)-2-(piperazin-1-ylcarbonyl)thieno[3,2-c]pyridine-6-carboxamide;
N-((3R,5R)-1-azabicyclo[3.2.1]oct-3-yl)-2-[(4-methylpiperazin-1-yl)carbonyl]thieno[3,2-c]pyridine-6-carboxamide;
N-((3R,5R)-1-azabicyclo[3.2.1]oct-3-yl)-2-(morpholin-4-ylcarbonyl)thieno[3,2-c]pyridine-6-carboxamide;
N-((3R,5R)-1-azabicyclo[3.2.1]oct-3-yl)-2-(thiomorpholin-4-ylcarbonyl)thieno[3,2-c]pyridine-6-carboxamide;
N-((3R,5R)-1-azabicyclo[3.2.1]oct-3-yl)-2-(aziridin-1-ylcarbonyl)thieno[3,2-c]pyridine-6-carboxamide;
N-((3R,5R)-1-azabicyclo[3.2.1]oct-3-yl)-2-(azetidin-1-ylcarbonyl)thieno[3,2-c]pyridine-6-carboxamide;
N-((3R,5R)-1-azabicyclo[3.2.1]oct-3-yl)-2-formylthieno[3,2-c]pyridine-6-carboxamide;
2-acetyl-N-((3R,5R)-1-azabicyclo[3.2.1]oct-3-yl)thieno[3,2-c]pyridine-6-carboxamide;
N-((3R,5R)-1-azabicyclo[3.2.1]oct-3-yl)-2-(trifluoroacetyl)thieno[3,2-c]pyridine-6-carboxamide;
N-((3R,5R)-1-azabicyclo[3.2.1]oct-3-yl)-2-[(phenyl)sulfonyl]thieno[3,2-c]pyridine-6-carboxamide;
N-((3R,5R)-1-azabicyclo[3.2.1]oct-3-yl)-2-(methylsulfonyl)thieno[3,2-c]pyridine-6-carboxamide;
N-((3R,5R)-1-azabicyclo[3.2.1]oct-3-yl)-3-vinylfuro[2,3-c]pyridine-5-carboxamide;
N-((3R,5R)-1-azabicyclo[3.2.1]oct-3-yl)-7-methyl-furo[2,3-c]pyridine-5-carboxamide;
N-((3R,5R)-1-azabicyclo[3.2.1]oct-3-yl)-7-methoxy-furo[2,3-c]pyridine-5-carboxamide;
N-((3R,5R)-1-azabicyclo[3.2.1]oct-3-yl)-3-ethynylfuro[2,3-c]pyridine-5-carboxamide;
N-((3R,5R)-1-azabicyclo[3.2.1]oct-3-yl)-3-prop-1-ynylfuro[2,3-c]pyridine-5-carboxamide;
N-((3R,5R)-1-azabicyclo[3.2.1]oct-3-yl)-3-cyanofuro[2,3-c]pyridine-5-carboxamide;
N-((3R,5R)-1-azabicyclo[3.2.1]oct-3-yl)-3-fluorofuro[2,3-c]pyridine-5-carboxamide;
N-((3R,5R)-1-azabicyclo[3.2.1]oct-3-yl)-3-iodofuro[2,3-c]pyridine-5-carboxamide;
N-((3R,5R)-1-azabicyclo[3.2.1]oct-3-yl)-3-trifluoromethylfuro[2,3-c]pyridine-5-carboxamide;
N-((3R,5R)-1-azabicyclo[3.2.1]oct-3-yl)-3-mercaptofuro[2,3-c]pyridine-5-carboxamide;
N-((3R,5R)-1-azabicyclo[3.2.1]oct-3-yl)-3-(methylthio)furo[2,3-c]pyridine-5-carboxamide;
N-((3R,5R)-1-azabicyclo[3.2.1]oct-3-yl)-3-(methylamino)furo[2,3-c]pyridine-5-carboxamide;
N-((3R,5R)-1-azabicyclo[3.2.1]oct-3-yl)-3-(formylamino)furo[2,3-c]pyridine-5-carboxamide;
3-(acetylamino)-N-((3R,5R)-1-azabicyclo[3.2.1]oct-3-yl)furo[2,3-c]pyridine-5-carboxamide;
3-(acetyl(methyl)amino)-N-((3R,5R)-1-azabicyclo[3.2.1]oct-3-yl)furo[2,3-c]pyridine-5-carboxamide;
N-((3R,5R)-1-azabicyclo[3.2.1]oct-3-yl)-3-[(trifluoroacetyl)amino]furo[2,3-c]pyridine-5-carboxamide;
N-((3R,5R)-1-azabicyclo[3.2.1]oct-3-yl)-3-(benzoylamino)furo[2,3-c]pyridine-5-carboxamide;
N-((3R,5R)-1-azabicyclo[3.2.1]oct-3-yl)-3-(diethylamino)furo[2,3-c]pyridine-5-carboxamide;
N-((3R,5R)-1-azabicyclo[3.2.1]oct-3-yl)-3-(diisopropylamino)furo[2,3-c]pyridine-5-carboxamide;
N-((3R,5R)-1-azabicyclo[3.2.1]oct-3-yl)-3-(pyrrolidin-1-yl)furo[2,3-c]pyridine-5-carboxamide;
N-((3R,5R)-1-azabicyclo[3.2.1]oct-3-yl)-3-(piperidin-1-yl)furo[2,3-c]pyridine-5-carboxamide;
N-((3R,5R)-1-azabicyclo[3.2.1]oct-3-yl)-3-(morpholin-4-yl)furo[2,3-c]pyridine-5-carboxamide;
N-((3R,5R)-1-azabicyclo[3.2.1]oct-3-yl)-3-(thiomorpholin-4yl)furo[3,2-c]pyridine-5-carboxamide;
N-((3R,5R)-1-azabicyclo[3.2.1]oct-3-yl)-3-(piperazin-1-yl)furo[2,3-c]pyridine-5-carboxamide;
N-((3R,5R)-1-azabicyclo[3.2.1]oct-3-yl)-3-(4-methylpiperazin-1-yl)furo[2,3-c]pyridine-5-carboxamide;
N-((3R,5R)-1-azabicyclo[3.2.1]oct-3-yl)-3-(cyclopropylamino)furo[2,3-c]pyridine-5-carboxamide;
N-((3R,5R)-1-azabicyclo[3.2.1]oct-3-yl)-3-[dimethylamino]furo[2,3-c]pyridine-5-carboxamide;
N-((3R,5R)-1-azabicyclo[3.2.1]oct-3-yl)-3-(pyrrolidin-1-ylcarbonyl)furo[2,3-c]pyridine-5-carboxamide;
N-((3R,5R)-1-azabicyclo[3.2.1]oct-3-yl)-3-(piperidin-1-ylcarbonyl)furo[2,3-c]pyridine-5-carboxamide;
N-((3R,5R)-1-azabicyclo[3.2.1]oct-3-yl)-3-(piperazin-1-ylcarbonyl)furo[2,3-c]pyridine-5-carboxamide;
N-((3R,5R)-1-azabicyclo[3.2.1]oct-3-yl)-3-[(4-methylpiperazin-1-yl)carbonyl]furo[2,3-c]pyridine-5-carboxamide;

N-((3R,5R)-1-azabicyclol[3.2.1]oct-3-yl)-3-(morpholin-4-ylcarbonyl)furo[2,3-c]pyridine-5-carboxamide;
N-((3R,5R)-1-azabicyclo[3.2.1]oct-3-yl)-3-(thiomorpholin-4-ylcarbonyl)furo[2,3-c]pyridine-5-carboxamide;
N-((3R,5R)-1-azabicyclo[3.2.1]oct-3-yl)-3-(aziridin-1-ylcarbonyl)furo[2,3-c]pyridine-5-carboxamide;
N-((3R,5R)-1-azabicyclo[3.2.1]oct-3-yl)-3-(azetidin-1-ylcarbonyl)furo[2,3-c]pyridine-5-carboxamide;
N-((3R,5R)-1-azabicyclo[3.2.1]oct-3-yl)-3-formylfuro[2,3-c]pyridine-5-carboximide;
3-acetyl-N-((3R,5R)-1-azabicyclo[3.2.1]oct-3-yl)furo[2,3-c]pyridine-5-carboxamide;
N-((3R,5R)-1-azabicyclo[3.2.1]oct-3-yl)-3-(trifluoroacetyl)furo[2,3-c]pyridine-5-carboxamide;
N-((3R,5R)-1-azabicyclo[3.2.1]oct-3-yl)-3-[(phenyl)sulfonyl]lfuro[2,3-c]pyridine-5-carboxamide;
N-((3R,5R)-1-azabicyclo[3.2.1]oct-3-yl)-3-(methylsulfonyl)furo[2,3-c]pyridine-5-carboxamide;
N-((3R,5R)-1-azabicyclo[3.2.1]oct-3-yl)-2-ethyl-furo[2,3-c]pyridine-5-carboximide;
N-((3R,5R)-1-azabicyclo[3.2.1]oct-3-yl)-2-ethynylfuro[2,3-c]pyridine-5-carboxamide;
N-((3R,5R)-1-azabicyclo[3.2.1]oct-3-yl)-2-prop-1-ynylfuro[2,3-c]pyridine-5-carboxamide;
N-((3R,5R)-1-azabicyclo[3.2.1]oct-3-yl)-2-cyanofuro[2,3-c]pyridine-5-carboxamide;
N-((3R,5R)-1-azabicyclo[3.2.1]oct-3-yl)-2-fluorofuro[2,3-c]pyridine-5-carboxamide;
N-((3R,5R)-1-azabicyclo[3.2.1]oct-3-yl)-2-chlorofuro[2,3-c]pyridine-5-carboxamide;
N-((3R,5R)-1-azabicyclo[3.2.1]oct-3-yl)-2-bromofuro[2,3-c]pyridine-5-carboxamide;
N-((3R,5R)-1-azabicyclo[3.2.1]oct-3-yl)-2-iodofuro[2,3-c]pyridine-5-carboxamide;
N-((3R,5R)-1-azahicyclo[3.2.1]oct-3-yl)-2-trifluoromethylfuro[2,3-c]pyridine-5-carboxamide;
N-((3R,5R)-1-azabicyclo[3.2.1]oct-3-yl)-2-mercaptofuro[2,3-c]pyridine-5-carboxamide;
N-((3R,5R)-1-azabicyclo[3.2.1]oct-3-yl)-2-(methylthio)furo[2,3-c]pyridine-5-carboxamide;
N-((3R,5R)-1-azabicyclo[3.2.1]oct-3-yl)-2-(methylamino)furo[2,3-c]pyridine-5-carboxamide;
N-((3R,5R)-1-azabicyclo[3.2.1]oct-3-yl)-2-(formylamino)furo[2,3-c]pyridine-5-carboxamide;
2-(acetylamino)-N-((3R,5R)-1-azabicyclo[3.2.1]oct-3-yl)furo[2,3-c]pyridine-5-carboxamide;
2-(acetyl(methyl)amino)-N-((3R,5R)-1-azabicyclo[3.2.1]oct-3-yl)furo[2,3-c]pyridine-5-carboxamide;
N-((3R,5R)-1-azabicyclo[3.2.1]oct-3-yl)-2-[(trifluoroacetyl)amino]furo[2,3-c]pyridine-5-carboxamide;
N-((3R,5R)-1-azabicyclo[3.2.1]oct-3-yl)-2-(benzoylamino)furo[2,3-c]pyridine-5-carboxamide;
N-((3R,5R)-1-azabicyclo[3.2.1]oct-3-yl)-2-(diethylamino)furo[2,3-c]pyridine-5-carboxamide;
N-((3R,5R)-1-azabicyclo[3.2.1]oct-3-yl)-2-(diisopropylamino)furo[2,3-c]pyridine-5-carboxamide;
N-((3R,5R)-1-azabicyclo[3.2.1]oct-3-yl)-2-(pyrrolidin-1-yl)furo[2,3-c]pyridine-5-carboxamide;
N-((3R,5R)-1-azabicyclo[3.2.1]oct-3-yl)-2-(piperidin-1-yl)furo[2,3-c]pyridine-5-carboxamide;
N-((3R,5R)-1-azabicyclo[3.2.1]oct-3-yl)-2-(morpholin-4-yl)furo[2,3-c]pyridine-5-carboxamide;
N-((3R,5R)-1-azabicyclo[3.2.1]oct-3-yl)-2-(thiomorpholin-4yl)furo[2,3-c]pyridine-5-carboxamide;
N-((3R,5R)-1-azabicyclo[3.2.1]oct-3-yl)-2-(piperazin-1-yl)furo[2,3-c]pyridine-5-carboxamide;
N-((3R,5R)-1-azabicyclo[3.2.1]oct-3-yl)-2-(4-methylpiperazin-1-yl)furo[2,3-c]pyridine-5-carboxamide;
N-((3R,5R)-1-azabicyclo[3.2.1]oct-3-yl)-2-(cyclopropylamino)furo[2,3-c]pyridine-5-carboxamide;
N-((3R,5R)-1-azabicyclo[3.2.1]oct-3-yl)-2[dimethylamino]furo[2,3-c]pyridine-5-carboxamide;
N-((3R,5R)-1-azabicyclo[3.2.1]oct-3-yl)-2-(pyrrolidin-1-ylcarbonyl)furo[2,3-c]pyridine-5-carboxamide;
N-((3R,5R)-1-azabicyclo[3.2.1]oct-3-yl)-2-(piperidin-1-ylcarbonyl)furo[2,3-c]pyridine-5-carboxamide;
N-((3R,5R)-1-azabicyclo[3.2.1]oct-3-yl)-2-(piperazin-1-ylcarbonyl)furo[2,3-c]pyridine-5-carboxamide;
N-((3R,5R)-1-azabicyclo[3.2.1]oct-3-yl)-2-[(4-methylpiperazin-1-yl)carbonyl]furo[2,3-c]pyridine-5-carboxamide;
N-((3R,5R)-1-azabicyclo[3.2.1]oct-3-yl)-2-(morpholin-4-ylcarbonyl)furo[2,3-c]pyridine-5-carboxamide;
N-((3R,5R)-1-azabicyclo[3.2.1]oct-3-yl)-2-(thiomorpholin-4-ylcarbonyl)furo[2,3-c]pyridine-5-carboxamide;
N-((3R,5R)-1-azabicyclo[3.2.1]oct-3-yl)-2-(aziridin-1-ylcarbonyl)furo[2,3-c]pyridine-5-carboxamide;
N-((3R,5R)-1-azabicyclo[3.2.1]oct-3-yl)-2-(azetidin-1-ylcarbonyl)furo[2,3-c]pyridine-5-carboxamide;
N-((3R,5R)-1-azabicyclo[3.2.1]oct-3-yl)-2-formylfuro[2,3-c]pyridine-5-carboxamide;
2-acetyl-N-((3R,5R)-1-azabicyclo[3.2.1]oct-3-yl)furo[2,3-c]pyridine-5-carboxamide;
N-((3R,5R)-1-azabicyclo[3.2.1]oct-3-yl)-2-(trifluoroacetyl)furo[2,3-c]pyridine-5-carboxamide;
N-((3R,5R)-1-azabicyclo[3.2.1]oct-3-yl)-2-[(phenyl)sulfonyl]lfuro[2,3-c]pyridine-5-carboxamide;
N-((3R,5R)-1-azabicyclo[3.2.1]oct-3-yl)-2-(methylsulfonyl)furo[2,3-c]pyridine-5-carboxamide;
N-((3R,5R)-1-azabicyclo[3.2.1]oct-3-yl)-7-methyl-thieno[2,3-c]pyridine-5-carboxamide;
N-((3R,5R)-1-azabicyclo[3.2.1]oct-3-yl)-7-methylthio-thieno[2,3-c]pyridine-5-carboxamide;
N-((3R,5R)-1-azabicyclo[3.2.1]oct-3-yl)-7-methoxy-thieno[2,3-c]pyridine-5-carboxamide;
N-((3R,5R)-1-azabicyclo[3.2.1]oct-3-yl)-7-chloro-thieno[2,3-c]pyridine-5-carboxamide;
N-((3R,5R)-1-azabicyclo[3.2.1]oct-3-yl)-3-vinylthieno[2,3-c]pyridine-5-carboxamide;
N-((3R,5R)-1-azabicyclo[3.2.1]oct-3-yl)-3-ethynylthieno[2,3-c]pyridine-5-carboxamide;
N-((3R,5R)-1-azabicyclo[3.2.1]oct-3-yl)-3-prop-1-ynylthieno[2,3-c]pyridine-5-carboxamide;
N-((3R,5R)-1-azabicyclo[3.2.1]oct-3-yl)-3-cyanothieno[2,3-c]pyridine-5-carboxamide;
N-((3R,5R)-1-azabicyclo[3.2.1]oct-3-yl)-3-fluorothieno[2,3-c]pyridine-5-carboxamide;
N-((3R,5R)-1-azabicyclo[3.2.1]oct-3-yl)-3-chlorothieno[2,3-c]pyridine-5-carboxamide;
N-((3R,5R)-1-azabicyclo[3.2.1]oct-3-yl)-3-bromothieno[2,3-c]pyridine-5-carboxamide;
N-((3R,5R)-1-azabicyclo[3.2.1]oct-3-yl)-3-iodothieno[2,3-c]pyridine-5-carboxamide;
N-((3R,5R)-1-azabicyclo[3.2.1]oct-3-yl)-3-trifluoromethylthieno[2,3-c]pyridine-5-carboxamide;
N-((3R,5R)-1-azabicyclo[3.2.1]oct-3-yl)-3-mercaptothieno[2,3-c]pyridine-5-carboxamide;
N-((3R,5R)-1-azabicyclo[3.2.1]oct-3-yl)-3-(methylthio)thieno[2,3-c]pyridine-5-carboxamide;
N-((3R,5R)-1-azabicyclo[3.2.1]oct-3-yl)-3-(methylamino)thieno[2,3-c]pyridine-5-carboxamide;
N-((3R,5R)-1-azabicyclo[3.2.1]oct-3-yl)-3-(formylamino)thieno[2,3-c]pyridine-5-carboxamide;

3-(acetylamino)-N-((3R,5R)-1-azabicyclo[3.2.1]oct-3-yl)thieno[2,3-c]pyridine-5-carboxamide;

3-(acetyl(methyl)amino)-N-((3R,5R)-1-azabicyclo[3.2.1]oct-3-yl)thieno[2,3-c]pyridine-5-carboxamide;

N-((3R,5R)-1-azabicyclo[3.2.1]oct-3-yl)-3-[(trifluoroacetyl)amino]thieno[2,3-c]pyridine-5-carboxamide;

N-((3R,5R)-1-azabicyclo[3.2.1]oct-3-yl)-3-(benzoylamino)thieno[2,3-c]pyridine-5-carboxamide;

N-((3R,5R)-1-azabicyclo[3.2.1]oct-3-yl)-3-(diethylamino)thieno[2,3-c]pyridine-5-carboxamide;

N-((3R,5R)-1-azabicyclo[3.2.1]oct-3-yl)-3-(diisopropylamino)thieno[2,3-c]pyridine-5-carboxamide;

N-((3R,5R)-1-azabicyclo[3.2.1]oct-3-yl)-3-(pyrrolidin-1-yl)thieno[2,3-c]pyridine-5-carboxamide;

N-((3R,5R)-1-azabicyclo[3.2.1]oct-3-yl)-3-(piperidin-1-yl)thieno[2,3-c]pyridine-5-carboxamide;

N-((3R,5R)-1-azabicyclo[3.2.1]oct-3-yl)-3-(morpholin-4-yl)thieno[2,3-c]pyridine-5-carboxamide;

N-((3R,5R)-1-azabicyclo[3.2.1]oct-3-yl)-3-(thiomorpholin-4yl)thieno[2,3-c]pyridine-5-carboxamide;

N-((3R,5R)-1-azabicyclo[3.2.1]oct-3-yl)-3-(piperazin-1-yl)thieno[2,3-c]pyridine-5-carboxamide;

N-((3R,5R)-1-azabicyclo[3.2.1]oct-3-yl)-3-(4-methylpiperazin-1-yl)thieno[2,3-c]pyridine-5-carboxamide;

N-((3R,5R)-1-azabicyclo[3.2.1]oct-3-yl)-3-(cyclopropylamino)thieno[2,3-c]pyridine-5-carboxamide;

N-((3R,5R)-1-azabicyclo[3.2.1]oct-3-yl)-3-[dimethylamino]thieno[2,3-c]pyridine-5-carboxamide;

N-((3R,5R)-1-azabicyclo[3.2.1]oct-3-yl)-3-(pyrrolidin-1-ylcarbonyl)thieno[2,3-c]pyridine-5-carboxamide;

N-((3R,5R)-1-azabicyclo[3.2.1]oct-3-yl)-3-(piperidin-1-ylcarbonyl)thieno[2,3-c]pyridine-5-carboxamide;

N-((3R,5R)-1-azabicyclo[3.2.1]oct-3-yl)-3-(piperazin-1-ylcarbonyl)thieno[2,3-c]pyridine-5-carboxamide;

N-((3R,5R)-1-azabicyclo[3.2.1]oct-3-yl)-3-[(4-methylpiperazin-1-yl)carbonyl]thieno[2,3-c]pyridine-5-carboxamide;

N-((3R,5R)-1-azabicyclo[3.2.1]oct-3-yl)-3-(morpholin-4-ylcarbonyl)thieno[2,3-c]pyridine-5-carboxamide;

N-((3R,5R)-1-azabicyclo[3.2.1]oct-3-yl)-3-(thiomorpholin-4-ylcarbonyl)thieno[2,3-c]pyridine-5-carboxamide;

N-((3R,5R)-1-azabicyclo[3.2.1]oct-3-yl)-3-(aziridin-1-ylcarbonyl)thieno[2,3-c]pyridine-5-carboxamide;

N-((3R,5R)-1-azabicyclo[3.2.1]oct-3-yl)-3-(azetidin-1-ylcarbonyl)thieno[2,3-c]pyridine-5-carboxamide;

N-((3R,5R)-1-azabicyclo[3.2.1]oct-3-yl)-3-formylthieno[2,3-c]pyridine-5-carboxamide;

3-acetyl-N-((3R,5R)-1-azabicyclo[3.2.1]oct-3-yl)thieno[2,3-c]pyridine-5-carboxamide;

N-((3R,5R)-1-azabicyclo[3.2.1]oct-3-yl)-3-(trifluoroacetyl)thieno[2,3-c]pyridine-5-carboxamide;

N-((3R,5R)-1-azabicyclo[3.2.1]oct-3-yl)-3-[(phenyl)sulfonyl]thieno[2,3-c]pyridine-5-carboxamide; and N-((3R,5R)-1-azabicyclo[3.2.1]oct-3-yl)-3-(methylsulfonyl)thieno[2,3-c]pyridine-5-carboxamide;

or a pharmaceutically acceptable salt thereof, wherein the compound is a racemic mixture or the pure enantiomer or thereof.

4. The compound of Formula I:

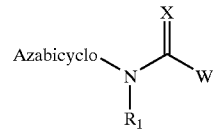

Formula I wherein Azabicyclo is

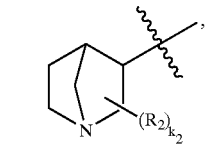

II

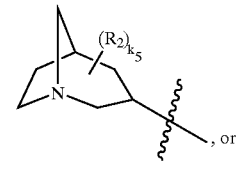

V

, or

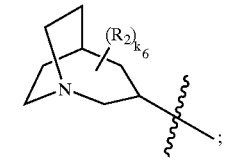

VI

;

W is

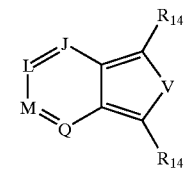

(b)

provided that the bond between the —C(=X)— group and the W group may be attached at any available carbon atom within the W group as provided in $R_6$;

X is O;

Each $R_1$ is H, alkyl, or cycloalkyl.

Each $R_2$ is alkyl, halogenated alkyl, substituted alkyl, cycloalkyl, aryl, F, Cl, Br, I, or $R_2$ is absent provided that $k_2$, $k_5$, or $k_6$ is 0;

$k_2$ is 0 or 1;

$k_5$ and $k_6$ are independently 0, 1, or 2;

J, L, M, and Q are N or C($R_6$) provided that only one of J, L, M, or Q, is N and the others are C($R_6$), further provided that when the core molecule is attached to the pyridinyl moiety at M, Q is C(H), and further provided that there is only one attachment to the core molecule;

$R_4$ is H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, or $R_9$;

Each $R_5$ is independently H, lower alkyl, or lower alkenyl;

Each $R_6$ is independently H, F, Br, I, Cl, —CN, —CF$_3$, —OR$_5$, —SR$_5$, —N(R$_5$)$_2$, or a bond to the core molecule provided that only one $R_6$ is said bond;

V is selected from O, S, or N(R4);

$R_7$ is 5-membered heteroaromatic mono-cyclic moieties containing within the ring 1–3 heteroatoms independently selected from the group consisting of =N—, —N($R_{17}$)—, —O—, and —S—, and having 0–1 substituent selected from $R_{18}$ and further having 0–3 substituents independently selected from F, Cl, Br, or I, or $R_7$ is 9-membered fused-ring moieties having a 6-membered ring fused to a 5-membered ring of the formulas:

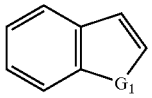

wherein $G_1$ is O, S or $NR_{17}$,

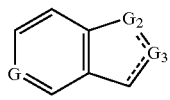

wherein G is C($R_{16}$) or N, and each $G_2$ and $G_3$ are independently selected from C($R_{16}$)$_2$, C($R_{16}$), O, S, N, and N($R_{18}$), provided that both $G_2$ and $G_3$ are not simultaneously O, simultaneously S, or simultaneously O and S, or

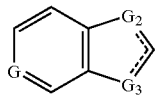

wherein G is C($R_{16}$) or N, and each $G_2$ and $G_3$ are independently selected from C($R_{16}$)$_2$, C($R_{16}$), O, S, N, and N($R_{17}$), each 9-membered fused-ring moiety having 0–1 substituent selected from $R_{18}$ and further having 0–3 substituent(s) independently selected from F, Cl, Br, or I, wherein the $R_7$ moiety attaches to other substituents as defined in formula I at any position on either ring as valency allows;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from $R_{18}$ and 0–3 substituent(s) independently selected from F, Cl, Br, or I, or $R_9$ is 10-membered heteroaromatic bi-cyclic moieties containing within one or both rings 1–3 heteroatoms selected from =N—, each 10-membered fused-ring moiety having 0–1 substituent selected from $R_{18}$ and 0–3 substituent(s) independently selected from F, Cl, Br, or I, and having a bond directly or indirectly attached to the core molecule where valency allows;

Each $R_{10}$ is independently H, alkyl, cycloalkyl, heterocyclo, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_{11}$ is independently H, alkyl, cycloalkyl, heterocycloalkyl, halogenated alkyl, halogenated cycloalkyl, or halogenated heterocycloalkyl;

$R_{13}$ is —CN, —CF$_3$, —NO$_2$, —OR$_{11}$, —SR$_{11}$, —NR$_{11}$R$_{11}$, —C(O)R$_{11}$, —C(O)NR$_{11}$R$_{11}$, —NR$_{11}$C(O)R$_{11}$, —S(O)$_2$NR$_{11}$R$_{11}$, or —NR$_{11}$S(O)$_2$R$_{11}$;

Each $R_{14}$ is H, alkyl, substituted alkyl, halogenated alkyl, alkenyl, substituted alkenyl, halogenated alkenyl, alkynyl, substituted alkynyl, halogenated alkynyl, F, Br, Cl, I, —CN, —NO$_2$, —OR$_{19}$, —C(O)N(R$_{10}$)$_2$, —N(R$_{10}$)$_2$, —SR$_{19}$, —S(O)$_2$R$_{19}$, —C(O)R$_{19}$, —CO$_2$R$_{19}$, aryl, $R_7$ or $R_9$;

Each $R_{16}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, F, Cl, Br, I, —NO$_2$, —CN, —OR$_{11}$, —SR$_{11}$, —NR$_{11}$R$_{11}$, —C(O)R$_{11}$, —C(O)NR$_{11}$R$_{11}$, —NR$_{11}$C(O)R$_{11}$, —S(O)$_2$NR$_{11}$R$_{11}$, —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$, R$_{11}$, —C(O)R$_{11}$, —NO$_2$, —C(O) NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

$R_{17}$ is H, alkyl, halogenated alkyl, substituted alkyl, cycloalkyl, halogenated cycloalkyl, substituted cycloalkyl, phenyl, —SO$_2$R$_8$, or phenyl having 1 substituent selected from $R_8$ and further having 0–3 substituents independently selected from F, Cl, Br, or I;

$R_{18}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —NO$_2$, alkyl substituted with 1–4 substituent(s) independently selected from F, Cl, Br, I, or $R_{13}$, cycloalkyl substituted with 1–4 substituent(s) independently selected from F, Cl, Br, I or $R_{13}$, or heterocycloalkyl substituted with 1–4 substituent(s) independently selected from F, Cl, Br, I, or $R_{19}$ is H, alkyl, cycloalkyl, substituted alkyl, halogenated alkyl, substituted phenyl, or substituted naphthyl;

or pharmaceutically acceptable salt, racemic mixture, and pure enantiomer thereof.

5. The compound of claim 4, wherein (b) is thieno[3,4-c]pyridin-6-yl, optionally substituted on up to 4 different carbon atoms as valency allows and as allowed by the definition of W with F, Br, Cl, I, —CN, —NO$_2$, —CF$_3$, —OR$_5$, —OR$_{19}$, —SR$_5$, —SR$_{19}$, —N(R$_5$)$_2$, —N(R$_{10}$)$_2$, —C(O)R$_{19}$, —CO$_2$R$_{19}$, —C(O)N(R$_{10}$)$_2$, —S(O)$_2$R$_{19}$, alkyl substituted alkyl, halogenated alkyl, alkenyl, substituted alkenyl, halogenated alkenyl, alkynyl, substituted alkynyl, halogenated alkynyl, aryl, $R_7$, $R_9$, provided that one carbon is used to bond W to the core molecule.

6. The compound of claim 5, wherein each $k_2$, $k_5$, and $k_6$ is independently 0 or 1.

7. The compound of claim 6, wherein $R_2$ is alkyl, halogenated alkyl, substituted alkyl, or is absent provided that $k_2$, $k_5$, or $k_6$ is 0.

8. The compound of claim 7, wherein $R_1$ is H or lower alkyl, and wherein $R_2$ is lower alkyl or is absent provided that $k_2$, $k_5$, or $k_6$ is 0.

9. The compound of claim 8, wherein the compound is
N-(1-azabicyclo[2.2.1]hept-3-yl)thieno[3,4-c]pyridine-6-carboxamide;
N-(1-(6-methyl)-azabicyclo[2.2.1]hept-3-yl)thieno[3,4-c]pyridine-6-carboxamide;
N-((3R,5R)-1-azabicyclo[3.2.1]oct-3-yl)thieno[3,4-c]pyridine-6-carboxamide;
N-(1-azabicyclo[3.2.2]non-3-yl)thieno[3,4-c]pyridine-6-carboxamide;
or a pharmaceutically acceptable salt thereof, wherein the compound is a racemic mixture or the pure enantiomer thereof.

10. The compound of Formula I:

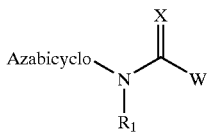

Formula I wherein Azabicyclo is

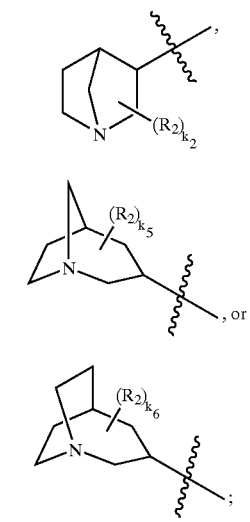

W is

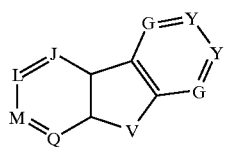

provided that the bond between the —C(=X)— group and the W group may be attached at any available carbon atom within the W group as provided in $R_6$;

X is O;

Each $R_1$ is H, alkyl, or cycloalkyl.

Each $R_2$ is alkyl, halogenated alkyl, substituted alkyl, cycloalkyl, aryl, F, Cl, Br, I, or $R_2$ is absent provided that $k_2$, $k_5$, or $K_6$ is 0;

$k_2$ is 0 or 1;

$k_5$ and $K_6$ are independently 0, 1, or 2;

J, L, M, and Q are N or C($R_6$) provided that only one of J, L, M, or Q, is N and the others are C($R_6$), further provided that when the core molecule is attached to the pyridinyl moiety at M, Q is C(H), and further provided that there is only one attachment to the core molecule;

G and Y are C($R_6$), provided that when the molecule is attached to the phenyl moiety at Y, G is CH;

$R_4$ is H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, or $R_9$;

Each $R_5$ is independently H, lower alkyl, or lower alkenyl;

Each $R_6$ is independently H, F, Br, I, Cl, —CN, —CF$_3$, —OR$_5$, —SR$_5$, —N(R$_5$)$_2$, or a bond to the core molecule provided that only one $R_6$ is said bond;

V is selected from O, S, or N($R_4$);

$R_7$ is 5-membered heteroaromatic mono-cyclic moieties containing within the ring 1–3 heteroatoms independently selected from the group consisting of =N—, —N($R_{17}$)—, —O—, and —S—, and having 0–1 substituent selected from $R_{18}$ and further having 0—3 substituents independently selected from F, Cl, Br, or I, or $R_7$ is 9-membered fused-ring moieties having a 6-membered ring fused to a 5-membered ring of the formulas

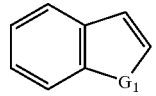

wherein $G_1$ is O, S or NR$_{17}$,

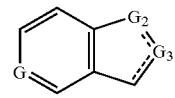

wherein G is C($R_{16}$) or N, and each $G_2$ and $G_3$ are independently selected from C($R_{16}$)$_2$, C($R_{16}$), O, S, N, and N($R_{18}$), provided that both $G_2$ and $G_3$ are not simultaneously O, simultaneously S, or simultaneously O and S, or

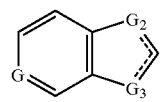

wherein G is C($R_{16}$) or N, and each $G_2$ and $G_3$ are independently selected from C($R_{16}$)$_2$, C($R_{16}$), O, S, N, and N($R_{17}$), each 9-membered fused-ring moiety having 0–1 substituent selected from $R_{18}$ and further having 0–3 substituent(s) independently selected from F, Cl, Br, or I, wherein the $R_7$ moiety attaches to other substituents as defined in formula I at any position on either ring as valency allows;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from $R_{18}$ and 0–3 substituent(s) independently selected from F, Cl, Br, or I, or R9 is 10-membered heteroaromatic bi-cyclic moieties containing within one or both rings 1–3 heteroatoms selected from =N—, each 10-membered fused-ring moiety having 0–1 substituent selected from $R_{18}$ and 0–3 substituent(s) independently selected from F, Cl, Br, or I, and having a bond directly or indirectly attached to the core molecule where valency allows;

Each $R_{10}$ is independently H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_{11}$ is independently H, alkyl, cycloalkyl, heterocycloalkyl, halogenated alkyl, halogenated cycloalkyl, or halogenated heterocycloalkyl;

$R_{13}$ is —CN, —CF$_3$, —NO$_2$, —OR$_{11}$, —SR$_{11}$, —NR$_{11}$R$_{11}$, —C(O)R$_{11}$, —C(O)NR$_{11}$R$_{11}$, —NR$_{11}$C(O)R$_{11}$, —S(O)$_2$NR$_{11}$R$_{11}$, or —NR$_{11}$S(O)$_2$R$_{11}$;

Each $R_{16}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, F, Cl, Br, I, —NO$_2$, —CN, —OR$_{11}$, —SR$_{11}$, —NR$_{11}$R$_{11}$, —C(O)R$_{11}$, —C(O)NR$_{11}$R$_{11}$, —NR$_{11}$C(O)R$_{11}$, —S(O)$_2$NR$_{11}$R$_{11}$, —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

$R_{17}$ is H, alkyl, halogenated alkyl, substituted alkyl, cycloalkyl, halogenated cycloalkyl, substituted cycloalkyl, phenyl, —SO$_2$R$_8$, or phenyl having 1 substituent selected from $R_{18}$ and further having 0–3 substituents independently selected from F, Cl, Br, or I;

$R_{18}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —NO$_2$, alkyl substituted with 1–4 substituent(s) independently selected from F, Cl, Br, I, or $R_{13}$, cycloalkyl substituted with 1–4 substituent(s) independently selected from F, Cl, Br, I, or $R_{13}$, or heterocycloalkyl substituted with 1–4 substituent(s) independently selected from F, Cl, Br, I, or $R_{13}$;

$R_{19}$ is H, alkyl, cycloalkyl, substituted alkyl, halogenated alkyl, substituted phenyl, or substituted naphthyl;

or pharmaceutically acceptable salt, racemic mixture, and pure enantiomer thereof.

11. The compound of claim 10, wherein (c) is benzothieno[3,2-c]pyridine-3-yl, benzothieno[2,3-c]pyridin-3-yl, benzofuro[3,2-c]pyridin-3-yl, or benzofuro[2,3-c]pyridin-3-yl, optionally substituted on up to 4 different carbon atoms as valency allows and as allowed by the definition of W with F, Br, Cl, I, —CN, —NO$_2$, —CF$_3$, —OR$_5$, —OR19, —SR$_5$, —SR$_{19}$, —N(R$_5$)$_2$, —N(R$_{10}$)$_2$, —C(O)R$_{19}$, —CO$_2$R$_{19}$, —C(O)N(R$_{10}$)$_2$, —S(O)$_2$R$_{19}$, alkyl, substituted alkyl, halogenated alkyl, alkenyl, substituted alkenyl, halogenated alkenyl, alkynyl, substituted alkynyl, halogenated alkynyl, aryl, $R_7$, $R_9$, provided that one carbon is used to bond W to the core molecule.

12. The compound of claim 11, wherein each $k_2$, $k_5$, and $k_6$ is independently 0 or 1.

13. The compound of claim 12, wherein $R_2$ is alkyl, halogenated alkyl, substituted alkyl, or is absent provided that $k_2$, $k_5$, or $k_6$ is 0.

14. The compound of claim 13, wherein $R_1$ is H or lower alkyl, and wherein $R_2$ is absent or lower alkyl or is absent provided that $k_2$, $k_5$, or $k_6$ is 0.

15. The compound of claim 14, wherein the compound is

N-(1-azabicyclo[2.2.1]hept-3-yl)-benzothieno[3,2-c]pyridine-3-carboxamide;

N-(1-(6-methyl)-azabicyclo[2.2.1]hept-3-yl)-benzothieno[3,2-c]pyridine3-carboxamide;

N-((3R,5R)-1-azabicyclo[3.2.1]oct-3-yl)-benzothieno[3,2c]pyridine-3-carboxamide;

N-(1-azabicyclo[3.2.2]non-3-yl)-benzothieno[3,2-c]pyridine-3-carboxamide;

N-[exo-4(S)-1-azabicyclo[2.2.1]hept-3-yl][1]benzofuro[2,3-c]pyridine-3-carboxamide;

N-[exo-4(S)-1-azabicyclo[2.2.1]hept-3-yl][1]benzothieno[2,3-c]pyridine-3-carboxamide;

or a pharmaceutically acceptable salt thereof, wherein the compound is a racemic mixture or the pure enantiomer thereof.

* * * * *